US012364748B2

(12) United States Patent
Kawaoka et al.

(10) Patent No.: US 12,364,748 B2
(45) **Date of Patent: *Jul. 22, 2025**

(54) INFLUENZA B VIRUS REPLICATION FOR VACCINE DEVELOPMENT

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US); Jihui Ping, Nanjing (CN)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 378 days.

This patent is subject to a terminal disclaimer.

(21) Appl. No.: 17/546,835

(22) Filed: Dec. 9, 2021

(65) Prior Publication Data

US 2022/0202926 A1 Jun. 30, 2022

Related U.S. Application Data

(63) Continuation of application No. 15/436,245, filed on Feb. 17, 2017, now Pat. No. 11,197,925.

(60) Provisional application No. 62/297,400, filed on Feb. 19, 2016.

(51) Int. Cl.

| | |
|---|---|
| ***A61K 39/145*** | (2006.01) |
| ***A61K 39/12*** | (2006.01) |
| ***C12N 7/00*** | (2006.01) |
| ***C12N 15/86*** | (2006.01) |
| *A61K 39/00* | (2006.01) |

(52) U.S. Cl.

CPC ............ *A61K 39/145* (2013.01); *A61K 39/12* (2013.01); *C12N 7/00* (2013.01); *C12N 15/86* (2013.01); *A61K 2039/5258* (2013.01); *C12N 2760/16023* (2013.01); *C12N 2760/16071* (2013.01); *C12N 2760/16221* (2013.01); *C12N 2760/16222* (2013.01); *C12N 2760/16234* (2013.01); *C12N 2760/16251* (2013.01)

(58) Field of Classification Search

None

See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,578,473 | A | 11/1996 | Palese et al. |
| 5,716,821 | A | 2/1998 | Wertz et al. |
| 5,750,394 | A | 5/1998 | Palese et al. |
| 5,786,199 | A | 7/1998 | Palese |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,001,634 | A | 12/1999 | Palese et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,270,958 | B1 | 8/2001 | Olivo et al. |
| 6,271,011 | B1 | 8/2001 | Lee et al. |
| 6,358,733 | B1 | 3/2002 | Motwani et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,843,996 | B1 | 1/2005 | Parkin et al. |
| 6,872,395 | B2 | 3/2005 | Kawaoka |
| 6,890,710 | B1 | 5/2005 | Palese et al. |
| 6,951,752 | B2 | 10/2005 | Reiter et al. |
| 6,951,754 | B2 | 10/2005 | Hoffmann |
| 6,974,695 | B2 | 12/2005 | Vogels et al. |
| 7,037,707 | B2 | 5/2006 | Webster et al. |
| 7,176,021 | B2 | 2/2007 | Kawaoka |
| 7,211,378 | B2 | 5/2007 | Kawaoka et al. |
| 7,226,774 | B2 | 6/2007 | Kawaoka |
| 7,312,064 | B2 | 12/2007 | Hoffmann |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

McCullers et al. Virology vol. 336, Issue 2, Jun. 5, 2005, pp. 318-326 (Year: 2005).*

Result 17, NCBI Blast nucleotide search of SEQ ID No. 2, database "nr", (Jul. 18, 2006), 3 pgs.

Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.

Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.

Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.

(Continued)

*Primary Examiner* — Janet L Andres
*Assistant Examiner* — Myron G Hill
(74) *Attorney, Agent, or Firm* — Schwegman Lundberg & Woessner, P.A.

(57) ABSTRACT

The invention provides a composition useful to prepare high titer influenza B viruses, e.g., in the absence of helper virus, which includes internal genes from an influenza B virus vaccine strain or isolate, e.g., one that is safe in humans, for instance, one that does not result in significant disease, that confer enhanced growth in cells in culture, such as MDCK cells, or in eggs.

19 Claims, 52 Drawing Sheets

Specification includes a Sequence Listing.

(56) References Cited

U.S. PATENT DOCUMENTS

| | | | |
|---|---|---|---|
| 7,335,356 | B2 | 2/2008 | Hart et al. |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,601,356 | B2 | 10/2009 | Jin et al. |
| 7,670,837 | B2 | 3/2010 | Schwartz |
| 7,682,618 | B2 | 3/2010 | Bavari et al. |
| 7,723,094 | B2 | 5/2010 | Kawaoka et al. |
| 7,833,788 | B2 | 11/2010 | Pau et al. |
| 7,883,844 | B2 | 2/2011 | Nouchi et al. |
| 7,955,833 | B2 | 6/2011 | Reiter et al. |
| 7,959,930 | B2 | 6/2011 | De Wit et al. |
| 7,968,101 | B2 | 6/2011 | Kawaoka et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,043,856 | B2 | 10/2011 | Kawaoka et al. |
| 8,048,430 | B2 | 11/2011 | Yang et al. |
| 8,057,806 | B2 | 11/2011 | Kawaoka et al. |
| 8,093,033 | B2 | 1/2012 | Kemble et al. |
| 8,114,415 | B2 | 2/2012 | Hoffmann et al. |
| 8,119,337 | B2 | 2/2012 | Gregersen |
| 8,119,388 | B2 | 2/2012 | Schwartz et al. |
| 8,298,805 | B2 | 10/2012 | Kawaoka |
| 8,309,099 | B2 | 11/2012 | Hoffmann |
| 8,354,114 | B2 | 1/2013 | Lu et al. |
| 8,357,376 | B2 | 1/2013 | Liu et al. |
| 8,409,843 | B2 | 4/2013 | Kemble et al. |
| 8,460,914 | B2 | 6/2013 | Gregersen |
| 8,465,960 | B2 | 6/2013 | Kawaoka et al. |
| 8,475,806 | B2 | 7/2013 | Kawaoka |
| 8,507,247 | B2 | 8/2013 | Kawaoka et al. |
| 8,524,497 | B2 | 9/2013 | Reiter et al. |
| 8,546,123 | B2 | 10/2013 | Lewis |
| 8,574,591 | B2 | 11/2013 | Hoffmann et al. |
| 8,574,593 | B2 | 11/2013 | Yang et al. |
| 8,580,277 | B2 | 11/2013 | Yang et al. |
| 8,591,914 | B2 | 11/2013 | Yang et al. |
| 8,597,661 | B2 | 12/2013 | Kawaoka et al. |
| 8,679,819 | B2 | 3/2014 | Kawaoka |
| 8,877,209 | B2 | 11/2014 | Kawaoka et al. |
| 8,900,595 | B2 | 12/2014 | Kawaoka et al. |
| 9,101,653 | B2 | 8/2015 | Kawaoka et al. |
| 9,109,013 | B2 | 8/2015 | Kawaoka et al. |
| 9,222,118 | B2 | 12/2015 | Kawaoka et al. |
| 9,254,318 | B2 | 2/2016 | Kawaoka et al. |
| 9,284,533 | B2 | 3/2016 | Bilsel et al. |
| 9,474,798 | B2 | 10/2016 | Watanabe et al. |
| 9,757,446 | B2 | 9/2017 | LeFebvre et al. |
| 9,890,363 | B2 | 2/2018 | Kawaoka |
| 9,926,535 | B2 | 3/2018 | Kawaoka et al. |
| 9,950,057 | B2 | 4/2018 | Kawaoka et al. |
| 10,053,671 | B2 | 8/2018 | Kawaoka et al. |
| 10,059,925 | B2 | 8/2018 | Kawaoka et al. |
| 10,119,124 | B2 | 11/2018 | Watanabe et al. |
| 10,130,697 | B2 | 11/2018 | Watanabe |
| 10,172,934 | B2 | 1/2019 | Kawaoka et al. |
| 10,246,686 | B2 | 4/2019 | Kawaoka et al. |
| 10,358,630 | B2 | 7/2019 | Kawaoka et al. |
| 10,494,613 | B2 | 12/2019 | Kawaoka et al. |
| 10,513,692 | B2 | 12/2019 | Kawaoka et al. |
| 10,633,422 | B2 | 4/2020 | Kawaoka et al. |
| 10,808,229 | B2 | 10/2020 | Kawaoka et al. |
| 11,007,262 | B2 | 5/2021 | Watanabe et al. |
| 11,046,934 | B2 | 6/2021 | Kawaoka et al. |
| 11,180,737 | B2 | 11/2021 | Kawaoka et al. |
| 11,197,925 | B2 | 12/2021 | Kawaoka et al. |
| 11,197,926 | B2 | 12/2021 | Kawaoka et al. |
| 11,241,492 | B2 | 2/2022 | Kawaoka et al. |
| 11,384,339 | B2 | 7/2022 | Kawaoka et al. |
| 11,389,523 | B2 | 7/2022 | Kawaoka et al. |
| 11,390,649 | B2 | 7/2022 | Kawaoka et al. |
| 11,739,303 | B2 | 8/2023 | Kawaoka et al. |
| 11,802,273 | B2 | 10/2023 | Kawaoka et al. |
| 11,807,872 | B2 | 11/2023 | Kawaoka et al. |
| 11,851,648 | B2 | 12/2023 | Kawaoka et al. |
| 12,258,557 | B2 | 3/2025 | Kawaoka et al. |
| 12,290,562 | B2 | 5/2025 | Kawaoka et al. |
| 2002/0010143 | A1 | 1/2002 | Barbosa et al. |
| 2002/0164770 | A1 | 11/2002 | Hoffmann |
| 2002/0197705 | A1 | 12/2002 | Kawaoka |
| 2003/0035814 | A1 | 2/2003 | Kawaoka et al. |
| 2003/0044962 | A1 | 3/2003 | Makizumi et al. |
| 2003/0073223 | A1 | 4/2003 | Groner et al. |
| 2003/0119183 | A1 | 6/2003 | Groner |
| 2003/0194694 | A1 | 10/2003 | Kawaoka |
| 2003/0215794 | A1 | 11/2003 | Kawaoka et al. |
| 2004/0002061 | A1 | 1/2004 | Kawaoka |
| 2004/0029251 | A1 | 2/2004 | Hoffman et al. |
| 2004/0057967 | A1 | 3/2004 | Bavari et al. |
| 2004/0063141 | A1 | 4/2004 | Lok |
| 2004/0077086 | A1 | 4/2004 | Reiter et al. |
| 2004/0132164 | A1 | 7/2004 | Doyle et al. |
| 2004/0142322 | A1 | 7/2004 | Malcolm et al. |
| 2004/0219170 | A1 | 11/2004 | Kawaoka |
| 2004/0241139 | A1 | 12/2004 | Hobom et al. |
| 2004/0242518 | A1 | 12/2004 | Chen et al. |
| 2005/0003349 | A1 | 1/2005 | Kawaoka |
| 2005/0037487 | A1 | 2/2005 | Kawaoka et al. |
| 2005/0095583 | A1 | 5/2005 | Pekosz et al. |
| 2005/0118140 | A1 | 6/2005 | Vorlop et al. |
| 2005/0158342 | A1 | 7/2005 | Kemble et al. |
| 2005/0186563 | A1 | 8/2005 | Hoffmann |
| 2005/0202553 | A1 | 9/2005 | Groner et al. |
| 2005/0232950 | A1 | 10/2005 | Kawaoka |
| 2005/0266023 | A1 | 12/2005 | Bavari et al. |
| 2005/0266026 | A1 | 12/2005 | Hoffmann et al. |
| 2006/0057116 | A1 | 3/2006 | Kawaoka et al. |
| 2006/0088909 | A1 | 4/2006 | Compans |
| 2006/0099609 | A1 | 5/2006 | Bavari et al. |
| 2006/0134138 | A1 | 6/2006 | Kawaoka et al. |
| 2006/0166321 | A1 | 7/2006 | Kawaoka et al. |
| 2006/0188977 | A1 | 8/2006 | Schwartz et al. |
| 2006/0216702 | A1 | 9/2006 | Compans et al. |
| 2006/0240515 | A1 | 10/2006 | Dimitrov et al. |
| 2006/0246092 | A1 | 11/2006 | Neirynck et al. |
| 2007/0141699 | A1 | 6/2007 | Kawaoka |
| 2007/0231348 | A1 | 10/2007 | Kawaoka et al. |
| 2008/0009031 | A1 | 1/2008 | Kawaoka |
| 2008/0187557 | A1 | 8/2008 | Sambhara |
| 2008/0233560 | A1 | 9/2008 | Hoffmann |
| 2008/0254067 | A1 | 10/2008 | Trepanier et al. |
| 2008/0274141 | A1 | 11/2008 | Groner et al. |
| 2008/0292658 | A1 | 11/2008 | De Wit et al. |
| 2008/0293040 | A1 | 11/2008 | Kawaoka et al. |
| 2008/0311148 | A1 | 12/2008 | Hoffmann |
| 2008/0311149 | A1 | 12/2008 | Hoffmann |
| 2009/0017444 | A1 | 1/2009 | Kawaoka et al. |
| 2009/0047728 | A1 | 2/2009 | Kawaoka et al. |
| 2009/0074812 | A1 | 3/2009 | Watanabe et al. |
| 2009/0081252 | A1 | 3/2009 | Gregersen |
| 2009/0181446 | A1 | 7/2009 | Nouchi et al. |
| 2009/0311669 | A1 | 12/2009 | Kawaoka |
| 2009/0324640 | A1 | 12/2009 | Kawaoka et al. |
| 2010/0080825 | A1 | 4/2010 | Kawaoka et al. |
| 2010/0112000 | A1 | 5/2010 | Schwartz |
| 2010/0183671 | A1 | 7/2010 | Gregersen et al. |
| 2010/0247572 | A1 | 9/2010 | Kawaoka |
| 2010/0267116 | A1 | 10/2010 | Kawaoka et al. |
| 2011/0020374 | A1 | 1/2011 | Frazer |
| 2011/0027314 | A1 | 2/2011 | Broeker |
| 2011/0045022 | A1 | 2/2011 | Tsai |
| 2011/0081373 | A1 | 4/2011 | Kawaoka et al. |
| 2011/0110978 | A1 | 5/2011 | Kawaoka et al. |
| 2011/0159031 | A1 | 6/2011 | Falkner et al. |
| 2011/0236417 | A1 | 9/2011 | Watanabe et al. |
| 2011/0263554 | A1 | 10/2011 | Kawaoka et al. |
| 2011/0300604 | A1 | 12/2011 | Kawaoka et al. |
| 2012/0020997 | A1 | 1/2012 | Hoffman et al. |
| 2012/0034600 | A1 | 2/2012 | Gregersen |
| 2012/0058124 | A1 | 3/2012 | Kurosawa et al. |
| 2012/0115206 | A1 | 5/2012 | Schwartz et al. |
| 2012/0156241 | A1 | 6/2012 | De Wit et al. |

(56) References Cited

U.S. PATENT DOCUMENTS

| | | | |
|---|---|---|---|
| 2012/0207785 | A1 | 8/2012 | Fabry et al. |
| 2012/0251568 | A1 | 10/2012 | Garcia-sastre et al. |
| 2013/0095135 | A1 | 4/2013 | Collignon et al. |
| 2013/0183741 | A1 | 7/2013 | Park et al. |
| 2013/0230552 | A1 | 9/2013 | Kawaoka et al. |
| 2013/0243744 | A1 | 9/2013 | Betenbaugh |
| 2013/0316434 | A1 | 11/2013 | Reiter et al. |
| 2014/0227310 | A1 | 8/2014 | Li et al. |
| 2015/0017205 | A1 | 1/2015 | Kawaoka et al. |
| 2015/0166967 | A1 | 6/2015 | Kawaoka et al. |
| 2015/0307851 | A1 | 10/2015 | Kawaoka et al. |
| 2015/0368621 | A1 | 12/2015 | Kawaoka et al. |
| 2016/0024193 | A1 | 1/2016 | Ayalon et al. |
| 2016/0024479 | A1 | 1/2016 | Kawaoka et al. |
| 2016/0115518 | A1 | 4/2016 | Kawaoka et al. |
| 2016/0208223 | A1 | 7/2016 | Kawaoka et al. |
| 2016/0215040 | A1 | 7/2016 | Kyratsous et al. |
| 2016/0355790 | A1 | 12/2016 | Kawaoka et al. |
| 2017/0058265 | A1 | 3/2017 | Kawaoka et al. |
| 2017/0067029 | A1 | 3/2017 | Kawaoka et al. |
| 2017/0096645 | A1 | 4/2017 | Watanabe et al. |
| 2017/0097334 | A1 | 4/2017 | Kawaoka et al. |
| 2017/0121391 | A1 | 5/2017 | Kawaoka et al. |
| 2017/0258888 | A1 | 9/2017 | Kawaoka |
| 2017/0298120 | A1 | 10/2017 | Sasisekharan |
| 2017/0354730 | A1 | 12/2017 | Kawaoka et al. |
| 2018/0245054 | A1 | 8/2018 | Kawaoka et al. |
| 2018/0273588 | A1 | 9/2018 | Kawaoka et al. |
| 2018/0340152 | A1 | 11/2018 | Kawaoka et al. |
| 2019/0032023 | A1 | 1/2019 | Kawaoka et al. |
| 2019/0048324 | A1 | 2/2019 | Kawaoka et al. |
| 2019/0117759 | A1 | 4/2019 | Wantanabe et al. |
| 2019/0167781 | A1 | 6/2019 | Kawaoka et al. |
| 2020/0188506 | A1 | 6/2020 | Kawaoka et al. |
| 2020/0237899 | A1 | 7/2020 | Kawaoka et al. |
| 2020/0263142 | A1 | 8/2020 | Kawaoka et al. |
| 2020/0263143 | A1 | 8/2020 | Kawaoka et al. |
| 2020/0291384 | A1 | 9/2020 | Kawaoka et al. |
| 2021/0061862 | A1 | 3/2021 | Kawaoka et al. |
| 2021/0102178 | A1 | 4/2021 | Kawaoka et al. |
| 2021/0121545 | A1 | 4/2021 | Knoll et al. |
| 2021/0228708 | A1 | 7/2021 | Smith et al. |
| 2021/0246432 | A1 | 8/2021 | Kawaoka et al. |
| 2021/0252130 | A1 | 8/2021 | Watanabe et al. |
| 2021/0290754 | A1 | 9/2021 | Kawaoka et al. |
| 2021/0299249 | A1 | 9/2021 | Kawaoka et al. |
| 2022/0025339 | A1 | 1/2022 | Kawaoka et al. |
| 2022/0202927 | A1 | 6/2022 | Kawaoka et al. |
| 2022/0241396 | A1 | 8/2022 | Kawaoka et al. |
| 2023/0321217 | A1 | 10/2023 | Kawaoka et al. |
| 2023/0346911 | A1 | 11/2023 | Kawaoka et al. |
| 2024/0010995 | A1 | 1/2024 | Kawaoka et al. |
| 2024/0076632 | A1 | 3/2024 | Kawaoka et al. |
| 2024/0238403 | A1 | 7/2024 | Kawaoka et al. |
| 2024/0318167 | A1 | 9/2024 | Kawaoka et al. |

FOREIGN PATENT DOCUMENTS

| | | | |
|---|---|---|---|
| AU | 2014290203 | B2 | 12/2020 |
| AU | 2017221444 | B2 | 11/2021 |
| BR | PI0410702 | B1 | 4/2022 |
| CA | 2379012 | A1 | 1/2001 |
| CA | 2816242 | C | 1/2019 |
| CN | 1826407 | A | 8/2006 |
| CN | 101472941 | A | 7/2009 |
| CN | 1826407 | B | 9/2013 |
| CN | 105296356 | A | 2/2016 |
| CN | 103540614 | B | 2/2018 |
| CN | 109477074 | A | 3/2019 |
| CN | 113874496 | A | 12/2021 |
| CN | 114929269 | A | 8/2022 |
| CN | 109477074 | B | 1/2023 |
| EP | 0687471 | A1 | 12/1995 |
| EP | 0700991 | A1 | 3/1996 |
| EP | 0702085 | A1 | 3/1996 |
| EP | 0704533 | A1 | 4/1996 |
| EP | 1201760 | A1 | 5/2002 |
| EP | 2010557 | B1 | 2/2014 |
| EP | 1572910 | B1 | 12/2015 |
| EP | 1631663 | B1 | 8/2016 |
| EP | 2747778 | B1 | 12/2017 |
| EP | 3009507 | B1 | 6/2020 |
| EP | 2493912 | B1 | 7/2020 |
| EP | 3022296 | B1 | 12/2022 |
| IL | 171831 | A | 5/2015 |
| JP | 07-203958 | | 8/1995 |
| JP | 2002536992 | A | 11/2002 |
| JP | 2003528570 | A | 9/2003 |
| JP | 2004500842 | A | 1/2004 |
| JP | 2004-531232 | A | 10/2004 |
| JP | 2005523698 | A | 8/2005 |
| JP | 2005245302 | A | 9/2005 |
| JP | 2005535288 | A | 11/2005 |
| JP | 2006525815 | A | 11/2006 |
| JP | 2007-518395 | A | 7/2007 |
| JP | 2007525175 | A | 9/2007 |
| JP | 2007529997 | A | 11/2007 |
| JP | 2008520248 | A | 6/2008 |
| JP | 2009511084 | A | 3/2009 |
| JP | 2009523252 | A | 6/2009 |
| JP | 2009532352 | A | 9/2009 |
| JP | 2010530248 | A | 9/2010 |
| JP | 2011530295 | A | 12/2011 |
| JP | 4927290 | | 5/2012 |
| JP | 4927290 | B2 | 5/2012 |
| JP | 2013-507990 | A | 3/2013 |
| JP | 2013511280 | A | 4/2013 |
| JP | 2014039551 | A | 3/2014 |
| JP | 2014131516 | A | 7/2014 |
| JP | 2016500007 | A | 1/2016 |
| JP | 2016-521553 | A | 7/2016 |
| JP | 2016144463 | A | 8/2016 |
| JP | 2016524915 | A | 8/2016 |
| JP | 2016169225 | A | 9/2016 |
| JP | 2017527557 | A | 9/2017 |
| JP | 2017197555 | A | 11/2017 |
| JP | 2018064493 | A | 4/2018 |
| JP | 6352974 | B2 | 6/2018 |
| JP | 6375329 | B2 | 7/2018 |
| JP | 2019510481 | A | 4/2019 |
| JP | 2020-010711 | A | 1/2020 |
| JP | 2020114250 | A | 7/2020 |
| JP | 2021500891 | A | 1/2021 |
| JP | 2021-036878 | A | 3/2021 |
| JP | 2021184761 | A | 12/2021 |
| JP | 2021533157 | A | 12/2021 |
| JP | 2021536228 | A | 12/2021 |
| JP | 2022066209 | A | 4/2022 |
| JP | 2022522112 | A | 4/2022 |
| JP | 2022527235 | A | 6/2022 |
| JP | 2022172369 | A | 11/2022 |
| JP | 2022551805 | A | 12/2022 |
| JP | 2023011603 | A | 1/2023 |
| KR | 101113432 | B1 | 2/2012 |
| MX | 285206 | | 3/2011 |
| NO | 341506 | | 11/2017 |
| WO | WO-9610631 | A1 | 4/1996 |
| WO | WO-9610632 | A1 | 4/1996 |
| WO | WO-9640955 | A1 | 12/1996 |
| WO | WO-9737000 | A1 | 10/1997 |
| WO | WO-9802530 | A1 | 1/1998 |
| WO | WO-9848834 | A1 | 11/1998 |
| WO | WO-9853078 | A1 | 11/1998 |
| WO | WO-9928445 | A1 | 6/1999 |
| WO | WO-0053786 | A1 | 9/2000 |
| WO | WO-00/060050 | A2 | 10/2000 |
| WO | WO-0060050 | A2 | 10/2000 |
| WO | WO-0060050 | A3 | 1/2001 |
| WO | WO-2001004333 | A1 | 1/2001 |
| WO | WO-2001025462 | A1 | 4/2001 |
| WO | WO-01/079273 | A2 | 10/2001 |
| WO | WO-0179273 | A2 | 10/2001 |
| WO | WO-01/083794 | A2 | 11/2001 |
| WO | WO-0183794 | A2 | 11/2001 |

(56) References Cited

FOREIGN PATENT DOCUMENTS

| | | | |
|---|---|---|---|
| WO | WO-0210143 | A1 | 1/2002 |
| WO | WO-02/064757 | A2 | 8/2002 |
| WO | WO-02074795 | A2 | 9/2002 |
| WO | WO-03068923 | A2 | 8/2003 |
| WO | WO-03076462 | A1 | 9/2003 |
| WO | WO-2003080846 | A1 | 10/2003 |
| WO | WO-03091401 | A2 | 11/2003 |
| WO | WO-2004142322 | A1 | 7/2004 |
| WO | WO-2004/094466 | A2 | 11/2004 |
| WO | WO-04094466 | A2 | 11/2004 |
| WO | WO-2004/112831 | A2 | 12/2004 |
| WO | WO-2004/112831 | A3 | 12/2004 |
| WO | WO-04112831 | A2 | 12/2004 |
| WO | WO-05028658 | A2 | 3/2005 |
| WO | WO-05028658 | A3 | 3/2005 |
| WO | WO-2005028658 | A2 | 3/2005 |
| WO | WO-2005062820 | A2 | 7/2005 |
| WO | WO-2006051069 | A2 | 5/2006 |
| WO | WO-2007044024 | A2 | 4/2007 |
| WO | WO-2007044024 | A3 | 4/2007 |
| WO | WO-2007126810 | A2 | 11/2007 |
| WO | WO-2007126810 | A3 | 11/2007 |
| WO | WO-2007146057 | A2 | 12/2007 |
| WO | WO-2007146057 | A3 | 12/2007 |
| WO | WO-08156681 | A3 | 12/2008 |
| WO | WO-2008147496 | A2 | 12/2008 |
| WO | WO-2008147496 | A3 | 12/2008 |
| WO | WO-2008156681 | A2 | 12/2008 |
| WO | WO-2008156778 | A2 | 12/2008 |
| WO | WO-2008156778 | A3 | 12/2008 |
| WO | WO-2008157583 | A1 | 12/2008 |
| WO | WO-09008921 | A3 | 1/2009 |
| WO | WO-09008921 | A9 | 1/2009 |
| WO | WO-2009007244 | A2 | 1/2009 |
| WO | WO-2009008921 | A2 | 1/2009 |
| WO | WO-2009014919 | A2 | 1/2009 |
| WO | WO-2008156778 | A9 | 2/2009 |
| WO | WO-09128867 | A2 | 10/2009 |
| WO | WO-2009152181 | A1 | 12/2009 |
| WO | WO-2009128867 | A3 | 3/2010 |
| WO | WO-2010053573 | A2 | 5/2010 |
| WO | WO-2010053573 | A3 | 7/2010 |
| WO | WO-2011014645 | A1 | 2/2011 |
| WO | WO-2011056591 | A1 | 5/2011 |
| WO | WO-2011087839 | A1 | 7/2011 |
| WO | WO-2011126370 | A1 | 10/2011 |
| WO | WO-2011130627 | A2 | 10/2011 |
| WO | WO-2012045882 | A2 | 4/2012 |
| WO | WO-2012177924 | A2 | 12/2012 |
| WO | WO-2013032942 | A1 | 3/2013 |
| WO | WO-2013032942 | A9 | 3/2013 |
| WO | WO-2013034069 | A1 | 3/2013 |
| WO | WO-2013087945 | A2 | 6/2013 |
| WO | WO-2013148302 | A1 | 10/2013 |
| WO | WO-2014195920 | A2 | 12/2014 |
| WO | WO-2015009743 | A1 | 1/2015 |
| WO | 2015031166 | | 3/2015 |
| WO | WO-2015134488 | A1 | 9/2015 |
| WO | WO-2015196150 | A2 | 12/2015 |
| WO | WO-2015196150 | A3 | 12/2015 |
| WO | WO-2016142671 | A2 | 9/2016 |
| WO | WO-2016144933 | A1 | 9/2016 |
| WO | WO-2016207853 | A2 | 12/2016 |
| WO | WO-2017007839 | A1 | 1/2017 |
| WO | WO-2017040203 | A1 | 3/2017 |
| WO | WO-2017136575 | A1 | 8/2017 |
| WO | WO-2017143236 | A1 | 8/2017 |
| WO | WO-2019084310 | A1 | 5/2019 |
| WO | WO-2019241579 | A1 | 12/2019 |
| WO | WO-2020033527 | A2 | 2/2020 |
| WO | WO-2020041311 | A1 | 2/2020 |
| WO | 2020061443 | | 3/2020 |
| WO | WO-2020033527 | A3 | 3/2020 |
| WO | WO-2020/167432 | A2 | 8/2020 |
| WO | WO-2020163804 | A1 | 8/2020 |
| WO | WO-2020223699 | A1 | 11/2020 |
| WO | WO-2020/167432 | A3 | 12/2020 |
| WO | WO-2020264141 | A1 | 12/2020 |
| WO | WO-2021041624 | A2 | 3/2021 |
| WO | WO-2021041624 | A3 | 5/2021 |
| WO | WO-2021150874 | A1 | 7/2021 |
| WO | WO-2021195410 | A1 | 9/2021 |
| WO | WO-2021242597 | A1 | 12/2021 |
| WO | 2022245888 | | 11/2022 |
| WO | 2023125889 | | 7/2023 |
| WO | 2023164556 | | 8/2023 |
| WO | WO-2024015510 | A1 | 1/2024 |
| WO | 2024197167 | | 9/2024 |

OTHER PUBLICATIONS

Result 7, NCBI Blast nucleotide search of SEQ ID: 1, database "nr", (Jul. 18, 2006), 3 pgs.

FlumistTM Package Insert Template, [Online]. Retrieved from the Internet: http://www.fda.gov/downloads/BiologicsBioodVaccines!Vaccines/ApprovedProducts/UCM294307.pdf, (Mar. 1, 2012), 26 pgs.

"1.A.32 The Type B Influenza Virus NB Channel (NB-C) Family", Transport Protein Database, (University of California, San Diego, The Saller Laboratory Bioinformatics Group) [online]. http://www.web.archive.org/web/20030131105525 4/http://tcdb.ucsd.edu/tcdb/tcfamilybrowse.php?tcname=1.A.32, (Archived Jan. 31, 2003), 1 pg.

"U.S. Appl. No. 09/834,095, Advisory Action mailed Jan. 8, 2004", 3 pgs.

"U.S. Appl. No. 09/834,095, Final Office Action mailed Aug. 26, 2003", 12 pgs.

"U.S. Appl. No. 09/834,095, Non-Final Office Action mailed Nov. 4, 2002", 12 pgs.

"U.S. Appl. No. 09/834,095, Notice of Allowance mailed Sep. 27, 2004", 13 pgs.

"U.S. Appl. No. 09/834,095, Office Action mailed Apr. 20, 2004", 11 pgs.

"U.S. Appl. No. 09/834,095, Response filed Feb. 4, 2003 to Office Action mailed Nov. 4, 2002", 14 pgs.

"U.S. Appl. No. 09/834,095, Response filed Jun. 12, 2003 to Restriction Requirement mailed Apr. 22, 2003", 2 pgs.

"U.S. Appl. No. 09/834,095, Response filed Jun. 18, 2004 to Office Action mailed Apr. 20, 2004", 11 pgs.

"U.S. Appl. No. 09/834,095, Response filed Aug. 1, 2002 to Restriction Requirement mailed Jul. 1, 2002", 3 pgs.

"U.S. Appl. No. 09/834,095, Response filed Nov. 26, 2003 to Final Office Action mailed Aug. 26, 2003", 10 pgs.

"U.S. Appl. No. 09/834,095, Restriction Requirement mailed Apr. 22, 2003", 5 pgs.

"U.S. Appl. No. 09/834,095, Restriction Requirement mailed Jul. 1, 2002", 9 pgs.

"U.S. Appl. No. 09/834,095, Supplemental Amendment filed Aug. 4, 2004", 7 pgs.

"U.S. Appl. No. 10/827,995, Final Office Action mailed Nov. 15, 2006", 10 pgs.

"U.S. Appl. No. 10/827,995, Non-Final Office Action mailed Jun. 2, 2006", 15 pgs.

"U.S. Appl. No. 10/827,995, Non-Final Office Action mailed Oct. 25, 2007", 7 pgs.

"U.S. Appl. No. 10/827,995, Notice of Allowance mailed Feb. 17, 2009", 9 pgs.

"U.S. Appl. No. 10/827,995, Notice of Allowance mailed Jul. 2, 2008", 9 pgs.

"U.S. Appl. No. 10/827,995, Notice of Allowance mailed Oct. 17, 2008", 7 pgs.

"U.S. Appl. No. 10/827,995, Notice of Non-Compliant Amendment Jul. 25, 2007", 4 pgs.

"U.S. Appl. No. 10/827,995, Proposed Examiner's Amendment malled Jun. 5, 2008", 6 pgs.

"U.S. Appl. No. 10/827,995, Response filed Mar. 3, 2008 to Office Action mailed Oct. 25, 2007", 10 pgs.

"U.S. Appl. No. 10/827,995, Response filed May 14, 2007 Final Office Action mailed Nov. 15, 2006", 16 pgs.

(56) References Cited

OTHER PUBLICATIONS

"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action mailed Jun. 2, 2006", 15 pgs.
"U.S. Appl. No. 10/855,875 , Response filed May 17, 2012 to Non Final Office Action mailed Mar. 15, 2012", 15 pgs.
"U.S. Appl. No. 10/855,875, Final Office Action mailed Mar. 11, 2008", FOAR, 20 Pgs.
"U.S. Appl. No. 10/855,875, Final Office Action mailed Dec. 10, 2010", 15 pgs.
"U.S. Appl. No. 10/855,875, Final Office Action malled Aug. 2, 2006", 34 pgs.
"U.S. Appl. No. 10/855,875, Non Final Office Action mailed Mar. 15, 2012", 15 pgs.
"U.S. Appl. No. 10/855,875, Non-Final Office Action mailed Feb. 19, 2010", 7 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Non-Final Office Action mailed May 3, 2007", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action malled Aug. 2, 2007", 14 pgs.
"U.S. Appl. No. 10/855,875, Response filed Mar. 18, 2011 to Final Office Action malled Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Dec. 7, 2009 to Non Final Office Action mailed Aug. 7, 2009", 15 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.
"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,875, Response filed Nov. 2, 2007 to Office Action mailed May 3, 2007", 16 pgs.
"U.S. Appl. No. 11/043,768 Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Jun. 23, 2009 to Non Final Office Action mailed Feb. 23, 2009", 9 pgs.
"U.S. Appl. No. 11/043,768, Response filed Sep. 13, 2007 to Restriction Requirement mailed Mar. 13, 2007", 10 pgs.
"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,786, Final Office Action mailed Feb. 3, 2011", 10 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non Final Office Action malled Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.
"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Respons filed Jun. 22, 2010 to Non Final Office Action mailed Feb. 22, 2010", 33 pgs.
"U.S. Appl. No. 11/729,557, Response filed Apr. 27, 2011 to Final Office Action mailed Feb. 2, 2011", 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557, Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Response filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.
"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action malled Jun. 12, 2014", 28 pgs.

(56) References Cited

OTHER PUBLICATIONS

"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Dec. 21, 2011 to Advisory Action mailed Oct. 21, 2011", 10 pgs.
"U.S. Appl. No. 12/467,492, Restriction Requirement mailed Nov. 22, 2010", 6 pgs.
"U.S. Appl. No. 12/912,411, Advisory Action mailed Feb. 5, 2014", 3 pgs.
"U.S. Appl. No. 12/912,411, Examiner Interview Summary mailed Feb. 11, 14", 2 pgs.
"U.S. Appl. No. 12/912,411, Final Office Action mailed Jan. 14, 2015", 10 pgs.
"U.S. Appl. No. 12/912,411, Final Office Action mailed Oct. 25, 2013", 11 pgs.
"U.S. Appl. No. 12/912,411, Non Final Office Action mailed Jun. 7, 2013", 8 pgs.
"U.S. Appl. No. 12/912,411, Non Final Office Action mailed Sep. 24, 2014", 11 pgs.
"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Jan. 27, 2014 to Final Office Action mailed Oct. 25, 2013", 11 pgs.
"U.S. Appl. No. 12/912,411, Response filed Feb. 18, 2013 to Restriction Requirement mailed Oct. 17, 2012", 9 pgs.
"U.S. Appl. No. 12/912,411, Response filed Feb. 25, 2014 to Final Office Action mailed Oct. 25, 2013", 11 pgs.
"U.S. Appl. No. 12/912,411, Response filed Mar. 16, 2015 to Final Office Action mailed Jan. 14, 2015", 9 pgs.
"U.S. Appl. No. 12/912,411, Response filed Oct. 7, 2013 to Non Final Office Action mailed Jun. 7, 2013", 10 pgs.
"U.S. Appl. No. 12/912,411, Response filed Dec. 31, 2014 to Non Final Office Action mailed Sep. 24, 2014", 12 pgs.
"U.S. Appl. No. 12/912,411, Restriction Requirement mailed Oct. 17, 2012", 9 pgs.
"U.S. Appl. No. 13/070,110, Advisory Action mailed Mar. 3, 2017", 5 pgs.
"U.S. Appl. No. 13/070,110, Examiner Interview Summary mailed Jan. 16, 2018", 3 pgs.
"U.S. Appl. No. 13/070,110, Final Office Action mailed Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Jul. 21, 2017", 14 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.
"U.S. Appl. No. 13/070,110, Non Final Office Action mailed Dec. 21, 2012", 7 pgs.
"U.S. Appl. No. 13/070,110, Notice of Allowance mailed Mar. 26, 2018", 6 pgs.
"U.S. Appl. No. 13/070,110, Preliminary Amendment filed Jun. 6, 2011", 4 pgs.
"U.S. Appl. No. 13/070,110, Response filed Jan. 22, 2018 to Non Final Office Action mailed Jul. 21, 2017", 10 pgs.
"U.S. Appl. No. 13/070,110, Response filed Feb. 14, 2017 to Final Office Action mailed Sep. 14, 2016", 8 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Jun. 20, 2017 to Advisory Action mailed Mar. 3, 2017", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action malled Apr. 3, 2015", 11 pgs.
"U.S. Appl. No. 13/070,110, Response filed Nov. 12, 2013 to Final Office Action mailed Jun. 12, 2013", 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 14/332,121, Non Final Office Action mailed May 16, 2016", 9 pgs.
"U.S. Appl. No. 14/332,121, Notice of Allowance mailed Feb. 15, 2017", 10 pgs.
"U.S. Appl. No. 14/332,121, Notice of Allowance mailed Jun. 15, 2017", 8 pgs.
"U.S. Appl. No. 14/332,121, Notice of Allowance mailed Oct. 11, 2017", 8 pgs.
"U.S. Appl. No. 14/332,121, Preliminary Amendment filed Sep. 30, 2014", 5 pgs.
"U.S. Appl. No. 14/332,121, Response filled Jan. 29, 2016 to Restriction Requirement mailed Jul. 30, 2015", 9 pgs.
"U.S. Appl. No. 14/332,121, Response filed Sep. 7, 2017 to Notice of Allowability mailed Jun. 15, 2017", 8 pgs.
"U.S. Appl. No. 14/332,121, Response filed Oct. 11, 2016 to Non Final Office Action mailed May 16, 2016", 9 pgs.
"U.S. Appl. No. 14/332,121, Restriction Requirement mailed Jul. 30, 2015", 9 pgs.
"U.S. Appl. No. 14/332,121, Supplemental Amendment filed Jan. 23, 2017", 10 pgs.
"U.S. Appl. No. 14/745,236, Advisory Action mailed Nov. 15, 2017", 2 pgs.
"U.S. Appl. No. 14/745,236, Final Office Action mailed Aug. 25, 2017", 16 pgs.
"U.S. Appl. No. 14/745,236, Non Final Office Action mailed Feb. 2, 2017", 14 pgs.
"U.S. Appl. No. 14/745,236, Notice of Allowability mailed Jul. 5, 2018", 4 pgs.
"U.S. Appl. No. 14/745,236, Notice of Allowance mailed Feb. 5, 2018", 9 pgs.
"U.S. Appl. No. 14/745,236, PTO Response to Rule 312 Communication mailed Jul. 10, 2018", 2 pgs.
"U.S. Appl. No. 14/745,236, Response filed May 2, 2017 to Non Final Office Action mailed Feb. 2, 2017", 10 pgs.
"U.S. Appl. No. 14/745,236, Response filed Nov. 6, 2017 to Final Office Action mailed Aug. 25, 2017", 12 pgs.
"U.S. Appl. No. 14/745,236, Response filed Dec. 14, 2017 to Final Office Action mailed Aug. 25, 2017", 12 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 14/816,807, Non Final Office Action mailed Oct. 3, 2017", 7 pgs.

(56) References Cited

OTHER PUBLICATIONS

"U.S. Appl. No. 14/816,807, Notice of Allowance mailed Apr. 20, 2018", 8 pgs.
"U.S. Appl. No. 14/816,807, Preliminary Amendment filed Aug. 11, 2015", 8 pgs.
"U.S. Appl. No. 14/816,807, Response filed Jan. 3, 2018 to Non Final Office Action mailed Oct. 3, 2017", 8 pgs.
"U.S. Appl. No. 14/816,807, Response filed May 1, 2017 to Restriction Requirement mailed Nov. 1, 2016", 9 pgs.
"U.S. Appl. No. 14/816,807, Restriction Requirement mailed Nov. 1, 2016", 8 pgs.
"U.S. Appl. No. 15/000,851, Non Final Office Action malled Jan. 26, 2017", 15 pgs.
"U.S. Appl. No. 15/000,851, Notice of Allowance mailed Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action mailed Jan. 26, 2017", 16 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"U.S. Appl. No. 15/170,556, Non Final Office Action mailed Feb. 8, 2019", 11 pgs.
"U.S. Appl. No. 15/170,556, Non Final Office Action mailed Jul. 27, 2018", 10 pgs.
"U.S. Appl. No. 15/170,556, Notice of Allowability mailed Jan. 29, 2020", 4 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement mailed Feb. 16, 2018", 8 pgs.
"U.S. Appl. No. 15/170,556, Response filed Oct. 29, 2018 to Non Final Office Action mailed Jul. 27, 2018", 9 pgs.
"U.S. Appl. No. 15/170,556, Response filed Apr. 15, 2019 to Non Final Office Action mailed Feb. 8, 2019", 9 pgs.
"U.S. Appl. No. 15/170,556, Restriction Requirement malled Feb. 16, 2018", 7 pgs.
"U.S. Appl. No. 15/170,556, PTO Response to Rule 312 Communication mailed Apr. 3, 2020", 2 pgs.
"U.S. Appl. No. 15/203,581, Examiners Interview Summary mailed Sep. 11, 2017", 1 pg.
"U.S. Appl. No. 15/203,581, Notice of Allowance mailed Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication mailed Dec. 27, 2017", 2 pgs.
"U.S. Appl. No. 15/203,581, Response filed Aug. 15, 2017 to Restriction Requirement mailed Jun. 16, 2017", 8 pgs.
"U.S. Appl. No. 15/203,581, Restriction Requirement mailed Jun. 16, 2017", 8 pgs.
"U.S. Appl. No. 15/292,595, Non Final Office Action mailed Sep. 25, 2017", 13 pgs.
"U.S. Appl. No. 15/292,595, Notice of Allowance malled Feb. 28, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action mailed Sep. 25, 2017", 9 pgs.
"U.S. Appl. No. 15/436,245, Corrected Notice of Allowability mailed Nov. 10, 2021", 2 pgs.
"U.S. Appl. No. 15/436,245, Final Office Action mailed Mar. 24, 2021", 9 pgs.
"U.S. Appl. No. 15/436,245, Final Office Action mailed Nov. 18, 2019", 9 pgs.
"U.S. Appl. No. 15/436,245, Non Final Office Action mailed Apr. 19, 2019", 9 pgs.
"U.S. Appl. No. 15/436,245, Non Final Office Action mailed Sep. 4, 2020", 9 pgs.
"U.S. Appl. No. 15/436,245, Notice of Allowance mailed Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication mailed Oct. 27, 2021", 2 pgs.
"U.S. Appl. No. 15/436,245, Response filed Apr. 27, 2020 to Final Office Action mailed Nov. 18, 2019", 10 pgs.
"U.S. Appl. No. 15/436,245, Response filed Jun. 24, 2021 to Final Office Action mailed Mar. 24, 2021", 11 pgs.
"U.S. Appl. No. 15/436,245, Response filled Dec. 4, 2020 to Non Final Office Action mailed Sep. 4, 2020", 12 pgs.
"U.S. Appl. No. 15/436,245, Response filed Jul. 29, 2019 to Non-Final Office Action mailed Apr. 19, 2019", 11 pgs.
"U.S. Appl. No. 15/436,245, Restriction Requirement mailed Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action malled Feb. 6, 2018", 8 pgs.
"U.S. Appl. No. 15/593,039, Notice of Allowance mailed Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication mailed Oct. 9, 2018", 2 pgs.
"U.S. Appl. No. 15/593,039, Response filed Apr. 30, 2018 to Non Final Office Action mailed Feb. 4, 2018", 8 pgs.
"U.S. Appl. No. 15/593,039, Response filed Dec. 18, 2017 to Restriction Requirement mailed Oct. 18, 2017", 8 pgs.
"U.S. Appl. No. 15/593,039, Restriction Requirement mailed Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Preliminary Amendment filed Apr. 10, 2018", 10 pgs.
"U.S. Appl. No. 15/966,092, Non Final Office Action mailed Jun. 26, 2020", 22 pgs.
"U.S. Appl. No. 15/966,092, Response filed Oct. 26, 2020 to Non Final Office Action mailed Jun. 26, 2020", 9 pgs.
"U.S. Appl. No. 12/214,414, Response filed Oct. 14, 2014 to Non Final Office Action mailed Jun. 12, 2014", 16 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2004249133, First Examiner's Report mailed May 5, 2008", 4 pgs.
"Australian Application Serial No. 2004249133, Response filed Mar. 30, 2009 to First Examiner's Report mailed May 5, 2008", 30 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Response filed Jul. 4, 2016 to Subsequent Examiners Report malled Feb. 1, 2016", 3 pgs.
"Australian Application Serial No. 2014202470, Response filed Jul. 20, 2016 to Subsequent Examiners Report mailed Jul. 19, 2016", 15 pgs.

(56) References Cited

OTHER PUBLICATIONS

"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb. 1, 2016", 2 pgs.
"Australian Application Serial No. 2014202470, Subsequent Examiners Report mailed Jul. 19, 2016", 3 pgs.
"Australian Application Serial No. 2017221444, First Examination Report mailed Jul. 8, 2020", 6 pgs.
"Australian Application Serial No. 2017221444, Fourth Examiners Report mailed Jun. 29, 2021", 3 pgs.
"Australian Application Serial No. 2017221444, Response filed Nov. 13, 2020 to First Examination Report mailed Jul. 8, 2020", 13 pgs.
"Australian Application Serial No. 2017221444, Subsequent Examiners Report mailed Nov. 27, 2020", 4 pgs.
"Brazilian Application Serial No. PI0410702-0, Office Action mailed Feb. 23, 2012", w/ English Translation, 4 pgs.
"Brazilian Application Serial No. PI0410702-0, Response filed May 7, 2012 to Office Action mailed Feb. 23, 2012", w/ English Claims, 11 pgs.
"Canadian Application Serial No. 2,406,180, Office Action mailed Sep. 9, 2008", 5 pgs.
"Canadian Application Serial No. 2,406,180, Office Action mailed Nov. 10, 2011", 3 pgs.
"Canadian Application Serial No. 2,406,180, Office action mailed Nov. 23, 2009", 3 pgs.
"Canadian Application Serial No. 2,406,180, Office Action mailed Dec. 10, 2010", 2 Pgs.
"Canadian Application Serial No. 2,406,180, Response filed Jan. 26, 2009 to Official Action mailed Sep. 9, 2008", 22 pgs.
"Canadian Application Serial No. 2,406,180, Response filed May 21, 2010 to Office action mailed Nov. 23, 2009", 13 pgs.
"Canadian Application Serial No. 2,406,180, Response filed Jun. 14, 2011 to Office Action mailed Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action mailed Jun. 6, 2011", 2 pgs.
"Canadian Application Serial No. 2,522,081, Office Action mailed Aug. 30, 2010", 2 pgs.
"Canadian Application Serial No. 2,522,081, Office Action mailed Oct. 8, 2009", 6 pgs.
"Canadian Application Serial No. 2,522,081, Response filed Feb. 28, 2011 to Office Action mailed Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action mailed Jun. 6, 2011", 11 pgs.
"Canadian Application Serial No. 2,525,953, Amendment and Response filed Feb. 1, 2017 to Office Action mailed Aug. 1, 2016", 28 pgs.
"Canadian Application Serial No. 2,525,953, Office Action mailed Jan. 21, 2016", 6 pgs.
"Canadian Application Serial No. 2,525,953, Office Action mailed Jul. 31, 2012", 4 pgs.
"Canadian Application Serial No. 2,525,953, Office Action mailed Aug. 1, 2016", 6 pgs.
"Canadian Application Serial No. 2,525,953, Office Action mailed Aug. 16, 2013", 3 pgs.
"Canadian Application Serial No. 2,525,953, Office Action mailed Oct. 3, 2017", 4 pgs.
"Canadian Application Serial No. 2,525,953, Office Action mailed Nov. 6, 2014", 3 pgs.
"Canadian Application Serial No. 2,525,953, Office Action mailed Jun. 22, 2011", 4 pgs.
"Canadian Application Serial No. 2,525,953, Office Action", 4 pgs.
"Canadian Application Serial No. 2,525,953, Response filed Jan. 31, 2013 to Office Action mailed Jul. 31, 2012", 11 pgs.
"Canadian Application Serial No. 2,525,953, Response filed Feb. 1, 2017 to Office Action mailed Aug. 1, 2016", 28 pgs.
"Canadian Application Serial No. 2,525,953, Response filed Feb. 14, 2014 to Office Action mailed Aug. 16, 2013", 16 pgs.
"Canadian Application Serial No. 2,525,953, Response filed Apr. 3, 2018 to Office Action mailed Oct. 3, 2017", 46 pgs.
"Canadian Application Serial No. 2,525,953, Response filed May 1, 2015 to Office Action mailed Nov. 6, 2014", 23 pgs.
"Canadian Application Serial No. 2,525,953, Response filed Jul. 11, 2016 to Office Action mailed Jan. 21, 2016", 21 pgs.
"Canadian Application Serial No. 2,525,953, Response filed Dec. 22, 2011 to Office Action mailed Jun. 22, 2011", 17 pgs.
"Canadian Application Serial No. 2,647,985 , Office Action mailed May 15, 2013", 3 pgs.
"Canadian Application Serial No. 2,647,985 , Response filed Sep. 30, 2013 to Office Action mailed May 15, 2013", 20 pgs.
"Canadian Application Serial No. 2406180, Response filed May 7, 2012 to Office Action mailed Nov. 10, 2011", 11 pgs.
"Canadian Application Serial No. 3,014,435, Office Action mailed Oct. 26, 2021", 4 pgs.
"Canadian Application Serial No. 3,014,435, Office Action mailed Nov. 6, 2020", 5 pgs.
"Canadian Application Serial No. 3,014,435, Office Action mailed Nov. 13, 2019", 4 pgs.
"Canadian Application Serial No. 3,014,435, Response filed Mar. 13, 2020 to Office Action mailed Nov. 13, 2019", 18 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton mailed May 6, 2010", (w/ English Translation of Claims), 26 pgs.
"Chinese Application Serial No. 200480021259.9, First Office Action issued on Aug. 24, 2007", (w/ English Translation), 9 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Office Action issued on Aug. 24, 2007", (w/ English Translation of Claims), 13 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.

(56) References Cited

OTHER PUBLICATIONS

"Chinese Application Serial No. 200780020095.1, Office Action mailed Apr. 26, 2016", (w/ English Summary), 4 pgs.
"Chinese Application Serial No. 200780020095.1, Office Action mailed May 3, 2012", (w/ English Translation), 10 pgs.
"Chinese Application Serial No. 200780020095.1, Office Action mailed Nov. 2, 2016", (w/ English Translation), 11 pgs.
"Chinese Application Serial No. 200780020095.1, Response filed Jan. 6, 2017 to Office Action mailed Nov. 2, 2016", (w/ English Translation of Claims), 15 pgs.
"Chinese Application Serial No. 200780020095.1, Response filed Jun. 9, 2013 to Office Action mailed Jan. 29, 2013", (w/ English Translation of Claims), 10 pgs.
"Chinese Application Serial No. 200780020095.1, Response filed Jun. 23, 2015 to Office Action mailed Mar. 5, 2015", (w/ English Translation of Claims), 16 pgs.
"Chinese Application Serial No. 200780020095.1, Response filed Jun. 30, 2016 to Office Action mailed Apr. 26, 2016", (w/ English Translation of Claims), 22 pgs.
"Chinese Application Serial No. 200780020095.1, Response filed Sep. 17, 2012 to Office Action mailed May 3, 2012", (w/ English Translation of Claims), 17 pgs.
"Chinese Application Serial No. 200780020095.1, Response filed Nov. 5, 2013 to to Decision on Rejection mailed Jul. 22, 2013", (w/ English Translation of Claims), 12 pgs.
"Chinese Application Serial No. 200780020095.1, Response filed Nov. 8, 2011 to Office Action mailed Jun. 24, 2011", (w/ English Translation of Amended Claims), 20 pgs.
"Chinese Application Serial No. 200480021259.9, Office Action mailed May 8, 2009", (w/ English Translation), 6 pgs.
"Eurasian Application No. 200501890, Notice of Allowance mailed Jun. 23, 2009", 1 pg.
"Eurasian Application Serial No. 200501890, Office Action mailed Mar. 23, 2007", (w English Translation), 2 pgs.
"Eurasian Application Serial No. 200501890, Office Action mailed Sep. 4, 2008", (English Translation), 1 pg.
"Eurasian Application Serial No. 200501890, Office Action mailed Dec. 17, 2007", (w/ English Translation), 6 pgs.
"Eurasian Application Serial No. 200501890, Response filed Mar. 26, 2008 to Office Action mailed Dec. 17, 2007", (w/ English Translation of Claims), 15 pgs.
"Eurasian Application Serial No. 200501890, Response filed Jun. 14, 2007 to Office Action mailed Mar. 23, 2007", (w/ English Translation of Claims), 11 pgs.
"Eurasian Application Serial No. 200501890, Response filed Dec. 17, 2008 to Office Action", (w/ English Translation of Claims), 13 pgs.
"Eurasian Application Serial No. 200501890, Response filed Dec. 17, 2008 to Office Action mailed Sep. 4, 2008", (w/ English Translation of Claims), 14 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial 17709236.8 , Response filed Apr. 26, 2019 to Communication Pursuant to Rules 161(1) and 162 EPC mailed Oct. 19, 2018", 9 pgs.
"European Application Serial No. 01928486.8 Office Action mailed Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action mailed Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication mailed Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action mailed Oct. 1, 2009", 11 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04750333.9, Response filed Nov. 17, 2009 to Communication mailed Jan. 22, 2009", 17 pgs.
"European Application Serial No. 04750333.9, Summons To Attend Oral Proceedings mailed Aug. 3, 2011", 13 pgs.
"European Application Serial No. 04776133.3, Communication mailed Mar. 30, 2006", 3 pgs.
"European Application Serial No. 04776133.3, Examination Notification Art. 94(3) mailed Jul. 28, 2015", 4 pgs.
"European Application Serial No. 04776133.3, Examination Notification Art. 94(3) mailed Nov. 25, 2013", 5 pgs.
"European Application Serial No. 04776133.3, Office Action mailed Jan. 5, 2010", 4 pgs.
"European Application Serial No. 04776133.3, Response filed Jan. 25, 2007 to Communication mailed Mar. 30, 2006", 20 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Jul. 15, 2010 to Office Action mailed Jan. 5, 2010", 9 pgs.
"European Application Serial No. 04776133.3, Response filed Sep. 18, 2015 to Examination Notification Art. 94(3) mailed Jul. 28, 2015", 47 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC mailed Apr. 4, 2018", 7 pgs.
"European Application Serial No. 10777154.5, Communication Pursuant to Article 94(3) EPC mailed Oct. 12, 2017", 7 pgs.
"European Application Serial No. 10777154.5, Examination Notification Art. 94(3) mailed Oct. 6, 2014", 7 pgs.
"European Application Serial No. 10777154.5, Office Action mailed May 2, 2016", 6 pgs.
"European Application Serial No. 10777154.5, Office Action mailed Jul. 4, 2012", 2 pgs.
"European Application Serial No. 10777154.5, Response filed Jan. 14, 2013 to Office Action mailed Jul. 4, 2012", 12 pgs.
"European Application Serial No. 10777154.5, Response filed Feb. 21, 2018 to Communication Pursuant to Article 94(3) EPC mailed Oct. 12, 2017", 12 pgs.
"European Application Serial No. 10777154.5, Response filed Sep. 8, 2016 to Office Action mailed May 2, 2016", 69 pgs.
"European Application Serial No. 14745060.5, Communication Pursuant to Article 94(3) EPC mailed Feb. 6, 2018", 5 pgs.
"European Application Serial No. 14745060.5, Office Action malled Feb. 23, 2016", 2 pgs.

(56) References Cited

OTHER PUBLICATIONS

"European Application Serial No. 14745060.5, Response filed Dec. 22, 2016 to Communication pursuant to Rules 161(1) and 162 EPC mailed Feb. 23, 2016", 6 pgs.
"European Application Serial No. 17709236.8, Communication Pursuant to Article 94(3) EPC mailed Jul. 6, 2021", 10 pgs.
"Evaluation of Medicines for human Use", EMEA/CPMP/BWP/2289/01, London, The European Agency for the Evaluation of Medicinal Products, Committee for Proprietary Medicinal Products (CPMP), (Feb. 20, 2003), 14.
"Fluzone® Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007 x Texas/1/1977) (H1N1)], (2012), 2 pgs.
"Gen Bank Accession JX414012", Influenza A virus (A/reassortant/IVR-148(Brisbane/59/2007 x Texas/1/1977)(H1 N1)) segment 7 matrix protein 2 (M2) and matrix protein 1 (M1) genes, complete cds, (2012), 2 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"Indian Application Serial No. 02082/KOLNP/2005, Examination Report mailed Mar. 17, 2008", 1 pg.
"Indian Application Serial No. 02082/KOLNP/2005, Examination Report mailed Dec. 28, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 10, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 1026/KOLNP/2009, First Examiner Report mailed Mar. 13, 2014", 2 pgs.
"Indian Application Serial No. 2272/KOLNP/2005, First Examination Report mailed Mar. 17, 2008", 10 pgs.
"Indian Application Serial No. 2272/KOLNP/2005, Response filed Mar. 16, 2009 to Subsequent Examination Report mailed Mar. 6, 2009", 12 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009", 1 pg.
"Influenza B/Ann Arbor/1/66 (cold-adapted) nonstructural protein (seg 8) RNA, complete cds", GenBank Accession M20224, (Aug. 2, 1993).
"Influenza B/lee/40, neuraminidase & nb (seg 6) rna", Database EM_VI E.B.I. Hinxton U.K., (Jun. 13, 1985), 10 pgs.
"International Application No. PCT/US2004/016680, International Search Report", (Feb. 2, 2005), 7 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report mailed Oct. 15, 2002", 13 pgs.
"International Application Serial No. PCT/US01/11963, International Search Report mailed May 7, 2002". 5 pgs.
"International Application Serial No. PCT/US01/11963, Response filed Sep. 9, 2002 to Written Opinion mailed Aug. 7, 2002", 12 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US2004/012050, International Search Report mailed Feb. 2, 2005", 8 pgs.
"International Application Serial No. PCT/US2004/012050, Written Opinion mailed Feb. 2, 2005", 12 pgs.
"International Application Serial No. PCT/US2004/016680, International Preliminary Report on Patentability mailed Dec. 15, 2005", 11 pgs.
"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.
"International Application Serial No. PCT/US2008/007582, International Preliminary Report on Patentability mailed Jan. 7, 2010", 9 pgs.
"International Application Serial No. PCT/US2008/007582, International Search Report and Written Opinion mailed Feb. 18, 2009", 16 pgs.
"International Application Serial No. PCT/US2010/054128, Preliminary Report on Patentability mailed May 10, 2012", 10 pgs.
"International Application Serial No. PCT/US2010/054128, Search Report mailed Feb. 23, 2011", 6 pgs.
"International Application Serial No. PCT/US2010/054128, Written Opinion mailed Feb. 23, 2011", 8 pgs.
"International Application Serial No. PCT/US2014/046731, International Preliminary Report on Patentability mailed Jan. 28, 2016", 12 pgs.
"International Application Serial No. PCT/US2014/046731, International Search Report mailed Nov. 25, 2014", 9 pgs.
"International Application Serial No. PCT/US2014/046731, Written Opinion mailed Nov. 25, 2014", 10 pgs.
"International Application Serial No. PCT/US2015/036803, International Preliminary Report on Patentability mailed Dec. 29, 2016", 10 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Preliminary Report on Patentability mailed Jan. 18, 2018", 10 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"International Application Serial No. PCT/US2017/018443, International Preliminary Report on Patentability mailed Aug. 30, 2018", 11 pgs.
"International Application Serial No. PCT/US2017/018443, International Search Report mailed May 22, 2017", 9 pgs.
"International Application Serial No. PCT/US2017/018443, Written Opinion mailed May 22, 2017", 9 pgs.
"Israel Application Serial No. 238584, Office Action mailed Jul. 24, 2017", 2 pgs.
"Israel Application Serial No. 238584, Response filed Nov. 21, 2017 to Office Action mailed Jul. 24, 2017", W/English Translation, 2 pgs.
"Israeli Application Serial No. 171831, Notification of Defects mailed Nov. 10, 2008", (English Translation), 10 pgs.
"Israeli Application Serial No. 171372, Office Action mailed Feb. 21, 2010", (Translation), 2 pgs.
"Israeli Application Serial No. 171372, Office Action mailed Nov. 6, 2008", (Translation), 12 pgs.
"Israeli Application Serial No. 171372, Response filed Nov. 18, 2010 to Office Action mailed Feb. 21, 2010", (Translation), 19 pgs.
"Israeli Application Serial No. 171831, Office Action mailed Feb. 21, 2010", (English Translation), 2 pgs.

(56) References Cited

OTHER PUBLICATIONS

"Israeli Application Serial No. 171831, Office Action mailed Apr. 18, 2012", (English Translation), 2 pgs.
"Israeli Application Serial No. 171831, Response filed Jan. 20, 2011 to Office Action mailed Feb. 21, 2010", (English Translation), 18 pgs.
"Israeli Application Serial No. 171831, Response filed Jun. 24, 2009 to Notification of Defects mailed Nov. 10, 2008", (w/ English Translation of Claims), 10 pgs.
"Israeli Application Serial No. 171831, Response filed Nov. 6, 2012 to Office Action mailed Apr. 18, 2012", (w/ English Translation of Amended Claims), 54 pgs.
"Israeli Application Serial No. 238584, Office Action mailed Apr. 14, 2016", (English Translation), 3 pgs.
"Israeli Application Serial No. 238584, Office Action mailed Jul. 24, 2017", (Translation), 2 pgs.
"Israeli Application Serial No. 238584, Response filed Aug. 3, 2016 to Office Action mailed Apr. 14, 2016", (English Translation of Claims), 19 pgs.
"Israeli Application Serial No. 238584, Response filed Nov. 21, 2017 to Office Action mailed Jul. 24, 2017", (Translation), 2 pgs.
"Israeli Application Serial No. 171372,Office Action mailed Feb. 20, 2011", (Translation), 2 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2001-576868, Office Action mailed Nov. 2, 2010", w/ English Translation), 10 pgs.
"Japanese Application Serial No. 2001-576868, Response filed Dec. 1, 2011 to Office Action mailed May 3, 2011", (w/ English Translation of Amended Claims), 37 pgs.
"Japanese Application Serial No. 2006-513125, Office Action mailed Mar. 9, 2010", (English (Translation), 11 pgs.
"Japanese Application Serial No. 2006-513125, Response filed Aug. 30, 2010 to Office Action mailed Mar. 9, 2010", (w/ English Translation of Amended Claims), 60 pgs.
"Japanese Application Serial No. 2006-533439, Decision of Final Rejection mailed Aug. 14, 2012", (w/ English Translation), 5 pgs.
"Japanese Application Serial No. 2006-533439, Office Action mailed Mar. 9, 2010", (w/ English Translations), 20 pgs.
"Japanese Application Serial No. 2006-533439, Office Action mailed Mar. 27, 2012", w/ English Translation, 8 pgs.
"Japanese Application Serial No. 2006-533439, Response filed May 21, 2012 to Office Action mailed Mar. 27, 2012", (w/ English Translation of Amended Claims), 19 pgs.
"Japanese Application Serial No. 2006-533439, Response filed Aug. 3, 2011 to Office Action mailed Feb. 15, 2011", (w/ English Translation of Amended Claims), 18 pgs.
"Japanese Application Serial No. 2006-533439, Office Action mailed Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2009-502945, Examiners Decision of Final Refusal mailed Nov. 12, 2013", (w/ English Translation), 8 pgs.
"Japanese Application Serial No. 2009-502945, Office Action mailed Oct. 23, 2012", (w/ English Translation), 16 pgs.
"Japanese Application Serial No. 2009-502945, Response filed Apr. 10, 2013 to Office Action mailed Oct. 23, 2012", (w/ English Translation of Claims), 18 pgs.
"Japanese Application Serial No. 2011-111048, Office Action mailed Jun. 25, 2013", (w/ English Translation), 7 pgs.
"Japanese Application Serial No. 2011-111048, Office Action mailed Sep. 18, 2012", (w/ English Translation), 10 pga.
"Japanese Application Serial No. 2011-111048, Response filed Sep. 25, 2012 to Office Action mailed Jun. 25, 2013", (w/ English Translation of Amended Claims), 18 pgs.
"Japanese Application Serial No. 2011-111048, Response filed Mar. 15, 2013", (w/ Translation of Amended Claims), 14 pgs.
"Japanese Application Serial No. 2012-273898, Office Action mailed Jun. 10, 2014", (w/ English Translation), 7 pgs.
"Japanese Application Serial No. 2012-273898, Response filed Sep. 4, 2014 to Office Action mailed Jun. 10, 2014", W/ English Claims, 9 pgs.
"Japanese Application Serial No. 2012-536963, Amendment and Argument filed Jun. 26, 2015 to Office Action mailed Jan. 6, 2015", (w/ English Translation of Amended Claims), 12 pgs.
"Japanese Application Serial No. 2012-536963, Examiners Decision of Final Refusal mailed Nov. 17, 2015", (w/ English Translation), 8 pgs.
"Japanese Application Serial No. 2012-536963, Office Action mailed Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action mailed Jan. 6, 2015", (w/ English Translation), 9 pgs.
"Japanese Application Serial No. 2014-049025 Response filed Sep. 4, 2015 to Office Action mailed Jun. 16, 2015", (w/ Amended Claims), 12 pgs.
"Japanese Application Serial No. 2014-049025, Examiners Decision of Final Refusal mailed Feb. 2, 2016", W/ English Translation, 5 pgs.
"Japanese Application Serial No. 2014-049025, Office Action mailed Jun. 16, 2015", (w/ English Translation), 6 pgs.
"Japanese Application Serial No. 2016-053990, Office Action mailed Jun. 6, 2017", (w/ English Translation), 4 pgs.
"Japanese Application Serial No. 2016-053990, Response filed Dec. 6, 2017 to Office Action mailed Jun. 6, 2017", (w/ English Translation of Amended Claims), 14 pgs.
"Japanese Application Serial No. 2016-110879, Office Action mailed May 30, 2017", (w/ English Translation), 7 pgs.
"Japanese Application Serial No. 2016-110879, Response filed Nov. 30, 2017 to Office Action mailed May 30, 2017", (w/ English Translation of Claims), 25 pgs.
"Japanese Application Serial No. 2018-543688, Notification of Reasons for Rejection mailed Oct. 29, 2019", w/ English Translation, 14 pgs.
"Japanese Application Serial No. 2018-543688, Office Action mailed Jun. 30, 2020", w/ English translation, 11 pgs.
"Japanese Application Serial No. 2018-543688, Response filed Apr. 28, 2020 to Notification of Reasons for Rejection mailed Oct. 29, 2019", w/ English Claims, 12 pgs.
"Japanese Application Serial No. 2006-513125,Final Office Action mailed Jan. 18, 2011", (English Translation), 4 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ English Translation), 9 pgs.
"Korean Application Serial No. 10-2005-7020077, Response filed Aug. 28, 2007 to Notice of Preliminary Rejection mailed Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action mailed Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.

(56) References Cited

OTHER PUBLICATIONS

"Mexican Application No. PA/a/2005/012712 Office Action mailed Jul. 21, 2009", (w/ English Translation), 9 pgs.
"Mexican Application Serial No. MX/a/2009/006341, Office Action mailed Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action mailed May 19, 2015", (w/ English Translation of Claims), 21 pgs.
"Mexican Application Serial No. MX/a/2012/009249, Office Action mailed Feb. 5, 2016", W/ English Claims, 2 pgs.
"Mexican Application Serial No. MX/a/2012/009249, Office Action mailed May 19, 2015", (English Translation), 1 pg.
"Mexican Application Serial No. MX/a/2012/009249, Response filed Mar. 29, 2016 to Office Action mailed Feb. 5, 2016", (English Translation of Claims), 18 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", (w/ English Translation of Claims), 14 pgs.
"Mexican Application Serial No. PA/a/2005/012712 , Office Action Mailed Aug. 11, 2009", (English Translation), 5 pgs.
"Mexican Application Serial No. PA/a/2005/012712 , Response filed Sep. 28, 2009 to Office Action Mailed Jul. 21, 2009", (w/ English Translation of Claims), 24 pgs.
"Mexican Application Serial No. PA/a/2005/012712, Office Action mailed May 12, 2010", (w/ English Translation), 19 pgs.
"Mexican Application Serial No. PA/a/2005/012712, Office Action mailed Jun. 9, 2010", (w/ English Translation), 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Official Action mailed Mar. 5, 2009", (English Translation), 2 pgs.
"Mexican Application Serial No. PA/a/2005/012712, Response filed Feb. 3, 2010 to Office Action mailed Nov. 30, 2009", (w/ English Translation of Amended Claims), 22 pgs.
"Mexican Application Serial No. PA/a/2005/012712, Response filed Sep. 27, 2010 to Office Action mailed May 12, 2010", (w/ English Translation of Claims), 19 pgs.
"Mexico Application Serial No. PA/a/2005/012712, Response filed Jun. 12, 2009 to Official Action mailed Mar. 5, 2009", (w/ English Translation of Claims), 11 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 12, 2008", 2 pgs.
"New Zealand Application Serial No. 543446, Response mailed Mar. 20, 2008 to Examination Report mailed Feb. 29, 2008", 2 pgs.
"Nonstructural protein 1 [influenza B virus (B/Hong Kong/330/2001)]", GenBank AAT69443.1, (2006), 1 pg.
"Norway Application Serial No. 20056074, Office Action mailed Jan. 17, 2017", (English Translation), 5 pgs.
"Norway Application Serial No. 20056074, Office Action Response mailed Apr. 18, 2017", W/ English Claims, 27 Pgs.

"Norway Application Serial No. 20056074, Response filed Jul. 25, 2017 to Office Action mailed Apr. 25, 2017", (w/ English Translation of Amended Claims), 111 pgs.
"Norweigan Application Serial No. 20056074, Office Action mailed Apr. 25, 2017", (Translation), 3 pgs.
"Polymerase acidic [influenza A virus (A/swine/Shizuoka/120/97(H3N2)]", GenBank AAO15329.1, (2003), 1 pg.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AltName: Full=NS1 B", GenPept Accesion P08013, (Dec. 9, 2015).
"RecName: Full=Polymerase acidic protein {ECO:0000256|RuleBase;RU361280, ECO:0000256|SAAS:SAAS00262764}", XP002744257, retrieved from EBI accession No. UNIPROT:A3R6C9 Database accession No. A3R6C9 the whole document, (Apr. 3, 2007), 1 pgs.
"RecName: Full=Polymerase acidic protein {ECO:0000256|RuleBase;RU361280, ECO:0000256|SAAS:SAAS00262764}", XP002744258, retrieved from EBI accession No. UNIPROT:U3S198 Database accession No. U3S198 the whole document, (Dec. 11, 2013), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singaporean Application Serial No. 200506858-0, Examination Report mailed Feb. 9, 2007", 4 pgs.
"Singaporean Application Serial No. 200506858-0, Response filed Dec. 22, 2006 to Written Opinion mailed Jul. 26, 2006", 18 pgs.
"Singaporean Application Serial No. 200506858-0, Written Opinion mailed Jul. 26, 2006", 8 pgs.
"Singaporean Application Serial No. 200507468-7, Examination Report mailed Mar. 19, 2008", 5 pgs.
"Singaporean Application Serial No. 200507468-7, Invitation to Respond to Written Opinion mailed Jun. 12, 2007", 6 pgs.
"Singaporean Application Serial No. 200507468-7, Response filed Nov. 7, 2007 to Invitation to Respond to Written Opinion mailed Jun. 12, 2007", 9 pgs.
"The Influenza Virus: Structure and Replication", Rapid Reference to Influenza. Elsevier Ltd, [Online]. Retrieved from the Internet: http://www.rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action mailed Jun. 17, 2009", W/ English Claims, 14 pgs.
"Ukrainian Application Serial No. 200512619, Office Action mailed Feb. 27, 2009", (w/ English Translation), 21 pgs.
"Ukrainian Application Serial No. 200512619, Office Action mailed Jun. 17, 2009", (w/ English Translation), 4 pgs.
"Ukrainian Application Serial No. 200512619, Response filed Apr. 8, 2009 to Office Action mailed Feb. 27, 2009", (w/ English Translation of Claims), 9 pgs.
Air, Gillian M., et al., "Antigenic, Sequence, and Crystal Variation in Influenza B Neuraminidase", Virology, 177(2), (1990), 578-587.

(56) References Cited

OTHER PUBLICATIONS

Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant, (2005), 411-415.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an integral component of the membrane of influenza B virus.", J Gen Virol., 77 ( Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4, (2010), 1425-1427.
Bourmakina, S. V, et al., "Reverse genetics studies on the Filamentous morphology of influenza A Virus", Journal of General Virology (2003) 84,, (2003), 517-527.
Bowie, J. U., et al., "Deciphering the Message in Protein Sequences: Tolerance to Amino Acid Substitutions", Science, 247(4948), (1990), 1306-1310.
Boyer, J. C., et al., "Infectious transcripts and cDNA clones of RNA viruses", Virology, 198(2), (Feb. 1994), 415-426.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Brooke, C B, "Biological activities of 'noninfectious' influenza A virus particles", Future Virol 9(1), (Jan. 2014), 41-51.
Brown, E. G., et al., "Genetic analysis of mouse-adapted influenza A virus identifies roles for the NA, PB1, and PB2 genes in virulence", Virus Research, 61(1), (May 1999), 63-76.
Buchholz, U. J., et al., "Generation of Bovine Respiratory Syncytial Virus (BRSV) From cDNA: BRSV NS2 is Not Essential for Virus Replication in Tissue Culture, and the Human RSV Leader Region Acts as a Functional BRSV Genome Promoter", Journal of Virology, 73(1), (1999), 251-259.
Bukreyev, A., et al., "Recovery of infectious respiratory syncytial virus expressing an additional, foreign gene", Journal of Virology, 70(10), (Oct. 1996), 6634-6641.
Cao, S., et al., "Characterization of the Nucleocytoplasmic Shuttle of the Matrix Protein of Influenza B Virus", Journal of Virology., 88(13), (Jul. 2014), 7464-7473.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Chan, Winnie, et al., "The cold adapted and temperature sensitive influenza A/AnnArbor/6/60 virus, the master donor virus for live attenuated influenza vaccines, has multiple defects in replication at the restrictive temperature", Virology, 380(2), (2008), 304-311.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Clarke, D. K., et al., "Rescue of Mumps Virus From cDNA", Journal of Virology, 74(10), (2000), 4831-4838.
Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Dimmock, Nigel J, et al., "In vivo antiviral activity: defective interfering virus protects better against virulent Influenza A virus than avirulent virus", Journal of General Virology 87, (Jan. 8, 2006), 1259-1265.

(56) References Cited

OTHER PUBLICATIONS

Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P., et al., "Recovery of infectious human parainfluenza virus type 3 from cDNA", Virology, 235(2), (Sep. 1, 1997), 323-332.
Elhefnawi, M, et al., "Identification of novel conserved functional motifs across most Influenza A viral strains", Virology Journal, 8:44, (2011), 10 pages.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., et al., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Fischer, W. B, et al., "Viral ion channels: structure and function.", Biochim Biophys Acta., 1561(1), (Mar. 19, 2002), 27-45.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Gao, Qinshan, et al., "A Nine-Segment In?uenza A Virus Carrying Subtype H1 and H3 Hemagglutininst†", Journal of Virology, 84(16), (Aug. 2010), 8062-8071.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garcia-Sastre, A., et al., "Genetic Manipulation of Negative-Strand RNA Virus Genomes", Annu. Rev. Microbiol., 47, (1993), 765-790.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Giddings, A M, et al., "The matrix protein of HIV-1 is not sufficient for assembly and release of virus-like particles", Virology, 248(1), (1998), 108-16.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Grambas, S., et al., "Influence of amantadine resistance mutations on the pH regulatory function of the M2 protein of influenza A viruses", Virology, 191(2), (Dec. 1992), 541-549.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Hai, Rong, et al., "Influenza B Virus NS1-Truncated Mutants: Live-Attenuated Vaccine Approach", Journal of Virology, 82(21), (2008), 10580-10590.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatada, E., et al., "Binding of Influenza A Virus NS1 Protein to dsRNA in vitro", Journal of General Virology, 73, (1992), 3325-3329.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hickman, Danielle, et al., "An avian live attenuated master backbone for potential use in epidemic and pandemic influenza vaccines", Journal of General Virology, 89(Part 11), (2008), 2682-2690.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.

(56) References Cited

OTHER PUBLICATIONS

Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Holsinger, L. J., et al., "Influenza A Virus M2 Ion Channel Protein: a Structure-Function Analysis", Journal of Virology, 68 (3), (1994), pp. 1551-1563.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Horimoto, "Designing Vaccines for Pandemic Influenza", Current Topics Microbiol Immunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14), (2003), 8031-8038.
Horimoto, T., et al., "The Development and Characterization of H5 Influenza Virus Vaccines Derived from a 2003 Human Isolate", Vaccine, 24(17), (2006), 3669-3676.
Huang, T.-S., et al., "Determination of Influenza Virus Proteins Required for Genome Replication", Journal of Virology, 64(11), (1990), 5669-5673.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, D., et al., "A reverse genetics approach for recovery of recombinant influenza B viruses entirely from cDNA.", J Virol., 76(22), (Nov. 2002), 11744-7.
Jang, S.-W., et al., "Deoxygedunin, a Natural Product with Potent Neurotrophic Activity in Mice", PLoS ONE 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaoka, Y, et al., "Sequence requirements for cleavage activation of influenza virus hemagglutinin expressed in mammalian cells", Proc Natl Acad Sci., 85(2), (1988), 324-328.
Kawaoka, Y., "Mutant Cells With Altered Sialic Acid", U.S. Appl. No. 11/644,179, filed Dec. 22, 2006, 51 pgs.
Kilbourne, E. D, et al., "Related studies of a recombinant influenza-virus vaccine. I. Derivation and characterization of virus and vaccine", J Infect Dis., 124(5), (Nov. 1971), 449-62.
Kim, H., et al., "Cold adaptation generates mutations associated with the growth of influenza B vaccine viruses", Vaccine, 33(43), (2015), 5786-5793.
Kimura, N., et al., "An In Vivo Study of the Replication Origin in the Influenza Virus Complementary RNA", The Journal of Biochemistry, 113(1), (1993), 88-92.
Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.
Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, Otfried, et al., "Cell culture (Vero) derived whole virus (H5N1) vaccine based on wild-type virus strain induces cross-protective immune responses", Vaccine, 25(32), (2007), 6028-6036.
Kittel, Christian, et al., "Generation of an In?uenza A Virus Vector Expressing Biologically Active Human Interleukin-2 from the NS Gene Segment", Journal of Virology, 79(16), (Aug. 2005), 10672-10677.
Kobayashi, M., et al., "Reconstitution of Influenza Virus RNA Polymerase From Three Subunits Expressed Using Recombinant Baculovirus System", Virus Research, 22, (1992), 235-245.
Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.
Konarska, M. M., et al., "Structure of RNAs Replicated by the DNA-Dependent T7 RNA Polymerase", Cell, 63(2), (1990), 609-618.
Kovacova, A., et al., "Sequence similarities and evolutionary relationships of influenza virus A hemagglutinins.", Virus Genes, 24(1), (2002), 57-63.
Kovacova, Andrea, et al., "Sequence Similarities and Evolutionary Relationships of Influenza Vrus A Hemagglutinins", Virus Genes, 24(1), (2002), 57-63.
Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.
Krystal, M., "Influenza B/Lee/40, hemagglutinin (seg 4), complete segment.", Database EM_VI E.B.I. Hinxton U.K., (Apr. 25, 1990).
Kunkel, T. A., "Rapid and Efficient Site-Specific Mutagenesis Without Phenotypic Selection", Proc. Natl. Acad. Sci. USA, 82, (1985), 488-492.
Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.
Lawson, N. D., "Recombinant Vesicular Stomatitis Viruses From DNA", Proc. Natl. Acad. Sci. USA, 92(10), (1995), 4477-4481.
Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.
Lee, C. W, et al., "Generation of reassortant influenza vaccines by reverse genetics that allows utilization of a DIVA (Differentiating

(56) References Cited

OTHER PUBLICATIONS

Infected from Vaccinated Animals) strategy for the control of avian influenza", Vaccine, vol. 22, (2004), 3175-3181.
Lee, Dong-Hun, et al., "Progress and hurdles in development of influenza virus-like particle vaccines for veterinary use", Korean Vaccine Society, (2014), 133-139.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al., "Genetic and pathogenic characterization of H6NI avian influenza viruses isolated in Taiwan between 1972 and 2005", Avian Diseases, 50(4), (Dec. 2006), 561-571.
Levis, R., et al., "Deletion Mapping of Sindbis Virus DI RNAs Derived From cDNAs Defines the Sequences Essential for Replication and Packaging", Cell, 44, (1986), 137-145.
Li, K. S., et al., "Genesis of a highly pathogenic and potentially pandemic H5N1 influenza virus in eastern Asia", Nature, vol. 430, (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Li, Y, et al., "Viral liposomes released from insect cells infected with recombinant baculovirus expressing the matrix protein of vesicular stomatitis virus", Journal of Virology, 67 (7), (1993), 4415-4420.
Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.
Liu, Bo, et al., "[Comparison of three methods in construction fusion gene of influenza A virus Nucleoprotein].", (English Abstract), Zhonghua Shi Yan He Lin Chuang Bing Du Xue Za Zhi, 26(1), 70-74, (Feb. 2012), 1 pg.
Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.
Lugovtsev, V. Y., et al., "Genetic Composition and Mutational Pattern of Influenza B Viruses Adapted to Replication in Embryonated Eggs", GenBank: AAT69446.1, (2005), 1 pg.
Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.
Manz, Benjamin, et al., "Disruption of the Viral Polymerase Complex Assembly as a Novel Approach to Attenuate Influenza A Virus", The Journal of Biological Chemistry, 286(10), 2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21), (2014), 12364-12373.
McCown, M F, et al., "The influenza A virus M2 cytoplasmic tail is required for infectious virus production and efficient genome packaging.", J Virol., 79(6), (Mar. 2005), 3595-605.
McCown, M. F, et al., "Distinct domains of the influenza a virus M2 protein cytoplasmic tail mediate binding to the M1 protein and facilitate infectious virus production.", J Virol., 80(16), (Aug. 2006), 8178-89.
McCullers, Jonathan A., et al., "A single amino acid change in the C-terminal domain of the matrix protein M1 of influenza B virus confers mouse adaption and virulence", Virology, 336(2), (Jun. 5, 2005), 318-326.
McKimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Monto, Arnold S, et al., "Comparative efficacy of inactivated and live attenuated influenza vaccines.", N Engl J Med., 361(13), (Sep. 24, 2009), 1260-7.
Moyer, S. A., et al., "Assembly and Transcription of Synthetic Vesicular Stomatitis Virus Nucleocapsids", Journal of Virology, 65(5), (1991), 2170-2178.
Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Murphy, Brian R, et al., "Virulence of Avian Influenza A Viruses for Squirrel Monkeys", Infection and Immunity 37 (3), (Sep. 1982), 1119-1126.
Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.
Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "An Improved Reverse Genetics System for Influenza A Virus Generation and Its Implications for Vaccine Production", Proc. Natl. Acad. Sci. USA, 102(46), (2005), 16825-16829.
Neumann, G., et al., "Emergence and pandemic potential of swine-origin HIN1 influenza virus", Nature (London), 459(7249), (Jun. 2009), 931-939.

(56) References Cited

OTHER PUBLICATIONS

Neumann, G., et al., "Generation of influenza A virus from cloned cDNAs—historical perspective and outlook for the new millenium.", Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.
Noda, Takeshi, et al., "Three-dimensional analysis of ribonucleoprotein complexes in nfluenza A virus", Nature Communications, 3, (2012), 1-6.
Odagiri, T., et al., "Nucleotide Sequence of the PA Gene of Influenza A/WSN/33 (H1N1)", Nucleic Acids Research, 18 (3), Department of Virology, (Jan. 9, 1990).
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Ozaki, "Generation of High-Yielding Influenza A Viruses in African Green Monkey Kidney (Vero) Cells by Reverse Genetics", J Virol 78(4), (2004), 1851-1857.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.
Percy, N., et al., "Expression of a Foreign Protein by Influenza A Virus", Journal of Virology, 68(7), (1994), 4486-4492.
Perez, Jasmine T., et al., "Unit 15G.4—Insertion of a GFP Reporter Gene in Influenza Virus", Curr Protoc Microbiol., (2013), 20 pgs.
Piller, S C., et al., "Vpr protein of human immunodeficiency virus type 1 forms cation-selective channels in planar lipid bilayers", PNAS, 93, (1996), 111-1115.
Ping, J., et al., "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza A virus vaccine viruses", Nature Communications, [online]. Retrieved from the Internet: <http://www.nature.eom/article-assets/npg/ncomms/2015/150902/ncomms9148/extref/ncomms9148-sl.pdf>, (Sep. 2, 2015).
Pinto, L. H., et al., "Influenza Virus M2 Protein Has Ion Channel Activity", Cell, 69, (May 1992), pp. 517-528.
Plant, E P, et al., "Mutations to A/PuertoRico/8/34 PB1 gene improves seasonal reassortant influenza A virus growth kinetics", Vaccine, 31(1), (Dec. 1, 2012), 207-212.
Pleschka, S., et al., "A Plasmid-Based Reverse Genetics System for Influenza A Virus", Journal of Virology, 70(6), (1996), 4188-4192.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981).
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Roberts, A., et al., "Minireview—Recovery of Negative-Strand RNA Viruses From Plasmid DNAs: A Positive Approach Revitalizes a Negative Field", Virology, 247(1), (1998), 1-6.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 ( Pt 4), (Apr. 1984), 799-802.
Ruigrok, R W, et al., "Structural Characterization and Membrane Binding Properties of the Matrix Protein VP40 of Ebola Virus", Journal of Molecular Biology, 300(1), (2000), 103-112.
Sansom, M. S., et al., "Influenza virus M2 Protein: a molecular modelling study of the Ion channel", Protein Engineering, 6 (1), (1993), pp. 65-74.
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17(5), (1998), 1289-1296.
Schotsaert, M, et al., "Universal M2 ectodomain-based influenza A vaccines: preclinical and clinical developments", Expert Rev Vaccines. Apr. 2009;8(4):, 499-508.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Skehel, J. J., et al., "On the Mechanism of Inhibition of Influenza Virus Replication by Amantadine Hydrochloride", The Journal of General Virology, 38 (1), (1977), pp. 97-110.

(56) References Cited

OTHER PUBLICATIONS

Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Takeda, M., et al., "Influenza a virus M2 ion channel activity is essential for efficient replication in tissue culture.", J Virol., 76(3), (Feb. 2002), 1391-9.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Tobler, K, et al., "Effect of cytoplasmic tail truncations on the activity of the M(2) ion channel of influenza A virus", J Virol., 73(12), (Dec. 1999), 9695-9701.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Verma, I. M, et al., "Gene Therapy—Promises, Problems and Prospects", Nature, 389, (1997), 239-242.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Wenlig, et al., "Robust Immunity and Heterologous Protection against Influenza in Mice Elicited by a Novel Recombinant NP-M2e Fusion Protein Expressed in *E. coli*", PLoS One 7(12): e52488, (Dec. 2012), 1-13.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Watanabe, S., et al., "Influenza A Virus Lacking M2 Protein as a Live Attenuated Vaccine" Journal of Virology, 83(11), (2009), 5947-5950.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals To Generate a Novel In?uenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Wei, Hung-Ju, et al., "Fabrication of influenza virus-like particles using M2 fusion proteins for imaging single viruses and designing vaccines", Vaccine, 29, (2011), 7163-7172.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wilson, Julie A, et al., "Epitopes Involved in Antibody-Mediated Protection from Ebola Virus", Science, 287(5458), (Mar. 2000), 1664-1666.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wu, Rui, et al., "A live bivalent influenza vaccine based on a H9N2 virus strain", Vaccine, 28, (2010), 673-680.
Xu, X., et al., "Reassortment and evolution of current human influenza A and B viruses", Virus Research, 103, (2004), 55-60.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yannarell, Dean A., et al., "Factors affecting the yield of cold-adapted influenza virus vaccine", Journal of Virological Methods, vol. 64, 161-169, (1997), 1 pg.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendal and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

(56) References Cited

OTHER PUBLICATIONS

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.
Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zobel, A., et al., "RNA Polymerase I Catalysed Transcription of Insert Viral cDNA", Nucleic Acids Research, 21(16), (1993), 3607-3614.
"U.S. Appl. No. 18/525,460, Preliminary Amendment filed Jun. 7, 2024", 6 pgs.
"U.S. Appl. No. 17/212,836, Non Final Office Action mailed Jun. 13, 2024", 14 pgs.
"International Application Serial No. PCT US2024 020952, International Search Report mailed Jul. 30, 2024", 3 pgs.
"International Application Serial No. PCT US2024 020952, Written Opinion mailed Jul. 30, 2024", 5 pgs.
"Japanese Application Serial No. 2022-161803, Notification of Reasons for Refusal mailed Jun. 4, 2024", w English Translation, 13 pgs.
"International Application Serial No. PCT US2023 063136, International Preliminary Report on Patentability mailed Sep. 6, 2024", 9 pgs.
Aria, Yasuha, "PB2 mutations arising during H9N2 influenza evolution in the Middle East confer enhanced replication and growth in mammals", PLOS Pathogens 15(7): e1007919. https: doi.org 10.1371 journal.ppat.1007919, (Jul. 2, 2019), 25 pages.
Fan, Haitian, "Structures of influenza A virus RNA polymerase offer insight into viral genome replication", Nature 573, 287-290 (2019). https: doi.org 10.1038 s41586-019-1530-7, (Sep. 4, 2019), 35 pages.
Kamiki, Haruhiko, "Novel Biological System with Terminal Sialic Acid Knockout Cells", J Virol 96:e00416-22.https:doi.org 10.1128 jvi.00416-22, (Jul. 18, 2022), 15 pages.
Klimov, A.I., "Correlation of amino acid residues in the M1 and M2 proteins of influenza virus with high yielding properties", Virus Research, vol. 19, Issue 1, 1991,pp. 105-114,ISSN 0168-1702,https: doi.org 10.10160168-1702(91)90098-G.(https: www.sciencedirect.com science article pii 016817029190098G), (Mar. 1991), 10 pages.
Ma, Wenjun, "The NS Segment of an H5N1 Highly Pathogenic Avian Influenza Virus (HPAIV) Is Sufficient To Alter Replication Efficiency, Cell Tropism, and Host Range of an H7N1 HPAIV", J Virol. Feb. 2010;84(4):2122-33. doi: 10.1128 JVI.01668-09. Epub Dec. 9, 2009. PMID: 20007264; PMCID: PMC2812369., (Feb. 2010), 12 pages.
Mahesutihan, Madina, "CypA Regulates AIP4-Mediated M1 Ubiquitination of Influenza A Virus", Virologica Sinica 33 (2018): 440-448., (Oct. 16, 2018), 9 pages.
"U.S. Appl. No. 13/070,110, Notice of Allowance mailed Jul. 20, 2018", 7 pgs.
"U.S. Appl. No. 13/070,110, PTO Response to Rule 312 Communication mailed Aug. 15, 2018", 2 pgs.
"U.S. Appl. No. 14/816,807, PTO Response to Rule 312 Communication mailed Jul. 6, 2018", 2 pgs.
"U.S. Appl. No. 15/170,556, Final Office Action mailed Jul. 30, 2019", 6 pgs.
"U.S. Appl. No. 15/170,556, Notice of Allowance mailed Nov. 27, 2019", 8 pgs.
"U.S. Appl. No. 15/170,556, Response filed Nov. 18, 2019 to Final Office Action mailed Jul. 30, 2019", 8 pgs.
"U.S. Appl. No. 15/292,595, Notice of Allowance mailed Jun. 20, 2018", 9 pgs.
"U.S. Appl. No. 15/865,364, Notice of Allowance mailed Nov. 15, 2018", 7 pgs.
"U.S. Appl. No. 15/905,454, Preliminary Amendment filed Nov. 2, 2018", 5 pgs.
"U.S. Appl. No. 15/905,454, Restriction Requirement mailed Jan. 3, 2019", 6 pgs.
"U.S. Appl. No. 15/966,092, Interview Summary mailed Mar. 2, 2021", 2 pgs.
"U.S. Appl. No. 15/966,092, Notice of Allowance mailed Feb. 11, 2021", 5 pgs.
"U.S. Appl. No. 16/046,250, Non-Final Office Action mailed Mar. 6, 2020", 10 pgs.
"U.S. Appl. No. 16/046,250, Notice of Allowance mailed Jun. 15, 2020", 9 pgs.
"U.S. Appl. No. 16/046,250, Response filed Jun. 3, 2020 to Non-Final Office Action mailed Mar. 6, 2020", 10 pgs.
"U.S. Appl. No. 16/046,250, Response filed Oct. 25, 2019 to Restriction Requirement mailed Jul. 25, 2019", 9 pgs.
"U.S. Appl. No. 16/046,250, Restriction Requirement mailed Jul. 25, 2019", 7 pgs.
"U.S. Appl. No. 16/749,910, Notice of Allowance mailed Sep. 22, 2021", 10 pgs.
"U.S. Appl. No. 16/749,910, Response filed Jun. 17, 2021 to Restriction Requirement mailed Apr. 19, 2021", 11 pgs.
"U.S. Appl. No. 16/749,910, Restriction Requirement mailed Apr. 19, 2021", 9 pgs.
"Australian Application Serial No. 2014290203, First Examination Report mailed Oct. 10, 2019", 4 pgs.
"Australian Application Serial No. 2014290203, Response filed Mar. 13, 2020 to First Examination Report mailed Oct. 10, 2019", 16 pgs.
"Australian Application Serial No. 2014290203, Response filed Jun. 24, 2020 to Subsequent Examiners Report mailed Mar. 23, 2020", 16 pgs.
"Australian Application Serial No. 2014290203, Response filed Sep. 29, 2020 to Subsequent Examiners Report mailed Jul. 21, 2020", 25 pgs.
"Australian Application Serial No. 2014290203, Response filed Dec. 9, 2020 to Subsequent Examiners Report mailed Oct. 6, 2020", 14 pgs.
"Australian Application Serial No. 2014290203, Subsequent Examiners Report mailed Mar. 23, 2020", 6 pgs.
"Australian Application Serial No. 2014290203, Subsequent Examiners Report mailed Jul. 21, 2020", 5 pgs.
"Australian Application Serial No. 2014290203, Subsequent Examiners Report mailed Oct. 6, 2020", 4 pgs.
"Australian Application Serial No. 2017221444, Response filed Jan. 25, 2021 to Subsequent Examiners Report mailed Nov. 27, 2020", 18 pgs.
"Australian Application Serial No. 2017221444, Response filed Jun. 2, 2021 to Subsequent Examiners Report mailed Feb. 24, 2021", 20 pgs.
"Australian Application Serial No. 2017221444, Response filed Jul. 6, 2021 to Fourth Examiners Report mailed Jun. 29, 2021", 7 pgs.
"Australian Application Serial No. 2017221444, Subsequent Examiners Report mailed Feb. 24, 2021", 4 pgs.
"Brazilian Application Serial No. PI 0410702-0, Office Action mailed Oct. 6, 2020", (w/ English Translation), 9 pgs.
"Brazilian Application Serial No. PI 0410702-0, Response filed Dec. 14, 2020 to Office Action mailed Oct. 6, 2020", (w/ English Translation of Claims), 42 pgs.
"Brazilian Application Serial No. PI 0410702-0, Office Action mailed Nov. 1, 2019", (w/ English Translation), 6 pgs.
"Brazilian Application Serial No. PI 0410702-0, Response filed Feb. 6, 2020 to Office Action mailed Nov. 1, 2019", (w/ English Translation of Claims), 92 pgs.
"Brazilian Application Serial No. PI0410702-0, Office Action mailed Apr. 1, 2020", (w/ English Summary), 6 pgs.
"Brazilian Application Serial No. PI0410702-0, Response filed Aug. 28, 2020 to Office Action mailed Apr. 1, 2020", (w/ English Translation of Claims), 86 pgs.
"Canadian Application Serial No. 2,525,953, Office Action mailed Jan. 29, 2020", 4 pgs.
"Canadian Application Serial No. 2,525,953, Office Action mailed Apr. 2028, 21", 7 pgs.

(56) References Cited

OTHER PUBLICATIONS

"Canadian Application Serial No. 2,525,953, Office Action mailed Nov. 2, 2018", 6 pgs.
"Canadian Application Serial No. 2,525,953, Response filed May 2, 2019 to Office Action mailed Nov. 2, 2018", 31 pgs.
"Canadian Application Serial No. 2,525,953, Response filed May 25, 2020 to Office Action mailed Jan. 29, 2020", 35 pgs.
"Canadian Application Serial No. 3,014,435, Response filed Feb. 25, 2022 to Office Action mailed Oct. 26, 2021", 15 pgs.
"Canadian Application Serial No. 3,014,435, Response filed Mar. 5, 2021 to Office Action mailed Nov. 6, 2020", 20 pgs.
"Chinese Application Serial No. 200480021259.9, Reexamination Decision mailed Mar. 25, 2013", (w/ English Translation), 17 pgs.
"Chinese Application Serial No. 201780024821.0, Office Action mailed Jun. 15, 2022", (w/ English Translation), 6 pgs.
"Chinese Application Serial No. 201780024821.0, Office Action mailed Nov. 30, 2021", (w/ English Translation), 21 pgs.
"Chinese Application Serial No. 201780024821.0, Response filed Apr. 12, 2022 to Office Action mailed Nov. 30, 2021", (w/ English Translation of Claims), 17 pgs.
"European Application Serial No. 10777154.5, Communication Pursuant to Article 94(3) EPC mailed Jun. 11, 2019", 3 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Jul. 29, 2019 to Communication Pursuant to Article 94(3) EPC mailed Jun. 11, 2019", 57 pgs.
"European Application Serial No. 10777154.5, Response filed Sep. 7, 2018 to Communication Pursuant to Article 94(3) EPC mailed Apr. 4, 2018", 18 pgs.
"European Application Serial No. 10777154.5, Summons to Attend Oral Proceedings mailed Jan. 7, 2019", 5 pgs.
"European Application Serial No. 14745060.5, Communication Pursuant to Article 94(3) EPC mailed Mar. 12, 2020", 4 pgs.
"European Application Serial No. 14745060.5, Communication Pursuant to Article 94(3) EPC mailed Jul. 18, 2019", 5 pgs.
"European Application Serial No. 14745060.5, Communication Pursuant to Article 94(3) EPC mailed Sep. 15, 2021", 4 pgs.
"European Application Serial No. 14745060.5, Communication Pursuant to Article 94(3) EPC mailed Sep. 18, 2018", 4 pgs.
"European Application Serial No. 14745060.5, Communication Pursuant to Article 94(3) EPC mailed Nov. 9, 2020", 4 pgs.
"European Application Serial No. 14745060.5, Response filed Jan. 28, 2020 to Communication Pursuant to Article 94(3) EPC mailed Jul. 18, 2019", 9 pgs.
"European Application Serial No. 14745060.5, Response filed Mar. 27, 2019 to Communication Pursuant to Article 94(3) EPC mailed Sep. 18, 2018", 13 pgs.
"European Application Serial No. 14745060.5, Response filed May 12, 2021 to Communication Pursuant to Article 94(3) EPC mailed Nov. 9, 2020", 12 pgs.
"European Application Serial No. 14745060.5, Response filed Jun. 15, 2018 to Communication Pursuant to Article 94(3) EPC mailed Feb. 6, 2018", 14 pgs.
"European Application Serial No. 14745060.5, Response filed Jul. 17, 2020 to Communication Pursuant to Article 94(3) EPC mailed Mar. 12, 2020", 52 pgs.
"European Application Serial No. 17709236.8, Communication Pursuant to Article 94(3) EPC mailed Jun. 8, 2022", 6 pgs.
"European Application Serial No. 17709236.8, Response filed Jan. 17, 2022 to Communication Pursuant to Article 94(3) EPC mailed Jul. 6, 2021", 13 pgs.
"International Application Serial No. PCT/US2020/014659, International Preliminary Report on Patentability mailed Aug. 5, 2021", 12 pgs.
"International Application Serial No. PCT/US2020/014659, International Search Report mailed Nov. 6, 2020", 7 pgs.
"International Application Serial No. PCT/US2020/014659, Invitation to Pay Additional Fees mailed Sep. 16, 2020", 11 pgs.
"International Application Serial No. PCT/US2020/014659, Written Opinion mailed Nov. 6, 2020", 10 pgs.
"Israeli Application Serial No. 238584, Notification of Defects in Patent Application mailed Jul. 21, 2019", (w/ English Translation), 5 pgs.
"Israeli Application Serial No. 238584, Office Action mailed Aug. 23, 2018", (w/ English Translation), 6 pgs.
"Israeli Application Serial No. 238584, Response filed Nov. 21, 2019 to Notification of Defects in Patent Application mailed Jul. 21, 2019", (w/ English Translation of Claims), 6 pgs.
"Israeli Application Serial No. 238584, Response Filed Dec. 10, 2018 to Office Action mailed Aug. 23, 2018", (w/ English Translation of Claims, 10 pgs.
"Japanese Application Serial No. 2016-527046, Examiners Decision of Final Refusal mailed May 21, 2019", (w/ English Translation), 20 pgs.
"Japanese Application Serial No. 2016-527046, Reasons For Rejection mailed Aug. 14, 2018", (w/ English Translation), 14 pgs.
"Japanese Application Serial No. 2016-527046, Response Filed Dec. 4, 2018 to Reasons For Rejection mailed Aug. 14, 2018", (w/ English Translation of Amended Claims), 18 pgs.
"Japanese Application Serial No. 2019-171818, Examiners Decision of Final Refusal mailed Oct. 5, 2021", (w/ English Translation), 15 pgs.
"Japanese Application Serial No. 2019-171818, Notification of Reasons for Rejection mailed Nov. 10, 2020", (w/ English Translation), 11 pgs.
"Japanese Application Serial No. 2019-171818, Response filed May 10, 2021 to Notification of Reasons for Rejection mailed Nov. 10, 2020", (w/ English Translation of Claims), 12 pgs.
"Japanese Application Serial No. 2020-182549, Examiners Decision of Final Refusal mailed Jun. 7, 2022", (w/ English Translation), 11 pgs.
"Japanese Application Serial No. 2020-182549, Notification of Reasons for Refusal mailed Nov. 30, 2021", (w/ English Translation), 10 pgs.
"Japanese Application Serial No. 2020-182549, Response filed Feb. 28, 2022 to Notification of Reasons for Refusal mailed Nov. 30, 2021", (w/ English Translation of Claims), 52 pgs.
"Norweigan Application Serial No. 20056074, Office Action mailed Apr. 25, 2017", (w/ English Translation), 3 pgs.
Air, Gillian M., et al., "Antigenic, Sequence, and Crystal Variation in Influenza B Neuraminidase", Virology vol. 177,, (1990), 578-587.
Govorkova, E A, et al., "Replication of Influenza A Viruses in a Green Monkey Kidney Continuous Cell Line (Vero)", J. Infect. Dis. 172(1), (1995), 250-253.
Hoffmann, Erich, et al., "A DNA transfection system for generation of influenza A virus from eight plasmids", Proceedings of the National Academy of Sciences, vol. 97, No. 11, (2000), 6108-6113.
Jiang, H, et al., "Influenza virus genome C4 promoter/origin attenuates its transcription and replication activity by the low polymerase recognition activity", Virology, 408(2), (2010), 190-196.
Li, Qi, et al., "Screening of the high yield influenza B virus on MDCK cell and cloning of its whole genome", (English Abstract), Chinese Journal of Virology, 3, (Sep. 30, 2004), 1 pg.
Li, Qi, et al., "Screening of the high yield influenza B virus on MDCK cell and cloning of its whole genome", International Congress Series 1263, (2004), 610-614.
Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.
Neumann, G., et al., "Mutational analysis of influenza virus promoter elements in vivo", Journal of General Virology, 76, (1995), 1709-1717.
Ramanunninair, Manojkumar, et al., "Molecular Signature of High Yield (Growth) Influenza A Virus Reassortants Prepared as Candidate Vaccine Seeds", PLoS ONE, 8(6): e65955, (2013), 1-16.

(56) References Cited

OTHER PUBLICATIONS

Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
"Chinese Application Serial No. 201780024821.0, Response filed Aug. 30, 2022 to Office Action mailed Jun. 15, 2022", w English Claims, 18 pgs.
"Chinese Application Serial No. 201780024821.0, Response to Examiner Telephone Interview filed Sep. 26, 2022", w English Claims, 10 pgs.
"European Application Serial No. 17709236.8, Response filed Oct. 11, 2022 to Communication Pursuant to Article 94(3) EPC mailed Jun. 8, 2022", 65 pgs.
"Japanese Application Serial No. 2020-182549, Response filed Oct. 6, 2022 to Examiners Decision of Final Refusal mailed Jun. 7, 2022", w English Claims, 21 pgs.
U.S. Appl. No. 16/785,449, filed Feb. 7, 2020, Humanized Cell Line.
U.S. Appl. No. 17/004,583, filed Aug. 27, 2020, Recombinant Influenza Viruses With Stabilized HA for Replication in Eggs.
U.S. Appl. No. 17/155,625, filed Jan. 22, 2021, Recombinant Influenza Viruses with Stabilized NA.
U.S. Appl. No. 17/212,836, filed Mar. 25, 2021, Recombinant Multivalent Influenza Viruses.
U.S. Appl. No. 18/173,535, filed Feb. 23, 2023, Broadly Protective Influenza B Virus Vaccines.
U.S. Appl. No. 17/936,194, filed Sep. 28, 2022, Compositions Comprising Complexes Displaying Antigens and Methods of Using the Compositions.
U.S. Appl. No. 14/332,121 U.S. Pat. No. 9,950,057, filed Jul. 15, 2014, High Titer Recombinant Influenza Viruses With Enhanced Replication in MDCK or Vero Cells or Eggs.
U.S. Appl. No. 15/593,039 U.S. Pat. No 10,172,934, filed May 11, 2017, High Titer Recombinant Influenza Viruses With Enhanced Replication in MDCK or Vero Cells or Eggs.
U.S. Appl. No. 16/178,323, filed Nov. 1, 2018, High Titer Recombinant Influenza Viruses With Enhanced Replication in MDCK or Vero Cells or Eggs.
U.S. Appl. No. 14/745,236 U.S. Pat. No. 10,053,671, filed Jun. 19, 2015, Mutations That Confer Genetic Stability to Additional Genes in Influenza Viruses.
U.S. Appl. No. 15/966,092 U.S. Pat. No. 11,046,934, filed Apr. 30, 2018, Mutations That Confer Genetic Stability to Additional Genes in Influenza Viruses.
U.S. Appl. No. 15/170,556 U.S. Pat. No. 10,633,422, filed Jun. 1, 2016, Influenza Virus Replication by Inhibiting MicroRNA LEC7C Binding to Influenza Viral CRNA and MRNA.
U.S. Appl. No. 17/352,845, filed Jun. 21, 2021, Mutations That Confer Genetic Stability to Additional Genes in Influenza Viruses.
U.S. Appl. No. 15/436,245 U.S. Pat. No. 11,197,925, filed Feb. 17, 2017, Influenza B Virus Replication for Vaccine Development.
"U.S. Appl. No. 10/855,975 Response filed Aug. 28, 2007 to Final Office Action mailed Jun. 28, 2007", 16 pgs.
"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.
"Final O.A Jun. 28, 2007", 5 pgs.
"Application Serial No. 04809419.7, Office Action Mailed Sep. 9, 2009", 3 pgs.
"U.S. Appl. No. 10/081,170, Advisory Action mailed Sep. 27, 2004", 3 pgs.
"U.S. Appl. No. 10/081,170, Final Office Action mailed Apr. 12, 2006", 7 pgs.
"U.S. Appl. No. 10/081,170, Final Office Action mailed Jul. 13, 2004", 8 pgs.
"U.S. Appl. No. 10/081,170, Non Final Office Action mailed Jan. 15, 2004", 9 pgs.
"U.S. Appl. No. 10/081,170, Non Final Office Action mailed Feb. 8, 2005", 9 pgs.
"U.S. Appl. No. 10/081,170, Non Final Office Action mailed Aug. 24, 2005", 9 pgs.
"U.S. Appl. No. 10/081,170, Notice of Allowance mailed Sep. 18, 2006", 8 pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action mailed Aug. 24, 2005", 11 pgs.
"U.S. Appl. No. 10/081,170, Response filed Apr. 12, 2004 to Non Final Office Action mailed Jan. 15, 2004", 12 pgs.
"U.S. Appl. No. 10/081,170, Response filed Jun. 8, 2005 to Non Final Office Action nailed Feb. 8, 2005", 11 pgs.
"U.S. Appl. No. 10/081,170, Response filed Aug. 17, 2006 to Final Office Action mailed Apr. 12, 2006", 9 pgs.
"U.S. Appl. No. 10/081,170, Response filed Sep. 13, 2004 to Final Office Action mailed Jul. 13, 2004", 10 pgs.
"U.S. Appl. No. 10/081,170, Response filed Oct. 10, 2003 to Restriction Requirement mailed Sep. 10, 2003", 3 pgs.
"U.S. Appl. No. 10/081,170, Restriction Requirement mailed Sep. 10, 2003", 4 pgs.
"U.S. Appl. No. 10/353,856, Final Office Action mailed Jun. 1, 2006", 10 pgs.
"U.S. Appl. No. 10/353,856, Non-Final Office Action mailed Sep. 30, 2005", 9 pgs.
"U.S. Appl. No. 10/353,856, Non-Final Office Action mailed Dec. 16, 2004", 11 pgs.
"U.S. Appl. No. 10/353,856, Notice of Allowance mailed Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment mailed Mar. 8, 2007", 2 pgs.
"U.S. Appl. No. 10/353,856, Response filed Feb. 28, 2006 to Non-Final Office Action mailed Sep. 30, 2005", 10 pgs.
"U.S. Appl. No. 10/353,856, Response filed Apr. 7, 2005 to Non-Final Office Action mailed Dec. 16, 2004", 10 pgs.
"U.S. Appl. No. 10/353,856, Response filed Aug. 17, 2006 to Final Office Action mailed Jun. 1, 2006", 11 pgs.
"U.S. Appl. No. 10/353,856, Response filed Oct. 8, 2004 to Restriction Requirement mailed Sep. 10, 2004", 2 pgs.
"U.S. Appl. No. 10/353,856, Restriction Requirement mailed Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/855,975, Advisory Action mailed Sep. 6, 2006", 3 pgs.
"U.S. Appl. No. 10/855,975, Advisory Action mailed Sep. 13, 2007", 3 pgs.
"U.S. Appl. No. 10/855,975, Advisory Action mailed Dec. 24, 2008", 4 pgs.
"U.S. Appl. No. 10/855,975, Final Office Action mailed May 17, 2006", 7 pgs.
"U.S. Appl. No. 10/855,975, Final Office Action mailed Jun. 28, 2007", 7 pgs.
"U.S. Appl. No. 10/855,975, Final Office Action mailed Aug. 7, 2008", 5 pgs.
"U.S. Appl. No. 10/855,975, Non-Final Office Action mailed Jan. 4, 2008", 10 pgs.
"U.S. Appl. No. 10/855,975, Non-Final Office Action mailed Jan. 19, 2007", 7 pgs.
"U.S. Appl. No. 10/855,975, Non-Final Office Action mailed May 29, 2009", 5 pgs.
"U.S. Appl. No. 10/855,975, Non-Final Office Action mailed Nov. 30, 2005", 11 pgs.

(56) References Cited

OTHER PUBLICATIONS

"U.S. Appl. No. 10/855,975, Notice of Allowance mailed Dec. 16, 2009", 19 pgs.
"U.S. Appl. No. 10/855,975, Response filed Jan. 29, 2009 to Advisory Action mailed Dec. 24, 2008", 15 pgs.
"U.S. Appl. No. 10/855,975, Response filed Feb. 28, 2006 to Non-Final Office Action mailed Nov. 30, 2005", 15 pgs.
"U.S. Appl. No. 10/855,975, Response filed Apr. 3, 2008 to Non Final Office Action mailed Jan. 4, 2008", 16 pgs.
"U.S. Appl. No. 10/855,975, Response filed Apr. 19, 2007 to Non-Final Office Action mailed Jan. 19, 2007", 16 pgs.
"U.S. Appl. No. 10/855,975, Response filed Aug. 13, 2009 to Non Final Office Action mailed May 29, 2009", 19 pgs.
"U.S. Appl. No. 10/855,975, Response filed Aug. 17, 2006 to Final Office Action mailed May 17, 2006", 13 pgs.
"U.S. Appl. No. 10/855,975, Response filed Aug. 28, 2007 to Final Office Action mailed Jun. 28, 2007", 15 pgs.
"U.S. Appl. No. 10/855,975, Response filed Sep. 28, 2005 to Restriction Requirement mailed Jul. 12, 2005", 3 pgs.
"U.S. Appl. No. 10/855,975, Response filed Dec. 11, 2008 to Final Office Action mailed Aug. 7, 2008", 14 pgs.
"U.S. Appl. No. 10/855,975, Restriction Requirement mailed Jul. 12, 2005", 8 pgs.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006", 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.
"U.S. Appl. No. 11/509,249, Final Office Action mailed Jun. 12, 2008", 5 pgs.
"U.S. Appl. No. 11/509,249, Non Final Office Action with Restriction Requirement mailed Aug. 24, 2007", 8 pgs.
"U.S. Appl. No. 11/509,249, Notice of Allowance mailed Apr. 9, 2009", 7 pgs.
"U.S. Appl. No. 11/509,249, Notice of Allowance mailed Nov. 17, 2008", 4 pgs.
"U.S. Appl. No. 11/509,249, Response filed Feb. 20, 2008 to Non Final Office Action mailed Aug. 24, 2007", 11 pgs.
"U.S. Appl. No. 11/509,249, Response filed Oct. 6, 2008 to Office Action mailed Jun. 12, 2008", 11 pgs.
"U.S. Appl. No. 11/644,179 , Response filed Oct. 21, 2013 to Final Office Action mailed May 21, 2013", 8 pgs.
"U.S. Appl. No. 11/644,179, Final Office Action mailed May 21, 2013", 11 pgs.
"U.S. Appl. No. 11/644,179, Final Office Action mailed Jul. 2, 2010", 8 pgs.
"U.S. Appl. No. 11/644,179, Non Final Office Action mailed Nov. 29, 2012", 19 pgs.
"U.S. Appl. No. 11/644,179, Non Final Office Action mailed Dec. 8, 2009", 7 pgs.
"U.S. Appl. No. 11/644,179, Notice of Allowance mailed Nov. 1, 2013", 11 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement mailed Oct. 30, 2007", 5 pgs.
"U.S. Appl. No. 11/644,179, Response filed Apr. 8, 2010 to Non Final Office Action mailed Dec. 8, 2009", 8 pgs.
"U.S. Appl. No. 11/644,179, Response filed Aug. 17, 2010 to Final Office Action mailed Jul. 2, 2010", 8 pgs.
"U.S. Appl. No. 11/644,179, Restriction Requirement mailed Oct. 30, 2007", 7 pgs.
"U.S. Appl. No. 11/644,179, Supplemental Preliminary Amendment filed Feb. 6, 2008", 6 pgs.
"U.S. Appl. No. 11/644,179. Response filed Feb. 20, 2013 to Non Final Office Action mailed Nov. 29, 2012", 10 pgs.
"U.S. Appl. No. 11/654,863 Final Office Action mailed Jul. 17, 2017", 11 pgs.
"U.S. Appl. No. 11/654,863 Restriction Requirement mailed Sep. 3, 2010", 5 pgs.
"U.S. Appl. No. 11/654,863, Appeal Brief filed Apr. 30, 2014", 22 pgs.
"U.S. Appl. No. 11/654,863, Appeal Decision mailed Aug. 3, 2016", 11 pgs.
"U.S. Appl. No. 11/654,863, Decision on Pre-Appeal Brief Request mailed Dec. 5, 2013", 2 pgs.
"U.S. Appl. No. 11/654,863, Declaration of Dr. Heinz Feldmann dated Jan. 9, 2018", 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief mailed Jun. 18, 2014", 10 pgs.
"U.S. Appl. No. 11/654,863, Final Office Action mailed Jul. 11, 2013", 9 pgs.
"U.S. Appl. No. 11/654,863, Final Office Action mailed Sep. 12, 2018", 12 pgs.
"U.S. Appl. No. 11/654,863, Final Office Action mailed Oct. 25, 2011", 9 pgs.
"U.S. Appl. No. 11/654,863, Non Final Office Action mailed Feb. 11, 2013", 10 pgs.
"U.S. Appl. No. 11/654,863, Non Final Office Action mailed Mar. 29, 2018", 12 pgs.
"U.S. Appl. No. 11/654,863, Non Final Office Action mailed Jun. 27, 2011", 9 pgs.
"U.S. Appl. No. 11/654,863, Non Final Office Action mailed Dec. 2, 2010", 8 pgs.
"U.S. Appl. No. 11/654,863, Non Final Office Action mailed Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action mailed Jul. 17, 2017", 9 pgs.
"U.S. Appl. No. 11/654,863, Response filed Apr. 18, 2012 to Final Office Action mailed Oct. 25, 2011", 8 pgs.
"U.S. Appl. No. 11/654,863, Response filed Jun. 2, 2011 to Non Final Office Action mailed Dec. 2, 2010", 6 pgs.
"U.S. Appl. No. 11/654,863, Response filed Jun. 7, 2013 to Non Final Office Action mailed Feb. 11, 2013", 10 pgs.
"U.S. Appl. No. 11/654,863, Response filed Jun. 21, 2017 to Non Final Office Action mailed Dec. 21, 2016", 11 pgs.
"U.S. Appl. No. 11/654,863, Response filed Jul. 9, 2018 to Non Final Office Action mailed Mar. 29, 2018", 10 pgs.
"U.S. Appl. No. 11/654,863, Response filed Sep. 28, 2010 to Restriction Requirement mailed Sep. 3, 2010", 6 pgs.
"U.S. Appl. No. 11/654,863, Response filed Oct. 6, 2011 to Non Final Office Action mailed Jun. 27, 2011", 9 pgs.
"U.S. Appl. No. 11/810,956, Final Office Action mailed Mar. 22, 2010", 8 pgs.

(56) References Cited

OTHER PUBLICATIONS

"U.S. Appl. No. 11/810,956, Non-Final Office Action mailed Aug. 11, 2009", 9 pgs.
"U.S. Appl. No. 11/810,956, Response filed Jan. 11, 2010 to Non Final Office Action mailed Aug. 11, 2009", 8 pgs.
"U.S. Appl. No. 11/810,956, Response filed Apr. 23, 2009 to Restriction Requirement mailed Mar. 23, 2009", 6 pgs.
"U.S. Appl. No. 11/810,956, Restriction Requirement mailed Mar. 23, 2009", 6 pgs.
"U.S. Appl. No. 12/058,389, Advisory Action mailed Jan. 2, 13", 2 pgs.
"U.S. Appl. No. 12/058,389, Final Office Action mailed Jan. 22, 2010", 8 pgs.
"U.S. Appl. No. 12/058,389, Final Office Action mailed Nov. 14, 2012", 7 pgs.
"U.S. Appl. No. 12/058,389, Non Final Office Action mailed Aug. 10, 2012", 5 pgs.
"U.S. Appl. No. 12/058,389, Non Final Office Action mailed Dec. 8, 2011", 8 pgs.
"U.S. Appl. No. 12/058,389, Non-Final Office Action mailed Apr. 13, 2009", 12 pgs.
"U.S. Appl. No. 12/058,389, Notice of Allowability mailed Mar. 22, 2013", 8 pgs.
"U.S. Appl. No. 12/058,389, Notice of Allowance mailed Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action mailed Aug. 10, 2012", 7 pgs.
"U.S. Appl. No. 12/058,389, Response filed Feb. 6, 2009 to Restriction Requirement mailed Dec. 3, 2008", 7 pgs.
"U.S. Appl. No. 12/058,389, Response filed Apr. 10, 2012 to Non Final Office Action mailed Dec. 8, 2011", 7 pgs.
"U.S. Appl. No. 12/058,389, Response filed Jun. 16, 2010 to Final Office Action mailed Jan. 22, 2010", 6 pgs.
"U.S. Appl. No. 12/058,389, Response filed Oct. 13, 2009 to Non Final Office Action mailed Apr. 13, 2009", 9 pgs.
"U.S. Appl. No. 12/058,389, Response filed Dec. 18, 2012 to Non Final Office Action mailed Nov. 14, 2012", 7 pgs.
"U.S. Appl. No. 12/058,389, Restriction Requirement mailed Dec. 3, 2008", 7 pgs.
"U.S. Appl. No. 12/113,690, Final Office Action mailed Apr. 15, 2011", 10 pgs.
"U.S. Appl. No. 12/113,690, Non-Final Office Action mailed Nov. 10, 2010", 11 pgs.
"U.S. Appl. No. 12/113,690, Notice of Allowability mailed Aug. 19, 2013", 9 pgs.
"U.S. Appl. No. 12/113,690, Notice of Allowance mailed Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action mailed Apr. 15, 2011", 17 pgs.
"U.S. Appl. No. 12/113,690, Response filed Aug. 5, 2010 to Restriction Requirement mailed Apr. 6, 2010", 14 pgs.
"U.S. Appl. No. 12/113,690, Response filed Dec. 22, 2010 to Non Final Office Action mailed Nov. 10, 2010", 19 pgs.
"U.S. Appl. No. 12/113,690, Restriction Requirement mailed Apr. 6, 2010", 10 pgs.
"U.S. Appl. No. 12/139,183, Non Final Office Action mailed Jan. 6, 2011", 12 pgs.
"U.S. Appl. No. 12/139,183, Non-Final Office Action mailed Jan. 4, 2010", 6 pgs.
"U.S. Appl. No. 12/139,183, Non-Final Office Action mailed Jul. 13, 2010", 15 pgs.
"U.S. Appl. No. 12/139,183, Notice of Allowance mailed Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action mailed Jan. 6, 2011", 21 pgs.
"U.S. Appl. No. 12/139,183, Response filed Apr. 12, 2010 to Non Final Office Action mailed Jan. 4, 2010", 17 pgs.
"U.S. Appl. No. 12/139,183, Response filed Aug. 18, 2009 to Restriction Requirement mailed Jul. 24, 2009", 16 pgs.
"U.S. Appl. No. 12/139,183, Response filed Sep. 21, 2010 to Non Final Office Action mailed Jul. 13, 2010", 21 pgs.
"U.S. Appl. No. 12/139,183, Restriction Requirement mailed Jul. 24, 2009", 12 pgs.
"U.S. Appl. No. 12/245,296, Final Office Action mailed Jul. 11, 2013", 15 pgs.
"U.S. Appl. No. 12/245,296, Final Office Action mailed Dec. 17, 2010", 16 pgs.
"U.S. Appl. No. 12/245,296, Non Final Office Action mailed Mar. 25, 2013", 14 pgs.
"U.S. Appl. No. 12/245,296, Non-Final Office Action mailed Jun. 1, 2010", 13 pgs.
"U.S. Appl. No. 12/245,296, Notice of Allowance mailed Aug. 1, 2014", 10 pgs.
"U.S. Appl. No. 12/245,296, Preliminary Amendment mailed Jan. 28, 2009", 14 pgs.
"U.S. Appl. No. 12/245,296, Response filed Jan. 8, 2013 to Final Office Action mailed Jul. 11, 2013", 10 pgs.
"U.S. Appl. No. 12/245,296, Response filed Apr. 8, 2010 to Restriction Requirement mailed Mar. 9, 2010", 6 pgs.
"U.S. Appl. No. 12/245,296, Response filed May 17, 2011 to Final Office Action mailed Dec. 17, 2010". 10 pgs.
"U.S. Appl. No. 12/245,296, Response filed Jun. 7, 2013 to Non Final Office Action mailed Mar. 25, 2013", 9 pgs.
"U.S. Appl. No. 12/245,296, Response filed Oct. 1, 2010 to Non Final Office Action mailed Jun. 1, 2010", 12 pgs.
"U.S. Appl. No. 12/245,296, Restriction Requirement mailed Mar. 9, 2010", 6 pgs.
"U.S. Appl. No. 12/470,287 , Response filed Jan. 23, 2012 to Non Final Office Action mailed Jul. 22, 2011", 13 pgs.
"U.S. Appl. No. 12/470,287 , Response filed May 31, 2012 to Final Office Action mailed Apr. 3, 2012", 14 pgs.
"U.S. Appl. No. 12/470,287, Corrected Notice of Allowability mailed Sep. 11, 2012", 2 pgs.
"U.S. Appl. No. 12/470,287, Final Office Action mailed Apr. 3, 2012", 7 pgs.
"U.S. Appl. No. 12/470,287, Non Final Office Action mailed Jul. 22, 2011", 9 pgs.
"U.S. Appl. No. 12/470,287, Notice of Allowance mailed Jun. 19, 2012", 5 pgs.
"U.S. Appl. No. 12/470,287, Response filed Apr. 28, 2011 to Restriction Requirement mailed Dec. 29, 2010", 8 pgs.
"U.S. Appl. No. 12/470,287, Restriction Requirement mailed Dec. 29, 2010", 6 pgs.
"U.S. Appl. No. 12/854,578 , Response filed Oct. 1, 2012 to Non Final Office Action mailed Jun. 29, 2012", 10 pgs.
"U.S. Appl. No. 12/854,578, Final Office Action mailed Nov. 29, 2012", 8 pgs.
"U.S. Appl. No. 12/854,578, Non Final Office Action mailed Jun. 29, 2012", 8 pgs.
"U.S. Appl. No. 12/854,578, Notice of Allowance mailed Apr. 10, 2013", 6 pgs.
"U.S. Appl. No. 12/854,578, PTO Response to 312 Amendment mailed Jul. 18, 2013", 2 pgs.
"U.S. Appl. No. 12/854,578, Response filed Feb. 28, 2013 to Final Office Action mailed Nov. 29, 2012", 8 pgs.
"U.S. Appl. No. 12/854,578, Restriction Requirement mailed Apr. 6, 2012", 6 pgs.
"U.S. Appl. No. 13/113,244, Final Office Action mailed Feb. 27, 2014", 8 pgs.
"U.S. Appl. No. 13/113,244, Non Final Office Action mailed Jul. 5, 2013", 6 pgs.
"U.S. Appl. No. 13/113,244, Non Final Office Action mailed Oct. 1, 2012", 7 pgs.
"U.S. Appl. No. 13/113,244, Notice of Allowance mailed Jun. 30, 2014", 9 pgs.

(56) References Cited

OTHER PUBLICATIONS

"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement mailed Oct. 31, 2011", 10 pgs.
"U.S. Appl. No. 13/113,244, Response filed Feb. 20, 2013 to Non Final Office Action mailed Oct. 1, 2012", 12 pgs.
"U.S. Appl. No. 13/113,244, Response filed Jun. 13, 2014 to Final Office Action mailed Feb. 27, 2014", 6 pgs.
"U.S. Appl. No. 13/113,244, Response filed Oct. 31, 2013 to Non Final Office Action mailed Jul. 5, 2013", 12 pgs.
"U.S. Appl. No. 13/113,244, Restriction Requirement mailed Oct. 31, 2011", 8 pgs.
"U.S. Appl. No. 13/127,951, Advisory Action mailed Jul. 16, 2014", 3 pgs.
"U.S. Appl. No. 13/127,951, Final Office Action mailed Apr. 9, 2014", 23 pgs.
"U.S. Appl. No. 13/127,951, Non Final Office Action mailed Sep. 26, 2013", 18 pgs.
"U.S. Appl. No. 13/127,951, Notice of Allowance mailed Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication mailed Oct. 23, 2015", 2 pgs.
"U.S. Appl. No. 13/127,951, Response filed Mar. 18, 2014 to Non Final Office Action mailed Sep. 26, 2013", 14 pgs.
"U.S. Appl. No. 13/127,951, Response filed Jul. 7, 2014 to Final Office Action mailed Apr. 9, 2014", 10 pgs.
"U.S. Appl. No. 13/127,951, Response filed Aug. 30, 2013 to Restriction Requirement mailed Apr. 30, 2013", Aug. 30, 2013.
"U.S. Appl. No. 13/127,951, Response filed Oct. 9, 2014 to Advisory Action mailed Jul. 16, 2014", 10 pgs.
"U.S. Appl. No. 13/127,951, Restriction Requirement mailed Apr. 30, 2013", 15 pgs.
"U.S. Appl. No. 13/594,611, Final Office Action mailed Aug. 15, 2014", 7 pgs.
"U.S. Appl. No. 13/594,611, Non Final Office Action mailed Apr. 24, 2014", 9 pgs.
"U.S. Appl. No. 13/594,611, Notice of Allowance mailed Jan. 13, 2015", 7 pgs.
"U.S. Appl. No. 13/594,611, PTO Response to Rule 312 Communication mailed Apr. 16, 2015", 2 pgs.
"U.S. Appl. No. 13/594,611, Response filed Feb. 25, 2014 to Restriction Requirement mailed Jan. 27, 2014", 8 pgs.
"U.S. Appl. No. 13/594,611, Response filed Jul. 7, 2014 to Non Final Office Action mailed Apr. 24, 2014", 9 pgs.
"U.S. Appl. No. 13/594,611, Response filed Dec. 15, 2014 to Final Office Action mailed Aug. 15, 2014", 10 pgs.
"U.S. Appl. No. 13/594,611, Restriction Requirement mailed Jan. 27, 2014", 8 pgs.
"U.S. Appl. No. 14/528,997, Advisory Action mailed Aug. 9, 2017", 3 pgs.
"U.S. Appl. No. 14/528,997, Final Office Action mailed Feb. 10, 2017", 9 pgs.
"U.S. Appl. No. 14/528,997, Non Final Office Action mailed Jun. 16, 2016", 12 pgs.
"U.S. Appl. No. 14/528,997, Non Final Office Action mailed Jun. 29, 2018", 7 pgs.
"U.S. Appl. No. 14/528,997, Notice of Allowance mailed Mar. 8, 2019", 7 pgs.
"U.S. Appl. No. 14/528,997, PTO Response to Rule 312 Communication mailed Jun. 19, 2019", 2 pgs.
"U.S. Appl. No. 14/528,997, Response filed Mar. 16, 2016 to Restriction Requirement mailed Sep. 16, 2015", 11 pgs.
"U.S. Appl. No. 14/528,997, Response filed Jul. 27, 2017 to Final Office Action mailed Feb. 10, 2017", 11 pgs.
"U.S. Appl. No. 14/528,997, Response filed Oct. 10, 2016 to Non Final Office Action mailed Jun. 16, 2016", 12 pgs.
"U.S. Appl. No. 14/528,997, Response filed Nov. 16, 2018 to Non Final Office Action mailed Jun. 29, 2018", 11 pgs.
"U.S. Appl. No. 14/528,997, Restriction Requirement mailed Sep. 16, 2015", 6 pgs.
"U.S. Appl. No. 14/699,213, Advisory Action mailed Mar. 7, 2018", 3 pgs.
"U.S. Appl. No. 14/699,213, Final Office Action mailed Dec. 1, 2017", 11 pgs.
"U.S. Appl. No. 14/699,213, Non Final Office Action mailed Jun. 2, 2017", 12 pgs.
"U.S. Appl. No. 14/699,213, Non-Final Office Action mailed Jan. 11, 2019", 10 pgs.
"U.S. Appl. No. 14/699,213, Notice of Allowance mailed Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication mailed Nov. 19, 2019", 2 pgs.
"U.S. Appl. No. 14/699,213, Response filed Feb. 15, 2017 to Restriction Requirement mailed Aug. 15, 2016", 9 pgs.
"U.S. Appl. No. 14/699,213, Response filed Feb. 27, 2018 to Final Office Action mailed Dec. 1, 2017", 34 pgs.
"U.S. Appl. No. 14/699,213, Response filed Aug. 22, 2017 to Non Final Office Action mailed Jun. 2, 2017", 12 pgs.
"U.S. Appl. No. 14/699,213, Response filed Apr. 11, 2019 to Non-Final Office Action mailed Jan. 11, 2019", 13 pgs.
"U.S. Appl. No. 14/699,213, Restriction Requirement mailed Aug. 15, 2016", 10 pgs.
"U.S. Appl. No. 14/919,431, Preliminary Amendment filed Jan. 4, 2016", 8 pgs.
"U.S. Appl. No. 15/204,381, Advisory Action mailed Feb. 7, 2019", 3 pgs.
"U.S. Appl. No. 15/204,381, Advisory Action mailed Aug. 25, 2020", 3 pgs.
"U.S. Appl. No. 15/204,381, Final Office Action mailed Feb. 27, 2020", 21 pgs.
"U.S. Appl. No. 15/204,381, Final Office Action mailed Jul. 9, 2021", 14 pgs.
"U.S. Appl. No. 15/204,381, Final Office Action mailed Sep. 21, 2018", 10 pgs.
"U.S. Appl. No. 15/204,381, Non Final Office Action mailed Feb. 23, 2018", 10 pgs.
"U.S. Appl. No. 15/204,381, Non Final Office Action mailed Jun. 13, 2019", 23 pgs.
"U.S. Appl. No. 15/204,381, Non Final Office Action mailed Oct. 6, 2020", 15 pgs.
"U.S. Appl. No. 15/204,381, Preliminary Amendment filed Oct. 25, 2016", 74 pgs.
"U.S. Appl. No. 15/204,381, Response filed Jan. 2, 2019 to Final Office Action mailed Sep. 21, 2018", 6 pgs.
"U.S. Appl. No. 15/204,381, Response filed Jan. 19, 2018 to Restriction Requirement mailed Oct. 13, 2017", 6 pgs.
"U.S. Appl. No. 15/204,381, Response filed Apr. 6, 2021 to Non Final Office Action mailed Oct. 6, 2020", 12 pgs.
"U.S. Appl. No. 15/204,381, Response filed May 30, 2018 to Non Final Office Action mailed Feb. 23, 2018", 9 pgs.
"U.S. Appl. No. 15/204,381, Response filed Jul. 27, 2020 to Final Office Action mailed Feb. 27, 2020", 11 pgs.
"U.S. Appl. No. 15/204,381, Response filed Aug. 27, 2020 to Advisory Action mailed Aug. 25, 2020", 2 pgs.
"U.S. Appl. No. 15/204,381, Response Filed Nov. 14, 2019 to Non Final Office Action mailed Jun. 13, 2019", 9 pgs.
"U.S. Appl. No. 15/204,381, Response Filed Mar. 21, 2019 to Advisory Action mailed Feb. 7, 2019", 7 pgs.
"U.S. Appl. No. 15/204,381, Restriction Requirement mailed Oct. 13, 2017", 10 pgs.
"U.S. Appl. No. 15/227,147, Preliminary Amendment filed Oct. 10, 2016", 7 pgs.
"U.S. Appl. No. 15/227,147, Restriction Requirement mailed Jan. 19, 2017", 14 pgs.
"U.S. Appl. No. 15/247,006 Response filed Jun. 4, 2019 to Final Office Action mailed Feb. 4, 2019", 7 pgs.

(56) References Cited

OTHER PUBLICATIONS

"U.S. Appl. No. 15/247,006, Examiner Interview Summary mailed Nov. 27, 2017", 4 pgs.
"U.S. Appl. No. 15/247,006, Final Office Action mailed Feb. 4, 2019", 8 pgs.
"U.S. Appl. No. 15/247,006, Non Final Office Action mailed Apr. 20, 2018", 7 pgs.
"U.S. Appl. No. 15/247,006, Non Final Office Action mailed Sep. 8, 2017", 8 pgs.
"U.S. Appl. No. 15/247,006, Notice of Allowance mailed Jun. 24, 2019", 7 pgs.
"U.S. Appl. No. 15/247,006, Notice of Allowance mailed Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement mailed Mar. 17, 2017", 12 pgs.
"U.S. Appl. No. 15/247,006, Response filed Oct. 22, 2018 to Non Final Office Action mailed Apr. 20, 2018", 14 pgs.
"U.S. Appl. No. 15/247,006, Response filed Dec. 7, 2017 to Non Final Office Action mailed Sep. 8, 2017", 13 pgs.
"U.S. Appl. No. 15/247,006, Restriction Requirement mailed Mar. 17, 2017", 9 pgs.
"U.S. Appl. No. 15/915,486 Supplemental Preliminary Amendment Filed Mar. 12, 2019", 5 pgs.
"U.S. Appl. No. 15/915,486, Advisory Action mailed Jun. 28, 2021", 7 pgs.
"U.S. Appl. No. 15/915,486, Advisory Action mailed Jul. 13, 2020", 3 pgs.
"U.S. Appl. No. 15/915,486, Final Office Action mailed Jan. 11, 2022", 9 pgs.
"U.S. Appl. No. 15/915,486, Final Office Action mailed Jan. 27, 2020", 8 pgs.
"U.S. Appl. No. 15/915,486, Final Office Action mailed Feb. 1, 2021", 8 pgs.
"U.S. Appl. No. 15/915,486, Non Final Office Action mailed Sep. 2, 2021", 8 pgs.
"U.S. Appl. No. 15/915,486, Non Final Office Action mailed Sep. 15, 2020", 10 pgs.
"U.S. Appl. No. 15/915,486, Non Final Office Action mailed Oct. 24, 2019", 10 pgs.
"U.S. Appl. No. 15/915,486, Response filed Jan. 3, 2020 to Non Final Office Action mailed Oct. 24, 2019", 8 pgs.
"U.S. Appl. No. 15/915,486, Response filed Jun. 1, 2021 to Final Office Action mailed Feb. 1, 2021", 10 pgs.
"U.S. Appl. No. 15/915,486, Response filed Jun. 23, 2020 to Final Office Action mailed Jan. 27, 2020", 7 pgs.
"U.S. Appl. No. 15/915,486, Response filed Jul. 27, 2021 to Advisory Action mailed Jun. 28, 2021", 10 pgs.
"U.S. Appl. No. 15/915,486, Response filed Nov. 30, 2021 to Non Final Office Action mailed Sep. 2, 2021", 6 pgs.
"U.S. Appl. No. 15/915,486, Response filed Dec. 21, 2020 to Non Final Office Action mailed Sep. 15, 2020", 7 pgs.
"U.S. Appl. No. 15/915,486, Restriction Requirement mailed Aug. 5, 2019", 9 pgs.
"U.S. Appl. No. 16/170,321, Advisory Action mailed Feb. 23, 2021", 3 pgs.
"U.S. Appl. No. 16/170,321, Corrected Notice of Allowability mailed Sep. 29, 2021", 2 pgs.
"U.S. Appl. No. 16/170,321, Final Office Action mailed Dec. 14, 2020", 13 pgs.
"U.S. Appl. No. 16/170,321, Non Final Office Action mailed Apr. 13, 2020", 13 pgs.
"U.S. Appl. No. 16/170,321, Notice of Allowance mailed Aug. 4, 2021", 10 pgs.
"U.S. Appl. No. 16/170,321, PTO Response to Rule 312 Communication mailed Sep. 1, 2021", 2 pgs.
"U.S. Appl. No. 16/170,321, Response filed Jan. 24, 2020 to Restriction Requirement mailed Nov. 27, 2019", 9 pgs.
"U.S. Appl. No. 16/170,321, Response filed Jan. 26, 2021 to Final Office Action mailed Dec. 14, 2020", 9 pgs.
"U.S. Appl. No. 16/170,321, Response filed Mar. 9, 2021 to Advisory Action mailed Feb. 23, 2021", 9 pgs.
"U.S. Appl. No. 16/170,321, Response filed Sep. 11, 2020 to Non Final Office Action mailed Apr. 13, 2020", 9 pgs.
"U.S. Appl. No. 16/170,321, Restriction Requirement mailed Nov. 27, 2019", 10 pgs.
"U.S. Appl. No. 16/173,605 Preliminary Amendment Filed Nov. 18, 2019", 5 pgs.
"U.S. Appl. No. 16/173,605, Final Office Action mailed Jul. 27, 2020", 7 pgs.
"U.S. Appl. No. 16/173,605, Non Final Office Action mailed Mar. 13, 2020", 10 pgs.
"U.S. Appl. No. 16/173,605, Notice of Allowance mailed Jan. 13, 2021", 6 pgs.
"U.S. Appl. No. 16/173,605, Response filed Jul. 13, 2020 to Non Final Office Action mailed Mar. 13, 2020", 13 pgs.
"U.S. Appl. No. 16/173,605, Response filed Dec. 21, 2020 to Final Office Action mailed Jul. 27, 2020", 7 pgs.
"U.S. Appl. No. 16/545,761, Final Office Action mailed Oct. 20, 2021", 10 pgs.
"U.S. Appl. No. 16/545,761, Non Final Office Action mailed Feb. 11, 2021", 12 pgs.
"U.S. Appl. No. 16/545,761, Notice of Allowance mailed Mar. 9, 2022", 6 pgs.
"U.S. Appl. No. 16/545,761, Preliminary Amendment filed Feb. 7, 2020", 9 pgs.
"U.S. Appl. No. 16/545,761, PTO Response to Rule 312 Communication mailed May 13, 2022", 2 pgs.
"U.S. Appl. No. 16/545,761, Response filed Feb. 16, 2022 to Final Office Action mailed Oct. 20, 2021", 10 pgs.
"U.S. Appl. No. 16/545,761, Response filed Jun. 30, 2021 to Non Final Office Action mailed Feb. 11, 2021", 13 pgs.
"U.S. Appl. No. 16/547,262, Non Final Office Action mailed Mar. 31, 2021", 13 pgs.
"U.S. Appl. No. 16/547,262, Notice of Allowance mailed Jul. 22, 2021", 7 pgs.
"U.S. Appl. No. 16/547,262, Response filed Jun. 30, 2021 to Non Final Office Action mailed Mar. 31, 2021", 12 pgs.
"U.S. Appl. No. 16/547,262, Response filed Dec. 17, 2020 to Restriction Requirement mailed Jul. 17, 2020", 12 pgs.
"U.S. Appl. No. 16/547,262, Restriction Requirement mailed Jul. 17, 2020", 6 pgs.
"U.S. Appl. No. 16/694,748, Non Final Office Action mailed Nov. 9, 2021", 6 pgs.
"U.S. Appl. No. 16/694,748, Notice of Allowance mailed Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action mailed Nov. 9, 2021", 7 pgs.
"U.S. Appl. No. 16/694,748, Response filed Jul. 27, 2021 to Restriction Requirement mailed Jan. 27, 2021", 8 pgs.
"U.S. Appl. No. 16/694,748, Restriction Requirement mailed Jan. 27, 2021", 9 pgs.
"U.S. Appl. No. 16/785,449, Final Office Action mailed Mar. 18, 2022", 12 pgs.
"U.S. Appl. No. 16/785,449, Non Final Office Action mailed Jul. 21, 2021", 9 pgs.
"U.S. Appl. No. 16/785,449, Non Final Office Action mailed Sep. 22, 2022", 13 pgs.
"U.S. Appl. No. 16/785,449, Response filed Jan. 20, 2023 to Non Final Office Action mailed Sep. 22, 2022", 8 pgs.
"U.S. Appl. No. 16/785,449, Response filed Jun. 27, 2022 to Final Office Action mailed Mar. 18, 2022", 7 pgs.
"U.S. Appl. No. 16/785,449, Response filed Jul. 2, 2021 to Restriction Requirement mailed Jun. 21, 2021", 6 pgs.
"U.S. Appl. No. 16/785,449, Response filed Dec. 17, 2021 to Non Final Office Action mailed Jul. 21, 2021", 8 pgs.
"U.S. Appl. No. 16/785,449, Restriction Requirement mailed Jun. 21, 2021", 8 pgs.

(56) References Cited

OTHER PUBLICATIONS

"U.S. Appl. No. 16/785,449, Final Office Action mailed Mar. 22, 2023", 16 pgs.
"U.S. Appl. No. 16/865,194, Notice of Allowance mailed Mar. 3, 2022", 9 pgs.
"U.S. Appl. No. 16/865,194, Response filed Dec. 20, 2021 to Restriction Requirement mailed Oct. 20, 2021", 11 pgs.
"U.S. Appl. No. 16/865,194, Restriction Requirement mailed Oct. 20, 2021", 7 pgs.
"U.S. Appl. No. 17/004,583, 312 Amendment filed Mar. 16, 2023", 7 pgs.
"U.S. Appl. No. 17/004,583, Advisory Action mailed Aug. 30, 2022", 2 pgs.
"U.S. Appl. No. 17/004,583, Final Office Action mailed Jun. 9, 2022", 6 pgs.
"U.S. Appl. No. 17/004,583, Non Final Office Action mailed Feb. 24, 2022", 5 pgs.
"U.S. Appl. No. 17/004,583, Non Final Office Action mailed Sep. 29, 2022", 8 pgs.
"U.S. Appl. No. 17/004,583, Notice of Allowability mailed Feb. 10, 2023", 4 pgs.
"U.S. Appl. No. 17/004,583, Notice of Allowance mailed Feb. 1, 2023", 10 pgs.
"U.S. Appl. No. 17/004,583, Preliminary Amendment filed Dec. 21, 2020", 6 pgs.
"U.S. Appl. No. 17/004,583, PTO Response to Rule 312 Communication mailed Feb. 23, 2023", 4 pgs.
"U.S. Appl. No. 17/004,583, PTO Response to Rule 312 Communication mailed Apr. 6, 2023", 3 pgs.
"U.S. Appl. No. 17/004,583, Response filed Jan. 31, 2022 to Restriction Requirement mailed Nov. 24, 2021", 7 pgs.
"U.S. Appl. No. 17/004,583, Response filed May 24, 2022 to Non Final Office Action mailed Feb. 24, 2022", 9 pgs.
"U.S. Appl. No. 17/004,583, Response filed Aug. 9, 2022 to Final Office Action mailed Jun. 9, 2022", 9 pgs.
"U.S. Appl. No. 17/004,583, Response filed Sep. 8, 2022 to Advisory Action mailed Aug. 30, 2022", 15 pgs.
"U.S. Appl. No. 17/004,583, Response filed Dec. 29, 2022 to Non Final Office Action mailed Sep. 29, 2022", 8 pgs.
"U.S. Appl. No. 17/004,583, Restriction Requirement mailed Nov. 24, 2021", 10 pgs.
"U.S. Appl. No. 17/004,583, Supplemental Amendment filed Mar. 28, 2023", 6 pgs.
"U.S. Appl. No. 17/155,625, Advisory Action mailed Jan. 20, 2023", 3 pgs.
"U.S. Appl. No. 17/155,625, Final Office Action mailed Sep. 28, 2022", 18 pgs.
"U.S. Appl. No. 17/155,625, Non Final Office Action mailed May 26, 2022", 10 pgs.
"U.S. Appl. No. 17/155,625, Notice of Allowance mailed Apr. 12, 2023", 11 pgs.
"U.S. Appl. No. 17/155,625, Response filed Feb. 28, 2023 to Advisory Action mailed Jan. 20, 2023", 8 pgs.
"U.S. Appl. No. 17/155,625, Response filed May 2, 2022 to Restriction Requirement mailed Mar. 3, 2022", 7 pgs.
"U.S. Appl. No. 17/155,625, Response filed Aug. 29, 2022 to Non Final Office Action mailed May 26, 2022", 8 pgs.
"U.S. Appl. No. 17/155,625, Response filed Dec. 28, 2022 to Final Office Action mailed Sep. 28, 2022", 8 pgs.
"U.S. Appl. No. 17/155,625, Restriction Requirement mailed Mar. 3, 2022", 9 pgs.
"U.S. Appl. No. 17/212,836, Non Final Office Action mailed Feb. 16, 2023", 12 pgs.
"U.S. Appl. No. 17/212,836, Response filed Oct. 19, 2022 to Restriction Requirement mailed Aug. 19, 2022", 6 pgs.
"U.S. Appl. No. 17/212,836, Restriction Requirement mailed Aug. 19, 2022", 7 pgs.
"U.S. Appl. No. 17/229,001, Preliminary Amendment filed Apr. 26, 2021", 7 pgs.
"U.S. Appl. No. 17/352,845, Non Final Office Action mailed Dec. 16, 2022", 15 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"U.S. Appl. No. 14/528,997, Preliminary Amendment filed Dec. 8, 2014", 3 pgs.
"U.S. Appl. No. 14/919,431, Restriction Requirement mailed Feb. 3, 2016", 18 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Australian Application Serial No. 2004274860, Office Action mailed May 21, 2008", 2 pgs.
"Australian Application Serial No. 2008203186, First Examiner Report mailed Jan. 28, 2011", 2 pgs.
"Australian Application Serial No. 2008203186, Office Action Received mailed Sep. 16, 2010", 1 page.
"Australian Application Serial No. 2008203186, Response filed Mar. 28, 2011 to First Examiner Report mailed Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2021201844, First Examination Report filed Sep. 29, 2022", 3 pgs.
"Australian Application Serial No. 2021201844, Voluntary Amendment filed Dec. 6, 2021", 17 pgs.
"Australian Application Serial No. 2021204721, First Examination Report mailed Mar. 16, 2023", 6 pgs.
"Australian Application Serial No. 2008203186, Subsequent Examiner Report mailed Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.
"Brazil Application Serial No. PI0307679-2, Office Action mailed May 16, 2017", 2 pgs.
"Brazil Application Serial No. PI0307679-2, Response filed Jul. 13, 2017 to Office Action mailed May 16, 2017", 9 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI0307679-2, Final Office Action mailed Jul. 7, 2020", w/o English Translation, 6 pgs.
"Brazilian Application Serial No. PI0307679-2, Office Action mailed May 13, 2019", (w/ English Translation), 17 pgs.
"Brazilian Application Serial No. PI0307679-2, Office Action mailed Oct. 3, 2019", (w/ English Translation), 6 pgs.
"Brazilian Application Serial No. PI0307679-2, Office Action mailed Dec. 20, 2016", 2 pgs.
"Brazilian Application Serial No. PI0307679-2, Response filed Feb. 1, 2017 to Office Action mailed Dec. 20, 2016", 6 pgs.
"Brazilian Application Serial No. PI0307679-2, Response filed Aug. 16, 2019 to Office Action mailed May 13, 2019", (w/ English Translation of Claims), 29 pgs.
"Brazilian Application Serial No. PI0307679-2, Response filed Dec. 11, 2019 to Office Action mailed Oct. 3, 2019", w/ English Claims, 59 pgs.
"Canadian Application Serial No. 11/509,249, Response filed May 16, 2011 to Office Acttion mailed Nov. 18, 2010", 15 pgs.
"Canadian Application Serial No. 2,406,180, Response mailed Jun. 10, 2011 to Office Action mailed Dec. 10, 2010", 10 pgs.
"Canadian Application Serial No. 2,492,097, Office Action mailed Jan. 10, 2012", 4 pgs.
"Canadian Application Serial No. 2,492,097, Office Action mailed Apr. 24, 2008", 3 pgs.
"Canadian Application Serial No. 2,492,097, Office Action mailed Jul. 31, 2009", 3 pgs.

(56) References Cited

OTHER PUBLICATIONS

"Canadian Application Serial No. 2,492,097, Response filed Jan. 29, 2010 to Office Action mailed Jul. 31, 2009", 13 pgs.
"Canadian Application Serial No. 2,492,097, Response filed May 2, 2012 to Office Action mailed Jan. 10, 2012", 12 pgs.
"Canadian Application Serial No. 2,492,097, Response filed Oct. 23, 2008 to Office Action mailed Apr. 24, 2008", 14 pgs.
"Canadian Application Serial No. 2,525,953, Non Final Office Action mailed Mar. 30, 2022", 4 pgs.
"Canadian Application Serial No. 2,525,953, Response filed Aug. 26, 2021 to Office Action mailed Apr. 28, 2021", 16 pgs.
"Canadian Application Serial No. 2,816,242, Office Action mailed Jun. 16, 2014", 3 pgs.
"Canadian Application Serial No. 2,816,242, Office Action mailed Jul. 12, 2017", 4 pgs.
"Canadian Application Serial No. 2,816,242, Office Action mailed Sep. 16, 2016", 4 pgs.
"Canadian Application Serial No. 2,816,242, Office Action mailed Oct. 5, 2015", 6 pgs.
"Canadian Application Serial No. 2,816,242, Response filed Jan. 3, 2018 to Office Action mailed Jul. 12, 2017", 13 pgs.
"Canadian Application Serial No. 2,816,242, Response filed Mar. 10, 2017 to Office Action mailed Sep. 16, 2016", 18 pgs.
"Canadian Application Serial No. 2,816,242, Response filed Apr. 5, 2016 to Office Action mailed Oct. 5, 2015", 13 pgs.
"Canadian Application Serial No. 2,816,242, Response filed Dec. 16, 2014 to Office Action mailed Jun. 16, 2014", 9 pgs.
"Canadian Application Serial No. 2492097, Office Action mailed Nov. 18, 2010", 4 pgs.
"Chinese Application Serial No. 202080048487.4, Voluntary Amendment filed Dec. 5, 2022", w/ English Claims, 33 pgs.
"Chinese Application Serial No. 03808356.6, Office Action mailed Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Reexamination Notice mailed Nov. 26, 2012", (w/ English Translation), 9 pgs.
"Chinese Application Serial No. 03808356.6, Response filed Mar. 11, 2013 to Office Action mailed Nov. 26, 2012", (w/ English Translation of Amended Claims), 9 pgs.
"Chinese Application Serial No. 03808356.6, Response filed Mar. 16, 2009 to Office Action mailed Sep. 5, 2008", (w/ English Translation of Claims), 8 pgs.
"Chinese Application Serial No. 03808356.6, Response filed Oct. 14, 2011 to Office Action mailed Jul. 1, 2011", (w/ English Translation of Amended Claims), 25 pgs.
"Chinese Application Serial No. 200480022014, First Office Action mailed Aug. 24, 2007", w/English Translation, 6 pgs.
"Chinese Application Serial No. 200580046922.5, Office Action mailed Jul. 24, 2009", 12 pgs.
"Chinese Application Serial No. 201310400039.8, Notice of Reexamination mailed Aug. 26, 2016", (w/ English Translation), 7 pgs.
"Chinese Application Serial No. 201310400039.8, Office Action mailed Feb. 12, 2015", (w/ English Translation), 10 pgs.
"Chinese Application Serial No. 201310400039.8, Office Action mailed Feb. 15, 2016", (w/ English Translation), 12 pgs.
"Chinese Application Serial No. 201310400039.8, Office Action mailed Apr. 1, 2017", (English Translation), 10 pgs.
"Chinese Application Serial No. 201310400039.8, Office Action mailed Aug. 7, 2015", (w/ English Translation), 10 pgs.
"Chinese Application Serial No. 201310400039.8, Office Action mailed Aug. 21, 2014", (w/ English Translation), 13 pgs.
"Chinese Application Serial No. 201310400039.8, Office Action Response mailed Jun. 16, 2017", W / English Claims, 8 pgs.
"Chinese Application Serial No. 201310400039.8, Response filed Jan. 4, 2015 to Office Action mailed Aug. 21, 2014", (w/ English Translation of Claims), 10 pgs.
"Chinese Application Serial No. 201310400039.8, Response filed Apr. 27, 2015 to Office Action mailed Feb. 12, 2015", (w/ English Translation of Claims), 16 pgs.
"Chinese Application Serial No. 201310400039.8, Response filed Jun. 1, 2016 to Office Action mailed Feb. 15, 2016", (w/ English Translation of Claims), 9 pgs.
"Chinese Application Serial No. 201310400039.8, Response filed Oct. 10, 2016 to Notice of Reexamination mailed Aug. 26, 2016", (w/ English Translation of Claims), 12 pgs.
"Chinese Application Serial No. 201310400039.8, Response filed Oct. 20, 2015 to Office Action mailed Aug. 7, 2015", (w/ English Translation of Claims), 11 pgs.
"Chinese Application Serial No. 201310400039.8, Response filed Aug. 14, 2017 to Office Action Response mailed Jun. 16, 2017", W/ English Claims, 11 pgs.
"Chinese Application Serial No. 201310400039.8, Response filed Aug. 7, 2017 to Office Action Response mailed Jun. 16, 2017", W/ English Claims, 10 pgs.
"Chinese Application Serial No. 202080048487.4, Notification to Make Rectification mailed Jan. 18, 2022", w/o English Translation, 1 pg.
"Chinese Application Serial No. 202080048487.4, Notification to Make Rectification mailed May 26, 2022", w/o English translation, 1 pg.
"Confirmed Cases of Avian Influenza A(H5N1)", World Health Organization, (Jan. 28, 2004), 1 pg.
"Declaration of Anne Koch Ballard dated Oct. 6, 2011", 1 pg.
"Eurasian Application Serial No. 200701097,Office Action mailed Sep. 4, 2008", OAR-MISC, 2 pgs.
"Eurasion Application Serial No. 200701097, Office Action mailed Jun. 16, 2009", 3 pgs.
"European Application Serial No. 03716017.3, Office Action mailed Aug. 23, 2012", 4 pgs.
"European Application Serial No. 02724994.5, Office Action mailed Mar. 27, 2009", 2 pgs.
"European Application Serial No. 03716017.3, Communication and Supplementary European Search Report mailed Jan. 2, 2008", 8 pgs.
"European Application Serial No. 03716017.3, Communication mailed May 23, 2006", 3 pgs.
"European Application Serial No. 03716017.3, Communication mailed Jul. 26, 2006", 2 pgs.
"European Application Serial No. 03716017.3, Communication mailed Oct. 20, 2008", 7 pgs.
"European Application Serial No. 03716017.3, Further Written Submissions filed Mar. 19, 2015", 45 pgs.
"European Application Serial No. 03716017.3, Office Action mailed Jul. 27, 2010", 4 pgs.
"European Application Serial No. 03716017.3, Response filed Feb. 4, 2011 to Office Action mailed Jul. 27, 2010", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) mailed Aug. 23, 2012", 19 pgs.
"European Application Serial No. 03716017.3, Response filed Mar. 24, 2015 to Office Action mailed Nov. 3, 2014", 38 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"European Application Serial No. 03716017.3, Response filed Sep. 28, 2015", 13 pgs.
"European Application Serial No. 03716017.3, Result of Consultation mailed Mar. 17, 2015", 5 pgs.
"European Application Serial No. 03716017.3, Summons to Attend Oral proceedings mailed Nov. 3, 2014", 5 pgs.
"European Application Serial No. 04809419.7, Communication mailed Apr. 3, 2007", 3 pgs.
"European Application Serial No. 04809419.7, Response filed Oct. 19, 2007 to Communication mailed Apr. 3, 2007", 20 pgs.
"European Application Serial No. 12761841.1, Communication pursuant to Article 94(3) EPC mailed Dec. 23, 2016", 6 pgs.
"European Application Serial No. 12761841.1, Response filed Feb. 23, 2017 to Communication pursuant to Article 94(3) EPC mailed Dec. 23, 2016", 9 pgs.

(56) References Cited

OTHER PUBLICATIONS

"European Application Serial No. 12761841.1, Voluntary Amendment filed Dec. 1, 2014", 5 pgs.
"European Application Serial No. 14745060.5, Response filed Jan. 5, 2022 to Communication Pursuant to Article 94(3) EPC mailed Sep. 15, 2021", 78 pgs.
"European Application Serial No. 15197386.4, Communication Pursuant to Article 94(3) EPC mailed Feb. 21, 2018", 5 pgs.
"European Application Serial No. 15197386.4, Communication Pursuant to Article 94(3) EPC mailed Apr. 21, 2017", 5 pgs.
"European Application Serial No. 15197386.4, Communication Pursuant to Article 94(3) EPC mailed Jun. 19, 2019", 4 pgs.
"European Application Serial No. 15197386.4, extended European Search Report mailed Feb. 26, 2016", 11 pgs.
"European Application Serial No. 15197386.4, Response filed Jul. 3, 18 to Communication Pursuant to Article 94(3) EPC mailed Feb. 21, 2018", 7 pgs.
"European Application Serial No. 15197386.4, Response filed Aug. 27, 2019 to Communication Pursuant to Article 94(3) EPC mailed Jun. 19, 2019", 61 pgs.
"European Application Serial No. 15197386.4, Response filed Oct. 20, 2016 to Extended European Search Report mailed Feb. 26, 2016", 4 pgs.
"European Application Serial No. 15197386.4, Response filed Oct. 31, 2017 to Communication Pursuant to Article 94(3) EPC mailed Apr. 21, 2017", 5 pgs.
"European Application Serial No. 16778485.9, Communication Pursuant to Article 94(3) EPC mailed Feb. 18, 2022", 4 pgs.
"European Application Serial No. 16778485.9, Communication Pursuant to Article 94(3) EPC mailed May 25, 2020", 5 pgs.
"European Application Serial No. 16778485.9, Communication Pursuant to Article 94(3) EPC mailed Aug. 22, 2019", 5 pgs.
"European Application Serial No. 16778485.9, Office Action mailed Apr. 30, 2018", 3 pgs.
"European Application Serial No. 16778485.9, Response filed Aug. 9, 2022 to Communication Pursuant to Article 94(3) EPC mailed Feb. 18, 2022", 14 pgs.
"European Application Serial No. 16778485.9, Response filed Oct. 5, 2020 to Communication Pursuant to Article 94(3) EPC mailed May 25, 2020", 14 pgs.
"European Application Serial No. 16778485.9, Response filed Nov. 8, 2018 to Office Action mailed Apr. 30, 2018", 18 pgs.
"European Application Serial No. 16778485.9, Response filed Dec. 19, 2019 to Communication Pursuant to Article 94(3) EPC mailed Aug. 22, 2019", 20 pgs.
"European Application Serial No. 18800815.5, Response to Communication pursuant to Rules 161(1) and 162 EPC filed Dec. 15, 2020", 14 pgs.
"European Application Serial No. 19778696.5, Response to Communication persuant to Rules 161 and 162 filed Oct. 15, 2021", 39 pgs.
"European Application Serial No. 20714015.3, Response to Communication persuant to Rules 161 and 162 filed Apr. 7, 2022", 10 pgs.
"European Application Serial No. 20731609.2, Response to Communication persuant to Rules 161 and 162 filed Mar. 16, 2022", 17 pgs.
"European Application Serial No. 20768781.5, Response to Communication pursuant to Rules 161 and 162 filed Oct. 17, 2022", 17 pgs.
"Gen Bank Accessions QHU79173", surface glycoprotein [Severe acute respiratory syndrome coronavirus 2], (Mar. 17, 2020), 3 pgs.
"Genbank", CY002484.1, (2005), 2 pgs.
"Genbank Accession # AAA43733, Neuraminidase Protein of Influenza B/Beijing/1/87 virus," (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam. [online]. [retrieved on Dec. 5, 2004]. Retrieved from the Internet: <URL: http://www.abcam.com/index.html?datasheet=6556>, (2004), 5 pgs.
"https://www.abcam.com/gfp-antibody-ab6556", [online]. [accessed on Dec. 5, 2004], Retrieved from the Internet: http://www.abcam.com/index.html?datasheet=6556, Dec. 5, 2004), 5 pgs.
"Indian Application Serial No. 2388/KOLNP/2005, First Examination Report mailed Mar. 28, 2007", 10 pgs.
"Influenza virus A/CHR/ 157/83 genomic RNA for haemagglutinin", (2012), 2 pgs.
"International Application Serial No. PCT/US2021/033365, International Search Report mailed Sep. 24, 2021", 6 pgs.
"International Application Serial No. PCT/US2021/033365, Written Opinion mailed Sep. 24, 2021", 6 pgs.
"International Application Serial No. PCT/US02/05455, International Preliminary Examination Report dated Aug. 17, 2004", 4 pgs.
"International Application Serial No. PCT/US02/05455, International Search Report mailed Mar. 25, 2003", 3 pgs.
"International Application Serial No. PCT/US03/04233, International Search Report mailed Dec. 16, 2005", 7 pgs.
"International Application Serial No. PCT/US2004/016649, International Preliminary Report on Patentability mailed Dec. 15, 2005", 7 pgs.
"International Application Serial No. PCT/US2004/016649, International Search Report mailed Apr. 18, 2005", 6 pgs.
"International Application Serial No. PCT/US2005/041991, International Search Report mailed Jun. 4, 2007", 5 pgs.
"International Application Serial No. PCT/US2005/041991, Written Opinion mailed Jun. 4, 2007", 6 pgs.
"International Application Serial No. PCT/US2007/013407, International Search Report mailed Oct. 24, 2008", 10 pgs.
"International Application Serial No. PCT/US2007/013407, Written Opinion mailed Oct. 24, 2008", 14 pgs.
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"International Application Serial No. PCT/US2008/005641, International Preliminary Report on Patentability dated Nov. 10, 2009", 9 pgs.
"International Application Serial No. PCT/US2008/005641, International Search Report mailed Feb. 4, 2009", 6 pgs.
"International Application Serial No. PCT/US2008/005641, Written Opinion mailed Feb. 4, 2009", 8 pgs.
"International Application Serial No. PCT/US2008/007417, International Search Report mailed Jan. 30, 2009", 20 pgs.
"International Application Serial No. PCT/US2008/007417, Written Opinion mailed Jan. 30, 2009", 10 pgs.
"International Application Serial No. PCT/US2009/000056, International Search Report mailed Feb. 9, 2010", 3 pgs.
"International Application Serial No. PCT/US2009/000056, Written Opinion mailed Feb. 9, 2010", 5 pgs.
"International Application Serial No. PCT/US2009/006019, International Preliminary Report on Patentability mailed May 19, 2011", 8 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 7 Pgs.
"International Application Serial No. PCT/US2009/006019, Written Opinion mailed Jun. 10, 2010", 6 pgs.
"International Application Serial No. PCT/US2012/052368, International Preliminary Report on Patentability mailed Mar. 13, 2014", 8 pgs.
"International Application Serial No. PCT/US2012/052368, International Search Report mailed Dec. 3, 2012", 4 pgs.
"International Application Serial No. PCT/US2012/052368, Written Opinion mailed Dec. 3, 2012", 6 pgs.
"International Application Serial No. PCT/US2016/048691, International Preliminary Report on Patentability mailed Mar. 15, 2018", 7 pgs.

(56) References Cited

OTHER PUBLICATIONS

"International Application Serial No. PCT/US2016/048691, International Search Report mailed Nov. 22, 2016", 7 pgs.
"International Application Serial No. PCT/US2016/048691, Written Opinion mailed Nov. 22, 2016", 6 pgs.
"International Application Serial No. PCT/US2018/057576, International Preliminary Report on Patentability mailed May 7, 2020", 12 pgs.
"International Application Serial No. PCT/US2018/057576, International Search Report mailed Mar. 25, 2019", 7 pgs.
"International Application Serial No. PCT/US2018/057576, Invitation to Pay Additional Fees and Partial Search Report mailed Jan. 31, 2019", 16 pgs.
"International Application Serial No. PCT/US2018/057576, Written Opinion mailed Mar. 25, 2019", 10 pgs.
"International Application Serial No. PCT/US2019/037084, International Preliminary Report on Patentability mailed Dec. 24, 2020", 12 pgs.
"International Application Serial No. PCT/US2019/037084, International Search Report mailed Nov. 14, 2019", 10 pgs.
"International Application Serial No. PCT/US2019/037084, Invitation to Pay Add'l Fees and Partial Search Report mailed Sep. 24, 2019", 10 pgs.
"International Application Serial No. PCT/US2019/037084, Written Opinion mailed Nov. 14, 2019", 10 pgs.
"International Application Serial No. PCT/US2019/045476, International Preliminary Report on Patentability mailed Feb. 18, 2021", 13 pgs.
"International Application Serial No. PCT/US2019/045476, International Search Report mailed Feb. 11, 2020", 8 pgs.
"International Application Serial No. PCT/US2019/045476, Invitation to Pay Additional Fees mailed Dec. 17, 2019", 14 pgs.
"International Application Serial No. PCT/US2019/045476, Written Opinion mailed Feb. 11, 2020", 13 pgs.
"International Application Serial No. PCT/US2019/047263, International Preliminary Report on Patentability mailed Mar. 4, 2021", 8 pgs.
"International Application Serial No. PCT/US2019/047263, International Search Report mailed Dec. 20, 2019", 5 pgs.
"International Application Serial No. PCT/US2019/047263, Written Opinion mailed Dec. 20, 2019", 6 pgs.
"International Application Serial No. PCT/US2020/017342, International Preliminary Report on Patentability mailed Aug. 19, 2021", 8 pgs.
"International Application Serial No. PCT/US2020/017342, International Search Report mailed Jun. 26, 2020", 6 pgs.
"International Application Serial No. PCT/US2020/017342, Written Opinion mailed Jun. 26, 2020", 6 pgs.
"International Application Serial No. PCT/US2020/031176, International Preliminary Report on Patentability mailed Nov. 11, 2021", 9 pgs.
"International Application Serial No. PCT/US2020/031176, International Search Report mailed Jul. 22, 2020", 6 pgs.
"International Application Serial No. PCT/US2020/031176, Written Opinion mailed Jul. 22, 2020", 7 pgs.
"International Application Serial No. PCT/US2020/048130, International Preliminary Report on Patentability mailed Mar. 10, 2022", 11 pgs.
"International Application Serial No. PCT/US2020/048130, International Search Report mailed Apr. 20, 2021", 9 pgs.
"International Application Serial No. PCT/US2020/048130, Invitation to Pay Additional Fees mailed Jan. 13, 2021", 7 pgs.
"International Application Serial No. PCT/US2020/048130, Written Opinion mailed Apr. 20, 2021", 9 pgs.
"International Application Serial No. PCT/US2021/014586, International Preliminary Report on Patentability mailed Aug. 4, 2022", 10 pgs.
"International Application Serial No. PCT/US2021/014586, International Search Report mailed May 20, 2021", 7 pgs.
"International Application Serial No. PCT/US2021/014586, Written Opinion mailed May 20, 2021", 8 pgs.
"International Application Serial No. PCT/US2021/024200, International Preliminary Report on Patentability mailed Oct. 6, 2022", 8 pgs.
"International Application Serial No. PCT/US2021/024200, International Search Report mailed Jul. 16, 2021", 6 pgs.
"International Application Serial No. PCT/US2021/024200, Written Opinion mailed Jul. 16, 2021", 6 pgs.
"International Application Serial No. PCT/US2021/033365, International Preliminary Report on Patentability mailed Dec. 8, 2022", 8 pgs.
"Israel Application Serial No. 163,546, Office Action mailed Nov. 12, 2009", w/English Translation, 1 pg.
"Israel Application Serial No. 163,546, Office Action mailed Dec. 26, 2007", w/English Translation, 1 pg.
"Israel Application Serial No. 163,546, Response filed May 9, 2008 to Office Action mailed Dec. 26, 2007", w/English Translation, 2 pgs.
"Israel Application Serial No. 163,546, Response filed Jun. 8, 2010 to Office Action mailed Nov. 12, 2009", w/English Claims, 3 pgs.
"Israel Application Serial No. 163,546, Response filed Aug. 16, 2009 to Substantive Examination Report mailed Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report mailed Jul. 28, 2008", w/English Claims, 13 pgs.
"Israel Application Serial No. 163546, Office Action mailed Jun. 8, 2010", w/English Translation, 2 pgs.
"Israel Application Serial No. 183026, Office Action mailed Feb. 9, 2009", w/English Translation, 2 pgs.
"Israeli Application Serial No. 163,546, First Examination Report mailed Jul. 28, 2008", (English Translation), 2 pgs.
"Israeli Application Serial No. 163,546, Substantive Examination Report mailed Feb. 23, 2009", w/English Translation, 3 pgs.
"Israeli Application Serial No. 211324, Office Action mailed Sep. 18, 2014", w/English Translation, 5 pgs.
"Israeli Application Serial No. 211324, Office Action mailed Oct. 18, 2015", w/English Translation, 4 pgs.
"Israeli Application Serial No. 211324, Response filed Feb. 16, 2016 to Office Action mailed Oct. 18, 2015", w/English Claims, 4 pgs.
"Israeli Application Serial No. 211324, Response filed Mar. 31, 2015 to Office Action mailed Sep. 8, 2014", w/English Translation, 21 pgs.
"Japanese Application Serial No. 2022-144599, Voluntary Amendment filed Nov. 9, 2022", w/ English Claims, 14 pgs.
"Japanese Application Serial No. 2022-544779, Voluntary Amendment filed Sep. 9, 2022", w/ English Claims, 8 pgs.
"Japanese Application Serial No. 2003-315106, Amended Claims filed Oct. 15, 2009 in Response to Office Action mailed Jun. 24, 2009", (English Translation), 6 pgs.
"Japanese Application Serial No. 2003-315106, Notice of Allowance mailed Jan. 5, 2010", (w/ English Translation), 5 pgs.
"Japanese Application Serial No. 2003-315106, Office Action mailed Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance mailed Nov. 30, 2009", w/out English Translation, 3 pgs.
"Japanese Application Serial No. 2003-568038, Office Action mailed May 15, 2009", (w/ English Translation), 7 pgs.
"Japanese Application Serial No. 2003-568038, Office Action mailed Jul. 10, 2008", (w/ English Translation), 11 pgs.
"Japanese Application Serial No. 2003-568038, Office Action mailed Jul. 21, 2005", w/out English Translation, 3 pgs.
"Japanese Application Serial No. 2003-568038, Request for Examination filed Aug. 19, 2005 in Response to Official Action mailed Jul. 21, 2005", (w/ Partial English Translation of Specification), 8 pgs.
"Japanese Application Serial No. 2003-568038, Response filed Sep. 14, 2009 to Office Action mailed May 15, 2009", (w/ English Translation of Amended Claims), 10 pgs.

(56) References Cited

OTHER PUBLICATIONS

"Japanese Application Serial No. 2003-568038, Response filed Dec. 10, 2008 to Office Action mailed Jul. 10, 2008", (w/ English Translation of Amended Claims), 15 pgs.
"Japanese Application Serial No. 2008-315106, Office Action mailed Jun. 24, 2009", (w/ English Translation), 10 pgs.
"Japanese Application Serial No. 2008-315106, Response filed Oct. 15, 2009 to Office Action mailed Jun. 24, 2009", w/English Translation, 103 pgs.
"Japanese Application Serial No. 2008-315106, Response filed Oct. 15, 2009 to Office Action mailed Jun. 24, 2009", (w/ English Translation of Amended Claims), 103 pgs.
"Japanese Application Serial No. 2008-315106, Response filed Dec. 3, 2009 to Office Action mailed Jun. 24, 2009", (w/ English Translation of Claims), 9 pgs.
"Japanese Application Serial No. 2009-238781, Office Action mailed Oct. 11, 2011", (w/ English Translation), 3 pgs.
"Japanese Application Serial No. 2014-527339, Examiners Decision of Final Refusal mailed Feb. 7, 2017", (w/ English Translation), 5 pgs.
"Japanese Application Serial No. 2014-527339, Office Action mailed May 31, 2016", (w/ English Translation), 10 pgs.
"Japanese Application Serial No. 2014-527339, Response filed Sep. 16, 2016 to Office Action mailed May 31, 2016", (w/ English Translation of Amended Claims), 33 pgs.
"Japanese Application Serial No. 2017-111526, Office Action mailed May 14, 2019", (w/ English Translation), 6 pgs.
"Japanese Application Serial No. 2017-111526, Office Action mailed Jun. 26, 2018", (w/ English Translation), 5 pgs.
"Japanese Application Serial No. 2017-111526, Response Filed Dec. 21, 2018 to Office Action mailed Jun. 26, 2018", (w/ English Translation of Amended Claims), 7 pgs.
"Japanese Application Serial No. 2018-510751, Examiners Decision of Final Refusal mailed Dec. 17, 2019", w/ English Translation, 10 pgs.
"Japanese Application Serial No. 2018-510751, Notification of Reasons for Refusal mailed Mar. 13, 2019", (w/ English Translation), 14 pgs.
"Japanese Application Serial No. 2018-510751, Response filed Apr. 17, 2020 to Examiners Decision of Final Refusal mailed Dec. 17, 2019", w/ English Claims, 7 pgs.
"Japanese Application Serial No. 2018-510751, Response filed Aug. 9, 2019 to Notification of Reasons for Refusal mailed Mar. 13, 2019", (w/ English Translation of Claims), 24 pgs.
"Japanese Application Serial No. 2019-171818, Preliminary Examination Report mailed May 10, 2022", (w/ English Translation), 2 pgs.
"Japanese Application Serial No. 2019-171818, Response filed Feb. 4, 2022 to Examiners Decision of Final Refusal mailed Oct. 5, 2021", (w/ English Translation of Claims), 21 pgs.
"Japanese Application Serial No. 2019-171818, Response filed Dec. 2, 2022 to Preliminary Examination Report mailed May 10, 2022", w/ English Claims, 44 pgs.
"Japanese Application Serial No. 2019-171818, Trial Brief filed Mar. 30, 2022", (w/ English (Translation), 14 pgs.
"Japanese Application Serial No. 2020-073952, Examiners Decision of Final Refusal mailed Aug. 4, 2022", w/ English translation, 3 pgs.
"Japanese Application Serial No. 2020-073952, Final Notification of Reasons for Refusal mailed Jan. 25, 2022", w/ English Translation, 11 pgs.
"Japanese Application Serial No. 2020-073952, Notification of Reasons for Refusal mailed May 20, 2021", w/o English Translation, 2 pgs.
"Japanese Application Serial No. 2020-073952, Response filed Apr. 20, 2022 to Final Notification of Reasons for Refusal mailed Jan. 25, 2022", w/ English Claims, 40 pgs.
"Japanese Application Serial No. 2020-073952, Response filed Sep. 9, 2021 to Notification of Reasons for Refusal mailed May 20, 2021", w/ English Claims, 27 pgs.
"Japanese Application Serial No. 2020-073952, Response filed Dec. 2, 2022 to Examiners Decision of Final Refusal mailed Aug. 4, 2022", w/ English Claims, 36 pgs.
"Japanese Application Serial No. 2020-182549, Preliminary Examination Report mailed Jan. 17, 2023", w/ English Translation, 3 pgs.
"Japanese Application Serial No. 2020-523276, Examiners Decision of Final Refusal mailed May 10, 2022", w/ English Translation, 13 pgs.
"Japanese Application Serial No. 2020-523276, Notification of Reasons for Refusal mailed Jul. 27, 2021", w/ English Translation, 12 pgs.
"Japanese Application Serial No. 2020-523276, Response filed Jan. 12, 2022 to Notification of Reasons for Refusal mailed Jul. 27, 2021", w/ English Claims, 27 pgs.
"Japanese Application Serial No. 2021-146743, Notification of Reasons for Rejection mailed Aug. 17, 2022", w/ English Translation, 3 pgs.
"Japanese Application Serial No. 2021-506434, Notification of Reasons for Refusal mailed May 10, 2022", w/ English translation, 10 pgs.
"Japanese Application Serial No. 2021-506434, Response filed Feb. 18, 2022 to Office Action mailed Dec. 21, 2021", 135 pgs.
"Japanese Application Serial No. 2021-506434, Response filed Nov. 7, 2022 to Notification of Reasons for Refusal mailed May 10, 2022", w/ English Claims, 13 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal mailed Dec. 13, 2022", w/ English Translation, 14 pgs.
"Korean Application Serial No. 10-2004-7012647, Office Action mailed Feb. 26, 2010", (w/ English Translation), 7 pgs.
"Korean Application Serial No. 10-2004-7012647, Response filed Jun. 10, 2010 to Office Action mailed Feb. 26, 2010", (w/ English Translation of Claims), 17 pgs.
"Korean Application Serial No. 10-2010-7011520, Office Action mailed Jul. 20, 2010", (w/ English Translation), 6 pgs.
"Korean Application Serial No. 10-2010-7011520, Response filed Oct. 20, 2010 to Office Action mailed Jul. 20, 2010", (w/ English Translation of Amended Claims), 30 pgs.
"Korean Application Serial No. 10-2010-7011520, Amended Claims filed May 24, 2011 in Response to Office Action malled Feb. 24, 2011", (English Translation of Amended Claims), 22 pgs.
"Korean Application Serial No. 10-2010-7011520, Office Action mailed Feb. 24, 2011", (w/ English Translation), 5 pgs.
"Mexican Application Serial No. PA/a/2004/007914, Office Action mailed Feb. 14, 2008", (w/ English Translation), 3 pgs.
"Mexican Application Serial No. PA/a/2004/007914, Office Action mailed Feb. 22, 2008", (English Translation), 3 pgs.
"Mexican Application Serial No. PA/a/2004/007914, Response filed Jun. 11, 2008 to Office Action mailed Feb. 22, 2008", (w/ English Translation of Claims), 68 pgs.
"Neuraminidase [Influenza A virus (A/Aichi/2/1968 (H3N2))]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"New Zealand Application Serial No. 543587, Examination Report mailed Mar. 1, 2007", 1 pg.
"New Zealand Application Serial No. 543587, Examination Report mailed Jul. 7, 2006", 2 pgs.
"New Zealand Application Serial No. 543587, Response filed Aug. 7, 2007 to Examination Reports mailed Jul. 7, 2006 and Mar. 1, 2007", 24 pgs.
"New Zealand Application Serial No. 543587, Second Examination Report mailed Feb. 25, 2008", 2 pgs.
"New Zealand Application Serial No. 555245, First Examination Report mailed Aug. 26, 2008", 12 pgs.
"New Zealand Application Serial No. 555245, Subsequent Examiner Report mailed Jul. 3, 2009", 1 pg.

(56) References Cited

OTHER PUBLICATIONS

"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structure of Small Viral RNA Segment", Database UniProt EBI / Accession No. NC_002023, (Jul. 10, 2008), 15 pgs.
"PCT Application Serial No. PCT/US2005/041991, International Preliminary Report on Patentability / Written Opinion mailed Jul. 19, 2007", 8 pgs.
"Polymerase PA [Influenza A virus (A/swine/Yangzhou/1/2008(H9N2))]", GenBank: ADK98493.1, [Online]. Retrieved from the Internet: <URL: https://www.ncbi.nlm.nih.gov/protein/ADK98493.1/>, 2 pgs.
"RNA World", http://faculty.uca.edu/~benw/biol4415/lecture10a/tsld003.htm, (Observed Feb. 25, 2003), 1 pg.
"Singapore Application Serial No. 200507467-9, Invitation to Respond to Written Opinion mailed Jun. 19, 2007", 5 pgs.
"ST3GAL6 Gene ID: 478535", ncbi, nlm, [Online]. Retrieved from the Internet: <URL: https://www.ncbi.nlm.nih.gov/gene/47853> Sep. 14, 2022, (Aug. 17, 2022), 14 pgs.
Abram, M. E, et al., "Nature, position, and frequency of mutations made in a single cycle of HIV-1 replication", J Virol., 84(19), (Oct. 2010), 9864-78.
Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.
Baron, M. D., et al., "Rescue of Rinderpest Virus from Cloned cDNA", Journal of Virology, 71(2), (1997), 1265-1271.
Bedford, M. T, et al., "FBP WW domains and the Abl SH3 domain bind to a specific class of proline-rich ligands", EMBO J., 16(9), (May 1, 1997), 2376-83.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bowie, et al., "Deciphering the Message in Protein Sequences: Tolerance to Amino Acid Substitutions", Science, 247, (Mar. 1990), 1306-1310.
Bradfute, S. B., "The Early Clinical Development of Ebola Virus Treatments", Exp. Opin. Invest. Drugs 26(1):, (2017), 5 pgs.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: A Safe Madin Darby Canine Kidney (MDCK) Cell Culture-Based Influenza Vaccine", Dev. Biol. Stand., 98, (1999), 93-100.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al., "Immunodominance of Antigenic Site B in the Hemagglutinin of the Current H3N2 In?uenza Virus in Humans and Mice", Journal of Virology, 92(20): e01100-18, (Oct. 2018), 1-13.
Brown, TA, "Studying DNA", Genomes—NCBI Bookshelf, Brown TA. Genomes. 2nd edition. Oxford: Wiley-Liss; 2002, (2002), 26 pgs.
Bruhl, P., et al., "Humoral and Cell-Mediated Immunity to Vero Cell-Derived Influenza Vaccine", Vaccine, 19, (2001), 1149-1158.
Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.
Bullido, R., et al., "Influenza A Virus NEP (NS2 protein) Downregulates RNA Synthesis of Model Template RNAs", Journal of Virology, 75(10), (May 2001), 4912-4917.
Bullido, R., et al., "Influenza A virus NEP(NS2 protein) downregulates RNA synthesis of model template RNAs", Journal of Virology, vol. 75 4912-4917, (May 2001), 6 pgs.
Burmeister, W. P., et al., "The 2.2 A resolution crystal structure of influenza B neuraminidase and its complex with sialic acid", The EMBO Journal, 11(1), (1992), 49-56.
Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.
Cardona, C. J., "Avian Influenza", http://www.vetmed.ucdavis.edu/vetex/INF-PO_AvianInfluenzaFS.html, ((Observed Feb. 22, 2003), 3 pgs.
Castrucci, M. R, et al., "Attenuation of Influenza A Virus by Insertion of a Foreign Epitope into the Neuraminidase", Journal of Virology, 66(8), (1992), 4647-4653.
Castrucci, M. R., et al., "Biologic Importance of Neuraminidase Stalk Length in Influenza A Virus", Journal of Virology, 67(2), (1993), 759-764.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.
Catchpole, A P, et al., "Alternative base pairs attenuate influenza A virus when introduced into the duplex region of the conserved viral RNA promoter of either the NS or the PA gene", Journal of General Virology, 84, (2003), 507-515.
Chang, M. W., et al., "Analysis of HIV Wild-Type and Mutant Structures via in Silico Docking against Diverse Ligand Libraries", J. Chem. Inf. Model., 47(3), (2007), 1258-1262.
Chiba, Shiho, et al., "Multivalent nanoparticle-based vaccines protect hamsters against SARS-CoV-2 after a single immunization", Communications Biology, 4: 597, (2021), 1-9.
Cho, Alice, et al., "Implications of Broadly Neutralizing Antibodies in the Development of a Universal Influenza Vaccine", Current Opinion In Virology, vol. 17 110-115, (Apr. 1, 2016), 6 pgs.
Chothia, Cyrus, et al., "Canonical Structures for the Hypervariable Regions of Immunoglobulins.", J Mol Biol., 196(4), (1987), 901-917.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.
Chung, C, et al., "Glycoengineering of Chinese Hamster Ovary Cells for Improving Biotherapeutics Efficacies", A dissertation submitted to Johns Hopkins University in conformity with the requirements for the degree of Doctor of Philosophy, Retrieved from the Internet: <https://jscholarship.library.jhu.edu/handle/177>, (2016), 137 pgs.
Claas, E C. J., et al., "Human Influenza A H5N1 Virus Related to a Highly Pathogenic Avian Influenza Virus", The Lancet, 351, (1998), 472-477.

(56) References Cited

OTHER PUBLICATIONS

Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).
Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.
Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.
Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.
Cunningham, Brian C, et al., "High-Resolution Epitope Mapping of hGH-Receptor Interactions by Alanine-Scanning Mutagenesis", Science 244:4908, (1989), 6 pgs.
Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.
Daddario-Dicaprio, K. M, et al., "Cross-protection against Marburg virus strains by using a live, attenuated recombinant vaccine", J Virol., 80(19), (Oct. 2006), 9659-66.
Del Guidice, G., et al., "What are the limits of adjuvanticity?", (Abstract), Vaccine, 20(Suppl 1), S38-S41, (2001), 1 pg.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dollenmaier, G., et al., "Membrane-Associated Respiratory Syncytial Virus F Protein Expressed From A Human Rhinovirus Type 14 Vector Is Immunogenic", Virology, 281(2), (Mar. 15, 2001), 216-230.
Du, Q., "Ribozyme Enzymology", http://academic.brooklyn.cuny.edu/chem/zhuang/QD/toppage1.htm, (Observed Feb. 25, 2003), 8 pgs.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, US, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dumoulin, Mireille, et al., "Single-domain antibody fragments with high conformational stability", Protein Science, 11, (2002), 500-515.
Durbin, A. P, et al., "Human Parainfluenza Virus Type 3 (PIV3) Expressing The Hemagglutinin Protein Of Measles Virus Provides A Potential Method For Immunization Against Measles Virus and PIV3 In Early Infancy", Journal of Virology, 74(15), (Aug. 2000), 6821-6831.
Dyall, J., et al., ""Identification of inhibitors of Ebola virus with a subgenomic replication system"", Antiviral Research, 70(1), 19th International Conference on Antiviral Research, San Juan, PR (May 7-11, 20006), (May 2006), p. A39.
Elliott, R. M., "Emerging Viruses: The Bunyaviridae", Molecular Medicine, 3(9), (1997), 572-577.
Enami, K., et al., "Influenza virus NS1 protein stimulates translation of the M1 protein", Journal of Virology, 68 1432-1437, (1994), 6 pgs.
Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation und Transkription von Marburgund Ebolavirus", [Online]. 2005, Philipps-Universitat Marburg, XP002563470, Retrieved from the Internet: <URL:http://deposit.ddb.de/cgi-bin/dokserv?>idn=977005607&dok_var=d1&dok_ext=pdf&filename=977005607 .pdf> [retrieved on Jan. 15, 2010], (2005), p. 70-p. 84.
Essere, Boris, et al., "Critical role of segment-specific packaging signals in genetic reassortment of influenza A viruses", Proc. Natl. Acad. Sci. USA, 110(40), (2013), E3840-E3848.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Viral RNA Segment", Cell, 28, (1982), 303-313.
Flandorfer, A., et al., "Chimeric Influenza A Viruses with a Functional Influenza B Virus Neuraminidase or Hemagglutinin", Journal of Virology, 77(17), (2003), 9116-9123.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Y, et al., "The packaging of influenza viral genome", Virus, 52 (1), Uirusu (Japanese Journal Name), (Jun. 2002), 203-206.
Gao, Qinshan, et al., "A Seven-Segmented Influenza A Virus Expressing the Influenza C Virus Glycoprotein HEF", Journal of Virology, 82(13), (Jul. 2008), 6419-6426.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Introduction of Foreign Sequences into the Genome of Influenza A Virus", Dev. Biol. Stand. vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", Virus Research, 37(1), (1995), 37-47.
Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garrett, L., "Deadly Ebola, Avian Influenza Re-Emerging", Newsday.com, (Feb. 20, 2003), 3 pgs.
Genbank, ABD36884.1, (2007), 2 pgs.
Gerdil, C., "The Annual Production Cycle for Influenza Vaccine", Vaccine, 21 1776-1779, (2003), 4 pgs.

(56) References Cited

OTHER PUBLICATIONS

Ghate, Anita A, et al., "Influenza Type B Neuraminidase Can Replace the Function of Type A Neuraminidase", Virology, 264 (2), (Nov. 1999), 265-277.
Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is The Major Driving Force in Virus Budding", Journal of Virology, 74 11538-11547, (Dec. 1, 2000), 10 pgs.
Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.
Green, R. F., et al., "Glycosylation Does Not Determine Segregation of Viral Envelope Proteins in the Plasma Membrane of Epithelial Cells", J. Cell Biol., 89(2), (1981), 230-239.
Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.
Groseth, A., et al., "RNA Polymerase I-Driven Minigenome System for Ebola Viruses", Journal of Virology, 79(7), (2005), 4425-4433.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.
Hagen, M., et al., "Recombinant Influenza Virus Polymerase: Requirement of both 5' and 3' Viral Ends for Endonuclease Activity", Journal of Virology, 68(3), (1994), 1509-1515.
Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.
Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.
Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.
Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.
Halstead, Scott B,, et al., "Dengue Antibody-Dependent Enhancement: Knowns and Unknowns", Microbiology Spectrum, 2(6), (2014), 1-18.
Harding, Alfred T, et al., "Rationally Designed Influenza Virus Vaccines That Are Antigenically Stable during Growth in Egg", MBIO, vol. 8, No. 3, eO0669-17, (Jul. 5, 2017), 1-16.
Harmsen, M. M., et al., "Properties, production, and applications of camelid single-domain antibody fragments", Appl Microbiol Biotechnol,77, (2007), 13-22.
Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.
Harvey, K. F, et al., "All three WW domains of murine Nedd4 are involved in the regulation of epithelial sodium channels by intracellular Na+.", J Biol Chem., 274(18), (Apr. 30, 1999), 12525-30.
Hatakeyama, S., et al., "Dissection and identification of regions required to form pseudoparticles by the interaction between the nucleocapsid (N) and membrane (M) proteins of SARS coronavirus", Virology, 380(1), (2008), 99-108.
Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.
Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.
Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.
He, X., et al., "Generation of SARS-CoV-2 reporter replicon for high-throughput antiviral screening and testing", Proc. Natl. Acad. Sci. USA, 118(15): e2025866118, (2021), 8 pgs.
Hiti, A. L., et al., "P03470—Neuraminidase", Entrez Protein Database, http://www.ncbi.nlm.nih.gov/entrez/viewer.fcgi?db=protein &val=84028231, (1982), 730-734.
Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>. (1982), 730-734 (8 pgs.).
Ho, Y., et al., "Assembly of human severe acute respiratory syndrome coronavirus-like particles", Biochem Biophys Res Commun, 318(4), (2004), 833-838.
Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.
Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.
Hoffman, E., et al., "Ambisense Approach for the Generation of Influenza A Virus: vRNA and mRNA Synthesis from One Template", Virology 267(2) 310-317, (Feb. 15, 2006), 8 pgs.
Honda, A., et al., "RNA Polymerase of Influenza Virus: Role of NP in RNA Chain Elongation", The Journal of Biochemistry, 104(6), (1988), 1021-1026.
Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Hossain, M. J., et al., "Establishment and Characterization of a Madin-Darby Canine Kidney Reporter Cell Line for Influenza A Virus Assays", J Clin Microbiol, 48(7), (2010), 2515-2523.
Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.
Huang, T. S, et al., "Determinaton of Influenza Virus Proteins Required for Genome Replication", Jounal of Virology, vol. 64 5669-5673, (1990), 5 pgs.
Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.
Huddleston, J. A., et al., "The Sequence of the Nucleoprotein Gene of Human Influenza A Virus, Strain A/NT/60/68", Nucleic Acids Research, 10(3), (1982), 1029-1038.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR .(Suppl 1), XP002574255 ISSN: 0022-1899 'abstract, (Feb. 1999), 240-247.
Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.

(56) References Cited

OTHER PUBLICATIONS

Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.
Huisman, W., et al., "Vaccine-induced enhancement of viral infections", Vaccine, 27(4), (2009), 505-512.
Hurt, A. C, et al., "Identification of a human influenza type B strain with reduced sensitivity to neuraminidase inhibitor drugs", Virus Research, vol. (103), (2004), 205-211.
Hutchinson, Edward C., et al., "Genome packaging in influenza A virus", Journal of General Virology, 91 (Pt 2), (2010), 313-328.
Hwang, Jung-Shan, et al., "Expression of Functional Influenza Virus RNA Polymerase in the Methylotrophic Yeast *Pichia pastoris*", Journal of Virology, 74(9), (2000), 4074-4084.
Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.
Jackson, et al., "Characterization of recombinant influenza B viruses with key neuraminidase inhibitor resistance mutations,", Journal of Antimicrobial Chemotherapy, Vol. (55), (2005), 162-169.
Jahrling, P. B., et al., "Ebola Hemorrhagic Fever: Evaluation of Passive Immunotherapy in Nonhuman Primates", J. Infect Dis. 196, (2007), 4 pgs.
Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Jin, H., et al., "Imparting temperature sensitivity and attenuation in ferrets to A/PuertoRico/8/34 influenza virus by transferring the genetic signature for temperature sensitivity from cold-adapted A/Ann Arbor/6/60", Journal of Virology, 78(2), (2004), 995-998.
Jin, H., et al., "Influenza virus hemagglutinin and neuraminidase cytoplasmic tails control particle shape", The EMBO Journal, 16(6), (1997), 1236-1247.
Jin, H., et al., "The influenza virus hemagglutinin cytoplasmic tail is not essential for virus assembly or infectivity", The EMBOL Journal, 13(22), (1994), 5504-5515.
Johnson, David A, et al., "TLR4 Agonists as Vaccine Adjuvants", Vaccine Adjuvants and Delivery Systems, (2007), 131-156.
Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.
Ju, X., et al., "A novel cell culture system modeling the SARS-CoV-2 life cycle", PloS Pathogens, 17(3): e1009439, (2021), 23 pgs.
Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.
Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.
Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/glrce/docs/2007/Kawaoka.pdf> [retrieved on Jan. 13, 2010] p. 10, under item C, -& Anonymous: "Index of GLRCE: documents from 2007" Great Lakes Regional Center of Excellence Index, [Online] 2007, XP002563469 Retrieved from the Internet: URL:http://www.rcebiodefense.org/glrce/docs/2007/> [retrieved on Jan. 14, 2010] -& Kawaoka Y.:, (2007), pp. 1-19.
Kawaoka, Y., "Prevention and Control of Ebola Virus Infection (Ongoing Research)", Great Lakes Regional Center of Excellence (GLRCE) Annual Meeting Schedule, (Abstract), [online] [retrieved on Jan. 14, 2010]. Retrieved from the Internet: <URL:http://www.rcebiodefense.org/glrce/annualmeeting/2007Agenda.pdf>, (Nov. 29, 2007), 4 pgs.
Keitel, W. A., et al., "Chapter 28—Live Cold-Adapted, Reassortant Influenza Vaccines (USA)", In: Textbook of Influenza, Nicholson, K. G., et al., Editors, Blackwell Science Ltd., (1998), 373-390.
Kijima, H., et al., "Therapeutic Application of Ribozymes", Pharmac. Ther., 68(2), (1995), 247-267.
Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.
Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.
Kistner, O., et al., "Development of a mammalian cell (Vero) derived candidate influenza virus vaccine", Vaccine, 16(9-10), (May-Jun. 1998), 960-8.
Kistner, O., et al., "Development of a Vero Cell-Derived Influenza Whole Virus Vaccine", Dev. Biol. Stand., 98, (1999), 101-110.
Kobayashi, H., et al., "A replication-incompetent influenza virus bearing the HN glycoprotein of human parainfluenza virus as a bivalent vaccine", Vaccine, 31(52), (2013), 6239-6246.
Kon, Theone C, et al., "Influenza Vaccine Manufacturing: Effect of Inactivation, Splitting and Site of Manufacturing. Comparison of Influenza Vaccine Production Processes", PLoS ONE, 11(3), e0150700, (Mar. 9, 2016), 19 pgs.
Konduru, K., et al., "Ebola virus glycoprotein Fc fusion protein confers protection against lethal challenge in vaccinated mice", Vaccine, 29(16), (Apr. 5, 2011), 2968-77.
Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.
Kopecky, S. A, et al., "Matrix protein and another viral component contribute to induction of apoptosis in cells infected with vesicular stomatitis virus", J Virol., 75(24), (Dec. 2001), Abstract Only.
Kovesdi, et al., "Adenoviral vectors for gene transfer", Current Opinion in Biotechnology, vol. 8, (1997), 583-589.
Kovesdi, I., et al., "Adenoviral Vectors for Gene Transfer", Current Opinion in Biotechnology, 8(5), (Oct. 1997), 583-589.
Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.
Kumar, P. K. R., et al., "Artificial Evolution and Natural Ribozymes", The FASEB Journal, 9, (1995), 1183-1195.
Kunik, Vered, et al., "Paratome: an online tool for systematic identification of antigen-binding regions in antibodies based on sequence or structure", Nucleic Acids Research, vol. 40, Issue W1, (2012), W521-W524.
Kuwahara, Tomoko, et al., "Characterization of cell-derived and egg-passaged influenza A/Saitama/103/2014 (H3N2) strain", The 65th Annual Meeting of the Japanese Society of Virology, (2017), 1 pg.
Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71(3), (2018), 234-238.
Latham, T, et al., "Formation of Wild-Type and Chimeric Influenza Virus-Like Particles following Simultaneous Expression of Only Four Structural Proteins", Journal of Virology 75 (13), (2001), 6154-6165.
Laxman, B., "Noninvasive Real-Time Imaging of Apoptosis", PNAS, 99(26), (2002), 16551-16555.
Le, T., "CaSpeR5, a family of *Drosophila* transgenesis and shuttle vectors with improved multiple cloning sites", Biotechniques, 42(2), (Feb. 2007), 164-166.
Leahy, M. B., et al., "An Endonuclease Switching Mechanism in the Virion RNA and cRNA Promoters of Thogoto Orthomyxovirus", Journal of Virology, 72(3), (1998), 2305-2309.

(56) References Cited

OTHER PUBLICATIONS

Leahy, M. B., et al., “In Vitro Polymerase Activity of Thogoto Virus: Evidence for a Unique Cap-Snatching Mechanism in a Tick-Borne Orthomyxovirus”, Journal of Virology, 71(11), (1997), 8347-8351.
Leahy, M. B., et al., “Striking Conformational Similarities between the Transcription Promoters of Thogoto and Influenza A Viruses: Evidence for Intrastrand Base Pairing in the 5' Promoter Arm”, Journal of Virology, 71(11), (1997), 8352-8356.
Leal, et al., “New challenges in therapeutic vaccines against HIV infection”, Expert Review of Vaccines, vol. 16, No. 6, (2017), 587-600.
Lee, D.-H., et al., “H9N2 avian influenza virus-like particle vaccine provides protective immunity and a strategy for the differentiation of infected from vaccinated animals”, Vaccine, vol. 29, (2011), 4003-4007.
Lee, Jeffrey E., et al., “Complex of a Protective Antibody with Its Ebola Virus GP Peptide Epitope: Unusual Features of a V?x Light Chain”, J. Mol. Biol., 375, (2007), 202-216.
Lefranc, Marie-Paule, et al., “IMGT unique numbering for immunoglobulin and T cell receptor variable domains and lg superfamily V-like domains”, Developmental & Comparative Immunology, 27, (2003), 55-77.
Lembo, A, et al., “Administration of a synthetic TLR4 agonist protects mice from pneumonic tularemia.”, J Immunol., 180(11), 7574-81.
Li, et al., “Selection of antigenically advanced variants of seasonal influenza viruses”, Nature Microbiology, 1 (6), (2016), 1-10.
Li, Feng, et al., “Generation of Replication-Competent Recombinant Influenza A Viruses Carrying a Reporter Gene Harbored in the Neuraminidase Segment”, Journal of Virology, 84(22), (Nov. 2010), 12075-12081.
Li, Junwei, et al., “Engineering Influenza Viral Vectors”, Bioengineered, vol. 4, No. 1, (Jan. 1, 2013), 9-14.
Li, S., et al., “Electroporation of Influenza Virus Ribonucleoprotein Complexes for Rescue of the Nucleoprotein and Matrix Genes”, Virus Research, 37(2), (1995), 153-161.
Li, S., et al., “Influenza A Virus Transfectants with Chimeric Hemagglutinins Containing Epitopes from Different Subtypes”, Journal of Virology, 66(1), (1992), 399-404.
Li, S., et al., “Recombinant Influenza A Virus Vaccines for the Pathogenic Human A/HongKong/97 (H5N1) Viruses”, J Infect Dis., 179(5), (1999), 1132-1138.
Li, Shengqiang, et al., “Influenza A Virus Transfectants with Chimeric Hemagglutinins containing Epitopes from different subtypes”, Journal of Virology 399-404, (1992), 6 pgs.
Li, Y, et al., “The I binding specificity of human VH4-34 (VH4-21) encoded antibodies is determined by both VH framework region 1 and complementarity determining region 3”, J. Mol. Biol. 256 577-589, (1996), 13 pgs.
Liu, C., et al., “Influenza type A virus neuraminidase does not play a role in viral entry, replication, assembly, or budding.”, Journal of Virology, 69(2), (1995), 1099-1106.
Liu, C., et al., “Selection and Characterization of a Neuraminidase-Minus Mutant of Influenza Virus and its Rescue by Cloned Neuraminidase Genes”, Virology, 194(1), (1993), 403-407.
Liu, Y., et al., “A live-attenuated SARS-CoV-2 vaccine candidate with accessory protein deletions”, bioRxiv [online]. [retrieved Jun. 10, 2022]. Retrieved from the Internet: <URL: https://www.biorxiv.org/content/10.1101/2022.02.14.480460v1.full.pdf>, (2022), 44 pgs.
Liu, Z, et al., “Fine mapping of the antigen-antibody interaction of scFv215 A recombinant antibody inhibiting RNA polymerase II from *Drosophila melanogaster*”, J. Mol. Recog. 12:103-111, (1999), 9 pgs.
Lobo, Ingrid A., “Predicting Vaccine Effectiveness Using Systems Biology”, Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.
Longnecker, R., et al., “WW- and SH3-domain interactions with Epstein-Barr virus LMP2A”, Exp Cell Res., 257(2), (Jun. 15, 2000), Abstract Only.
Lott, W. B., et al., “A Two-Metal Ion Mechanism Operates in the Hammerhead Ribozyme-Mediated Cleavage of an RNA Substrate”, Proc. Natl. Acad. Sci. USA, 95, (1998), 542-547.
Mansky, L. M, “Retrovirus mutation rates and their role in genetic variation”, J Gen Virol., 79 (Pt 6), (Jun. 1998), 1337-45.
Marsh, Glenn A., et al., “Specific Residues of the Influenza A Virus Hemagglutinin Viral RNA Are Important for Efficient Packaging into Budding Virions”, Journal of Virology, 81(18), (Sep. 2007), 9727-9736.
Martin, J., et al., “Studies of the Binding Properties of Influenza Hemagglutinin Receptor-Site Mutants”, Virology, 241 (1), (Feb. 1, 1998), 101-111.
Martinez-Sobrido, L., et al., “Hemagglutinin-Pseudotyped Green Fluorescent Protein-Expressing Influenza Viruses for the Detection of Influenza Virus Neutralizing Antibodies”, J Virol., 84(4), (2010), 2157-2163.
Martorelli Di, Genova B., et al., “Intestinal delta-6-desaturase activity determines host range for Toxoplasma sexual reproduction”, PLOS Biology, vol. 17, No. 8, E3000364, (Aug. 20, 2019), XP055619380, (Aug. 20, 2019), 1-19.
Masuda, H., et al., “Substitution of Amino Acid Residue in Influenza A Virus Hemagglutinin Affects Recognition of Sialyl-Oligosaccharides Containing N-Glycolylneuraminic Acid”, FEBS Letters, 464, (1999), 71-74.
Matrosovich, M, et al., “Overexpression of the [alpha]-2,6-sialyltransferase in MDCK cells increases influenza virus sensitivity to neuraminidase inhibitors”, Journal of Virology, the American Society for Microbiology, US, vol. 77, No. 15, (Aug. 1, 2003), 8418-8425.
Matta, M, et al., “Cell-surface sialoglycoconjugate structures in wild-type and mutant Crithidia fasciculata”, Parasitol. Res., 85(4), (1999), 293-299.
McCullers, et al., “Multiple Genotypes of Influenza B Virus Circulated between 1979 and 2003,”, Journal of Virology, vol. (78), No. (23) 12817-12828, (2004), 13 pgs.
McKee, Dwight L, et al., “Candidate drugs against SARS-CoV-2 and COVID-19”, Pharmacological Research, Academic Press, London, GB, vol. 157, (Apr. 29, 2020), 9 pgs.
McSharry, J. J, et al., “Phenotypic Drug Susceptibility Assay for Influenza Virus Neuraminidase Inhibitors”, Cinical and Diagnostic Laboratory Immunology Vol. (11), No.(2),. (2004), 10 pgs.
Mena, I., et al., “Synthesis of biologically active influenza virus core proteins using a vaccinia virus-T7 RNA polymerase expression system”, Journal of General Virology, 75 2109-2114, (1994), 6 pgs.
Mishin, V. P, et al., “Protection afforded by intranasal immunization with the neuraminidase-lacking mutant of influenza A virus in a ferret model”, Vaccine, 23(22), (Apr. 22, 2005), 2922-7.
Mitnaul, L. J., et al., “Balanced Hemagglutinin and Neuraminidase Activities are Critical for Efficient Replication of Influenza A Virus”, Journal of Virology, 74 (13), (2000), 6015-6020.
Mittler, E., et al., “Role of the transmembrane domain of marburg virus surface protein GP in assembly of the viral envelope.”, J Virol., 81(8), (Apr. 2007), 3942-8.
Miyoshi, H., et al., “Development of Self-Inactivating Lentivirus Vector”, Journal of Virology, 72(10), (1998), 8150-8157.
Monto, A. S, et al., “Detection of influenza viruses resistant to neuraminidase inhibitors in global surveillance during the first 3 years of their use”, Antimicrobal Agents and Chemotherapy, 50(7) 2395-2402, (2006), 8 pgs.
Morita, S., et al., “Plat-E: an efficient and stable system for transient packaging of retroviruses”, Gene Therapy, 7(12), (2000), 1063-1066.
Moss, B., et al., “New Mammalian Expression Vectors”, Nature, 348, (1990), 91-92.
Muhlberger, E., et al., “Comparision orf the Transcription and Replication Strategies of Marburg Virus and Ebola Virus by Using Artificial Replication Systems”, Journal of Virology, 73(3) 2333-2342, (1999), 10 pgs.
Muhlberger, E., et al., “Three of the four nucleocapsid proteins of Marburg virus,NP, VP35, and L, are sufficient to mediate replication

(56) References Cited

OTHER PUBLICATIONS and transcription of Marburg virus-specific monocistronic minigenomes", Journal of Virology, 72(11) 8756-8764, (1998), 11 pgs.
Muhlberger, Elke, "Filovirus replication and transcription", Future Virol., 2:205, (2007), 16 pgs.
Muramoto, Y., et al., "Hierarchy among Viral RNA (vRNA) Segments in Their Role in vRNA Incorporation into Influenza A Virions", J. Virol., 80(5), (2006), 2318-2325.
Muramoto, Yukiko, "Hierarchy among Viral RNA (vRNA) Segments in Their Role in vRNA Incorporation into Influenza A Virions", Journal of Virology, 80(5), (2006), 2318-2325.
Murphy, B. R, et al., "An influenza A live attenuated reassortant virus possessing three temperature-sensitive mutations in the PB2 polymerase gene rapidly loses temperature sensitivity following replication in hamsters", Vaccine,15(12-13) 1372-8, (1997), 7 pgs.
Muyldermans, S, "Nanobodies: Natural single-domain antibodies", Ann. Rev. Biochem. 82, (2013), 1 pg.
Naim, H. Y., et al., "Basis for Selective Incorporation of Glycoproteins into the Influenza Virus Envelope", Journal of Virology, 67(8), (1993), 4831-4841.
Nara, et al., "How Can Vaccines Against Influenza and Other Viral Diseases Be Made More Effective?", PLoS Biology, 8 (12), (2010), e1000571.
Neumann, G., et al., "A Decade After the Generation of a Negative-Sense RNA Virus From Cloned cDNA-What Have We Learned?", Journal of General Virology, 83(11), (Nov. 2002), 2635-2662.
Neumann, G., et al., "Genetic Engineering of Influenza and Other Negative-Strand RNA Viruses Containing Segmented Genomes", Advances in Virus Research, 53, (1999), 265-300.
Neumann, G., et al., "Influenza A virus NS2 protein mediates vRNP nuclear export through NES-independent interaction with hCRM1", The EMBO Journal, 19 (24), (2000), 6751-6758.
Neumann, G., et al., "Nuclear Import and Export of Influenza Virus Nucleoprotein", Journal of Virology, 71(12), (1997), 9690-9700.
Neumann, G., et al., "Reverse genetics of influenza virus.", Virology, 287(2), (Sep. 1, 2001), 243-50.
Neumann, G., et al., "Synthesis of Influenza Virus: New impetus from an old enzyme, RNA polymerase I", Virus Research 82(1-2), (Jan. 30, 2002), 153-158.
Neumann, Gabriele, "Minireview Reverse Genetics of Influenza Virus", Virology, vol. 287, (2001), 243-250.
Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.
Niwa, H., et al., "Efficient Selection for High-Expression Transfectants With a Novel Eukaryotic Factor", Gene, 108(2), (1991), 193-199.
Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.
Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.
Onishi, M., et al., "Applications of retrovirus-mediated expression cloning", Experimental Hematology, 24(2), (1996), 324-329.
Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.
Ozawa, M., et al., "An adenovirus vector-mediated reverse genetics system for Influenza A virus generation", Journal of Virology, The American society For Microbiology, US vol. 81 (17), XP002471230, ISSN: 0022-538X, (Jun. 27, 2007), 9556-9559.
Ozawa, M., et al., "Replication-incompetent influenza A viruses that stably express a foreign gene", Journal of General Virology, 92(Part 12)., (2011), 2879-2888.
Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.
Pattnaik, A. K., et al., "The Termini of VSV DI Particle RNAs are Sufficient to Signal RNA Encapsidation, Replication, and Budding to Generate Infectious Particles", Virology, 206, (1995), 760-764.
Peiris, J. S. M., et al., "Re-Emergence of Fatal Human Influenza A Subtype H5N1 Disease", The Lancet, 363 617-619, (2004), 3 pgs.
Pelet, T., et al., "High throughput screening assay for negative single stranded RNA virus polymerase inhibitors", Journal of Virological Methods, 128 29-36, (2005), 8 pgs.
Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.
Perez, D. R., et al., "The Matrix 1 Protein of Influenza A Virus Inhibits the Transcriptase Activity of a Model Influenza Reporter Genome in Vivo", Virology, 249(1), (1998), 52-61.
Peterson, B. C., et al., "Homologous sequences other than insertion elements can serve as recombination sites in plasmid drug resistance gene amplification", Journal of Bacteriology, Oct. 1983. 156(1) 177-185, (1983), 5 pgs.
Piatti, G., "Identification of immunodominant epitopes In the filamentous Hemagglutinin of Bordetella pertusis", FEMS Immunology and Medical Microbiology, 23(3), (1999), 235-241.
Pittman, Kelly J., et al., "Z-DNA Binding Protein Mediates Host Control of Toxoplasma gondii Infection", Infection and Immunity, 84(10), (Oct. 2016), 3063-3070.
Pley, H. W., et al., "Three-Dimensional Structure of a Hammerhead Ribozyme", Nature, 372, (1994), 68-74.
Popova, Lyubov, et al., "Immunodominance of Antigenic Site B over Site of Hemagglutinin of Recent H3N2 Influenza Viruses", PLOS ONE, vol. 7 No. 7, (Jul. 25, 2012), e41895.
Portela, A., et al., "Replication of orthomyxoviruses", Advances in Virus Research, 54, (1999), 319-348.
Potter, C. W., "Chapter 1—Chronicle of Influenza Pandemics", In: Textbook of Influenza, Nicoholson, K. G., et al., Editors, (Blackwell Scientific Publication), (1998), 3-18.
Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.
Preston, Andrew, "Choosing a Cloning Vector", Methods in Molecular Biology, vol. 235, *E. coli* Plasmid Vectors 19-27, Edited by: N. Casali and A. Preston, (2003), 9 pgs.
Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.
Puzelli, S., et al., "Changes in the Hemagglutinins and Neuraminidase of Human Influenza B Viruses Isolated in Italy During the Feb. 2001, Mar. 2002, and Apr. 2003 Seasons", Journal of Medical Virology, 74(4) 629-640, (2004), 12 pgs.
Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.
Rayner, J., et al., "Alphavirus vectors and vaccination", Reviews in Medical Virology, 12, (2002), 279-296.
Restifo, N. P., et al., "Transfectant Influenza A Viruses are Effective Recombinant Immunogens in the Treatment of Experimental Cancer", Virology, 249(1), (1998), 89-97.
Ricardo-Lax, I., et al., "Replication and single-cycle delivery of SARS-CoV-2 replicons", Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.

(56) References Cited

OTHER PUBLICATIONS

Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.
Saphire, E. O., et al., "Feverish Quest for Ebola Immunotherapy: Straight or Cocktail", Trends Microbial, 24(9), (Sep. 2016), 684-686.
Satterlee, B., "Production of H5N1 avian influenza virus vaccine by plasmid-based reverse genetics technology", Basic Biotechnology eJournal, vol. 4, pp. 93-98, (2008), 93-98 Pgs.
Saunders, Kevin O., et al., "Neutralizing antibody vaccine for pandemic and pre-emergent coronaviruses", Nature, 594, (2021), 553-559 (27 pgs.).
Schares, G., et al., "Oocysts of Neospora caninum, Hammondia heydorni, Toxoplasma gondii and Hammondia hammondi in faeces collected from dogs in Germany", International Journal of Parasitology, vol. 35, No. 14, (Dec. 1, 2005), XP027737007, (Dec. 1, 2005), 1525-1537.
Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.
Schultz-Cherry, S., et al., "Influenza Virus NS1 Protein Induces Apoptosis in Cultured Cells", Journal of Virology, 75(17), (2001), 7875-7881.
Sheridan, Cormac, et al., "Innovators target vaccines for variants and shortages in global South", Nature Biotechnology, 39(4), (Apr. 2021), 393-396.
Shi, Pei-Yong, "Infectious cDNA Clone of the Epidemic West Nile Virus from New York City", Journal of Virology 5847-5856, (Jun. 2002), 10 pgs.
Shimojima, M., et al., "Tyro3 family-mediated cell entry of Ebola and Marburg viruses", J Virol., 80(20), (Oct. 2006), 10109-16.
Shortridge, K. F., et al., "Characterization of Avian H5N1 Influenza Viruses From Poultry in Hong Kong", Virology, 252 331-342, (1998), 12 pgs.
Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.
Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.
Smatti, Maria K., et al., "Viral-Induced Enhanced Disease Illness", Front Microbiol, vol. 9: Article 2991, (Dec. 2018), 1-19.
Smura, T, "Surface glycoprotein [Severe acute respiratory syndrome coronavirus 2]", GenBank Accessions QH062107, (Feb. 11, 2020), 2 pgs.
Stray, S. J., et al., "Influenza virus infection of desialylated cells", Glycobiology, 10(7), (2000), 649-658.
Strobel, I., et al., "Efficient Expression Of The Tumor-Associated Antigen MAGE-3 In Human Dendritic Cells, Using An Avian Influenza Virus Vector", Human Gene Therapy, 11(16), (2000), 2207-2218.
Stroud, Chad K., et al., "Disruption of FADS2 gene in mice impairs male reproduction and causes dermal and intestinal ulceration", Journal of Lipid Research, vol. 50, (2009), 1870-1880.
Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.
Subbarao, K., et al., "Characterization of an Avian Influenza A (H5N1) Virus Isolated From a Child With a Fatal Respiratory Illness", Science, 279, (1998), 393-396.
Sugawara, K., et al., "Development of Vero Cell-Derived Inactivated Japanese Encephalities Vaccine", Biologicals, 30 303-314, (2002), 12 pgs.
Sun, Weina, et al., "Development of Influenza B Universal Vaccine Candidates Usingthe "Mosaic" Hemagglutinin Approach", American Society For Microbiology, Journal of Virology, Vaccines and Antiviral Agents, vol. 93, Issue 12, (Jun. 2019), 17 pgs.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Takada, A., et al., "Downregulation of beta1 integrins by Ebola virus glycoprotein: implication for virus entry", Virology, 278(1), (Dec. 2000), Abstract Only.
Takada, Ayato, et al., "A system for functional analysis of Ebola? virus?glycoprotein", Proc. Natl. Acad. Sci. USA, 94(26), (1997), 14764-14769.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Infectivity-Enhancing Antibodies to Ebola Virus Glycoprotein", Journal of Virology, 75(5), (2001), 2324-2330.
Takada, Ayato, et al., "Protective efficacy of neutralizing antibodies against Ebola virus infection", Vaccine, 25(6), (2007), 993-999.
Takada, Ayato, et al., "The pathogenesis of Ebola hemorrhagic fever", Trends in Microbiology, 9(10), (2001), 506-511.
Takada, Kosuke, et al., "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273.
Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.
Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.
Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.
Terry, G., et al., "The Contruction of Defective Interfering Rubella Virus Particles", Archives of Virology, 145(3), (2000), 625-633.
Tetsutani, K., et al., "Adjuvants in Influenza Vaccines", Vaccine 2012, vol. 30, (2012), 4 pgs.
Thao, Tran Thi Nhu, et al., "Rapid reconstruction of SARS-CoV-2 using a synthetic genomics platform", Nature, vol. 582 561-565, (2020), 24 pgs.
Theriault, S., "The role of reverse genetics systems in determining filovirus pathogenicity", Archives of Virology, Supplementum. 157-177, (2005), 22 pgs.
Thompson, Christine M, et al., "Critical assessment of influenza VLP production in Sf9 and HEK293 expression systems", BMC Biotechnology, 15(1), (May 16, 2015), 12 pgs.
Thompson, W. W., et al., "Mortality Associated With Influenza and Respiratory Syncytial Virus in the United States", JAMA, 289(2) 179-186, (2003), 8 pgs.
Towner, J S, et al., "Generation of eGFP express ing recombinant Zaire ebolavirus for analysis of early pathogenesis events and high-throughput antiviral drug screening", Virology, Academic Press ,Orlando, US , vol. 332, No. 1 20-27, XP004715289 ISSN: 0042-6822 the whole document, (Feb. 5, 2005), 8 pgs.
Treanor, J. J, et al., "The B allele of the NS gene of avian influenza viruses, but not the A allele, attenuates a human influenza a virus for squirrel monkeys", Virology, 171(1), (1989), 1-9.

(56) References Cited

OTHER PUBLICATIONS

Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.
Vaishnava, Shipra, et al., "The Antibacterial Lectin RegIlly Promotes the Spatial Segregation of Microbiota and Host in the Intestine", Science, 334 255-258, (2011), 4 pgs.
Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.nlm.nih.gov/pmc/articles/PMC7181998/pdf/main.pdf>, (Apr. 24, 2020), 17 pgs.
Varner, Chad, "Developing Synthetic Multivalent Cellular Effectors", Thesis, School of Chemical and Biomolecular Engineering, Georgia Institute of Technology, (Aug. 2017), 88 pgs.
Via, L. E, et al., "Isolation of restriction fragments from large plasmids recovered from bacteria with multiple plasmids", Biotechniques, 11(4), (Oct. 1991), Abstract Only.
Victor, Sylvia, et al., "A Replication-Incompetent PB2-Knockout Influenza A Virus Vaccine Vector", Journal of Virology, vol. 86, No. 8, (Apr. 2012), 4123-4128.
Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org:, Downloaded from http://jvi.asm.org/ on Aug. 20, 2012 by Univ. of Wisonsin—Mad, (Feb. 1, 2012), 7.
Vincke, C, et al., "Introduction to heavy chain antibodies and derived nanobodies", Meth. Mol. Biol. 911, (2012), 13 pgs.
Waap, Helga, et al., "In vitro isolation and seroprevalence ofin stray cats and pigeons in Lisbon, Portugal", Veterinary Parasitology, vol. 187, No. 3 XP028492469 542-547, (Jan. 17, 2012), 6 pgs.
Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.
Wan, Yushun, et al., "Molecular mechanism for Antibody-Dependent Enhancement of Coronavirus EntrM", Journal of Virology, 94(5): e02015-19, (2019), 1-15.
Wang, et al., "Glycoengineering of CHO Cells to Improve Product Quality", Methods in Molecular Biology book series (MIMB, vol. 1603) 25-44, (May 11, 2017), 256 pgs.
Wang, B., et al., "Construction of Non-infectious SARS-CoV-2 Replicons and Their Application in Drug Evaluation", Virologica Sinica, 36, (2021), 890-900.
Wang, Sheng-Fan, et al., "Antibody-dependent SARS coronavirus infection is mediated by antibodies against spike proteins", Biochem Biophys Res Commun, 451 208-214, (2014), 8 pgs.
Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.
Wanitchang, Asawin, et al., "Characterization of influenza A virus pseudotyped with the spike protein of porcine epidemic diarrhea virus", Archives of Virology, 163(12), (2018), 3255-3264.
Warfield, et al., PNAS, vol. 100(26), (2003), pp. 5889-15894.
Watanabe, S., et al., "Ebola virus (EBOV) VP24 inhibits transcription and replication of the EBOV genome", J Infect Dis., 196(Suppl 2), (Nov. 15, 2007), S284-90.
Watanabe, S., et al., "Production of Novel Ebola Virus-Like Particles from cDNAs: an Alternative to Ebola Virus Generation by Reverse Genetics", Journal of Virology, 78(2), (Jan. 2004), 999-1005.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Weber, F., et al., "Conserved vRNA end sequences of Thogoto-orthomyxovirus suggest a new panhandle structure", Archives of Virology, 142(5), (1997), 1029-1033.
Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.
Wei, Kai, et al., "Influenza A Virus Acquires Enhanced Pathogenicity and Transmissibility after Serial Passages in Swine", Journal of Virology, 88(20), (Oct. 2014), 11981-11994.
Wiedmer, T., et al., "Identification of three new members of the phospholipid scramblase gene family", Biochim Biophys Acta, 1467(1), (Jul. 31, 2000), Abstract Only.
Wills, J. W., et al., "An Assembly Domain of the Rous Sarcoma Virus Gag Protein Required Late in Budding", Journal of Virology, 68(10), (1994), 6605-6618.
Wilson, et al., "Vaccine Potential of Ebola Virus VP24, VP30, VP35 and VP40 Proteins", Virology 286, (2001), 384-90.
Winkler, K, et al., "Changing the antigen binding specificity by single point mutations of an anti-p24 (HIV-1) antibody", J. Immunol. 165 4505-4514, (2000), 11 pgs.
Wood, J. M., et al., "From Lethal Virus to Life-Saving Vaccine: Developing Inactivated Vaccines for Pandemic Influenza", Nature Reviews Microbiology, 2(10), (2004), 842-847.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J, et al., "Modification in framework region I results in a decreased affinity of chimeric anti-Tag72 antibody", Mol. Immunol. 28(1/2), (1991), 141-148.
Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10.3390/v15010095, (2023), 23.
Xu, Ruodan, et al., "Construction of SARS-CoV-2 Virus-Like Particles by Mammalian Expression System", Frontiers in Bioengineering and Technology, 8:862, (2020), 1-6.
Yagi, Y., et al., "In silico panning for a non-competitive peptide inhibitor", BMC Bioinformatics, 8(11), (2007), 11 pgs.
Yamamoto, K., et al., "Orientation Dependence in Homologous Recombination", Genetics May 1996; 143(1): 27-36, (1996), 27-36.
Yang, P., et al., "Hemagglutinin Specificity and Neuraminidase Coding Capacity of Meuraminidase-Deficient Influenza Viruses", Virology, 229(1), (1997), 155-165.
Yang, Z. Y, et al., "Identification of the Ebola virus glycoprotein as the main viral determinant of vascular cell cytotoxicity and injury", Nat Med., 6(8), (Aug. 2000), Abstract Only.
Yasuda, J., "Growth Control of Influenza A Virus by M1 Protein: Analysis of Transfectant Viruses Carrying the Chimeric M Gene", Journal of Virology, 68(12), (1994), 8141-8146.
Yen, H L, et al., "Neuraminidase Inhibitor-Resistant Recombinant A/Vietnam/1203/04 (K5N1) Influenza Viruses Retain Their Replication Efficiency and Pathogenicity In Vitro and In Vivo", Journal Of Virology., vol. 81, No. 22, (Nov. 15, 2007), 12418-12426.
Yip, Ming S., et al., "Antibody-dependent infection of human macrophages by severe acute respiratory syndrome coronavirus", Virology Journal, 11: 82, (2014), 11 pgs.
Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.
Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.
Zeitlin, L., et al., "Antibody Therapeutics for Ebola Virus Disease", Curr. Opin. Viral. 17:, (2016), 11 pgs.
Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.
Zhang, Q.-Y., et al., "SARS-CoV-2 replicon for high-throughput antiviral screening", J Gen Virol,, 102(5), (2021), 1-4.

(56) References Cited

OTHER PUBLICATIONS

Zhang, V. Q, et al., "Easy two-step method for randomizing and cloning gene fragments", Methods Mol Biol., 634, (2010), Abstract Only.
Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.
Zhang, Y., et al., "A bacterial artificial chromosome (BAC)-vectored noninfectious replicon of SARS-CoV-2", Antiviral Research, vol. 185, 104974, (Jan. 2021), 1-9.
Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.
Zhou, Yan, "Membrane-Anchored Incorporation of a Foreign Protein in Recombinant Influenza Virions", Virology 246(1), (1998), 83-94.
"U.S. Appl. No. 17/212,836, Response filed Aug. 22, 2023 to Final Office Action mailed Jun. 22, 2023", 7 pgs.
"U.S. Appl. No. 17/212,836, Advisory Action mailed Aug. 29, 2023", 3 pgs.
"International Application Serial No. PCT US2023 063136, International Search Report mailed Sep. 8, 2023", 6 pgs.
"International Application Serial No. PCT US2023 063136, Written Opinion mailed Sep. 8, 2023", 7 pgs.
"U.S. Appl. No. 16/785,449, Corrected Notice of Allowability mailed Sep. 11, 2023", 10 pgs.
"U.S. Appl. No. 17/352,845, Supplemental Notice of Allowability mailed Sep. 28, 2023", 2 pgs.
"Japanese Application Serial No. 2022-161803, Notification of Reasons for Refusal mailed Sep. 12, 2023", w English Translation, 4 pgs.
"International Application Serial No. PCT US2023 027622, International Search Report mailed Nov. 7, 2023", 5 pgs.
"International Application Serial No. PCT US2023 027622, Written Opinion mailed Nov. 7, 2023", 6 pgs.
"U.S. Appl. No. 16/785,449, Corrected Notice of Allowability mailed Nov. 8, 2023", 10 pgs.
"U.S. Appl. No. 16/785,449, Corrected Notice of Allowability mailed Nov. 17, 2023", 10 pgs.
Liu, Shufeng, "Stable Cell Clones Harboring Self-Replicating SARS-CoV-2 RNAs for Drug Screen", Journal of Virology, vol. 96, No. 6, [Online] Retrieved from the internet:https: www.ncbi.nlm.nih.gov pmc articles PMC8941906pdf jvi.02216-21.pdf, (Mar. 23, 2022), 13 pgs.
Netland, Jason, "Immunization with an attenuated severe acute respiratory syndrome coronavirus deleted in E protein protects against lethal respiratory disease", Virolog, vol. 399, No. 1, (Jan. 27, 2010), 9 pgs.
Zhang, Xianwen, "A trans-complementation system for SARS-CoV-2 recapitulates authentic viral replication without virulence", Cell, Elsevier, Amsterdam NL, vol. 184, No. 8, (Feb. 23, 2021), 24 pgs.
"European Application Serial No. 17709236.8, Communication Pursuant to Article 94(3) EPC mailed Mar. 14, 2024", 6 pgs.
"Japanese Application Serial No. 2020-182549, Notification of Reasons for Refusal mailed Feb. 20, 2024", w/ English Translation, 8 pgs.
"Japanese Application Serial No. 2022-161803, Response Filed Mar. 12, 2024 to Notification of Reasons for Refusal mailed Sep. 12, 2023", w/ English Claims, 15 pgs.
"U.S. Appl. No. 17/004,583, Notice of Allowance mailed May 15, 2023", 7 pgs.
"U.S. Appl. No. 17/352,845, Response filed May 16, 2023 to Non Final Office Action mailed Dec. 16, 2022", 8 pgs.
"U.S. Appl. No. 17/212,836, Response filed May 16, 2023 to Non Final Office Action mailed Feb. 16, 2023", 7 pgs.
"U.S. Appl. No. 16/785,449, Response filed May 22, 2023 to Final Office Action mailed Mar. 22, 2023", 9 pgs.
"U.S. Appl. No. 17/352,845, Notice of Allowance mailed Jun. 7, 2023", 5 pgs.
"U.S. Appl. No. 16/785,449, Advisory Action mailed Jun. 7, 2023", 17 pgs.
"U.S. Appl. No. 17/212,836, Final Office Action mailed Jun. 22, 2023", 15 pgs.
"U.S. Appl. No. 18/173,535, Preliminary Amendment filed Jun. 26, 2023", 16 pgs.
"U.S. Appl. No. 16/785,449, Response filed Jul. 13, 2023 to Advisory Action mailed Jun. 7, 2023", 12 pgs.
"U.S. Appl. No. 17/004,583, Notice of Allowability mailed Aug. 1, 2023", 2 pgs.
"U.S. Appl. No. 18/365,082, Preliminary Amendment filed Aug. 3, 2023", 4 pgs.
"U.S. Appl. No. 16/785,449, Notice of Allowance mailed Aug. 7, 2023", 14 pgs.
Abdoli, Mohsen, "Intranasal administration of cold-adapted live-attenuated SARS-CoV-2 candidate vaccine confers protection against SARS-CoV-2", Virus Research 319 198857, (2022), 10 pgs.
Faizuloev, Evgeny, "Cold-adapted SARS-CoV-2 variants with different sensitivity exhibit an attenuated phenotype and confer protective immunity", Science Direct Vaccine 41 892-902, (2023), 12 pgs.
Lu, Shan, "The SARS-CoV-2 nucleocapsid phosphoprotein forms mutually exclusive condensates with RNA and the membrane-associated M protein", nature communications 12:502, (2021), 15 pgs.
Plescia, Caroline B, "SARS-CoV-2 viral budding and entry can be modeled using BSL-2 level virus-like particles", JBC Research Article, (Nov. 19, 2020), 10 pgs.
Seo, Sang Heui, "Cold-Adapted Live Attenuated SARS-COV-2 Vaccine Completely Protects Human ACE2 Transgenic Mice from SARS-Cov-2 Infection", Vaccines 2020 8, 584, (Oct. 3, 2020), 17 pgs.
Swann, Heather, "Minimal system for assembly of SARS CoV 2 virus like particles", Scientific Reports 10:21877 nature portfolio, (2020), 1-5.
Zhang, Zhikuan, "Structure of SARS-CoV-2 membrane protein essential for virus assembly", nature communications 13:4399, (Aug. 5, 2022), 12 pgs.
"European Application Serial No. 17709236.8, Response filed Sep. 16, 2024 to Communication Pursuant to Article 94(3) EPC mailed Mar. 14, 2024", 16 pgs.
"Japanese Application Serial No. 2020-182549, Response filed Aug. 20, 2024 to Notification of Reasons for Refusal mailed Feb. 20, 2024", w English claims, 12 pgs.
"U.S. Appl. No. 17/212,836, Response filed Nov. 26, 2024 to Non Final Office Action mailed Jun. 13, 2024", 9 pgs.
"U.S. Appl. No. 18/365,082, Restriction Requirement mailed Oct. 24, 2024", 12 pgs.
"U.S. Appl. No. 17/212,836, Notice of Allowance mailed Jan. 2, 2025", 8 pgs.
"U.S. Appl. No. 18/461,321, Non Final Office Action mailed Nov. 14, 2024", 6 pgs.
"U.S. Appl. No. 18/525,460, Notice of Allowance mailed Oct. 23, 2024", 11 pgs.
"Japanese Application Serial No. 2022-161803, Response filed Dec. 4, 2024 to Notification of Reasons for Refusal mailed Jun. 4, 2024", w English claims, 13 pgs.
"U.S. Appl. No. 18/461,321, Response filed Jan. 7, 2025 to Non Final Office Action mailed Nov. 14, 2024", 6 pgs.
"European Application Serial No. 17709236.8, Supplementary Response filed Jan. 7, 2025 to Communication Pursuant to Article 94(3) EPC mailed Mar. 14, 2024", 8 pgs.
"Japanese Application Serial No. 2020-182549, Notification of Reasons for Refusal mailed Oct. 15, 2024", w English translation, 6 pgs.
"U.S. Appl. No. 17/212,836, Notice of Allowability mailed Feb. 7, 2025", 5 pgs.
"Japanese Application Serial No. 2020-182549, Response filed Dec. 4, 2024 to Notification of Reasons for Refusal mailed Oct. 15, 2024", w English claims, 10 pgs.

(56) References Cited

OTHER PUBLICATIONS

"U.S. Appl. No. 18/365,082, Notice of Allowance mailed Feb. 4, 2025", 10 pgs.
"International Application Serial No. PCT US2023 027622, International Preliminary Report on Patentability mailed Jan. 23, 2025", 8 pgs.
"U.S. Appl. No. 18/525,460, Corrected Notice of Allowability mailed Feb. 26, 2025", 7 pgs.
"Japanese Application Serial No. 2020-182549, Office Action mailed Jan. 28, 2025", w Machine English Translation, 5 pgs.
"U.S. Appl. No. 18/461,321, Final Office Action mailed Mar. 6, 2025", 8 pgs.
Chen, Xiaorui, "Comparison of four adjuvants revealed the strongest protection against lethal pneumococcal challenge following immunization with PsaA-PspA fusion protein and AS02 as adjuvant", https: pubmed.ncbi.nlm.nih.gov 30707297 (abstract), (2019), 1 pg.
"Japanese Application Serial No. 2022-161803, Final Notification of Reasons for Rejection mailed Mar. 4, 2025", W English Translation, 6 pgs.
"U.S. Appl. No. 18/461,321, Response filed Mar. 19, 2025 to Final Office Action mailed Mar. 6, 2025", 6 pgs.
"U.S. Appl. No. 18/365,082, Notice of Allowance mailed Mar. 20, 2025", 8 pgs.
"U.S. Appl. No. 18/461,321, Advisory Action mailed Mar. 27, 2025", 2 pgs.
"U.S. Appl. No. 18/365,082, Corrected Notice of Allowability mailed May 28, 2025", 2 pgs.

* cited by examiner

B/Yamagata/1/1973 PB2:

AGCAGAAGCGGAGCGTTTTCAAGATGACATTGGCTAAAATTGAATTGTTAAAACAACTGTTAAGGGACAACGAAGCCAAA
ACAGTATTGAAACAAACAACGGTAGACCAATATAACATAATAAGAAAATTCAATACATCAAGAATTGAAAAGAACCCTTC
ATTAAGGATGAAGTGGGCCATGTGTTCTAATTTTCCCTTGGCTCTGACCAAGGGTGATATGGCAAATAGAATCCCCTTGG
AATACAAGGGAATACAACTTAAAACAAATGCTGAAGACATAGGAACCAAAGGCCAAATGTGCTCAATAGCAGCAGTTACC
TGGTGGAATACATATGGACCAATAGGAGACACTGAAGGTTTCGAAAAGGTCTACGAAAGCTTCTTTCTCAGAAAGATGAG
ACTTGACAATGCCACTTGGGGCCGAATAACTTTTGGCCCAGTTGAAAGAGTAAGAAAAAGGGTACTGCTAAACCCTCTCA
CCAAGGAAATGCCTCCAGATGAAGCGAGCAATGTGATAATGGAAATATTGTTCCCTAAGGAAGCAGGAATACCAAGAGAA
TCTACTTGGATACATAGGGAACTGATAAAAGAAAAAAGAGAAAAATTGAAAGGAACGATGATAACTCCCATTGTACTGGC
ATACATGCTTGAGAGAGAATTGGTTGCCCGAAGAAGGTTCCTGCCAGTGGCAGGAGCAACATCAGCTGAGTTCATAGAAA
TGCTACACTGCTTACAAGGTGAAAATTGGAGACAAATATATCACCCAGGAGGGAATAAACTAACTGAATCTAGGTCTCAA
TCAATGATTGTAGCTTGTAGAAAAATAATCAGAAGATCAATAGTCGCATCAAACCCACTAGAGCTAGCTGTAGAAATTGC
AAACAAGACTGTGATAGATACTGAACCTTTAAAATCATGTCTGGCAGCCATAGACGGAGGTGATGTAGCCTGTGACATAA
TGAGAGCTGCATTAGGACTAAAGATCAGACAAAGACAAAGATTTGGACGGCTTGAACTAAAGAGAATATCAGGAAGAGGA
TTCAAAAATGATGAAGAAATATTGATCGGGAACGGAACAATACAGAAGATTGGAATATGGGACGGAGAAGAGGAGTTCCA
TGTAAGATGTGGTGAATGCAGGGGAATATTAAAAAAGAGCAAAATGAGAATGGAAAAACTACTAATAAATTCAGCCAAAA
AGGAGGACATGAAAGATTTAATAATCTTGTGCATGGTATTTTCTCAAGACACTAGGATGTTCCAAGGAGTGAGAGGAGAA
ATAAATTTTCTTAATCGAGCAGGCCAACTTTTATCTCCAATGTACCAACTCCAAAGATATTTTTTGAATAGGAGCAACGA
TCTTTTTGATCAATGGGGGTATGAGGAATCACCCAAAGCAAGTGAACTACATGGGATAAATGAATTAATGAATGCATCTG
ATTATACGTTGAAAGGGGTTGTAGTAACAAAAAATGTGATTGATGACTTTAGTTCTACTGAAACAGAAAAAGTATCTATA
ACAAAAAATCTTAGTTTAATAAAAAGAACTGGGGAAGTCATAATGGGGGCTAATGACGTAAGTGAATTAGAATCACAAGC
TCAGCTAATGATAACATATGATACACCTAAGATGTGGGAGATGGGAACAACCAAAGAACTGGTGCAAAACACCTACCAAT
GGGTGCTAAAAAATTTGGTAACACTGAAGGCTCAGTTTCTTCTAGGAAAAGAAGACATGTTCCAATGGGATGCATTTGAA
GCATTTGAAAGCATAATCCCCCAGAAGATGGCTGGCCAGTACAGTGGATTTGCAAGGGCAGTGCTCAAACAAATGAGAGA
CCAAGAGGTTATGAAAACTGACCAGTTCATAAAGTTGTTGCCTTTCTGTTTCTCACCACCAAAATTAAGGAGCAATGGGG
AGCCTTATCAATTCTTGAGGCTTATATTGAAGGGAGGAGGAGAAAATTTCATCGAAGTAAGGAAAGGGTCCCCTCTATTC
TCCTACAATCCACAAACAGAAGTCCTAACTATATGCGGCAGAATGATGTCATTAAAAGGGAAAATTGAAGATGAAGAAAG
GAATAGATCAATGGGGAATGCAGTATTGGCAGGCTTTCTCGTTAGTGGCAAGTATGACCCAGATCTTGGAGATTTCAAAA
CTATTGAAGAACTTGAAAAGCTAAAACCGGGGGAGAAAGCAAACATCTTACTTTATCAAGGAAAGCCCGTTAAAGTAGTT
AAAAGGAAAAGATATAGTGCTTTATCCAATGACATTTCACAAGGAATTAAGAGACAAAGAATGACAGTTGAGTCCATGGG
GTGGGCCTTGAGCTAATATAAATTTATCCATTAATTCAATAAACACAATTGAGTGAAAAATGCTCGTGTTTCTACT (SEQ ID NO:1)

FIG. 1A

B/Yamagata/1/1973 PB1:

AGCAGAAGCGGAGCCTTTAAGATGAATATAAATCCTTATTTTCTCTTCATAGATGTACCCATACAGGCAGCAATTTCAAC
AACATTCCCATACACCGGTGTTCCCCCTTATTCCCATGGAACGGGAACAGGCTACACAATAGACACCGTGATCAGAACAC
ATGAGTACTCAAACAAGGGAAAACAGTACATTTCTGATGTTACAGGATGTACAATGGTAGATCCAACAAATGGGCCATTA
CCCGAAGACAATGAGCCGAGTGCCTATGCACAATTAGATTGCGTTCTGGAGGCTTTGGATAGAATGGATGAAGAACATCC
AGGTCTGTTTCAAGCAGCCTCACAGAATGCCATGGAGGCACTAATGGTCACAACTGTAGACAAATTAACCCAGGGGAGAC
AGACTTTTGATTGGACAGTATGCAGAAACCAACCTGCTGCAACGGCACTGAACACAACAATAACCTCTTTTAGGTTGAAT
GATTTGAATGGAGCCGACAAGGGTGGATTAGTACCCTTTTGCCAAGATATCATTGATTCATTGGACAGACCTGAAATGAC
TTTCTTCTCAGTAAAGAATATAAAGAAAAAATTGCCTGCTAAAAACAGAAAGGGTTTCCTCATAAAGAGAATACCAATGA
AGGTAAAAGACAGAATAACCAGAGTGGAATACATCAAAAGAGCATTATCATTAAACACAATGACAAAAGATGCTGAAAG
A
GGCAAACTAAAAAGAAGAGCGATTGCCACCGCTGGAATACAAATCAGAGGGTTTGTATTAGTAGTTGAAAACTTGGCTAA
AAATATCTGTGAAAATCTAGAACAAAGTGGTTTGCCAGTAGGTGGAAACGAGAAGAAGGCCAAACTGTCAAATGCAGTG
G
CCAAAATGCTCAGTAACTGCCCACCAGGAGGGATCAGCATGACAGTAACAGGAGACAATACCAAATGGAATGAATGCTTA
AATCCAAGAATCTTTTTGGCTATGACTGAAAGAATAACCAGAGACAGCCCAATTTGGTTCCGGGATTTTTGTAGTATAGC
ACCGGTCTTGTTCTCCAATAAAATAGCCAGATTGGGAAAAGGGTTTATGATAACAAGCAAAACAAAAAGACTGAAGGCTC
AAATACCTTGTCCTGATCTGTTTAGTATACCATTAGAAAGATATAATGAAGAAACAAGGGCAAAATTGAAAAAGCTGAAA
CCATTCTTCAATGAAGAAGGAACGGCATCTTTGTCGCCTGGGATGATGATGGGAATGTTTAATATGCTATCTACCGTGTT
GGGAGTAGCCGCACTAGGTATCAAAAACATTGGAAACAAAGAATACTTATGGGATGGACTGCAATCTTCTGATGATTTTG
CTCTGTTTGTTAATGCAAAAGATGAAGAGACATGTATGGAAGGAATAAACGACTTTTACCGAACATGTAAACTATTGGGA
ATAAACATGAGCAAAAAGAAAAGTTACTGTAATGAAACTGGAATGTTTGAATTTACAAGCATGTTCTACAGAGATGGATT
TGTATCTAATTTTGCAATGGAACTTCCTTCATTTGGAGTTGCTGGAGTAAATGAATCAGCAGATATGGCAATAGGAATGA
CAATAATAAAGAACAATATGATCAACAATGGGATGGGTCCAGCAACAGCACAAACAGCCATACAATTATTCATAGCTGAT
TATAGATACACCTACAAATGCCACAGGGGAGATTCCAAAGTGGAAGGAAAGAGAATGAAAATTATAAAGGAGCTATGGG
A
AAACACTAAAGGAAGAGATGGTCTGTTAGTAGCAGATGGTGGGCCTAACATTTACAATTTGAGAAACTTGCATATCCCAG
AAATAGTATTAAAGTACAACCTAATGGACCCTGAATACAAAGGGCGGTTACTTCATCCTCAAAATCCCTTTGTAGGACAT
TTGTCTATTGAGGGCATCAAAGAGGCAGATATAACCCCAGCACATGGTCCAGTAAAGAAAATGGACTATGATGCGGTGTC
TGGAACTCATAGTTGGAGAACCAAAAGGAACAGATCTATACTAAACACTGATCAGAGGAACATGATTCTTGAGGAACAAT
GCTACGCTAAGTGTTGCAACCTTTTTGAGGCCTGTTTTAACAGTGCATCATACAGGAAACCAGTAGGTCAGCACAGCATG
CTTGAGGCTATGGCCCACAGATTAAGAATGGATGCACGACTAGATTATGAATCAGGAAGAATGTCAAAGGATGATTTTGA
GAAAGCAATGGCTCACCTTGGTGAGATTGGGTACATATAAGCTTCGAAGATGTCTATGGGGTTATTGGTCATCATTGAAT
ACATGCGGTACACAAATGATTAAAATGAAAAAAGGCTCGTGTTTCTACT (SEQ ID NO:2)

FIG. 1B

B/Yamagata/1/1973 PA:

AGCAGAAGCGGTGCGTTTGATTTGCCATAATGGATACTTTTATTACAAGAAACTTCCAGACTACAATAATACAAAAGGCC
AAAAACACAATGGCAGAATTTAGTGAAGATCCTGAATTACAACCAGCAATGCTATTCAACATCTGCGTCCATCTGGAGGT
CTGCTATGTAATAAGTGATATGAATTTTCTTGATGAAGAAGGAAAAGCATATACAGCATTAGAAGGACAAGGAAAAGAAC
AAAACTTGAGACCACAATATGAAGTGATTGAGGGAATGCCAAGAAACATAGCATGGATGGTTCAAAGATCCTTAGCCCAA
GAGCATGGGATAGAGACTCCAAGGTATCTGGCTGATTTGTTCGATTATAAAACTAAGAGGTTTATAGAAGTTGGAATAAC
AAAGGGATTGGCTGATGATTACTTCTGGAAAAAGAAAGAAAAGCTGGGGAATAGCATGGAACTGATGATATTCAGCTACA
ATCAAGACTATTCGTTAAGTAATGAATCCTCATTGGATGAGGAAGGAAAAGGGAGAGTGCTAAGCAGACTCACAGAACTT
CAGGCTGAGTTAAGTCTGAAAAATCTATGGCAAGTTCTCATAGGAGAAGAAGATATTGAAAAAGGAATTGACTTCAAACT
TGGACAAACAATATCTAAACTAAGGGATATATCTGTTCCAGCTGGTTTCTCCAATTTTGAAGGAATGAGGAGCTACATAG
ACAATATAGATCCTAAAGGAGCAATAGAGAGAAATCTAGCAAGGATGTCTCCCTTAGTATCAGTTACACCTAAAAAGTTG
AAATGGGAGGACCTAAGACCAATAGGGCCTCACATTTACAACCATGAGCTACCAGAAGTTCCATATAATGCCTTTCTTCT
AATGTCTGATGAATTGGGGCTGGCTAATATGACTGAAGGGAAGTCCAAGAAACCGAAGACCTTAGCCAAAGAGTGCCTAG
AAAAGTACTCAACACTACGGGATCAAACTGACCCAATATTAATAATGAAAAGCGAAAAAGCTAATGAACACTTCCTATGG
AAACTGTGGAGGGACTGTGTAAATACAATAAGTAATGAGGAAACAAGTAACGAATTACAGAAAACCAATTATGCCAAGTG
GGCCACAGGAGATGGATTAACATATCAGAAAATAATGAAAGAAGTAGCAATAGATGACGAAACAATGTACCAAGAAGAGC
CCAAAATACCTAACAAATGTAGAGTGGCTGCTTGGGTTCAAACAGAGATGAATCTATTGAGCACTCTGACAAGTAAAAGG
GCCCTGGATCTGCCAGAAATAGGGCCAGACGTAGCACCCGTGGAGCATGTAGGGAGTGAAAGAAGGAAATACTTTGTTAA
TGAAATCAACTACTGTAAGGCCTCTACCGTTATGATGAAGTATGTACTTTTTCACACTTCATTATTAAATGAAAGCAATG
CCAGCATGGGAAAATATAAAGTAATACCAATAACCAACAGAGTAGTAAATGAAAAGGGAGAAAGTTTTGACATGCTTTAT
GGTCTAGCGGTTAAAGGGCAATCTCATCTGAGGGGAGATACTGATGTTGTAACAGTTGTGACTTTCGAATTTAGTAGTAC
AGATCCCAGAGTGGACTCAGGAAAGTGGCCAAAATATACTGTATTTAGAATTGGCTCCTTATTTGTGAGTGGGAGGGAAA
AATCTGTATACCTATATTGCCGAGTGAATGGTACAAATAAGATCCAAATGAAATGGGGAATGGAAGCTAGAAGATGTCTG
CTTCAATCAATGCAACAAATGGAAGCAATTGTTGAACAAGAATCATCGATACAAGGATATGACATGACCAAAGCTTGTTT
CAAGGGAGACAGAGTGAATAGTCCAAAAACTTTCAGTATTGGGACTCAAGAAGGAAAACTAGTGAAAGGATCCTTTGGGA
AAGCACTAAGAGTAATATTCACCAAATGTTTGATGCACTATGTATTTGGAAATGCCCAATTGGAGGGGTTTAGTGCCGAA
TCTAGGAGACTTCTACTGTTAATTCAGGCATTAAAAGACAGAAAGGGCCCTTGGGTATTCGACTTAGAGGGAATGTATTC
TGGAATAGAAGAATGTATTAGTAACAACCCTTGGGTAATACAGAGTGCATACTGGTTTAATGAATGGTTGGGCTTTGAAA
AAGAGGGGAGTAAAGTATTAGAATCAGTAGATGAAATAATGGATGAATGAAAGAAGGGCATAGTGCTCAATTTGGTACTA
TTTTGTTCATTATGTATCTAAACATCCAATAAAAAGAATTGAGAATTAAAAATGCACGTGTTTCTACT (SEQ ID NO:3)

FIG. 1C

B/Yamagata/1/1973 NP:

AGCAGAAGCACAGCATTTTCTTGTGAACTTCAAGTACCAACAAAAAACTGAAAATCAAAATGTCCAACATGGACATTGAC
GGCATCAACACTGGAATAATTGACAAAACACCAGAAGAAATAACTTCCGGAACCAGTGGGGCAACCAGACCAATCATCAG
ACCAGCAACCCTTGCCCCACCAAGCAACAAACGAACCAGAAACCCATCCCCGGAAAGGGCAACCACAAGCAGTGAAGCTG
ATGTCGGAAGGAAAACCCAAAAGAAACAAACTCCGACAGAGATAAAGAAGAGCGTCTACAATATGGTAGTGAAACTGGGT
GAATTCTACAACCAGATGATGGTCAAAGCTGGACTCAACGATGACATGGAGAGAAACCTAATCCAAAATGCACATGCTGT
GGAAAGAATTCTATTGGCTGCTACTGATGACAAGAAAACTGAATTCCAAAAGAAAAAGAATGCCAGAGACGTCAAAGAAG
GGAAAGAAGAAATAGACCACAACAAAACAGGAGGCACCTTTTACAAGATGGTAAGAGATGATAAAACCATCTACTTCAGC
CCTATAAGAATTACCTTTTTAAAAGAAGAGGTGAAAACAATGTACAAAACCACCATGGGGAGTGACGGTTTCAGTGGACT
AAATCACATCATGATTGGGCATTCACAGATGAACGATGTCTGTTTCCAAAGATCAAAGGCACTAAAAAGAGTTGGACTTG
ACCCTTCATTAATCAGTACTTTTGCAGGAAGCACACTCCCCAGAAGATCAGGTACAACTGGTGTTGCGACCAAAGGAGGT
GGAACTTTAGTGGCAGAAGCCATTCGATTTATAGGAAGAGCAATGGCAGACAGAGGGCTATTGAGAGACATCAGAGCCAA
GACGGCCTATGAAAAGATTCTTCTGAATCTGAAAAACAAGTGCTCTGCGCCCCAACAAAAGGCTCTGGTTGATCAAGTGA
TCGGAAGTAGAAATCCAGGGATTGCAGACATAGAAGATCTCACCCTGCTTGCTCGAAGTATGGTCGTTGTTAGGCCCTCT
GTAGCAAGCAAAGTGGTGCTTCCCATAAGCATCTATGCTAAAATACCTCAACTGGGGTTCAACGTTGAAGAATACTCTAT
GGTTGGGTATGAAGCCATGGCTCTTTATAATATGGCAACACCTGTTTCCATATTAAGAATGGGAGACGATGCAAAAGATA
AATCACAATTATTCTTCATGTCTTGCTTTGGAGCTGCCTATGAAGACCTAAGAGTTCTGTCTGCACTAACAGGCACGGAA
TTCAAGCCTAGGTCAGCATTAAAGTGCAAAGGTTTCCACGTTCCAGCAAAGGAGCAAGTGGAAGGAATGGGGGCAGCTCT
GATGTCCATCAAGCTCCAGTTTTGGGCTCCAATGACCAGATCTGGGGGGAATGAAGTAGGTGGAGACGGAGGGTCTGGTC
AAATAAGTTGCAGCCCCGTGTTTGCAGTAGAAAGACCTATTGCTCTAAGCAAGCAAGCTGTAAGAAGAATGCTGTCAATG
AATATTGAGGGACGTGATGCAGATGTCAAAGGAAATCTACTCAAGATGATGAATGATTCAATGGCTAAGAAAACCAATGG
AAATGCTTTCATTGGGAAGAAAATGTTCCAAATATCAGACAAAAACAAAACCAATCCCGTTGAGATTCCAATTAAGCAGA
CCATCCCCAGTTTCTTCTTTGGGAGGGACACAGCAGAGGATTATGATGACCTCGATTATTAAAGCAACAAAATAGACACT
ATGGCTGTGATTGTTTCAGTACGTTTGGAATGTGGGTGTTTACTCTTATTGAAATAAATGTAAAAAATGCTGTTGTTTCT (SEQ
ID NO:4)

B/Yamagata/1/1973 M:

AGCAGAAGCACGCACTTTCTTAAAATGTCGCTGTTTGGAGACACAATTGCCTACCTGCTTTCACTAACAGAAGATGGAGA
AGGCAAAGCAGAACTAGCGGAAAAATTACACTGTTGGTTCGGTGGGAAAGAATTCGATCTAGACTCTGCTTTGGAATGGA
TAAAAAACAAAAGATGCCTAACTGATATACAAAAAGCACTAATTGGTGCCTCTATCTGCTTTTTGAAACCCAAAGACCAA
GAAAGAAAAAGAAGATTCATCACAGAGCCCCTGTCAGGAATGGGAACAACAGCAACAAAAAAGAAAGGCCTGATTCTAGC
TGAAAGAAAAATGAGAAGATGTGTGAGTTTTCATGAGGCATTTGAAATAGCAGAAGGCCATGAAAGCTCAGCACTACTAT
ATTGTCTCATGGTCATGTACCTGAACCCTGGAAATTATTCAATGCAAGTAAAACTAGGAACGCTCTGTGCTTTATGCGAG
AAACAAGCATCACATTCACACAGAGCTCATAGCAGAGCAGCAAGATCTTCAGTGCCTGGAGTGAGGCGAGAAATGCAAAT
GGTTTCAGCTATGAACACAGCAAAAACAATGAATGGAATGGGGAAGGGAGAAGACGTCCAAAAACTGGCAGAAGAGCTGC
AAAGCAACATTGGAGTATTGAGATCTCTGGGGGCAAGTCAAAAGAATGGAGAAGGAATTGCAAAGGATGTAATGGAAGTG
CTAAAGCAGAGCTCCATGGGAAATTCAGCTCTTGTGAAGAAATACCTATAATGCTCGAGCCATTTCAGATTCTTTCAATT
TGCTCTTTCATTTTATCGGCTCTCCATTTCATGGGCTGGACAATAGGGCATTTAAATCAAATAAAAAGAGGAGTAAACCT
AAAAATACGAATAAGAAATCCAAATAAAGAGACAATAAATAGAGAGGTATCAATTTTGAGACACAGTTACCAAAAAGAAA
TCCAAGCCAAAGAAACAATAAAGGAAGTACTCTCTGACAACATGGAGAGATTGAGTGACCACATAGTAATTGAGGGGCTT
TCTGCTGAAGAGATAATAAAAATGGGTGAAACAGTTTTGGAGGTAGAAGAATTGCATTAAACCCAATTTTCACCGTATTT
CTTACTATGCATTTAAGCAAATTGTAATCAATGTCAGCAAATAAACTGGAAAAAGTGCGTTGTTTCTACT (SEQ ID NO:5)

FIG. 1D

B/Yamagata/1/1973 NS:

AGCAGAAGCAGAGGATTTGTTTAGTCACTGGCAAACGGAAAAAAATGGCGGACAACATGACCACAACACAAATTGAGGTG
GGTCCGGGAGCAACCAATGCCACTATAAACTTTGAAGCAGGAATTTTGGAGTGCTATGAAAGGCTTTCATGGCAAAGAGC
CCTTGACTACCCTGGTCAAGACCGCCTAAACAGACTAAAGAGAAAATTAGAATCAAGAATAAAGACTCACAACAAAAGTG
AGCCTGAAAGTAAAAGGATGTCTCTTGAAGAGAGAAAAGCAATTGGGGTAAAAATGATGAAAGTGCTCCTATTTATGAAC
CCATCTGCTGGAATTGAAGGGTTTGAGCCATACTGTATGAAAAATTCCTCCAATAGCAACTGCCCAAACTGCAATTGGGC
CGATTACCCTCCAACATCAGGAAAGTGCCTTGATGACATAGAAGAAGAACCGGAGAATGTTGATGACCCAACTGAAATAG
TATTAAGGGACATGAACAACAAAGATGCAAGGCAAAAGATAAAAGAGGAAGTAAACACTCAGAAAGAAGGGAAGTTCCGT
TTGACAATAAAAAGGGATATACGTAATGTGTTGTCCTTGAGAGTGTTGGTAAACGGAACATTCCTCAAGCACCCTAATGG
ATACAAGTCCTTATCAACTCTGCATAGATTGAATGCATATGACCAGAGTGGAAGGCTTGTTGCTAAACTTGTTGCTACTG
ATGATCTTACAGTGGAGGATGAAGAAGATGGCCATCGGATCCTCAACTCACTCTTCGAGCGTTTTAATGAAGGACATTCA
AAGCCAATTCGAGCAGCTGAAACTGCGGTGGGAGTCTTATCCCAATTTGGTCAAGAGCACCGATTATCACCAGAGGAGGG
AGACAATTAGACTGGTTACGGAAGAACTTTATCTTTTAAGTAAAAGAATTGATGATAACATATTGTTCCACAAAACAGTA
ATAGCTAACAGCTCCATAATAGCTGACATGATTGTATCATTATCATTATTGGAAACATTGTATGAGATGAAGGATGTGGT
TGAAGTGTACAGCAGGCAGTGCTTGTGAATTTAAAATAAAAATCCTCTTGTTACTACT (SEQ ID NO:6)

HA

MKAIIVLLMVVTSNADRICTGITSSNSPHVVKTATQGEVNVTGVIP
LTTTPTKSHFANLKGTKTRGKLCPNCLNCTDLDVALGRPMCMGTI
PSAKASILHEVRPVTSGCFPIMHDRTKIRQLPNLLRGYENIRLSTHN
VINAERAPGGPYRLGTSGSCPNVTSRNGFFATMAWAVPRDNKTA
TNPLTVEVPYICTKGEDQITVWGFHSDDKTQMKNLYGDSNPQKFT
SSANGVTTHYVSQIGDFPNQTEDGGLPQSGRIVVDYMVQKPGKT
GTIVYQRGVLLPQKVWCASGRSKVIKGSLPLIGEADCLHEKYGGLN
KSKPYYTGEHAKAIGNCPIWVKTPLKLANGTKYRPPAKLLKERGFF
GAIAGFLEGGWEGMIAGWHGYTSHGAHGVAVAADLKSTQEAINK
ITKNLNSLSELEVKNLQRLSGAMDELHNEILELDEKVDDLRADTISS
QIELAVLLSNEGIINSEDEHLLALERKLKKMLGPSAVDIGNGCFETK
HKCNQTCLDRIAAGTFNAGEFSLPTFDSLNITAASLNDDGLDNHTI
LLYYSTAASSLAVTLMIAIFIVYMVSRDNVSCSICL(SEQ ID NO:7)

Encoded by

```
  1 tttctaatat ccacaaaatg aaggcaataa ttgtactact catggtagta acatccaacg
 61 cagatcgaat ctgcactggg ataacatctt caaactcacc tcatgtggtc aaaacagcta
121 ctcaagggga agttaatgtg actggtgtga taccactgac aacaacacca acaaaatctc
181 attttgcaaa tctcaaagga acaaagacca gagggaaact atgcccaaac tgtctcaact
241 gcacagatct ggatgtggcc ttgggcagac caatgtgtat ggggaccata ccttcggcaa
301 aagcttcaat actccacgaa gtcagacctg ttacatccgg gtgctttcct ataatgcacg
361 acagaacaaa aatcagacag ctacccaatc ttctcagagg atatgaaaat atcagattat
421 caacccataa cgttatcaac gcagaaaggg caccaggagg accctacaga cttggaacct
481 caggatcttg ccctaacgtt accagtagaa acggattctt cgcaacaatg gcttgggctg
541 tcccaaggga caacaaaaca gcaacgaatc cactaacagt agaagtacca tacatttgca
601 caaaaggaga agaccaaatt actgtttggg ggttccattc tgatgacaaa acccaaatga
```

FIG. 1E

```
 661 aaaacctcta tggagactca aatcctcaaa agttcacctc atctgccaat ggagtaacca
 721 cacattatgt ttctcagatt ggtgacttcc caaatcaaac agaagacgga gggctaccac
 781 aaagcggcag aattgttgtt gattacatgg tgcaaaaacc tgggaaaaca ggaacaattg
 841 tctatcaaag aggtgttttg ttgcctcaaa aggtgtggtg cgcaagtggc aggagcaagg
 901 taataaaagg gtccttgcct ttaattggtg aagcagattg ccttcacgaa aaatacggtg
 961 gattaaacaa aagcaagcct tactacacag gagaacatgc aaaagccata ggaaattgcc
1021 caatatgggt gaaaacacct ttgaagcttg ccaatggaac caaatataga cctcctgcaa
1081 aactattaaa ggaaaggggt ttcttcggag ctattgctgg tttcttagag ggaggatggg
1141 aaggaatgat tgcaggttgg cacggataca catctcatgg agcacatgga gtggcagtgg
1201 cagcagacct taagagcacg caagaagcca taaacaagat aacaaaaaat ctcaattctt
1261 tgagtgagct agaagtaaag aatcttcaaa gactaagtgg tgccatggat gaactccaca
1321 acgaaatact cgagctggat gagaaagtgg atgatctcag agctgacaca ataagctcgc
1381 aaatagagct tgcagtcttg ctttccaacg aaggaataat aaacagtgaa gatgagcatc
1441 tattggcact tgagagaaaa ctaaagaaaa tgctgggtcc ctctgctgta gacataggga
1501 atggatgctt cgaaaccaaa cacaagtgca accagacctg cttagacagg atagctgctg
1561 gcacctttaa tgcaggagaa ttttctcttc ccacttttga ttcactgaat attactgctg
1621 catctttaaa tgatgatgga ttggataatc atactatact gctctactac tcaactgctg
1681 cttctagttt ggccgtaaca ttgatgatag ctatttttat tgtttatatg gtctccagag
1741 acaatgtttc ttgctccatc tgtctataag gaaaattaag ccctgtattt tcctttattg
1801 tagtgcttgt ttgcttgtta ccattacaaa gaaacgttat tga (SEQ ID NO:9)
```

NA

```
M L P S T I Q T L T L F L T S G G V L L S L Y V S A S L S
Y L L Y S D I L L K F S P T E I T A P K V P L D C A N A S
N V Q A V N R S A T K G M T L L L S E P E W T Y P R L S C
Q G S T F Q K A L L I S P H R F G E T K G N S A P L I I R
E P F I A C G P K E C K H F A L T H Y A A Q P G G Y Y N G
T R E D R N K L R H L I S V K L G K I P T V E N S I F H M
A A W S G S A C H D G R E W T Y I G V D G P D S N A L I K
I K Y G E A Y T D T Y H S Y A N N I L R T Q E S A C N C I
G G D C Y L M I T D G S A S G I S K C R F L K I R E G R I
I K E I F P T G R V E H T E E C T C G F A S N K T I E C A
C R D N S Y T A K R P F V K L N V E T D T A E I R L M C T
E T Y L D T P R P D D G S I T G P C E S N G D K G R G G I
K G G F V H Q R M A S K I G R W Y S R T M S K T E R M G M
E L Y V K Y D G D P W T D S D A L A P S G V M V S M K E P
G W Y S F G F E I K D K K C D V P C I G I E M V H D G G K
K T W H S A A T A I Y C L M G S G Q L L W D T V T G V D M
A L (SEQ ID NO:8)
```

FIG. 1F

Encoded by

```
   1 aaactgaggc aaataggcca aaaatgaaca atgctacctt caactataca aacgttaacc
  61 ctatttctca catcaggggg agtgttatta tcactatatg tgtcagcttc actgtcatac
 121 ttactgtatt cggatatatt gctaaaattt tcaccaacag aaataactgc accaaaagtg
 181 ccattggatt gtgcaaacgc atcaaatgtt caggctgtga accgttctgc aacaaaaggg
 241 atgacacttc ttctctcaga accggagtgg acatacccctc gtttatcttg ccagggctca
 301 acctttcaga aagcactcct aattagccct catagattcg gagaaaccag aggaaactca
 361 gctccccttga taataaggga accttttatt gcttgtggac caaaggaatg caaacacttt
 421 gctctaaccc attatgcagc tcaaccaggg ggatactaca atggaacaag agaggacaga
 481 aacaagctga ggcatctgat ttcagtcaaa ttgggcaaaa tcccaacagt agaaaactcc
 541 attttccaca tggcagcttg gagcgggtcc gcatgccatg atggtagaga atggacatat
 601 atcggagttg atggccctga cagtaatgca ttgatcaaaa taaaatatgg agaagcatat
 661 actgacacat accattccta tgcaaacaac atcctaagaa cacaagaaag tgcctgcaat
 721 tgcatcgggg gagattgtta tcttatgata actgatggct cagcttcagg aattagtaaa
 781 tgcagatttc ttaagattcg agagggtcga ataataaaag aaatatttcc aacaggaaga
 841 gtagaacata ctgaagaatg cacatgcgga tttgccagca ataaaaccat agaatgtgcc
 901 tgtagagata acagttacac agcaaaaaga ccctttgtca aattaaatgt ggagactgat
 961 acagctgaaa taagattgat gtgcacagag acttatttgg acaccccag accagatgat
1021 ggaagcataa cagggccttg cgaatctaat ggggacaaag ggcgtggagg catcaaggga
1081 ggatttgttc atcaaagaat ggcatccaag attggaagat ggtactctcg aacgatgtct
1141 aaaactgaaa gaatggggat ggaactgtat gtcaagtatg atggagaccc atggactgac
1201 agtgacgccc ttgctcctag tggagtaatg gtttcaatga aagaacctgg ttggtattcc
1261 tttggcttcg aaataaaaga taagaaatgt gatgtcccct gtattgggat agagatggta
1321 catgatggtg gaaaaaagac ttggcactca gcagcaacag ccatttactg tttaatgggc
1381 tcaggacaat tgctatggga cactgtcaca ggtgttgata tggctctgta atggaggaat
1441 ggttgagtct gttctaaacc ctttgttcct attttgtttg aacaattgtc cttactgaac
1501 ttaa(SEQ ID NO:10)
```

FIG. 1G

A/B-Chimeric HA

NCR SP — TM CT NCR
[Influenza B HA ectodomain]
PR8 HA sequence 83 bp — PR8 HA sequence 159 bp A/B-Chimeric NA NCR CT TM — NCR
[Influenza B NA ectodomain]
PR8 NA sequence 203 bp — PR8 NA sequence 185 bp Yamagata/1/73 PB2:

AGCAGAAGCGGAGCGTTTTCAAGATGACATTGGCTAAAATTGAATTGTTAAAACAACTGTTAAGGGACAACGAAGCCAAA

ACAGTATTGAAACAAACAACGGTAGACCAATATAACATAATAAGAAAATTCAATACATCAAGAATTGAAAAGAACCCTTC

ATTAAGGATGAAGTGGGCCATGTGTTCTAATTTTCCCTTGGCTCTGACCAAGGGTGATATGGCAAATAGAATCCCCTTGG

AATACAAGGGAATACAACTTAAAACAAATGCTGAAGACATAGGAACCAAAGGCCAAATGTGCTCAATAGCAGCAGTTACC

TGGTGGAATACATATGGACCAATAGGAGACACTGAAGGTTTCGAAAAGGTCTACGAAAGCTTCTTTCTCAGAAAGATGAG

ACTTGACAATGCCACTTGGGGCCGAATAACTTTTGGCCCAGTTGAAAGAGTAAGAAAAAGGGTACTGCTAAACCCTCTCA

CCAAGGAAATGCCTCCAGATGAAGCGAGCAATGTGATAATGGAAATATTGTTCCCTAAGGAAGCAGGAATACCAAGAGAA

TCTACTTGGATACATAGGGAACTGATAAAAGAAAAAAGAGAAAAATTGAAAGGAACGATGATAACTCCCATTGTACTGGC

ATACATGCTTGAGAGAGAATTGGTTGCCCGAAGAAGGTTCCTGCCAGTGGCAGGAGCAACATCAGCTGAGTTCATAGAAA

TGCTACACTGCTTACAAGGTGAAAATTGGAGACAAATATATCACCCAGGAGGGAATAAACTAACTGAATCTAGGTCTCAA

TCAATGATTGTAGCTTGTAGAAAAATAATCAGAAGATCAATAGTCGCATCAAACCCACTAGAGCTAGCTGTAGAAATTGC

AAACAAGACTGTGATAGATACTGAACCTTTAAAATCATGTCTGGCAGCCATAGACGGAGGTGATGTAGCCTGTGACATAA

TGAGAGCTGCATTAGGACTAAAGATCAGACAAAGACAAAGATTTGGACGGCTTGAACTAAAGAGAATATCAGGAAGAGGA

TTCAAAAATGATGAAGAAATATTGATCGGGAACGGAACAATACAGAAGATTGGAATATGGGACGGAGAAGAGGAGTTCCA

TGTAAGATGTGGTGAATGCAGGGGAATATTAAAAAAGAGCAAAATGAGAATGGAAAAACTACTAATAAATTCAGCCAAAA

AGGAGGACATGAAAGATTTAATAATCTTGTGCATGGTATTTTCTCAAGACACTAGGATGTTCCAAGGAGTGAGAGGAGAA

ATAAATTTTCTTAATCGAGCAGGCCAACTTTTATCTCCAATGTACCAACTCCAAAGATATTTTTTGAATAGGAGCAACGA

TCTTTTTGATCAATGGGGGTATGAGGAATCACCCAAAGCAAGTGAACTACATGGGATAAATGAATTAATGAATGCATCTG

ATTATACGTTGAAAGGGGTTGTAGTAACAAAAAATGTGATTGATGACTTTAGTTCTACTGAAACAGAAAAAGTATCTATA

ACAAAAAATCTTAGTTTAATAAAAAGAACTGGGGAAGTCATAATGGGGGCTAATGACGTAAGTGAATTAGAATCACAAGC

TCAGCTAATGATAACATATGATACACCTAAGATGTGGGAGATGGGAACAACCAAAGAACTGGTGCAAAACACCTACCAAT

GGGTGCTAAAAAATTTGGTAACACTGAAGGCTCAGTTTCTTCTAGGAAAAGAAGACATGTTCCAATGGGATGCATTTGAA

GCATTTGAAAGCATAATCCCCCAGAAGATGGCTGGCCAGTACAGTGGATTTGCAAGGGCAGTGCTCAAACAAATGAGAGA

CCAAGAGGTTATGAAAACTGACCAGTTCATAAAGTTGTTGCCTTTCTGTTTCTCACCACCAAAATTAAGGAGCAATGGGG

AGCCTTATCAATTCTTGAGGCTTATATTGAAGGGAGGAGGAGAAAATTTCATCGAAGTAAGGAAAGGGTCCCCTCTATTC

TCCTACAATCCACAAACAGAAGTCCTAACTATATGCGGCAGAATGATGTCATTAAAAGGGAAAATTGAAGATGAAGAAAG

GAATAGATCAATGGGGAATGCAGTATTGGCAGGCTTTCTCGTTAGTGGCAAGTATGACCCAGATCTTGGAGATTTCAAAA

CTATTGAAGAACTTGAAAAGCTAAAACCGGGGGAGAAAGCAAACATCTTACTTTATCAAGGAAAGCCCGTTAAAGTAGTT

AAAAGGAAAAGATATAGTGCTTTATCCAATGACATTTCACAAGGAATTAAGAGACAAAGAATGACAGTTGAGTCCATGGG

GTGGGCCTTGAGCTAATATAAATTTATCCATTAATTCAATAAACACAATTGAGTGAAAAATGCTCGTGTTTCTACT (SEQ ID NO:11)

FIG. 16A

Yamagata/1/73 PB1:

AGCAGAAGCGGAGCCTTTAAGATGAATATAAATCCTTATTTTCTCTTCATAGATGTACCCATACAGGCAGCAATTTCAAC
AACATTCCCATACACCGGTGTTCCCCCTTATTCCCATGGAACGGGAACAGGCTACACAATAGACACCGTGATCAGAACAC
ATGAGTACTCAAACAAGGGAAAACAGTACATTTCTGATGTTACAGGATGTACAATGGTAGATCCAACAAATGGGCCATTA
CCCGAAGACAATGAGCCGAGTGCCTATGCACAATTAGATTGCGTTCTGGAGGCTTTGGATAGAATGGATGAAGAACATCC
AGGTCTGTTTCAAGCAGCCTCACAGAATGCCATGGAGGCACTAATGGTCACAACTGTAGACAAATTAACCCAGGGGAGAC
AGACTTTTGATTGGACAGTATGCAGAAACCAACCTGCTGCAACGGCACTGAACACAACAATAACCTCTTTTAGGTTGAAT
GATTTGAATGGAGCCGACAAGGGTGGATTAGTACCCTTTTGCCAAGATATCATTGATTCATTGGACAGACCTGAAATGAC
TTTCTTCTCAGTAAAGAATATAAAGAAAAAATTGCCTGCTAAAAACAGAAAGGGTTTCCTCATAAAGAGAATACCAATGA
AGGTAAAAGACAGAATAACCAGAGTGGAATACATCAAAAGAGCATTATCATTAAACACAATGACAAAAGATGCTGAAAGA
GGCAAACTAAAAAGAAGAGCGATTGCCACCGCTGGAATACAAATCAGAGGGTTTGTATTAGTAGTTGAAAACTTGGCTAA
AAATATCTGTGAAAATCTAGAACAAAGTGGTTTGCCAGTAGGTGGAAACGAGAAGAAGGCCAAACTGTCAAATGCAGTGG
CCAAAATGCTCAGTAACTGCCCACCAGGAGGGATCAGCATGACAGTAACAGGAGACAATACCAAATGGAATGAATGCTTA
AATCCAAGAATCTTTTTGGCTATGACTGAAAGAATAACCAGAGACAGCCCAATTTGGTTCCGGGATTTTTGTAGTATAGC
ACCGGTCTTGTTCTCCAATAAAATAGCCAGATTGGGAAAAGGGTTTATGATAACAAGCAAAACAAAAAGACTGAAGGCTC
AAATACCTTGTCCTGATCTGTTTAGTATACCATTAGAAAGATATAATGAAGAAACAAGGGCAAAATTGAAAAAGCTGAAA
CCATTCTTCAATGAAGAAGGAACGGCATCTTTGTCGCCTGGGATGATGATGGGAATGTTTAATATGCTATCTACCGTGTT
GGGAGTAGCCGCACTAGGTATCAAAAACATTGGAAACAAAGAATACTTATGGGATGGACTGCAATCTTCTGATGATTTTG
CTCTGTTTGTTAATGCAAAAGATGAAGAGACATGTATGGAAGGAATAAACGACTTTTACCGAACATGTAAACTATTGGGA
ATAAACATGAGCAAAAAGAAAAGTTACTGTAATGAAACTGGAATGTTTGAATTTACAAGCATGTTCTACAGAGATGGATT
TGTATCTAATTTTGCAATGGAACTTCCTTCATTTGGAGTTGCTGGAGTAAATGAATCAGCAGATATGGCAATAGGAATGA
CAATAATAAAGAACAATATGATCAACAATGGGATGGGTCCAGCAACAGCACAAACAGCCATACAATTATTCATAGCTGAT
TATAGATACACCTACAAATGCCACAGGGGAGATTCCAAAGTGGAAGGAAAGAGAATGAAAATTATAAAGGAGCTATGGGA
AAACACTAAAGGAAGAGATGGTCTGTTAGTAGCAGATGGTGGGCCTAACATTTACAATTTGAGAAACTTGCATATCCCAG
AAATAGTATTAAAGTACAACCTAATGGACCCTGAATACAAAGGGCGGTTACTTCATCCTCAAAATCCCTTTGTAGGACAT
TTGTCTATTGAGGGCATCAAAGAGGCAGATATAACCCCAGCACATGGTCCAGTAAAGAAAATGGACTATGATGCGGTGTC
TGGAACTCATAGTTGGAGAACCAAAAGGAACAGATCTATACTAAACACTGATCAGAGGAACATGATTCTTGAGGAACAAT
GCTACGCTAAGTGTTGCAACCTTTTTGAGGCCTGTTTTAACAGTGCATCATACAGGAAACCAGTAGGTCAGCACAGCATG
CTTGAGGCTATGGCCCACAGATTAAGAATGGATGCACGACTAGATTATGAATCAGGAAGAATGTCAAAGGATGATTTTGA
GAAAGCAATGGCTCACCTTGGTGAGATTGGGTACATATAAGCTTCGAAGATGTCTATGGGGTTATTGGTCATCATTGAAT
ACATGCGGTACACAAATGATTAAAATGAAAAAAGGCTCGTGTTTCTACT (SEQ ID NO:12)

FIG. 16B

**Yamagata/1/73 PA *a1406g/c1445t/a2272t*;:**

AGCAGAAGCGGTGCGTTTGATTTGCCATAATGGATACTTTTATTACAAGAAACTTCCAGACTACAATAATACAAAAGGCC
AAAAACACAATGGCAGAATTTAGTGAAGATCCTGAATTACAACCAGCAATGCTATTCAACATCTGCGTCCATCTGGAGGT
CTGCTATGTAATAAGTGATATGAATTTTCTTGATGAAGAAGGAAAAGCATATACAGCATTAGAAGGACAAGGAAAAGAAC
AAAACTTGAGACCACAATATGAAGTGATTGAGGGAATGCCAAGAAACATAGCATGGATGGTTCAAAGATCCTTAGCCCAA
GAGCATGGGATAGAGACTCCAAGGTATCTGGCTGATTTGTTCGATTATAAAACTAAGAGGTTTATAGAAGTTGGAATAAC
AAAGGGATTGGCTGATGATTACTTCTGGAAAAAGAAAGAAAAGCTGGGGAATAGCATGGAACTGATGATATTCAGCTACA
ATCAAGACTATTCGTTAAGTAATGAATCCTCATTGGATGAGGAAGGAAAAGGGAGAGTGCTAAGCAGACTCACAGAACTT
CAGGCTGAGTTAAGTCTGAAAAATCTATGGCAAGTTCTCATAGGAGAAGAAGATATTGAAAAAGGAATTGACTTCAAACT
TGGACAAACAATATCTAAACTAAGGGATATATCTGTTCCAGCTGGTTTCTCCAATTTTGAAGGAATGAGGAGCTACATAG
ACAATATAGATCCTAAAGGAGCAATAGAGAGAAATCTAGCAAGGATGTCTCCCTTAGTATCAGTTACACCTAAAAAGTTG
AAATGGGAGGACCTAAGACCAATAGGGCCTCACATTTACAACCATGAGCTACCAGAAGTTCCATATAATGCCTTTCTTCT
AATGTCTGATGAATTGGGGCTGGCTAATATGACTGAAGGGAAGTCCAAGAAACCGAAGACCTTAGCCAAAGAGTGCCTAG
AAAAGTACTCAACACTACGGGATCAAACTGACCCAATATTAATAATGAAAAGCGAAAAAGCTAATGAACACTTCCTATGG
AAACTGTGGAGGGACTGTGTAAATACAATAAGTAATGAGGAAACAAGTAACGAATTACAGAAAACCAATTATGCCAAGTG
GGCCACAGGAGATGGATTAACATATCAGAAAATAATGAAAGAAGTAGCAATAGATGACGAAACAATGTACCAAGAAGAGC
CCAAAATACCTAACAAATGTAGAGTGGCTGCTTGGGTTCAAACAGAGATGAATCTATTGAGCACTCTGACAAGTAAAAGG
GCCCTGGATCTGCCAGAAATAGGGCCAGACGTAGCACCCGTGGAGCATGTAGGGAGTGAAAGAAGGAAATACTTTGTTAA
TGAAATCAACTACTGTAAGGCCTCTACCGTTATGATGAAGTATGTGCTTTTTCACACTTCATTATTAAATGAAAGCAATG
CCAGTATGGGAAAATATAAAGTAATACCAATAACCAACAGAGTAGTAAATGAAAAGGGAGAAAGTTTTGACATGCTTTAT
GGTCTAGCGGTTAAAGGGCAATCTCATCTGAGGGGAGATACTGATGTTGTAACAGTTGTGACTTTCGAATTTAGTAGTAC
AGATCCCAGAGTGGACTCAGGAAAGTGGCCAAAATATACTGTATTTAGAATTGGCTCCTTATTTGTGAGTGGGAGGGAAA
AATCTGTATACCTATATTGCCGAGTGAATGGTACAAATAAGATCCAAATGAAATGGGGAATGGAAGCTAGAAGATGTCTG
CTTCAATCAATGCAACAAATGGAAGCAATTGTTGAACAAGAATCATCGATACAAGGATATGACATGACCAAAGCTTGTTT
CAAGGGAGACAGAGTGAATAGTCCAAAAACTTTCAGTATTGGGACTCAAGAAGGAAAACTAGTGAAAGGATCCTTTGGGA
AAGCACTAAGAGTAATATTCACCAAATGTTTGATGCACTATGTATTTGGAAATGCCCAATTGGAGGGGTTTAGTGCCGAA
TCTAGGAGACTTCTACTGTTAATTCAGGCATTAAAAGACAGAAAGGGCCCTTGGGTATTCGACTTAGAGGGAATGTATTC
TGGAATAGAAGAATGTATTAGTAACAACCCTTGGGTAATACAGAGTGCATACTGGTTTAATGAATGGTTGGGCTTTGAAA
AAGAGGGGAGTAAAGTATTAGAATCAGTAGATGAAATAATGGATGAATGAAAGAAGGGCATAGTGCTCAATTTGGTACTA
TTTTGTTCATTATGTATCTAAACATCCAATATAAAGAATTGAGAATTAAAAATGCACGTGTTTCTACT (SEQ ID NO:13)

FIG. 16C

**Yamagata/1/73 NP P40S, *c500t*:**

AGCAGAAGCACAGCATTTTCTTGTGAACTTCAAGTACCAACAAAAACTGAAAATCAAAATGTCCAACATGGACATTGAC
GGCATCAACACTGGAATAATTGACAAAACACCAGAAGAAATAACTTCCGGAACCAGTGGGGCAACCAGACCAATCATCAG
ACCAGCAACCCTTGCCTCACCAAGCAACAAACGAACCAGAAACCCATCCCCGGAAAGGGCAACCACAAGCAGTGAAGCTG
ATGTCGGAAGGAAAACCCAAAAGAAACAAACTCCGACAGAGATAAAGAAGAGCGTCTACAATATGGTAGTGAAACTGGGT
GAATTCTACAACCAGATGATGGTCAAAGCTGGACTCAACGATGACATGGAGAGAAACCTAATCCAAAATGCACATGCTGT
GGAAAGAATTCTATTGGCTGCTACTGATGACAAGAAAACTGAATTCCAAAAGAAAAAGAATGCCAGAGACGTCAAAGAAG
GGAAAGAAGAAATAGACCATAACAAAACAGGAGGCACCTTTTACAAGATGGTAAGAGATGATAAAACCATCTACTTCAGC
CCTATAAGAATTACCTTTTTAAAAGAAGAGGTGAAAACAATGTACAAAACCACCATGGGGAGTGACGGTTTCAGTGGACT
AAATCACATCATGATTGGGCATTCACAGATGAACGATGTCTGTTTCCAAAGATCAAAGGCACTAAAAAGAGTTGGACTTG
ACCCTTCATTAATCAGTACTTTTGCAGGAAGCACACTCCCCAGAAGATCAGGTACAACTGGTGTTGCGACCAAAGGAGGT
GGAACTTTAGTGGCAGAAGCCATTCGATTTATAGGAAGAGCAATGGCAGACAGAGGGCTATTGAGAGACATCAGAGCCAA
GACGGCCTATGAAAAGATTCTTCTGAATCTGAAAAACAAGTGCTCTGCGCCCCAACAAAAGGCTCTGGTTGATCAAGTGA
TCGGAAGTAGAAATCCAGGGATTGCAGACATAGAAGATCTCACCCTGCTTGCTCGAAGTATGGTCGTTGTTAGGCCCTCT
GTAGCAAGCAAAGTGGTGCTTCCCATAAGCATCTATGCTAAAATACCTCAACTGGGGTTCAACGTTGAAGAATACTCTAT
GGTTGGGTATGAAGCCATGGCTCTTTATAATATGGCAACACCTGTTTCCATATTAAGAATGGGAGACGATGCAAAAGATA
AATCACAATTATTCTTCATGTCTTGCTTTGGAGCTGCCTATGAAGACCTAAGAGTTCTGTCTGCACTAACAGGCACGGAA
TTCAAGCCTAGGTCAGCATTAAAGTGCAAAGGTTTCCACGTTCCAGCAAAGGAGCAAGTGGAAGGAATGGGGGCAGCTCT
GATGTCCATCAAGCTCCAGTTTTGGGCTCCAATGACCAGATCTGGGGGGAATGAAGTAGGTGGAGACGGAGGGTCTGGTC
AAATAAGTTGCAGCCCCGTGTTTGCAGTAGAAAGACCTATTGCTCTAAGCAAGCAAGCTGTAAGAAGAATGCTGTCAATG
AATATTGAGGGACGTGATGCAGATGTCAAAGGAAATCTACTCAAGATGATGAATGATTCAATGGCTAAGAAAACCAATGG
AAATGCTTTCATTGGGAAGAAAATGTTCCAAATATCAGACAAAAACAAAACCAATCCCGTTGAGATTCCAATTAAGCAGA
CCATCCCCAGTTTCTTCTTTGGGAGGGACACAGCAGAGGATTATGATGACCTCGATTATTAAAGCAACAAAATAGACACT
ATGGCTGTGATTGTTTCAGTACGTTTGGAATGTGGGTGTTTACTCTTATTGAAATAAATGTAAAAAATGCTGTTGTTTCT
ACT (SEQ ID NO:14)

FIG. 16D

**Yamagata/1/73 NP P40S/M204T, *c500t:***

AGCAGAAGCACAGCATTTTCTTGTGAACTTCAAGTACCAACAAAAACTGAAAATCAAAATGTCCAACATGGACATTGAC
GGCATCAACACTGGAATAATTGACAAAACACCAGAAGAAATAACTTCCGGAACCAGTGGGGCAACCAGACCAATCATCAG
ACCAGCAACCCTTGCCTCACCAAGCAACAAACGAACCAGAAACCCATCCCCGGAAAGGGCAACCACAAGCAGTGAAGCTG
ATGTCGGAAGGAAAACCCAAAAGAAACAAACTCCGACAGAGATAAAGAAGAGCGTCTACAATATGGTAGTGAAACTGGGT
GAATTCTACAACCAGATGATGGTCAAAGCTGGACTCAACGATGACATGGAGAGAAACCTAATCCAAAATGCACATGCTGT
GGAAAGAATTCTATTGGCTGCTACTGATGACAAGAAAACTGAATTCCAAAAGAAAAAGAATGCCAGAGACGTCAAAGAAG
GGAAAGAAGAAATAGACCATAACAAAACAGGAGGCACCTTTTACAAGATGGTAAGAGATGATAAAACCATCTACTTCAGC
CCTATAAGAATTACCTTTTTAAAAGAAGAGGTGAAAACAATGTACAAAACCACCATGGGGAGTGACGGTTTCAGTGGACT
AAATCACATCATGATTGGGCATTCACAGACGAACGATGTCTGTTTCCAAAGATCAAAGGCACTAAAAAGAGTTGGACTTG
ACCCTTCATTAATCAGTACTTTTGCAGGAAGCACACTCCCCAGAAGATCAGGTACAACTGGTGTTGCGACCAAAGGAGGT
GGAACTTTAGTGGCAGAAGCCATTCGATTTATAGGAAGAGCAATGGCAGACAGAGGGCTATTGAGAGACATCAGAGCCAA
GACGGCCTATGAAAAGATTCTTCTGAATCTGAAAAACAAGTGCTCTGCGCCCCAACAAAAGGCTCTGGTTGATCAAGTGA
TCGGAAGTAGAAATCCAGGGATTGCAGACATAGAAGATCTCACCCTGCTTGCTCGAAGTATGGTCGTTGTTAGGCCCTCT
GTAGCAAGCAAAGTGGTGCTTCCCATAAGCATCTATGCTAAAATACCTCAACTGGGGTTCAACGTTGAAGAATACTCTAT
GGTTGGGTATGAAGCCATGGCTCTTTATAATATGGCAACACCTGTTTCCATATTAAGAATGGGAGACGATGCAAAAGATA
AATCACAATTATTCTTCATGTCTTGCTTTGGAGCTGCCTATGAAGACCTAAGAGTTCTGTCTGCACTAACAGGCACGGAA
TTCAAGCCTAGGTCAGCATTAAAGTGCAAAGGTTTCCACGTTCCAGCAAAGGAGCAAGTGGAAGGAATGGGGGCAGCTCT
GATGTCCATCAAGCTCCAGTTTTGGGCTCCAATGACCAGATCTGGGGGGAATGAAGTAGGTGGAGACGGAGGGTCTGGTC
AAATAAGTTGCAGCCCCGTGTTTGCAGTAGAAAGACCTATTGCTCTAAGCAAGCAAGCTGTAAGAAGAATGCTGTCAATG
AATATTGAGGGACGTGATGCAGATGTCAAAGGAAATCTACTCAAGATGATGAATGATTCAATGGCTAAGAAAACCAATGG
AAATGCTTTCATTGGGAAGAAAATGTTCCAAATATCAGACAAAAACAAAACCAATCCCGTTGAGATTCCAATTAAGCAGA
CCATCCCCAGTTTCTTCTTTGGGAGGGACACAGCAGAGGATTATGATGACCTCGATTATTAAAGCAACAAAATAGACACT
ATGGCTGTGATTGTTTCAGTACGTTTGGAATGTGGGTGTTTACTCTTATTGAAATAAATGTAAAAAATGCTGTTGTTTCT
ACT (SEQ ID NO:15)

FIG. 16E

Yamagata/1/73 M R77K:

AGCAGAAGCACGCACTTTCTTAAAATGTCGCTGTTTGGAGACACAATTGCCTACCTGCTTTCACTAACAGAAGATGGAGA
AGGCAAAGCAGAACTAGCGGAAAAATTACACTGTTGGTTCGGTGGGAAAGAATTCGATCTAGACTCTGCTTTGGAATGGA
TAAAAAACAAAAGATGCCTAACTGATATACAAAAAGCACTAATTGGTGCCTCTATCTGCTTTTTGAAACCCAAAGACCAA
GAAAGAAAAAGAAAATTCATCACAGAGCCCCTGTCAGGAATGGGAACAACAGCAACAAAAAAGAAAGGCCTGATTCTAGC
TGAAAGAAAAATGAGAAGATGTGTGAGTTTTCATGAGGCATTTGAAATAGCAGAAGGCCATGAAAGCTCAGCACTACTAT
ATTGTCTCATGGTCATGTACCTGAACCCTGGAAATTATTCAATGCAAGTAAAACTAGGAACGCTCTGTGCTTTATGCGAG
AAACAAGCATCACATTCACACAGAGCTCATAGCAGAGCAGCAAGATCTTCAGTGCCTGGAGTGAGGCGAGAAATGCAAAT
GGTTTCAGCTATGAACACAGCAAAAACAATGAATGGAATGGGGAAGGGAGAAGACGTCCAAAAACTGGCAGAAGAGCTGC
AAAGCAACATTGGAGTATTGAGATCTCTGGGGGCAAGTCAAAAGAATGGAGAAGGAATTGCAAAGGATGTAATGGAAGTG
CTAAAGCAGAGCTCCATGGGAAATTCAGCTCTTGTGAAGAAATACCTATAATGCTCGAGCCATTTCAGATTCTTTCAATT
TGCTCTTTCATTTTATCGGCTCTCCATTTCATGGGCTGGACAATAGGGCATTTAAATCAAATAAAAAGAGGAGTAAACCT
AAAAATACGAATAAGAAATCCAAATAAAGAGACAATAAATAGAGAGGTATCAATTTTGAGACACAGTTACCAAAAAGAAA
TCCAAGCCAAAGAAACAATAAAGGAAGTACTCTCTGACAACATGGAGAGATTGAGTGACCACATAGTAATTGAGGGGCTT
TCTGCTGAAGAGATAATAAAAATGGGTGAAACAGTTTTGGAGGTAGAAGAATTGCATTAAACCCAATTTTCACCGTATTT
CTTACTATGCATTTAAGCAAATTGTAATCAATGTCAGCAAATAAACTGGAAAAAGTGCGTTGTTTCTACT (SEQ ID NO:16)

FIG. 16F

Yamagata/1/73 M M86T:

AGCAGAAGCACGCACTTTCTTAAAATGTCGCTGTTTGGAGACACAATTGCCTACCTGCTTTCACTAACAGAAGATGGAGA
AGGCAAAGCAGAACTAGCGGAAAAATTACACTGTTGGTTCGGTGGGAAAGAATTCGATCTAGACTCTGCTTTGGAATGGA
TAAAAAACAAAAGATGCCTAACTGATATACAAAAAGCACTAATTGGTGCCTCTATCTGCTTTTTGAAACCCAAAGACCAA
GAAAGAAAAAGAAGATTCATCACAGAGCCCCTGTCAGGAACGGGAACAACAGCAACAAAAAAGAAAGGCCTGATTCTAGC
TGAAAGAAAAATGAGAAGATGTGTGAGTTTTCATGAGGCATTTGAAATAGCAGAAGGCCATGAAAGCTGAGCACTACTAT
ATTGTCTCATGGTCATGTACCTGAACCCTGGAAATTATTCAATGCAAGTAAAACTAGGAACGCTCTGTGCTTTATGCGAG
AAACAAGCATCACATTCACACAGAGCTCATAGCAGAGCAGCAAGATCTTCAGTGCCTGGAGTGAGGCGAGAAATGCAAAT
GGTTTCAGCTATGAACACAGCAAAAACAATGAATGGAATGGGGAAGGGAGAAGACGTCCAAAAACTGGCAGAAGAGCTGC
AAAGCAACATTGGAGTATTGAGATCTCTGGGGGCAAGTCAAAAGAATGGAGAAGGAATTGCAAAGGATGTAATGGAAGTG
CTAAAGCAGAGCTCCATGGGAAATTCAGCTCTTGTGAAGAAATACCTATAATGCTCGAGCCATTTCAGATTCTTTCAATT
TGCTCTTTCATTTTATCGGCTCTCCATTTCATGGGCTGGACAATAGGGCATTTAAATCAAATAAAAAGAGGAGTAAACCT
AAAAATACGAATAAGAAATCCAAATAAAGAGACAATAAATAGAGAGGTATCAATTTTGAGACACAGTTACCAAAAAGAAA
TCCAAGCCAAAGAAACAATAAAGGAAGTACTCTCTGACAACATGGAGAGATTGAGTGACCACATAGTAATTGAGGGGCTT
TCTGCTGAAGAGATAATAAAAATGGGTGAAACAGTTTTGGAGGTAGAAGAATTGCATTAAACCCAATTTTCACCGTATTT
CTTACTATGCATTTAAGCAAATTGTAATCAATGTCAGCAAATAAACTGGAAAAAGTGCGTTGTTTCTACT (SEQ ID NO.17)

FIG. 16G

**Yamagata/1/73 NS *a39g* K176Q :**

AGCAGAAGCAGAGGATTTGTTTAGTCACTGGCAAACGGGAAAAAATGGCGGACAACATGACCACAACACAAATTGAGGTG

GGTCCGGGAGCAACCAATGCCACTATAAACTTTGAAGCAGGAATTTTGGAGTGCTATGAAAGGCTTTCATGGCAAAGAGC

CCTTGACTACCCTGGTCAAGACCGCCTAAACAGACTAAAGAGAAAATTAGAATCAAGAATAAAGACTCACAACAAAAGTG

AGCCTGAAAGTAAAAGGATGTCTCTTGAAGAGAGAAAAGCAATTGGGGTAAAAATGATGAAAGTGCTCCTATTTATGAAC

CCATCTGCTGGAATTGAAGGGTTTGAGCCATACTGTATGAAAAATTCCTCCAATAGCAACTGCCCAAACTGCAATTGGGC

CGATTACCCTCCAACATCAGGAAAGTGCCTTGATGACATAGAAGAAGAACCGGAGAATGTTGATGACCCAACTGAAATAG

TATTAAGGGACATGAACAACAAAGATGCAAGGCAAAAGATAAAAGAGGAAGTAAACACTCAGAAAGAAGGGAAGTTCCGT

TTGACAATACAAAGGGATATACGTAATGTGTTGTCCTTGAGAGTGTTGGTAAACGGAACATTCCTCAAGCACCCTAATGG

ATACAAGTCCTTATCAACTCTGCATAGATTGAATGCATATGACCAGAGTGGAAGGCTTGTTGCTAAACTTGTTGCTACTG

ATGATCTTACAGTGGAGGATGAAGAAGATGGCCATCGGATCCTCAACTCACTCTTCGAGCGTTTTAATGAAGGACATTCA

AAGCCAATTCGAGCAGCTGAAACTGCGGTGGGAGTCTTATCCCAATTTGGTCAAGAGCACCGATTATCACCAGAGGAGGG

AGACAATTAGACTGGTTACGGAAGAACTTTATCTTTTAAGTAAAAGAATTGATGATAACATATTGTTCCACAAAACAGTA

ATAGCTAACAGCTCCATAATAGCTGACATGATTGTATCATTATCATTATTGGAAACATTGTATGAGATGAAGGATGTGGT

TGAAGTGTACAGCAGGCAGTGCTTGTGAATTTAAAATAAAAATCCTCTTGTTACTACT (SEQ ID NO:18)

FIG. 16H

**Yamagata/1/73 NS *38(+1)g*:**

AGCAGAAGCAGAGGATTTGTTTAGTCACTGGCAAACGGGAAAAAAATGGCGGACAACATGACCACAACACAAATTGAGGT
GGGTCCGGGAGCAACCAATGCCACTATAAACTTTGAAGCAGGAATTTTGGAGTGCTATGAAAGGCTTTCATGGCAAAGAG
CCCTTGACTACCCTGGTCAAGACCGCCTAAACAGACTAAAGAGAAAATTAGAATCAAGAATAAAGACTCACAACAAAAGT
GAGCCTGAAAGTAAAAGGATGTCTCTTGAAGAGAGAAAAGCAATTGGGGTAAAAATGATGAAAGTGCTCCTATTTATGAA
CCCATCTGCTGGAATTGAAGGGTTTGAGCCATACTGTATGAAAAATTCCTCCAATAGCAACTGCCCAAACTGCAATTGGG
CCGATTACCCTCCAACATCAGGAAAGTGCCTTGATGACATAGAAGAAGAACCGGAGAATGTTGATGACCCAACTGAAATA
GTATTAAGGGACATGAACAACAAAGATGCAAGGCAAAAGATAAAAGAGGAAGTAAACACTCAGAAAGAAGGGAAGTTCCG
TTTGACAATAAAAAGGGATATACGTAATGTGTTGTCCTTGAGAGTGTTGGTAAACGGAACATTCCTCAAGCACCCTAATG
GATACAAGTCCTTATCAACTCTGCATAGATTGAATGCATATGACCAGAGTGGAAGGCTTGTTGCTAAACTTGTTGCTACT
GATGATCTTACAGTGGAGGATGAAGAAGATGGCCATCGGATCCTCAACTCACTCTTCGAGCGTTTTAATGAAGGACATTC
AAAGCCAATTCGAGCAGCTGAAACTGCGGTGGGAGTCTTATCCCAATTTGGTCAAGAGCACCGATTATCACCAGAGGAGG
GAGACAATTAGACTGGTTACGGAAGAACTTTATCTTTTAAGTAAAAGAATTGATGATAACATATTGTTCCACAAAACAGT
AATAGCTAACAGCTCCATAATAGCTGACATGATTGTATCATTATCATTATTGGAAACATTGTATGAGATGAAGGATGTGG
TTGAAGTGTACAGCAGGCAGTGCTTGTGAATTTAAAATAAAAATCCTCTTGTTACTACT (SEQ ID NO:19)

FIG. 16I

INFLUENZA B VIRUS REPLICATION FOR VACCINE DEVELOPMENT

CROSS-REFERENCE TO RELATED APPLICATIONS

This application is a continuation of U.S. application Ser. No. 15/436,245, filed Feb. 17, 2017, which claims the benefit of the filing date of U.S. application Ser. No. 62/297,400, filed on Feb. 19, 2016, the disclosure of which is incorporated by reference herein.

STATEMENT OF GOVERNMENT RIGHTS

This invention was made with government support under HHSN272201400008C awarded by the National Institutes of Health. The government has certain rights in the invention.

BACKGROUND

Influenza B viruses are a major cause of respiratory disease in humans. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains (Park et al., 2004).

There are three general types of influenza viruses, Type A, Type B and Type C, which are defined by the absence of serological crossreactivity between their internal proteins. Influenza Type B viruses are further classified into two lineages based on antigenic and genetic differences of the glycoprotein HA.

The burden of human infections with influenza A and B viruses is substantial, and the impact of influenza B virus infections can exceed that of influenza A virus infections in some seasons. Over the past few decades, viruses of two influenza B virus lineages (Victoria and Yamagata) have circulated in humans, and both lineages are now represented in influenza vaccines, as recommended by the World Health Organization. Influenza B virus vaccines for humans have been available for more than half a century, yet no systematic efforts have been undertaken to develop high-yield candidates. On the basis of their antigenic properties, influenza viruses are divided into three types (influenza A, B, and C); however, only type A and B influenza viruses cause human health concerns. Influenza A viruses are further divided into 18 hemagglutinin (HA, the major viral antigen) and 11 neuraminidase (NA, the second viral antigen) subtypes that are referred to as H1-H18 and N1-N11, respectively. Influenza A viruses are responsible for annual epidemics (caused by antigenic escape variants possessing point mutations in the antigenic epitopes of HA) and occasional pandemics. Pandemics are caused by avian or avian/human/swine reassortant influenza viruses that encode an HA protein to which humans lack protective immune responses. The epidemiology of influenza B viruses differs from that of influenza A viruses. Influenza B viruses primarily circulate in humans and do not cause pandemics. Nevertheless, the impact of influenza B virus infections on influenza-related morbidity and mortality is substantial and has exceeded that of influenza A viruses in some seasons (Paul-Glezen et al., 2013; Tafalla et al., 2016; van de Sandt et al., 2015). Until 1983, only one influenza B virus lineage was circulating in humans. Since then, two lineages (Victoria, named after B/Victoria/2/1987, and Yamagata, named after B/Yamagata/16/1988) can be distinguished genetically and antigenically on the basis of their HA (Paul-Glezen et al., 2013; van de Sandt et al., 2015; Rota et al., 1990). Until 2000, one of these two lineages tended to dominate each season; however, since 2001 both influenza B virus lineages have been cocirculating in human populations each year (Belshe, 2010; Belshe et al., 2010).

Until recently, most influenza vaccines were trivalent: that is, they were comprised of influenza A strains of the H1N1 and H3N2 subtypes, and an influenza B virus strain. Two studies demonstrated that the recommended influenza B vaccine strain matched the dominant strain of the particular influenza season only half the time (Belshe, 2010; Ambrose et al., 2010). On the basis of these findings and the continuing cocirculation of Yamagata- and Victoria-lineage viruses, in 2012 the World Health Organization (WHO) recommended including influenza B viruses of both lineages in human influenza vaccines. Accordingly, most seasonal influenza vaccines are now quadrivalent.

Many influenza vaccines are generated by combining the HA and NA viral RNA (vRNA) segments of WHO-recommended vaccine strains with the remaining six vRNA segments of a "backbone" strain. For live attenuated influenza A and B vaccine viruses, virus backbones were developed in the 1960s (Maassab, 1969). Many inactivated influenza A virus vaccines are based on the A/Puerto Rico/8/34 (H1N1; PR8) virus backbone, which was selected because of its efficient replication in embryonated chicken eggs. For inactivated influenza B vaccines, the B/Lee/40, B/Panama/45/90, or wild-type strains have been used as backbones (www.who.int/influenza/vaccines/virus/recommendations/summary_b_vic_cvv_nh1516. pdf).

SUMMARY

The present invention relates to several mutations in the 'internal' genes of influenza B virus, as well as several mutations in the viral glycoproteins HA and NA of influenza B viruses, that enhance viral titers and/or HA yields in cultured cells and may also enhance viral titers and/or HA yields in embryonated chicken eggs. The exemplary reassortant or recombinant parental influenza B viruses represent the two major influenza B virus lineages (i.e., the 'B/Victoria' and 'B/Yamagata' lineages). Virus libraries were generated for each lineage, which libraries were then passaged in selected cells, and mutations were identified that enhanced viral growth. The use of one or more of these mutations in vaccine virus master strains (where the internal viral genes, the "backbone," are used with selected HA and NA, e.g., those of circulating strains or predicted to be circulating strains), result in higher virus titers in virus cultured in cells in vitro and/or embryonated chicken eggs, allowing more efficient influenza B virus growth, and more rapid and cost-effective vaccine production.

Several strategies may be employed (including random mutagenesis and the comprehensive testing of growth-enhancing mutations) to develop influenza B viruses, e.g., based on reassortant or recombinant B/Yamagata- and B/Victoria-viruses, with enhanced properties, e.g., viruses that replicate to high titers, e.g., $10^8$ PFU/mL or more, e.g., $5\times10^8$, $10^9$, $5\times10^9$ or $10^{10}$ PFU/mL in cultured cells and/or embryonated chicken eggs. As discussed herein, a number of growth-enhancing mutations (both amino acid and non-coding nucleotide substitutions) were identified that increase the yield of influenza B viruses. Individual growth-enhancing amino acid residues in an influenza B virus polypeptide or in non-coding nucleotide sequence(s) in an influenza B virus segment, may be combined with one or more other growth-enhancing residues in the same influenza virus polypeptide or non-coding nucleotides in the same viral segment(s), or with one or more other growth-enhancing residues and/or nucleotide substitution(s) in other influenza virus polypeptide(s) or viral segment(s), respectively, e.g., growth-enhancing nucleotides in promoter sequences or in nucleotides between promoter sequences and an open reading frame. In particular, virus libraries possessing random mutations in the six "internal" influenza B viral RNA segments (those not encoding the major viral antigens, hemagglutinin (HA) and neuraminidase NA)) were screened for mutants that confer efficient replication. Candidate viruses that supported high yield in cell culture were tested with the HA and NA genes of eight different viruses of the Victoria and Yamagata lineages. Combinations of mutations that increased the titers of candidate vaccine viruses in mammalian cells used for human influenza vaccine virus propagation were identified and used in embryonated chicken eggs, the most common propagation system for influenza viruses, were identified. These influenza B virus vaccine backbones can be used for improved vaccine virus production.

For example, one or more growth-enhancing residues in a NP protein, for instance, 1, 2, 3, or 4 or more, growth-enhancing residues in NP, 1, 2, 3, or 4 or more, growth-enhancing residues in a M protein (such as 1, 2, 3, or 4 growth-enhancing residues in BM2 or 1, 2, 3, or 4 growth-enhancing residues in M1), 1, 2, 3, or 4 or more growth-enhancing residues in PA, or 1, 2, 3, or 4 growth-enhancing residues in NS1, or growth-enhancing nucleotides in viral non-coding sequences of NP, PA, NS, or in other viral segments, may be combined when preparing influenza B viruses, e.g., for a vaccine, to enhance viral titers. In one embodiment, growth-enhancing nucleotides in non-coding sequences may be introduced to a viral segment, or when present in a viral segment may be selected for inclusion in an influenza B virus. In one embodiment, one or more, e.g., 1, 2, 3, 4 or 5 or more growth-enhancing residues in HA and/or in NA may be introduced into, or when present in a HA or NA selected for inclusion in, a HA viral segment or a NA viral segment in an influenza virus. In one embodiment, the one or more growth-enhancing residues may enhance viral growth by at least 1.2, 2, 2.8, 4, 3, 5, 6, 8, 10, 100, or 200 fold or more.

In one embodiment, this disclosure provides isolated recombinant, e.g., reassortant, influenza B viruses with selected amino acid residues at one or more specified positions (including those described herein) in one or more viral segments for PA, PB1, PB2, NP, M (encoding M1 and BM2 proteins), and/or NS (encoding NS1 and NS2 proteins), e.g., in selected amino acid residues at specified positions of, for example, M1 and BM2; M1, BM2, and NS1; NP; M1 and NS1; NP, M1 and BM2; NP and M1; NP, M1 and NS1; BM2 and NS1; BM2, NS1 and PA; M1, BM2 and PA; M1, BM2, NP and PA; and optionally also including growth-enhancing non-coding nucleotide substitution(s), and in one embodiment, including HA and NA genes/proteins of interest, e.g., from annual and pandemic strains, or HA and NA viral segments with selected amino acid residues described herein, which viruses are produced more efficiently and cost-effectively via cell culture (in MDCK or Vero cells) or in embryonated chicken eggs.

In one embodiment, the reassortant or recombinant influenza B virus has an amino acid residue at position 28, 40, 51, 52, 57, 204, and/or 343, in NP, and/or a nucleotide other than c at position 500 in NP vRNA, or any combination thereof, that results in enhanced growth in cells including MDCK cells, Vero cells and/or eggs relative to a corresponding virus with, for instance, an alanine, proline, proline, glutamic acid, serine, methionine or proline at position 28, 40, 51, 52, 57, 204 and 343, respectively, in NP, i.e., the residue at position 28, 40, 51, 52, 57, 204 or 343, respectively, in the NP segment in the recombinant influenza B virus is not an alanine, proline, proline, glutamic acid, serine, methionine or proline but is a residue that is correlated with enhanced replication in MDCK cells, Vero cells or eggs. The recombinant virus may also optionally include other selected amino acid residues at one or more specified positions in one or more of M1, BM2, PA, PB2, and/or NS1, such as those described herein, and optionally PB1. In one embodiment, the recombinant influenza B virus has an amino acid residue at position 28, 40, 51, 52, 57, 204, and/or 343 in NP that results in enhanced interaction with one or more host proteins in MDCK cells, Vero cells or eggs relative to a corresponding virus with, for instance, alanine, proline, proline, glutamic acid, serine, methionine or proline at position 28, 40, 51, 52, 57, 204, and/or 343, respectively, in NP. In one embodiment, the recombinant influenza B virus has growth-enhancing residues in NP including but not limited to a residue other than alanine at position 28, other than proline at position 40, other than proline at position 51, other than glutamic acid at position 52, other than serine at position 57, other than methionine at position 204, and/or other than proline at position 343, and/or a nucleotide other than g at nucleotide position 1795 (italics indicates a nucleotide; position is relative to positive sense cRNA), or any combination thereof. In one embodiment, the recombinant influenza B virus has threonine at position 28, serine at position 40, glutamine at position 51, lysine at position 52, glycine at position 57, threonine at position 214, and/or threonine at position 343 in NP, nucleotide a at nucleotide position 1795, and/or nucleotide t at nucleotide position 500 in NP vRNA, or any combination thereof, as well as optionally selected amino acid residues at one or more specified positions in M, PA, PB1, PB2, and/or NS viral segments.

In one embodiment, the reassortant or recombinant influenza B virus has an amino acid residue at position 34, 54, 77, 86, and/or 97 in M1 that results in enhanced growth in cells including MDCK cells, Vero cells or eggs relative to a corresponding virus with, for instance, glycine, aspartic acid, arginine, methionine or isoleucine at position 34, 54, 77, 86, or 97, respectively, in M1, i.e., the residue at position 34, 54, 77, 86, or 97, respectively, in M1 in the M segment in the recombinant influenza virus is not glycine, aspartic acid, arginine, methionine or isoleucine but is a residue that is correlated with enhanced replication in MDCK cells, Vero cells or eggs. The recombinant virus may also optionally include selected amino acid residues at one or more specified positions PA. BM2, PB2, NP, and/or NS1, such as those described herein, and optionally PB1. In one embodiment, the recombinant influenza B virus has an amino acid residue at position 34, 54, 77, 86, and/or 97 in M1 that results in enhanced interaction with one or more host proteins in MDCK cells, Vero cells or eggs relative to a corresponding virus with, for instance, glycine, aspartic acid, arginine, methionine or isoleucine at position 34, 54, 77, 86, or 97, respectively, in M1. In one embodiment, the recombinant influenza B virus has a valine or asparagine, glycine, lysine, threonine or asparagine at position 34, 54, 77, 86, or 97, respectively, in M1 as well as optionally selected amino acid residues at one or more specified positions NP, PA, PB1, PB2, and/or NS.

In one embodiment, the reassortant or recombinant influenza B virus has an amino acid residue at position 26, position 27, position 58, or position 80 in BM2 that results in enhanced growth in cells including MDCK cells, Vero cells or eggs relative to a corresponding virus with, for instance, glycine, histidine, histidine or arginine, at residue 26, 27, 58 or 80, respectively, in BM2. The recombinant virus may also optionally include as selected amino acid residues at one or more specified positions NS1, PA, NP, PB2, and/or M1 which are described herein. In one embodiment, the residue in BM2 at position 26 is arginine, at position 27 is arginine, position 58 is arginine, or position 80 is glycine.

In one embodiment, the reassortant or recombinant influenza B virus has an amino acid residue other than tyrosine at position 42, other than methionine at position 117, other than lysine at position 176, and/or other than serine at position 252, a nucleotide other than a at position 39, a nucleotide insertion after position 38, or any combination thereof, in NS1 that results in enhanced growth in cells including MDCK cells, Vero cells or eggs relative to a corresponding virus with, for instance, tyrosine at position 42, methionine at position 117, lysine at position 176, serine at position 252, or an a at position 39. The recombinant virus may also optionally include selected amino acid residues at one or more specified positions PA, PB2, BM2, NP, and/or M1, e.g., those which are described herein, and optionally PB1. In one embodiment, the recombinant influenza virus has asparagine at position 42, tyrosine at position 117, glutamine at position 176, threonine at position 252, a g at nucleotide position 39, an additional g after nucleotide position 38, or any combination thereof, in NS1, and optionally selected amino acid residues at one or more specified positions PA, PB2, BM2, NP, and/or M1 which are described herein.

In one embodiment, the reassortant or recombinant influenza B virus has an amino acid residue in PA other than tyrosine at position 387, other than valine at position 434, other than aspartic acid at position 494, other than threonine at position 524, and/or a nucleotide other than a at position 2272, a nucleotide other than g at position 2213, a nucleotide other than a at position 1406, and/or a nucleotide other than c at position 1445 in PA vRNA, or any combination thereof, that results in enhanced growth in cells including MDCK cells, Vero cells or eggs relative to a corresponding virus with, for instance, tyrosine at position 387, valine at position 434, aspartic acid at position 494, threonine at position 524, and/or a nucleotide a at position 2272, g at position 2213, a at position 1406, or c at position 1445, or any combination thereof. The recombinant virus may also optionally include selected amino acid residues at one or more specified positions NS1, BM2, NP, PB2, and/or M1, e.g., those which are described herein, and optionally PB1. In one embodiment, the recombinant influenza virus has histidine at position 387, alanine at position 434, or asparagine at position 494, alanine at position 534 in PA, and/or t at position 2272, a at position 2213, g at position 1406, and/or t at position 1445 in PA vRNA, or any combination thereof.

In one embodiment, the reassortant or recombinant influenza B virus has an amino acid residue in PB2 other than asparagine at position 16 that results in enhanced growth in cells including MDCK cells, Vero cells or eggs relative to a corresponding virus with, for instance, asparagine at position 16. The recombinant virus may also optionally include selected amino acid residues at one or more specified positions PA, NS1, BM2, NP, and/or M1, e.g., those which are described herein, and optionally PB1. In one embodiment, the recombinant influenza virus has serine at position 16 in PB2.

In one embodiment, the reassortant or recombinant influenza B virus has an amino acid residue in HA1 other than threonine at position 34, other than arginine at position 98, other than lysine at position 129, other than asparagine at position 168, other than asparagine at position 194, and/or other than threonine at position 196, and/or in HA2 a residue other than lysine at position 39, other than serine at position 56, other than lysine at position 61, or other than aspartic acid at position 112, or any combination thereof, that results in enhanced growth in cells including MDCK cells, Vero cells or eggs relative to a corresponding virus with, for instance, in HA1 threonine at position 34, arginine at position 98, lysine at position 129, asparagine at position 168, asparagine at position 194, and/or threonine at position 196, and/or in HA2 lysine at position 39, serine at position 56, lysine at position 61, aspartic acid at position 112. The recombinant virus may also include selected amino acid residues at one or more specified positions PA, BM2, PB2, NS1, NP, and/or M1, e.g., those which are described herein, and/or PB1. In one embodiment, the recombinant influenza virus has isoleucine at position, 34, glutamic acid at position 129, glutamic acid or aspartic acid at position 168, proline, alanine, isoleucine or asparagine at position 196, lysine at position 98, aspartic acid at position 194, glycine at position 39 (in HA2), glycine at position 56 (in HA2), asparagine at position 51 (in HA2), or glutamic acid at position 112 (in HA2), or any combination thereof.

In one embodiment, the reassortant or recombinant influenza B virus has an amino acid residue other than threonine (T) at position 76, other than arginine (R) at position 102, other than glutamic acid (E) at position 105, other than proline (P) at position 139, other than asparagine (N) at position 169, other than glycine (G) at position 434, other than threonine at position 436, and/or other than aspartic acid (D) at position 457, or any combination thereof, in NA that results in enhanced growth in cells including MDCK cells, Vero cells or eggs relative to a corresponding virus with, for instance, T at position 76, R at position 102, E at position 105, P at position 139, N at position 169, G at position 434, T at position 436, and/or D at position 457 in NA, which recombinant virus may also optionally include selected amino acid residues at one or more specified positions PA, PB2, BM2, NP, NS1, and/or M1, e.g., those which are described herein, PB1. In one embodiment, the recombinant influenza B virus has methionine (M) at position 76, lysine (K) at position 102, lysine (K) at position 105, serine (S) at position 139, threonine (T) at position 169, glutamic acid (E) at position 434, methionine (M) at position 436, and/or asparagine (N) at position 457, or any combination thereof.

In one embodiment, the invention provides an isolated recombinant reassortant influenza virus having six "internal" gene segments from a vaccine influenza virus with two or more of the selected amino acid residues at specified positions described herein, and a NA gene segment selected from a first influenza virus isolate, and a HA gene segment from the same isolate or a different isolate.

In one embodiment, the influenza virus of the invention is a recombinant influenza B virus having a particular amino acid residue at specified positions in one, two, three or more of PA, PB1, PB2, NP, M1 and/or NS1 and having an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6 (the internal genes of B/Yamagata/1/73), such as a polypeptide with other than A at position 28, other than P at position 40, other than P at position 51, other than E at position 52, other than S at position 57, other than M at position 204, and/or other than P at position 343, in NP and/or g at position 1795 or t at position 500 in NP vRNA, or any combination thereof; residue other than G at position 34, other than D at position 54, other than R at position 77, other than M at position 86, other than I at position 97, or any combination thereof, in M1; other than H at position 58, other than R at position 80, other than H at position 27, other than G at position 26, in BM2, e.g. R at position 58, G at position 80, R at position 27, and/or R at position 26 in BM2; other than Y at position 42, other than M at position 117, other than K at position 176, and/or other than S at position 252, in SN1 and/or a39g, an additional g after 38, in NS1 vRNA, or any combination thereof; other than N at position 16 in PB2; and/or other than Y at position 387, other than V at position 434, other than D at position 494, other than T at position 524, in PA and/or a2272t, g2213a, a1406g, and/or c1445t, in PA vRNA, or any combination thereof. The residue other than the specified residue may be a conservative substitution. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine. Non-conservative substitutions are also envisioned.

In one embodiment, the influenza B virus of the invention is a recombinant influenza B virus having a particular amino acid residue at specified positions in one, two, three or more of PA, NS1, M or NP which polypeptides have an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1 or 4-6, respectively. In one embodiment, the influenza B virus of the invention is a recombinant influenza B virus having a particular amino acid residue at specified positions in one or more of PA, PB1, PB2, NP, M1 and/or NS1 and an amino acid sequence with at least 80%, e.g., 90%, 92%, 95%, 97%, 98%, or 99%, including any integer between 80 and 99, contiguous amino acid sequence identity to a corresponding polypeptide encoded by one of SEQ ID Nos. 1-6, such as a polypeptide with a residue that is a conservative substitution.

Also included are any combination of the selected amino acid residues at specified positions described herein.

Viral segments for PA, NP, M and/or NS that have the residues at the specified positions may be combined with viral segment for PB1, a viral segment for PB2, a viral segment for HA, and a viral segment for NA, to provide the reassortant vaccine viruses of the invention. In one embodiment, the HA viral segment in the reassortant virus is heterologous to the viral segments for PA, PB1, PB2, NP, M and NS. In one embodiment, the NA gene segment in the reassortant virus is heterologous to the viral segments for PA, PB1, PB2, NP, M and NS. In one embodiment, the HA viral segment in the reassortant virus has viral segments for PA, PB1, PB2, NP, M and NS from one influenza virus isolate or strain ("parent"), or a variant thereof, e.g., one with viral segments encoding influenza virus proteins with at least 95%, 96%, 97%, 98%, 99%, or 99.5% amino acid sequence identity, or having 1, 2, 5, 10, or 20 substitutions relative, to sequences in a parent influenza virus isolate or strain. In one embodiment, the parent strain has viral segments with sequences corresponding to at least one of SEQ ID Nos. 1-6, and the recombinant virus has at least one of the viral segments with at least one of the substitutions in PA, NS, NP or M described herein, and at least one of the parental viral segments. In one embodiment, the HA gene segment in the reassortant virus is a chimeric HA gene segment, e.g., a chimera of heterologous HA ectodomain sequences linked to HA signal peptide sequences and/or HA transmembrane domain sequences from the HA gene segment of the parent isolate or strain, or variant thereof. In one embodiment, the NA gene segment in the isolated recombinant virus is a chimeric NA gene segment e.g., a chimera of heterologous NA ectodomain sequences linked to NA transmembrane domain sequences from the NA gene segment of the parent isolate or strain, or variant thereof, and/or stalk sequences from the parent isolate or strain, or variant thereof, for instance, chimeras of influenza B virus NA and influenza A virus NA. In one embodiment, the NA gene segment in the isolated recombinant virus is a chimeric NA gene segment e.g., a chimera of heterologous NA ectodomain sequences linked to NA transmembrane domain sequences from the NA gene segment of the parent isolate or strain, or variant thereof, and/or stalk sequences from a second isolate or strain, or variant thereof. In one embodiment, the isolated recombinant virus has a heterologous HA gene segment, a heterologous NA gene segment, a chimeric HA gene segment, a chimeric NA gene segment, or any combination thereof. The nucleic acid sequences employed to prepare vRNA or cRNA may be ones that introduce the residues at the specified positions via recombinant methodology or may be selected as having the residues at the specified positions.

As described herein, an influenza virus isolate useful as a vaccine virus (e.g., reassortants of B/Yamagata/1/73 with viruses of the B/Yamagata- or B/Victoria-lineage) to carry heterologous gene segments for NA and/or HA, was serially passaged in MDCK cells, e.g., about 10-12-times although fewer passages may be employed, to obtain virus with enhanced replication in those cells. In one embodiment, viruses obtained after serial passage which have enhanced replication, have titers that are at least 0.5 to 1 or 2 logs higher than viruses that were not serially passaged. In one embodiment, viruses obtained after serial passage had substitutions in two or more internal gene segments relative to the parent virus.

Thus, for vaccine viruses that are to be grown or passaged in cells in culture, e.g., MDCK or Vero cells or eggs, selection of sequences with, or replacement of, the disclosed residues at the specified positions in one or more of PA, BM2, NP, M1 and/or NS1, that confer enhanced growth of the virus in cultured cells when employed with HA and NA sequences of interest, can result in significantly higher viral titers. Thus, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are canine or primate, e.g., human or monkey, cells.

The invention provides a plurality of influenza virus vectors of the invention, e.g., those useful to prepare reassortant viruses including 6:1:1 reassortants, 6:2 reassortants and 7:1 reassortants. A 6:1:1 reassortant within the scope of the present invention is an influenza virus with 6 internal gene segments from a vaccine virus, a NA gene segment from a different (second) viral isolate, and a HA gene segment from a third isolate; a 6:2 reassortant within the scope of the present invention is an influenza virus with 6 internal gene segments from a vaccine virus, and a NA gene segment and a HA gene segment from a different (second) viral isolate; and a 7:1 reassortant within the scope of the present invention is an influenza virus with 6 internal gene segments and a NA gene segment from a vaccine virus, and a HA gene segment from a different viral source than the vaccine virus, or an influenza virus with 6 internal gene segments and a HA gene segment from the vaccine virus, and a NA gene segment is from a different viral source than the vaccine virus.

In one embodiment of the invention, the plurality includes vectors for vRNA or cRNA production selected from a vector comprising a promoter operably linked to an influenza virus PA DNA, e.g., cDNA, linked to a transcription termination sequence, a vector comprising a promoter operably linked to an influenza virus PB1 DNA, e.g., cDNA, linked to a transcription termination sequence, a vector comprising a promoter operably linked to an influenza virus PB2 DNA, e.g., cDNA, linked to a transcription termination sequence, a vector comprising a promoter operably linked to an influenza virus HA DNA, e.g., cDNA, linked to a transcription termination sequence, a vector comprising a promoter operably linked to an influenza virus NP DNA, e.g., cDNA, linked to a transcription termination sequence, a vector comprising a promoter operably linked to an influenza virus NA DNA, e.g., cDNA, linked to a transcription termination sequence, a vector comprising a promoter operably linked to an influenza virus M DNA, e.g., cDNA, linked to a transcription termination sequence, and a vector comprising a operably linked to an influenza virus NS DNA linked to a transcription termination sequence. In one embodiment, the DNAs for vRNA or cRNA production of PB1, PB2, PA, NP, M, and NS, have sequences from an influenza virus that replicates to high titers in cultured mammalian cells such as MDCK cells, Vero cells or PER.C6® cells and also optionally embryonated eggs, and/or from a vaccine virus, e.g., one that does not cause significant disease in humans. The DNA, e.g., cDNA, for vRNA or cRNA production of NA may be from any NA, and the DNA for vRNA or cRNA production of HA may be from any HA. In one embodiment, the DNAs for vRNA or cRNA production may be for an influenza A or C virus. The DNAs for vRNA or cRNA production of NA and HA may be from different strains or isolates (6:1:1 reassortants) or from the same strain or isolate (6:2 reassortants), or the NA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and BM2, HA or NA. The vectors encoding viral proteins may further include a transcription termination sequence.

Viruses that may provide the internal genes for reassortants within the scope of the invention include viruses that have high titers in MDCK cells, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in cells such as MDCK cells, e.g., titers of at least about $10^7$ PFU/mL, e.g., at least $10^8$ PFU/mL, or high titers in two of more of those host cells.

In one embodiment, the titers of the reassortant viruses of the invention in cells such as MDCK cells or Vero cells may be over 1 log, 2 logs, 3 logs, or greater, than titers of the corresponding virus without particular residues at the specified positions.

In one embodiment, the DNAs for the internal genes for PB1, PB2, PA, NP, M, and NS encode proteins with substantially the same activity as a corresponding polypeptide encoded by one of SEQ ID NOs:1-6. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97%, 98%, or 99%, including any integer between 80 and 99, contiguous amino acid sequence identity to, a polypeptide encoded by one of SEQ ID NOs:1-6. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 and, in one embodiment, also encodes a polypeptide having at least 80%, e.g., 90%, 92%, 95%, 97%, 98%, or 99%, including any integer between 80 and 99, contiguous amino acid sequence identity to a polypeptide encoded by one of SEQ ID NOs:1-6. In one embodiment, the influenza virus polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide encoded by one of SEQ ID NOs:1-6, and has a characteristic residue in one or more of PA, PB2, BM2, NP, M1, and/or NS1, relative to a polypeptide encoded by one of SEQ ID NOs:1-6. In one embodiment, the influenza virus polypeptide has one or more, for instance, 2, 3, 4, 5, 6, 7 or 8 conservative and/or nonconservative amino acid substitutions, relative to a polypeptide encoded by one of SEQ ID NOs:1-6.

The invention thus includes the use of isolated and purified vectors or plasmids, which express or encode influenza virus proteins, or express or encode influenza vRNA or cRNA, both native and recombinant vRNA or cRNA. The vectors may comprise influenza cDNA, e.g., influenza A, B or C DNA (see Fields *Virology* (Fields et al. (eds.), Lippincott, Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance, may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA or cRNA corresponding to the heterologous sequences of the vector.

The promoter in a vector for vRNA or cRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA, cRNA or virus protein expression vector may be the same or different relative to the promoter or any other vector. In one embodiment, the vector or plasmid which expresses influenza vRNA or cRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA or cRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA or cRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA or cRNA vector may be the same or different as the RNA polymerase II promoter in any other vRNA or cRNA vector. Similarly, each ribozyme sequence in each vRNA or cRNA vector may be the same or different as the ribozyme sequences in any other vRNA or cRNA vector. In one embodiment, the ribozyme sequences in a single vector are not the same.

In one embodiment, the invention provides a plurality of influenza virus vectors for a reassortant, comprising a vector for vRNA or cRNA production comprising a promoter operably linked to an influenza virus PA DNA, e.g., cDNA, linked to a transcription termination sequence, a vector for vRNA or cRNA production comprising a promoter operably linked to an influenza virus PB1 DNA, e.g., cDNA, linked to a transcription termination sequence, a vector for vRNA or cRNA production comprising a promoter operably linked to an influenza virus PB2 DNA, e.g., cDNA, linked to a transcription termination sequence, a vector for vRNA or cRNA production comprising a promoter operably linked to an influenza virus HA DNA, e.g., cDNA, linked to a transcription termination sequence, a vector for vRNA or cRNA production comprising a promoter operably linked to an influenza virus NP DNA, e.g., cDNA, linked to a transcription termination sequence, a vector for vRNA or cRNA production comprising a promoter operably linked to an influenza virus NA DNA, e.g., cDNA, linked to a transcription termination sequence, a vector for vRNA or cRNA production comprising a promoter operably linked to an influenza virus M DNA, e.g., cDNA, linked to a transcription termination sequence, and a vector for vRNA or cRNA production comprising a promoter operably linked to an influenza virus NS DNA, e.g., cDNA, linked to a transcription termination sequence, wherein the DNAs for PB1, PB2, PA, NP, NS, and M are from one or more influenza vaccine seed viruses and contain two or more of the characteristic residues at the specified position(s); and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus BM2, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:1-6, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:1-6. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus BM2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA or cRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as wet as a host cell contacted with the plurality of vectors or virus of the invention. In another embodiment, the invention includes contacting the cell with one or more vectors, either vRNA or cRNA or protein production vectors, prior to other vectors, either vRNA or protein production vectors. In one embodiment, the promoter for vRNA or cRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA or cRNA vector employed in the method is on a separate plasmid. In one embodiment, the vRNA or cRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

In one embodiment, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate cells.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., the virus may be administered separately, for instance, administered before and/or after, or in conjunction with, those anti-virals.

BRIEF DESCRIPTION OF THE FIGURES

FIG. 1A-G. Nucleotide sequences for B/Yamagata/1/1973 (SEQ ID NOs: 1-6, 9, and 10) and amino acid sequences for HA (SEQ ID NO: 7) and NA (SEQ ID NO: 8).

**P<0.01). The color of the asterisks indicates the comparison of the respective virus with the comparator virus (depicted in black).

FIGS. 13A-D. Luciferase activity in mini-replicon assay at 35° C. Effect of mutations in the NP protein or PA and NS vRNAs on viral polymerase activity. 293T (A) or MDCK (B) cells were transfected with protein expression plasmids for the polymerase proteins and wild-type or mutant NP, and with a plasmid transcribing a virus-like RNA that encodes luciferase. Luciferase activity was measured 48 hours later. In parallel, MDCK cells were transfected with the protein expression plasmids described above, and with wild-type or mutant virus-like RNA encoding luciferase and possessing the indicated mutations in the non-coding regions of the PA vRNA (C) or NS vRNA (D). Luciferase activity was measured 48 hours later. Data were obtained from three independent experiments; shown are average titers±s.d. Statistical significance was determined by using one-way ANOVA, followed by Dunnett's test (*p<0.05; **p<0.01).

Figure 14A:
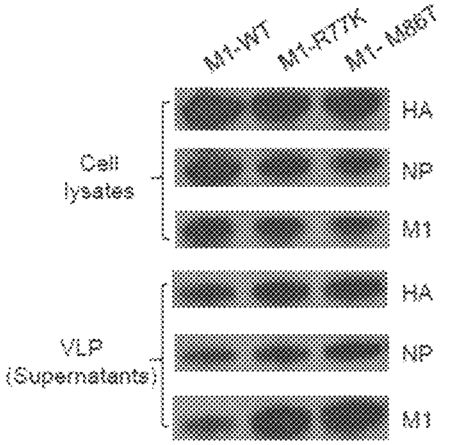
Figure 14B:
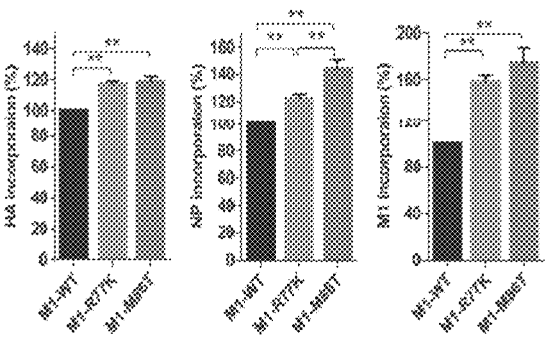

FIGS. 14A-B. Contribution of M1 mutations in HY backbones to HA, NP and M1 VLP incorporation and composition. 293T cells were transfected with protein expression plasmids for HA, NA, NP, BM2, NS2, and wild-type or mutant M1. At 48 hours post-transfection, cell lysates and VLPs in cell culture supernatants were Western blotted with anti-HA, anti-NP, and anti-M1 monoclonal antibodies (A). The intensity of the bands for HA, NP, and M1 was quantified by using ImageJ software (NH), and the relative percentages of HA, NP, and M1 in VLPs are shown in (B). Data were obtained from three independent experiments; shown are average titers±s.d. Statistical significance was determined by using one-way ANOVA, followed by Tukey's post hoc test (*p<0.05; **p<0.01).

Figure 15A:
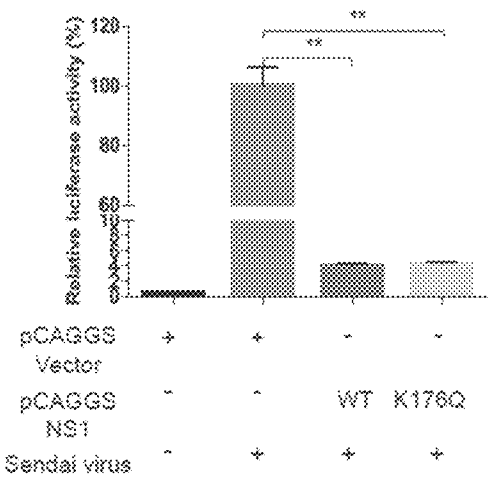
Figure 15B:
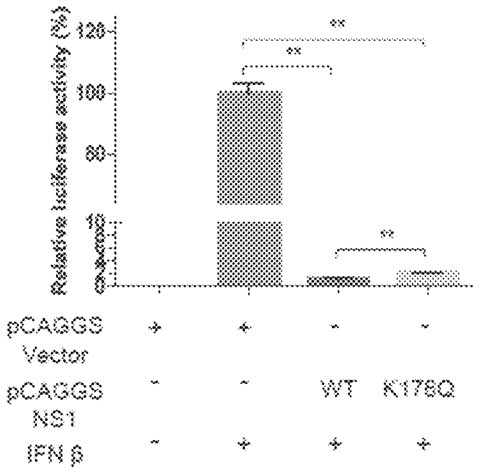

FIGS. 15A-B. Effect of NS1 mutation on IFN activity, A) To compare the ability of wild-type and mutant NS1 to interfere with IFN-β synthesis, 293T cells were transfected with a wild-type or NS1 protein expression plasmid and with the reporter plasmid pGL-IFN-β, which encodes the firefly luciferase protein under the control of the IFN-β promoter. Cells were incubated for 24 hours, infected with Sendai virus at an MOI of 5, again incubated for 24 hours, and then lysed to measure firefly luciferase. B) To determine the ability of wild-type and mutant NS1 to interfere with the synthesis of IFN-β-stimulated genes, 293T cells were transfected with a wild-type or mutant NS1 protein expression plasmid and with the reporter plasmid pISRE-Luc (which encodes the firefly luciferase protein under the control of an interferon-regulated promoter). Twenty-four hours later, cells were stimulated with human IFN-β. Forty-eight hours after transfection, we measured luciferase activity. Data were obtained from three independent experiments; shown are average titers±s.d. Statistical significance was determined by using one-way ANOVA, followed by Tukey's post hoc test (*p<0.05; **p<0.01).

FIG. 16A-I. Nucleotide sequences for viral segments in select HY clones (P132 and PB1 from Yamagata/1/73; SEQ ID Nos. 11-12); PA from Yamagata/1/73 having a1406g/c1445t/a2272t (SEQ ID NO:13); NP from Yamagata/1/73 having P40S, c500t (SEQ ID NO:14) or P40S/M204T, c500t (SEQ ID NO:15); M from Yamagata/1/73 having R77K (SEQ ID NO:16) or M86T (SEQ ID NO:17); and NS from Yamagata/1/73 having a39g K176Q (SEQ ID NO:18) or 38(+1)g, (SEQ ID NO:19).

DETAILED DESCRIPTION

Definitions

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (F) of 10, a cutoff of 100, M=5, N=−4, and a comparison of both strands. For amino acid sequences, the BLASTP program may use as defaults a wordlength (W) of 3, an expectation (F) of 10, and the BLOSUM62 scoring matrix. See http://www.ncbi.n1m.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza B Virus Structure and Propagation

Influenza B viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Influenza B Viruses of the Invention

Mutations that increase the replicative ability of viruses in cell culture and/or embryonated chicken eggs are useful to amplify influenza viruses and to establish robust influenza vaccine platforms. Currently, most influenza B vaccines are generated in embryonated chicken eggs. Influenza vaccines generated in MDCK cells are now approved for human use in the U.S. and in Europe, and influenza vaccines derived from Vero cells are approved for human use in Europe. As described herein, virus libraries possessing random mutations in the 'internal' viral genes (viral genes except those encoding the viral surface glycoproteins HA and NA) of a vaccine virus isolate, e.g., internal genes of B/Yamagata/1/73 with NA and HA genes from B/Yokohama/UT-K31/2012 (representing Yamagata-lineage) or NA and HA genes from B/Yokohama/UT-K1A/2011 (representing Victoria-lineage), were generated and passaged in cells, e.g., MDCK or Vero cells. The identified mutations result in higher virus titers in cells (that may also increase virus titers in heterologous cells and/or embryonated chicken eggs), allowing more efficient influenza B virus growth and more cost-effective vaccine production. In addition to mutations in the coding regions of the internal viral segments and viral glycoproteins, mutations in non-coding regions were observed to increase viral titers, e.g., g1795a in the NP segment, a39g in the NS segment, an additional g after position 38 in the NS segment, or g2213a or a2272t in the PA segment. The resulting coding sequences conferring enhanced growth may be also codon-usage optimized, e.g., optimized for expression in mammalian cells such as canine cells or primate cells, or avian cells, e.g., chicken embryos. The mutations can be used in various combinations, with results influenced by the cell line (or egg) in use and the desired level of improvement in the replication of the virus. One or more selected mutations may be introduced into one or more internal viral genes of a vaccine virus isolate, or one or more internal viral genes having one or more of the mutations may be selected for inclusion in a reassortant useful as a vaccine virus. That virus may then be combined with other viruses, e.g., one or more influenza A viruses and/or one or more other influenza B viruses, to form a multivalent vaccine.

Cell Lines that can be Used in the Present Invention

Any cell, e.g., any avian or mammalian cell, such as a human, e.g., 293T or PER.C6® cells, or canine, e.g., MDCK, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment; Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels theft level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into theft composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value, therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU), or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg per component for older children (greater than or equal to 3 years of age), and 7.5 μg per component for children less than 3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

Exemplary Embodiments

In one embodiment, the recombinant or reassortant influenza B virus has an amino acid that results in enhanced replication in MDCK cells, e.g., residues in HA including but not limited to a residue other than T at position 34, other than K at position 129, other than N at position 168, other than T at position 196, or any combination thereof; residues in NA including but not limited to a residue other than residue N at position 169, and/or other than G at position 434; residues in NP including but are not limited to a residue other than alanine (A) at position 28, other than P at position 40, other than P a position 51, other than E at position 52 other than S at position 57, other than M at position 204, other than g at nucleotide position 1795, or any combination thereof; residues in M1 including but not limited to a residue other than G at position 34, other than aspartic acid (D) at position 54, other than R at position 77, other than M at position 86; residues in BM2 including but not limited to a residue other than H at position 58 and/or other than R at position 80; residues in NS1 including but not limited to other than M at position 117, other than K at position 176, and/or other than S at position 252, a nucleotide other than a at position 39, or any combination thereof. In one embodiment, the recombinant influenza B virus has an amino acid that results in enhanced replication in MDCK cells, e.g., in HA1, residue I at position, 34, residue E at position 129, E, D at position 168, P, isoleucine (I), A or N at position 196, or any combination thereof; in NA, residue T at position 169 and/or residue E at position 434; in NP, residue T at position 28, residue S at position 40, residue Q at position 51, residue K at position 52, residue G at position 57, residue T at position 214, g at nucleotide position 1795, or any combination thereof; in M1 residue valine (V) or N at position 34, residue G at position 54, residue K at position 77, residue T at position 86, residue N at position 97, or any combination thereof; in BM2 include residue R at position 58 and/or residue G at position 80; in NS1 include residue tyrosine (Y) at position 117, residue glutamine (Q) at position 176, residue T at position 252, a g at nucleotide position 39, additional g after nucleotide position 38, or any combination thereof.

In one embodiment, the recombinant or reassortant influenza B virus has an amino acid that results in enhanced replication in Vero cells, e.g., residues in HA1 including but not limited to a residue other than R at position 98, other than N at position 194, and/or other than T at position 196, and/or in HA2 including but not limited to a residue other than K at position 39, other than S at position 56, other than K at position 61, or other than D at position 112, or any combination thereof; residues in NA including but not limited to a residue other than residue T at position 76, other than residue R at position 102, other than residue E at position 105, other than residue P at position 139, other than residue T at position 436, other than D at position 457, or any combination thereof; residues in NP including but not limited to a residue other than P at position 343; residues in M1 other than G at position 34, other than I at position 97, or any combination thereof; residues in BM2 other than H at position 58, other than R at position 80, other than H at position 27, other than G at position 26, or any combination thereof; residues in NS1 including but not limited to a residue other than Y at position 42; residues in PA other than Y at position 387, other than V at position 434, other than D at position 494, other than T at position 524, a nucleotide other than a at nucleotide position 2272, a nucleotide other than g at nucleotide position 2213, a residue in PB2 other than N at position 16; or any combination thereof. In one embodiment, the recombinant influenza B virus has an amino acid that results in enhanced replication in Vero cells, e.g., in HA, P, I, A or N at position 196 (in HA1), residue K at position 98 (in HA1), residue D at position 194 (in HA1), residue G at position 39 (in HA2) residue G at position 56 (in HA2), residue N at position 51 (in HA2), or residue E at position 112 (in HA2), or any combination thereof; in NA residue M at position 76, residue K at position 102, residue K at position 105, residue S at position 139, residue M at position 436, and/or residue N at position 457, or any combination thereof; in NP residue T at position 343; in M1 include residue V or N at position 34 and/or residue N at position 97; in BM2 residue R at position 58, residue G at position 80, residue R at position 27, residue R at position 26, or any combination thereof; in NS1 residue N at position; in PA residue H at position 387, residue A at position 434, residue N at position 494, residue A at position 534, g at nucleotide position 2272, a t at nucleotide position 2213; residue S at position 16 in PB2; or any combination thereof.

In one embodiment, for viruses related to B/Yamagata-lineage, the recombinant or reassortant influenza B virus has an amino acid in HA1 other than K at position 129, other than N at position 168, other than N at position 194, other than T at position 196, other than D at position 112, or any combination thereof; in NA other than T at position 76, other than R at position 102, other than E at position 105, other than P at position 139, other than G at position 434, other than T at position 436, other than D at position 457, or any combination thereof; in NP other than E at position 52, other than S at position 57, other than P at position 343, or any combination thereof; in M1 other than G at position 34, other than R at position 77, other than I at position 97, or in NP vRNA, a nucleotide other than c a position 500, or any combination thereof; in BM2 other than H at position 58, other than R at position 80, other than H at position 27, other than G at position 26, or any combination thereof; in NS1 other than M at position 117, other than S at position 252, and/or other than D at position 494 in PA, and/or a nucleotide other than a at position 2272, other than g at nucleotide position 2213, other than a at position 1406, and/or other than c at position 1445 in PA vRNA, or any combination thereof; in PB2 a residue other than N at position 16; or any combination thereof. In one embodiment, the recombinant influenza B virus has in HA1 E at position 129, D at position 168; P at position 196, D at position 194, in HA2 at position 112, or any combination thereof; in NA M at position 76, K at position 102, K at position 105, S at position 139, E at position 434, M at position 436, and/or N at position 457, or any combination thereof; in NP K at position 52, (3 at position 57, T at position 343, or any combination thereof; in M1 V or N at position 34, K at position 77, N at position 97, or any combination thereof; in BM2 R at position 58, G at position 80, R at position 27, R at position 26, or any combination thereof; in NS1 Y at position 117, T at position 252, or any combination thereof; in PA in N at position 494, t at position 2272, a at position 2213; in PB2 S at position 16; or any combination thereof.

In one embodiment, for influenza B viruses that are related to B/Victoria-lineage, the recombinant or reassortant influenza B virus has an amino acid in HA1 other than T at position 34, other than R at position 98, other than T at position 196, and/or in HA2 a residue other than K at position 39, other than S at position 56, other than K at position 61, or any combination thereof; in NA other than N at position 169 and/or other than D at position 457; in NP other than A at position 28, than P at position 40, other than P at position 51, other than M at position 204, or in NP vRNA a nucleotide other than g at position 1795 or other than c at position 500, or any combination thereof; in M1 other than D at position 54 and/or other than M at position 86; in BM2 other R at position 80; in NS1 other than V at position 42, other than K at position 176, nucleotide other than a at position 39; in PA other than V at position 387, other than V at position 434, other than T at position 524, or in PA vRNA a nucleotide other than a at nucleotide position 2272, a nucleotide other than g at nucleotide position 2213, a nucleotide other than a at position 1406, a nucleotide other than c at position 1445, or any combination thereof. In one embodiment, the recombinant influenza B virus has an amino acid has in HA I at position 34, P, I, A or N at position 196, K at position 98, and in HA2 G at position 39, residue G at position 56, residue N at position 61, or any combination thereof; in NA T at position 169 and/or N at position 457; in NP T at position 28, S at position 40, Q at position 51, T at position 204, a at position 1795, or any combination thereof; in M1 G at position 54 and/or T at position 86; in BM2 G at position 80; in NS1 N at position 42, Q at position 176, g at position 39, an additional g after position 38; in PA H at position 387, A at position 434, A at position 534, t at position 2272, a at position 2213, or any combination thereof.

In one embodiment, the recombinant or reassortant influenza B virus has one or more, e.g., 2, 3, 4, 5, 6, 7, 8, 9, 10 or more of the following: a residue other than V at position 387, other than V at position 434, other than D at position 494, other than T at position 524, a nucleotide other than a2272, g2213, a1406, c1445, or any combination thereof, in PA or PA vRNA, e.g., 2272t, 2213a, 1406g, 1445t, 387H, 434A, 494N, 524A, or any combination thereof (e.g., residue H at position 387, residue A at position 434, residue N at position 494, residue A at position 524, or any combination thereof); a residue other than T at position 34, other than R at position 98, other than K at position 129, other than N at position 168, other than N at position 194, and/or other than T at position 196, in HA1, other than K at position 39, other than S at position 56, other than K at position 61, or other than D at position 112, in HA2, e.g., in HA1 34I, K129E, 168D, 196P/I/A/N, 98K, or 194D, and in HA2 including 39G, 56G, 61N, or 112E, or any combination thereof; a residue other than residue T at position 76, other than residue R at position 102, other than residue E at position 105, other than residue P at position 139, other than residue N at position 169, other than G at position 434, other than residue T at position 436, and/or residue D at position 457 in NA, e.g., 169T, 434E, 76M, 102K, 105K, 139S, 436M, 457N, or any combination thereof; a residue other than H at position 58, other than R at position 80, other than H at position 27, other than G at position 26 in BM2, such as residue R at position 58, residue G at position 80, residue R at position 27, and/or residue R at position 26; other than A at position 28; other than P at position 40, other than P at position 51, other than E at position 52, other than S at position 57, other than M at position 204, and/or other than P at position 343, and/or g at position 1795, or any combination thereof, in NP, e.g., residue T at position 28, residue S at position 40, residue Q at position 51, residue K at position 52, residue G at position 57, residue T at position 214, residue T at position 343, or any combination thereof; residue other than G at position 34, other than D at position 54, other than R at position 77, other than M at position 86, other than I at position 97, or any combination thereof in M1, e.g., residue V or N at position 34, residue G at position 54, residue K at position 77, residue T at position 86, and/or residue N at position 97; in PB2 other than N at position 16. In one embodiment, the recombinant virus has M1 34V/I97N, BM2 58R/80G, NP 40S, NS1 86T.

In one embodiment, the influenza virus of the invention is a recombinant or reassortant influenza virus having two or more of selected amino acid residues at specified positions in one or more segments for PA, NP, M (M1 and BM2), and/or NS, which can be employed with HA and NA genes of interest. In one embodiment, the recombinant reassortant influenza virus has two or more of in NP, A28T, P40S, P51Q, E52K, S57G, M204T, and/or P343T, and/or g1795a; in M1, G34V/N, D54G, R77K, M86T, I97N; in BM2, H58R, R80G, H27R, G26R; in NS1, M117Y, K176Q, S252T, a39g, an additional g after 38, Y42N, in PA, a2272t, g2213g, Y387H, V434A, D494N, T524A; in PB2 N16S.

In one embodiment, the influenza virus of the invention is a recombinant or reassortant influenza virus having two or more of selected amino acid residues at specified positions in one or more of PA, BM2, NP, M1, and/or NS1, which can be employed with HA and NA genes of interest. For example, in one embodiment, the recombinant influenza B virus has M1 34V/I97N, BM2 58R/80G, NP 40S, M1 M86T, or has NP P40S or has NP E52K, or has a substitution in NP, M1, and optionally NS1 and BM2, as in clones 1-8 in Table 3 and substitutions in NP, M1, and optionally NS1, as in clones 1-8 in Table 4.

In one embodiment, the influenza virus of the invention is a recombinant or reassortant influenza virus having two or more of a1406g, c1445t, a2272t in PA vRNA, P40S or P40S/M204T in NP, c500t in NP vRNA, M77K or M86T, and a39g or 38(+1)g in NS vRNA, or K176 Q in NS, e.g., an influenza virus having PA a1406g/c1445t/a2272t, NP P40S, c500t, M R77K and NS a39g K176Q, or having PA a 1406g/c1445t/a2272, NP P40S/M204T, c500t, M M86T and NS 38(+1)g.

The invention will be described by the following nonlimiting examples.

EXAMPLE 1

The yield of vaccine viruses is important from an economic point of view. Even more important, the ability to produce high numbers of vaccine doses under tight timelines may save many lives during a virus outbreak. Mutations that increase the replicative ability of viruses in cell culture and/or embryonated chicken eggs are useful to amplify influenza viruses, and to establish robust influenza vaccine platforms. Currently, most influenza vaccines are generated in embryonated chicken eggs. Influenza vaccines generated in MDCK cells are now approved for human use in the U.S. and in Europe, and influenza vaccines derived from Vero cells are approved for human use in Europe.

To develop a high-yield influenza B virus backbone for growth of vaccine virus in these specific host cells, random mutagenesis of the internal genes of B/Yamagata/1/73 was conducted; the HA and NA genes of the mutant virus libraries were derived from B/Yokohama/UT-K31/2012 (Yamagata-lineage) or B/Yokohama-K1A/2011 (Victoria-lineage), representing the two major influenza B virus lineages. The virus libraries that were generated possessed random mutations in the 'internal' viral genes as well as those encoding the viral surface glycoproteins hemagglutinin (HA) and neuraminidase (NA), as well as non-coding mutation. Those that conferred improved growth, and this are vaccine virus candidates, were further evaluated. In particular, these vaccine virus candidates confer higher yield in commonly used propagation systems for influenza vaccine virus production: that is, embryonated chicken eggs, Madin-Darby canine kidney cells, and African green monkey (Vero) cells. These vaccine candidates could be used to improve the influenza B virus vaccine production process.

Materials and Methods

Cells. MDCK cells were grown in MEM containing 5% (vol/vol) newborn calf serum. Vero cells were maintained in MEM containing 10% (vol/vol) FBS. 293T human embryonic kidney cells were grown in DMEM supplemented with 10% (vol/vol) FBS.

Construction of Plasmids. The sequences of the eight viral RNAs of B/Yamagata/1/73 virus were used to design gBlocks Gene Fragments (Integrated DNA Technologies), which were amplified and joined by PCR; the resulting viral cDNAs were inserted into the RNA polymerase I vector pHH21 (Neumann et al., 1999). The vRNAs of the B/Yokohama/UT-K31/2012, B/Yokohama/UT-K1A/2011, B/Yokohama/P-2922/2005, B/Tokyo/UTE2/2008, B/Tochigi/UT-T1/2011, B/Massachusetts/2/2012, and B/Brisbane/60/2008 viruses were extracted from virus stocks by using the RNeasy Kit (Qiagen). The viral HA and NA genes were amplified with gene-specific oligonucleotides by using the One-Step RT-PCR Kit (Invitrogen), and the PCR-products were cloned into the pHH21 vector. The HA and NA genes of B/Yamagata/16/1988 were synthesized by PCR-amplification of joined gBlocks Gene Fragments, followed by cloning into pHH21. The type A/B chimeric HA and NA genes of B/Yokohama/UT-K31/2012, B/Yokohama/UT- K1A/2011, B/Massachusetts/2/2012 and B/Brisbane/60/2008 viruses were generated by overlapping PCRs.

Construction of Plasmid Libraries. One to four random mutations were introduced into each of the six internal genes of B/Yamagata/1/73 virus by error-prone PCR using the GeneMorph II Random Mutagenesis Kit. The randomly mutated PCR products were inserted into the pHH21 vector, and the diversity of the resulting plasmid libraries was confirmed by sequence analysis of at least 24 *Escherichia coli* colonies for each viral gene.

Virus Rescue and Virus Library Generation. Wild-type viruses and virus libraries possessing random mutations in the internal genes were generated with the help of reverse-genetics approaches (Neumann et al., 1999). Virus libraries were generated by transfecting 293T cells with a mutant plasmid library instead of the wild-type construct. Forty-eight hours later, supernatants from plasmid-transfected 293T cells were collected and amplified in MDCK cells to generate virus stock; the titers of the virus stocks were determined by using plaque assays in MDCK cells.

Evaluation of Viral Growth Kinetics. Wild-type or recombinant viruses were inoculated in triplicate into MDCK cells at a multiplicity of infection (MOI) of 0.001. After infection, cells were incubated with MEM/BBA medium with 0.6 μg/mL TPCK-trypsin. Supernatants were collected at the indicated time points and the virus titers were assessed by means of plaque assays in MDCK cells.

To analyze viral replication in embryonated chicken eggs, 10-day-old embryonated chicken eggs (four per virus) were inoculated with $1\times10^4$ pfu of virus and incubated them at 35° C. The allantoic fluids were collected at the indicated time points and virus titers were determined by use of plaque assays in MDCK cells.

The hemagglutination titers of viruses amplified in MDCK cells or embryonated chicken eggs were determined by using a hemagglutination assay. Briefly, 50 μL of virus sample was serially diluted twofold in 96-well U-bottom microtiter plates (Thermo Scientific) containing 50 μL of PBS per well. Next, 50 μL of 0.5% turkey red blood cells were added to each well, plates were incubated for 45 minutes at room temperature, and hemagglutination titers were calculated as the reciprocal value of the highest dilution at which agglutination occurred.

Virus Concentration and Purification. MDCK cells were grown in two 4-Layers Easy-Fill Cell Factories (Thermo Scientific) and infected with wild-type or high yield influenza B viruses at an MOI of 0.001 when the cells reached about 95% confluency. Cell-culture supernatants were harvested 48 hours later and clarified by centrifugation (3,500 rpm in a Beckman SX4750 rotor, 15 minutes, 4° C.). Viruses were pelleted by ultracentrifugation (18,500 rpm, 90 minutes at 4° C. in a Beckman Type 19 rotor), resuspended in 5 mL of PBS, and loaded onto 20-50% (wt/vol) continuous sucrose gradients which were centrifuged at 25,000 rpm for 90 minutes at 4° C. in a Beckman SW32 rotor. The virus-containing band was collected, diluted in PBS, and pelleted again by centrifugation (25,000 rpm, 90 minutes, 4° C., Beckman SW32 rotor). The virus pellet was resuspended in 400 μL of PBS, aliquoted, and stored at −80° C.

Total Protein Assay. Total protein yield of virus concentrates was determined by using the Pierce BCA protein assay kit (Thermo Scientific) according to the manufacturer's instructions.

Deglycosylation of Viral Proteins Using PNGase F. To remove sugar moieties, 10 μL of virus concentrate was denatured. The sample was then incubated at 37° C. for 20 hours with 2 μL of a one-tenth dilution of PNGase F enzyme (New England Biolabs) in the buffer provided by the manufacturer and with Nonidet P-40 at a final concentration of 1%.

SDS/PAGE. 2 μL of virus concentrate was mixed with PBS to a total volume of 10 μL and 2.5 μL of loading dye with 2% (vol/vol) β-mercaptoethanol (as reducing agent) was added, which mixture was heated to 95° C. for 5 minutes. Samples were then loaded onto NuPage 4-12% (wt/vol) Bris-Tris precast gels (Life technology), which were run at 150 V for 120 minutes using 1×Mes buffer (Bio-Rad), and then stained with SYPRO-Ruby (Sigma). Quantitation of protein amounts was carried out by using ImageJ software (NIH). The HA content was calculated by dividing the HA amount (calculated by summing the amounts of HA1 and HA2) by the sum of the amounts of HA1, HA2, NP, and M1, and multiplying this value by the amount of total viral protein.

Virulence Studies in Mice. Six-week-old female BALB/c mice (Jackson Laboratory) were anesthetized with isoflurane and inoculated intranasally with $10^6$ pfu of influenza B viruses in a volume of 50 μL. Five mice were infected per group; this sample size is adequate to detect large effects between groups. Mice were randomized and investigators were not blinded. Body weight changes and survival were monitored daily for 14 days. To assess virus replication in mice, 10 mice per virus were infected with $10^6$ pfu; on days 3 and 6 post-infection, five mice in each group were killed and virus titers in the lungs were determined by use of plaque assays in MDCK cells.

Genetic Stability Testing. To evaluate the genetic stability of the high-yield vaccine backbones, viruses possessing the HY(Yam) and HY(Vic) backbones combined with the HA and NA vRNAs of B/Yokohama/UT-K31/2012 and B/Yokohama/UT-K1A/2011, respectively, were passaged 10 times in MDCK cells at an MOI of 0.01. Viruses collected after each passage were sequenced by means of Sanger sequencing.

Minireplicon Assay. For the minireplicon assay, 293T cells and MDCK cells were transfected with 0.25 μg each of plasmids expressing the B/Yamagata/1/73 PB2, PB1, PA and NP proteins, together with 0.05 μg of pPolI-B/Yamagata/1/73-NS-Luc (which encodes the firefly luciferase gene under the control of the human RNA polymerase I promoter) or pPolIC250-B/Yamagata/1/73-NS-Luc (which encodes the firefly luciferase gene under the control of the canine RNA polymerase I promoter), respectively. Cells were cotransfected with 0.025 μg of pGL4.74(hRluc/TK) (an internal control to monitor transfection efficiency; Promega). The transfected cells were incubated at 35° C. for 48 hours, lysed, and assayed for luciferase activity by using the dual-luciferase system detector kit according to the manufacturer's protocol (Promega). The firefly luciferase expression levels were normalized to the Renilla luciferase activity. The data presented are the averages of three independent experiments±SD.

To investigate the significance of the mutations in the noncoding regions of the B/Yamagata/1/73 PA and NS1 vRNAs, cells were transfected as described above; however, pPolIC250-NP(0)Fluc(0) was replaced with a reporter construct in which the firefly luciferase gene was flanked by the wild-type or mutant noncoding regions of the PA or NS vRNAs, respectively. At 48 hours post-transfection, luciferase activity was measured as described above.

VLP Budding Assay. For the VLP budding assay, 2931 cells were transfected with 2 μg each of protein expression plasmids for wild-type or mutant B/Yamagata/1/73 M1, HA, NA, NP, BM2, and NS2. At 48 hours post-transfection, culture supernatant was harvested, clarified, loaded on a 20% (wt/vol) sucrose cushion, and ultracentrifuged at 60,000 rpm for 2 hours in a Beckman SW 60 Ti rotor; the pelleted VLPs were then resuspended in PBS overnight at 4° C. In parallel, we lysed the transfected cells with RIPA buffer.

Purified VLPs and cell lysates were separately mixed with 5×loading dye buffer and fractionated on NuPage 4-12% (wt/vol) Bris-Tris precast gels (Life Technology). The proteins were transferred to nitrocellulose membranes by using an iBlot dry blotting system (Invitrogen). The membranes were then blocked for 3 hours at room temperature with PBS with 0.05% Tween 20 (PBS-T) containing 5% (wt/vol) skimmed milk. Then, the membranes were incubated with monoclonal antibodies to B/Brisbane/60/2008 HA (1:1,000; my BioSource, MBS430175), or to influenza B virus NP (1:1,000; Abcam, ab47876) or M1 (1:2,000; Abcam, ab82608) protein overnight at 4° C. After four washes with PBS-T for 10 minutes each, the membranes were incubated with goat antimouse secondary antibodies conjugated with horseradish peroxidase (1:2,000; Life Technology) for 1 hour at room temperature. After four washes with PBS-T for 10 minutes each, the blots were developed by using lumi-light Western blotting substrate (Roche Applied Science) and visualized following autoradiography. Quantitation of protein amounts was carried out by using ImageJ software (NIH). To calculate the percentages of HA, NP, and M1 protein incorporation into VLPs, the following formula was used: (ratio of the amount of protein in the mutant VLP to the total amount of mutant protein (VLP+cell lysate)/ratio of the amount of protein in the wild-type VLP to the total amount of wild-type protein (VLP+cell lysate))×100.

IFN Antagonist Assays. To assess the IFN-antagonist activity of wild-type and mutant NS1 proteins, 293T cells were transfected with the NS1 protein expression plasmid and the reporter plasmid pGL-IFN-β, which encodes the firefly luciferase protein under the control of the IFN-β promoter (Bale et al., 2012). Twenty-four hours posttransfection, cells were infected with Sendai virus at an MOI of 5 for 1 hour. Cells were incubated for 24 hours and lysed with Glo lysis buffer (Promega); then, Steady-Glo assay buffer (Promega) was added and luciferase expression measured. In another set of experiments, 293T cells were transfected with wild-type or mutant NS1 protein expression plasmids and the reporter plasmid pISRE-Luc (Promega), which encodes the firefly luciferase protein under the control of an IFN-regulated promoter. Twenty-four hours later, cells were treated with 104 U/mL of human IFN-β for another 24 hours, followed by lysis and measurement of luciferase expression levels.

Statistical Analysis. Statistical analyses of the data were accomplished using the R software (www.r-project.org), v3.1. To compare multiple groups with measurements collected independently at several time points, a two-way ANOVA followed by Tukey's post hoc test was used. To compare measurements from multiple groups collected at a single time point, a one-way ANOVA followed by either Tukey's or Dunnett's post hoc test was used. To compare multiple groups with dependent measurements (e.g., viral growth curves in cell culture for which aliquots were collected from the same culture at different time points), a linear mixed-effects model to the data by using the R package NLME; the time, virus strains, and interaction between these two factors were considered. The R package PHIA was used to build a contrast matrix for comparing strains in a pairwise fashion at the same time point (e.g., group_1 vs. group_2 at 24 hours postinfection, group_1 vs. group_3 at 24 hours postinfection, group_2 vs. group_3 at 24 hours postinfection). Comparisons were performed individually; therefore, the final P values were adjusted by using Holm's method to account for multiple comparisons.

Raw data from growth curves were converted to the logarithmical scale before being analyzed; results were considered statistically significant for P (or adjusted P values)$<0.05$. Variance between groups was assessed by using Levene's test (which was similar for the groups being compared, with $P>0.05$).

Ethics and Biosafety. The experiments in mice followed the University of Wisconsin—Madison's Animal Care and Use Protocol. All experiments were approved by the Animal Care and Use Committee of the University of Wisconsin—Madison (protocol number V00806), which acknowledged and accepted both the legal and ethical responsibility for the animals, as specified in the Fundamental Guidelines for Proper Conduct of Animal Experiment and Related Activities in the Animal Welfare Act and associated Animal Welfare Regulations and Public Health Service Policy.

Results

Figure 2A:
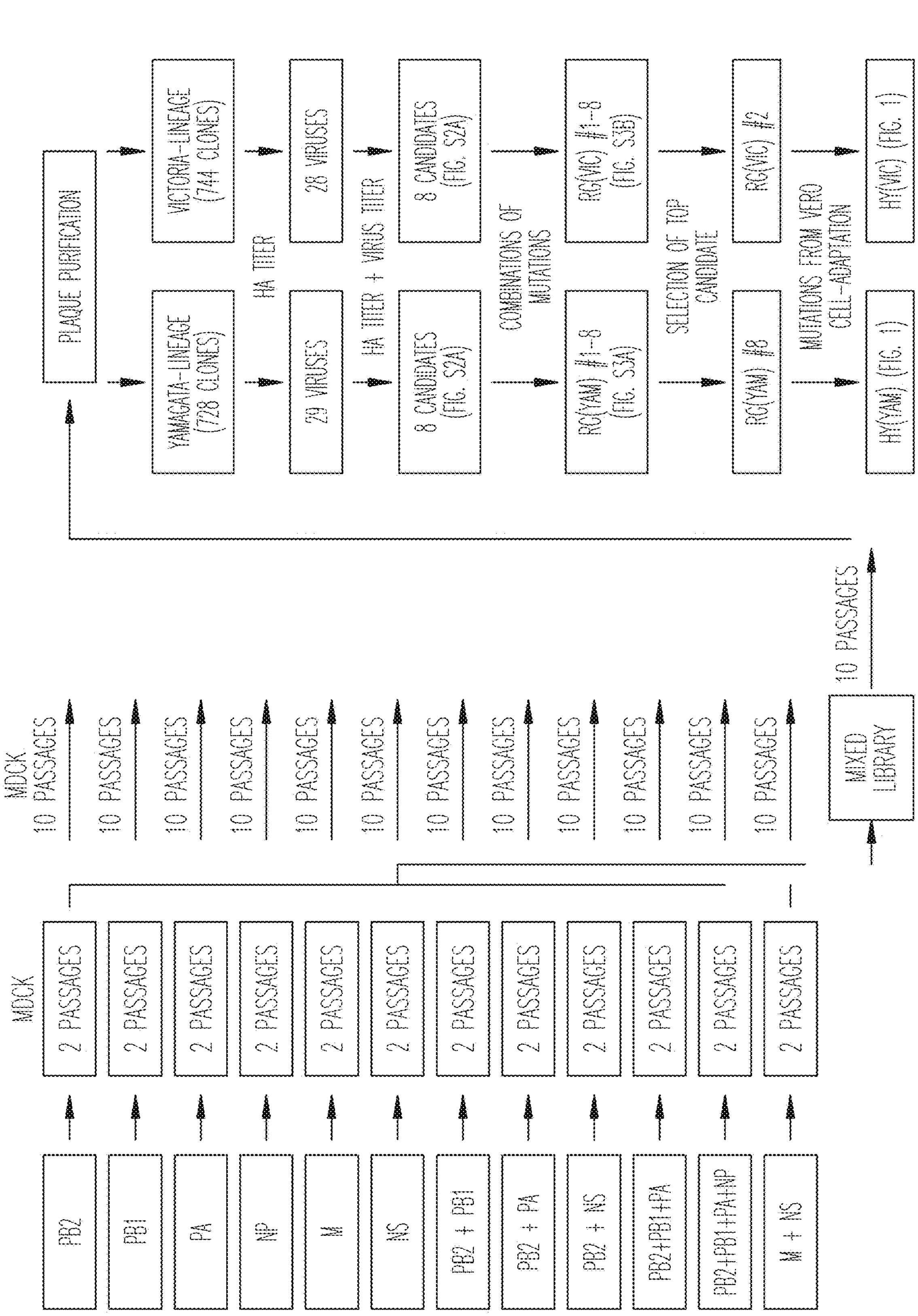
FIGS. 2A-B. Overview of library passages in MDCK cells and the identification of high-yield (HY) candidates (HY(Yam) and HY(Vic)). Yamagata- and Victoria-lineage virus libraries with random mutations in the indicated vRNAs were passaged twelve times in MDCK cells, or passaged twice, mixed, and passaged ten more times. More than 700 virus plaques were picked for each virus lineage. Based on hemagglutination and virus titers, the top eight candidates for each lineage were identified in a step-wise selection process. Testing of combinatorial mutations led to the selection of RG(Yam) #8 and RG(Vic) #2. The introduction of additional mutations (identified in virus library screens in Vero cells) resulted in the high-yield vaccine backbones HY(Yam) and HY(Vic). HA titer, hemagglutination titer.
Figure 2B:
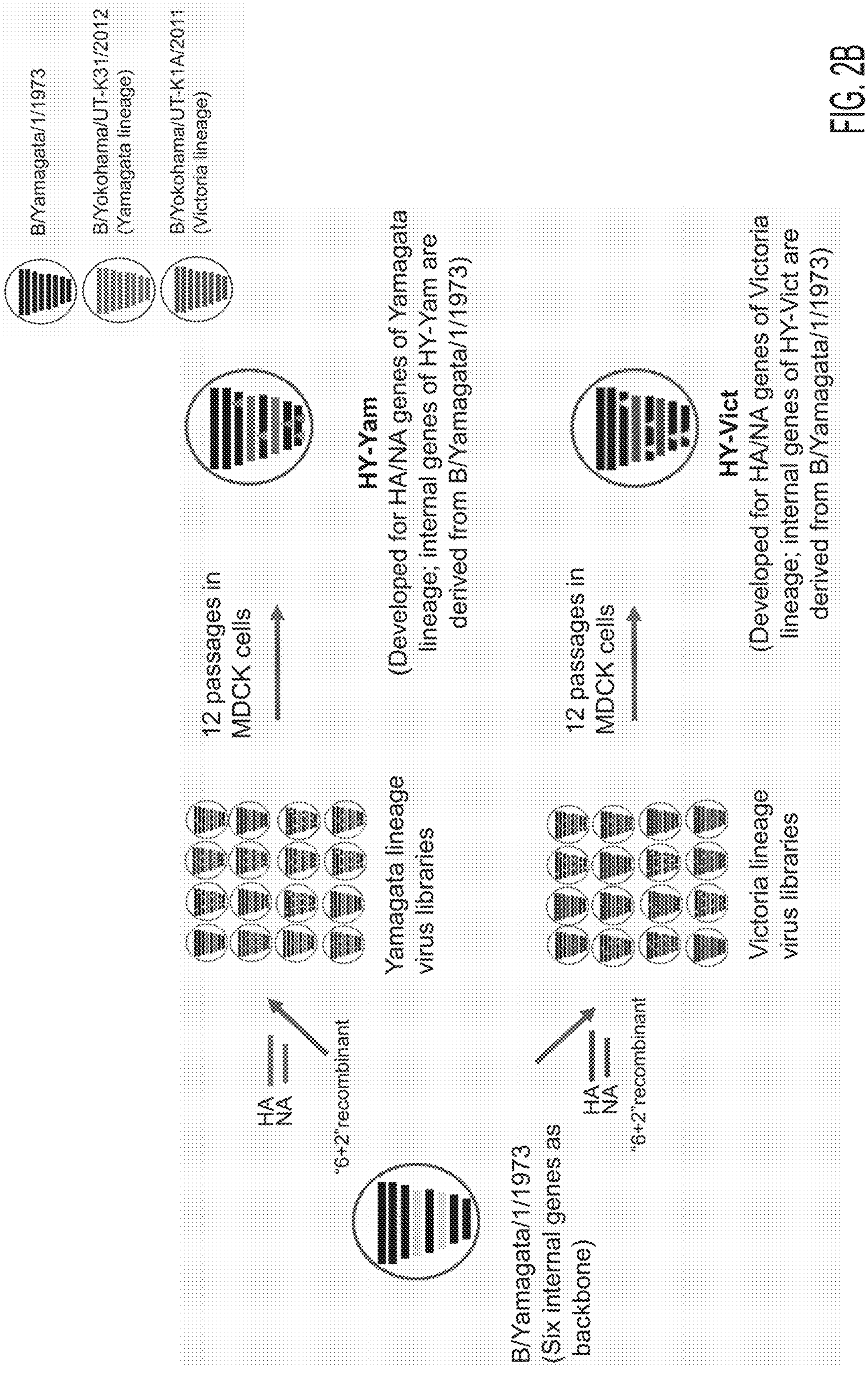

Virus Library Screens for High-Yield Variants in MDCK Cells. Comparable to a strategy to develop a high-yield influenza A virus PR8 vaccine backbone, mutagenesis and screening approaches were used to identify mutations associated with high yield of an influenza B virus. The six internal vRNA segments were from the B/Yamagata/1/73 virus, which grows efficiently in MDCK cells and was isolated before the Victoria and Yamagata lineages separated. A mutagenesis approach based on error-prone PCR was then used to generate libraries of cDNAs possessing one to four random amino acid changes in the viral proteins (FIG. 2). These cDNA libraries were then used to generate virus libraries. Six separate libraries representing each of the internal vRNAs (i.e., PB2, PB1, PA, NP, M, and NS) were generated (FIG. 2); three libraries for combinations of the polymerase vRNAs (i.e., PB2+PB1, PB2+PA, PB2+PB1+PA); one library for the polymerase and nucleoprotein (NP) vRNAs (i.e., PB2+PB1+PA+NP) because the PB2, PB1, PA, and NP proteins form the viral replication complex; one library for the PB2 and NS vRNAs (PB2+NS) because the PB2 and NS1 proteins (encoded by the NS vRNA) of influenza A viruses are important determinants of host virulence (Wright et al., 2013); and one library for the M and NS vRNAs because the M1 protein (encoded by the M vRNA) of influenza A viruses is associated with high-growth properties (Ramanunninair et al., 2013). Each of these 12 virus libraries was generated with the HA and NA vRNAs of a representative virus of the Victoria (B/Yokohama/UT-K1A/2011) or Yamagata (B/Yokohama/UTK31/2012) lineage, respectively, resulting in a total of 24 virus libraries. Libraries generated with the HA and NA vRNAs of the Victoria-lineage or Yamagata-lineage viruses will be referred to as "Victoria-lineage" or "Yamagata-lineage" libraries, respectively.

Figure 3A:
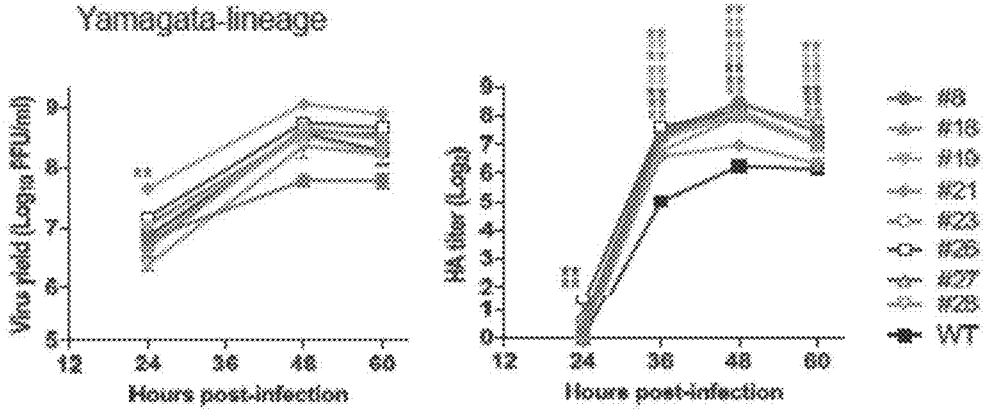
FIGS. 3A-B. Viral titers (growth kinetics) and hemagglutination (HA) titers for select high-yield candidates for the B/Yamagata-(A) and B/Victoria-(B) lineages. Viruses possessing high-yield vaccine backbones of the Yamagata-(A) and Victoria-lineages (B). Mutations detected in the candidate viruses are shown in Tables 1 and 2, respectively. Data were obtained from three independent experiments; shown are average titers±s.d. Statistical significance was determined by using the linear mixed model (*$p<0.05$; **$p<0.01$); P values are not shown if the titer of the high-yield vaccine candidate was lower than that of wild-type virus. The color of the asterisks indicates the comparison of the respective virus with WT virus.
Figure 3B:
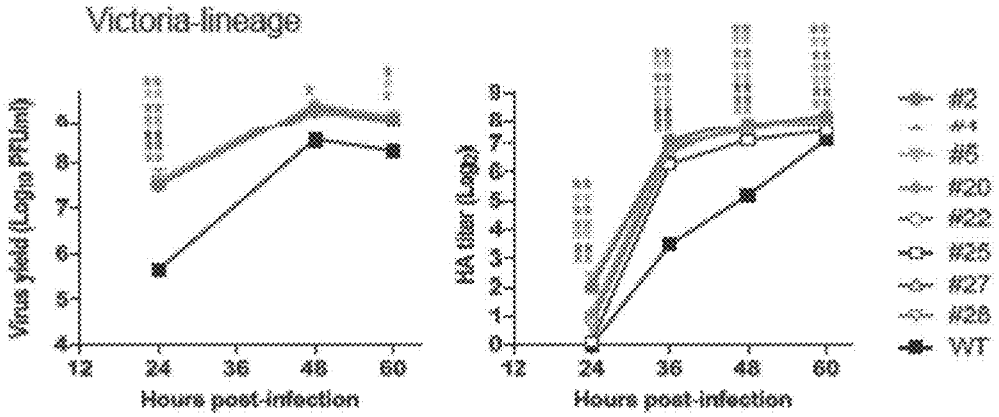

To select variants with enhanced growth properties, each library was passaged 12 times in MDCK cells. In parallel, virus libraries were combined after two passages in MDCK cells, and then 10 additional passages were performed in MDCK cells (FIG. 2). More than 700 viral plaques were randomly selected each from the Victoria- and Yamagata-lineage libraries, respectively, resulting in a total of 1,472 individual, plaque-purified viruses (FIG. 2). The plaque-purified viruses were then amplified in MDCK cells, and their yields were assessed in hemagglutination assays (as a surrogate for high HA yield) and compared with those of the parental Victoria- and Yamagata-lineage viruses (which possess the Victoria- or Yamagata-lineage lineage HA and NA vRNAs in combination with the six remaining vRNAs of B/Yamagata/1/73 virus). 29 Yamagata- and 28 Victoria-lineage viruses were identified with hemagglutination titers that were at least twofold higher than those of the respective control virus. These candidate viruses were reamplified in MDCK cells, and their high-yield properties were confirmed by assessing hemagglutination titers and replication kinetics in MDCK cells (used as another surrogate for high HA yield) (FIG. 3).

Next, the entire viral genomes of the top eight candidates of each lineage were sequenced and different sets of mutations were found for high-yield candidates of the Yamagata- and Victoria-lineages (amino acid changes and changes in the noncoding regions were evaluated) (Tables 1 and 2). Seven of the eight high-yield candidates isolated from the Yamagata-lineage libraries possessed G34V and I97N mutations in the M1 matrix protein, and H58R and R80G mutations in the BM2 ion channel protein (also encoded by the M gene) (Table 1), suggesting that these amino acid substitutions may confer efficient replication in MDCK cells.

All eight high-yield candidates obtained from the Victoria-lineage libraries encoded a P40S mutation in NP and an M86T mutation in M1 (Table 2). In addition, six of these eight high-yield candidates encoded nucleotide changes in the noncoding region of the NS vRNA: an additional nucleotide after position 38 was detected in five viruses (NS-38(+1)g; all nucleotide changes in noncoding regions are shown in italicized lowercase letters), and an a39g nucleotide replacement was detected in one virus (Table 2). A g1795a mutation was identified in the noncoding region of the NP segment in three high-yield candidates (Table 2).

Although the HA and NA vRNAs were not targeted by PCR-mediated random mutagenesis, several mutations were detected in the HA and NA proteins (Tables 1 and 2). Specifically, threonine at position 196 of HA was replaced with various other amino acids (e.g., alanine, isoleucine, proline, or asparagine) in seven of eight high-yield candidates derived from the Victoria-lineage libraries (Table 2), suggesting strong selective pressure at this position.

Figure 4A:
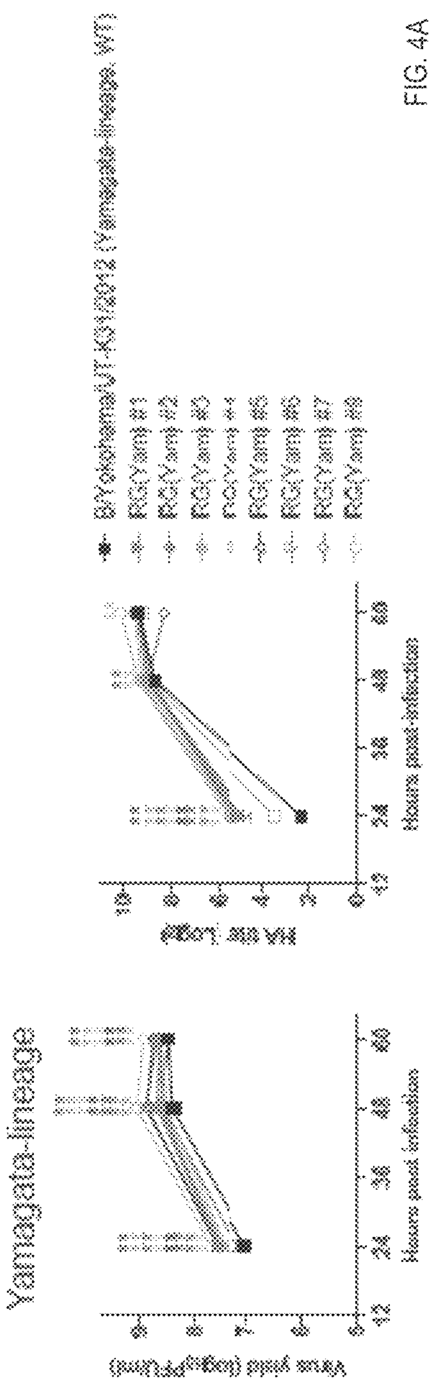
FIGS. 4A-B. Viral titers and HA titers for regenerated high-yield candidates for the B/Yamagata-(A) and B/Victoria-(B) lineages. Mutations introduced into the Yamagata-(A) and Victoria-lineage (B) viruses are shown in Tables 3 and 4, respectively. Data were obtained from three independent experiments; shown are average titers±s.d. P values were calculated by using the linear mixed model (*$p<0.05$; **$p<0.01$); P values are not shown if the titer of the high-yield vaccine candidate was lower than that of wild-type virus. The color of the asterisks indicates the comparison of the respective virus with WT virus.
Figure 4B:
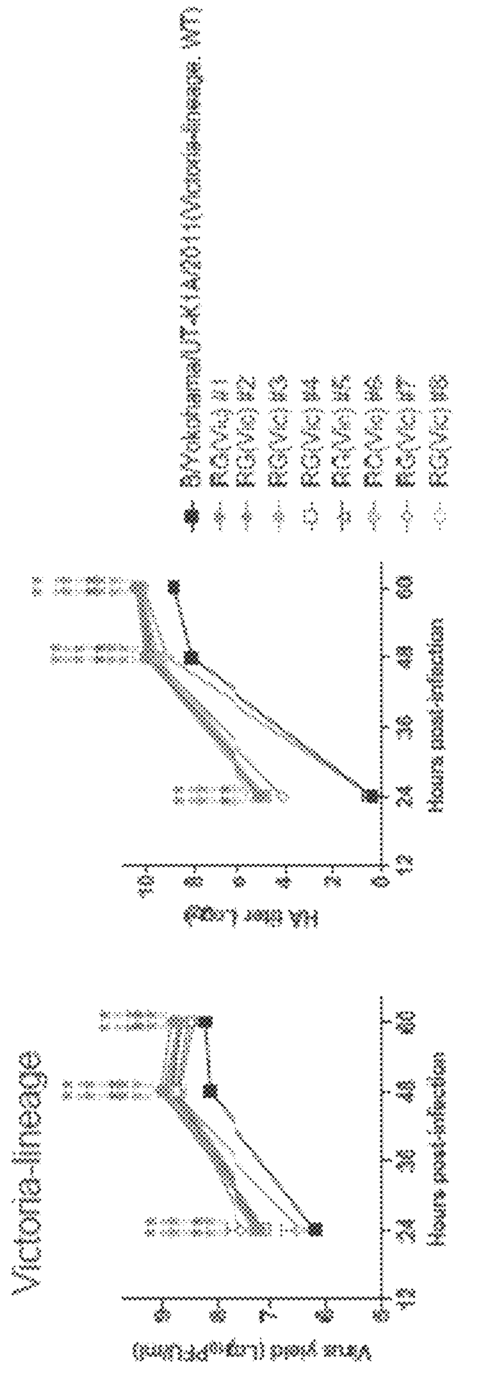

Potential Combinatorial Effects of Mutations. Next, reverse-genetics approaches were used to generate viruses possessing various combinations of the mutations found in the top eight high-yield Yamagata- or Victoria-lineage candidates (Tables 3 and 4). For example, the NP-E52K and M1-R77K mutations found in high-yield candidate #21 (which replicated to the highest titers in MDCK cells) (FIG. 3) were combined with the NS1-M117Y/S252T mutations found in high-yield candidates #23 and #26 (FIG. 3). Because the internal vRNAs of the Yamagata- and Victoria-lineage libraries are derived from the same virus, mutations found in high-yield Yamagata- and Victoria-lineage candidates were also combined (Tables 3 and 4). The resulting viruses were tested for their hemagglutination titers and viral titers in MDCK cells (FIG. 4). All high-yield Yamagata- and Victoria-lineage candidates replicated in MDCK cells more efficiently and had higher hemagglutination titers than the wild-type viruses at one or more time points, and most of these differences were statistically significant (FIG. 4).

Yamagata-lineage RG(Yam) #8 (encoding NP-P40S, M1-R77K, NS1-K176Q, and NS-a39g mutations) and Victoria-lineage RG(Vic) #2 (encoding NP-P40S/M204T, M1-M86T, and NS-38 (+1)g mutations) were selected as lead candidate vaccine backbones because they had the highest titers in their respective groups.

Virus Library Screens for Hitch-Yield Variants in Vero Cells. The ideal vaccine virus backbone should confer a high yield in all three propagation systems currently used in the commercial production of human influenza vaccines: that is, MDCK cells, Vero cells, and embryonated chicken eggs. In parallel to the development of a high-yield influenza B vaccine backbone in MDCK cells, all 24 virus libraries (FIG. 2) were passaged in Vero cells. Because the titers of influenza B virus libraries were low in Vera cells, first the libraries were passaged in cocultured MDCK and Vero cells five times, followed by five passages in Vero cells. In parallel, virus libraries were combined after two passages in cocultured MDCK and Vero cells, passaged three more times in cocultured cells, and then passaged five times in Vero cells. A total of 382 individual virus plaques were randomly picked from the various virus libraries and amplified in Vero cells. Based on the results of hemagglutination assays, the top six candidates were picked from the Yamagata and Victoria lineage, Vero cell-passaged libraries and determined their full genomic sequences (Tables 5 and 6).

The high-yield candidates possessed several of the mutations that were identified after the MDCK cell passages, which may have been selected in the MDCK cells during the passages in cocultured cells. These mutations include amino acid changes at positions M1-34/97, BM2-58 or -80, and HA1-196 (compare Tables 1 and 2 with Tables 5 and 6). The mutations at positions M1-34/97 and BM2-58 were only detected in the Yamagata-lineages libraries, whereas mutations at position BM2-80 occurred in both the Yamagata- and Victoria-lineage viruses. The mutation at position HA1-196 predominated among viruses of the Victoria lineage, but also occurred in one virus of the Yamagata lineage. In addition, mutations not previously found after passages in MDCK cells were observed, most notably an a2272t nucleotide replacement in the noncoding region of PA, which was found in high-yield candidates of both virus lineages (Tables 5 and 6).

Selection of High-Yield Yamagata- and Victoria-Lineage Vaccine Virus Candidates. Next, it was tested whether the PA-a2272t mutation found after the Vero cell passages would enhance the growth properties of RG(Yam) #8 and/or RG(Vic) #2. The resulting viruses (HY(Yam) and HY(Vic), respectively) displayed higher hemagglutination and virus titers in MDCK cells compared with RG(Yam) #8 and RG(Vic) #2, and compared with the parental Yamagata- and Victoria-lineage viruses; some of these differences were small (although statistically significant). Therefore, HY(Yam) (encoding NP-P40S, M1-R77K, NS1-K176Q, NS-a39g, PA-a2272t) and HY(Vic) (encoding NP-P40S/M204T, M1-M86T, NS-(38+1)g, PA-a2272t) were selected as lead high-yield candidates.

Evaluation of High-Yield Vaccine Virus Backbones with Different Influenza B Virus HA and NA Genes. HY(Yam) and HY(Vic) were developed with the HA and NA genes of B/Yamagata/UT-K31/2012 and B/Yokohama/UT-K1A/2011, respectively. Because high-yield vaccine virus backbones should have a general growth-enhancing effect, the HY(Yam) and HY(Vic) vaccine virus backbones with the HA and NA genes of six influenza B viruses isolated over several decades, including WHO-recommended vaccine viruses, were tested (FIG. 7). At one or more time points tested, the HY(Yam) and HY(Vic) vaccine virus backbones conferred higher viral or hemagglutination titers compared with the parental viruses, although not all of the differences were statistically significant. For the viruses tested, HY(Vic) had a greater growth-enhancing effect than HY(Yam).

Exchange of HY(Yam) and HY(Vic) Backbones. Next, it was tested whether the HY(Yam) and HY(Vic) backbones supported efficient replication of viruses possessing HA and NA genes derived from the other influenza B virus lineage (FIG. 8). High viral and hemagglutination titers were detected for HY(Yam) viruses encoding Victoria-lineage HA and NA genes, and for HY(Vic) viruses encoding Yamagata-lineage HA and NA genes. Overall, the HY(Yam) vaccine backbone resulted in slightly higher virus or hemagglutination titers than the HY(Vic) vaccine backbone at several time points, but most of these differences were not statistically significant. These data indicate that the HY(Yam) and HY(Vic) vaccine backbones confer efficient replication to viruses of both lineages.

Figure 5:
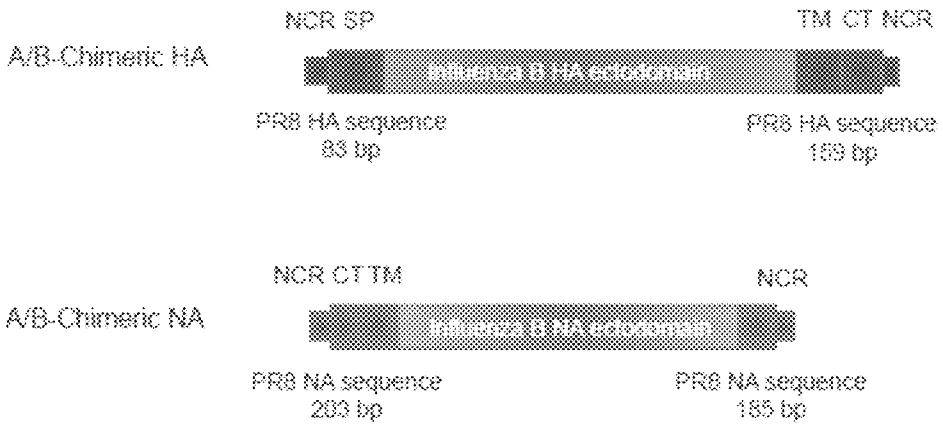
FIG. 5. Chimeric HA and NA constructs. The ectodomains of the influenza B virus HA (green) and NA (blue) proteins were inserted between the remaining sequences of the influenza A virus PR8 HA (purple) and NA (dark orange) vRNAs. Wide bars indicate coding regions; small bars indicate non-coding regions (NCRs). SP, signal peptide; TM, transmembrane domain; CT, cytoplasmic tail.
Figure 9A:
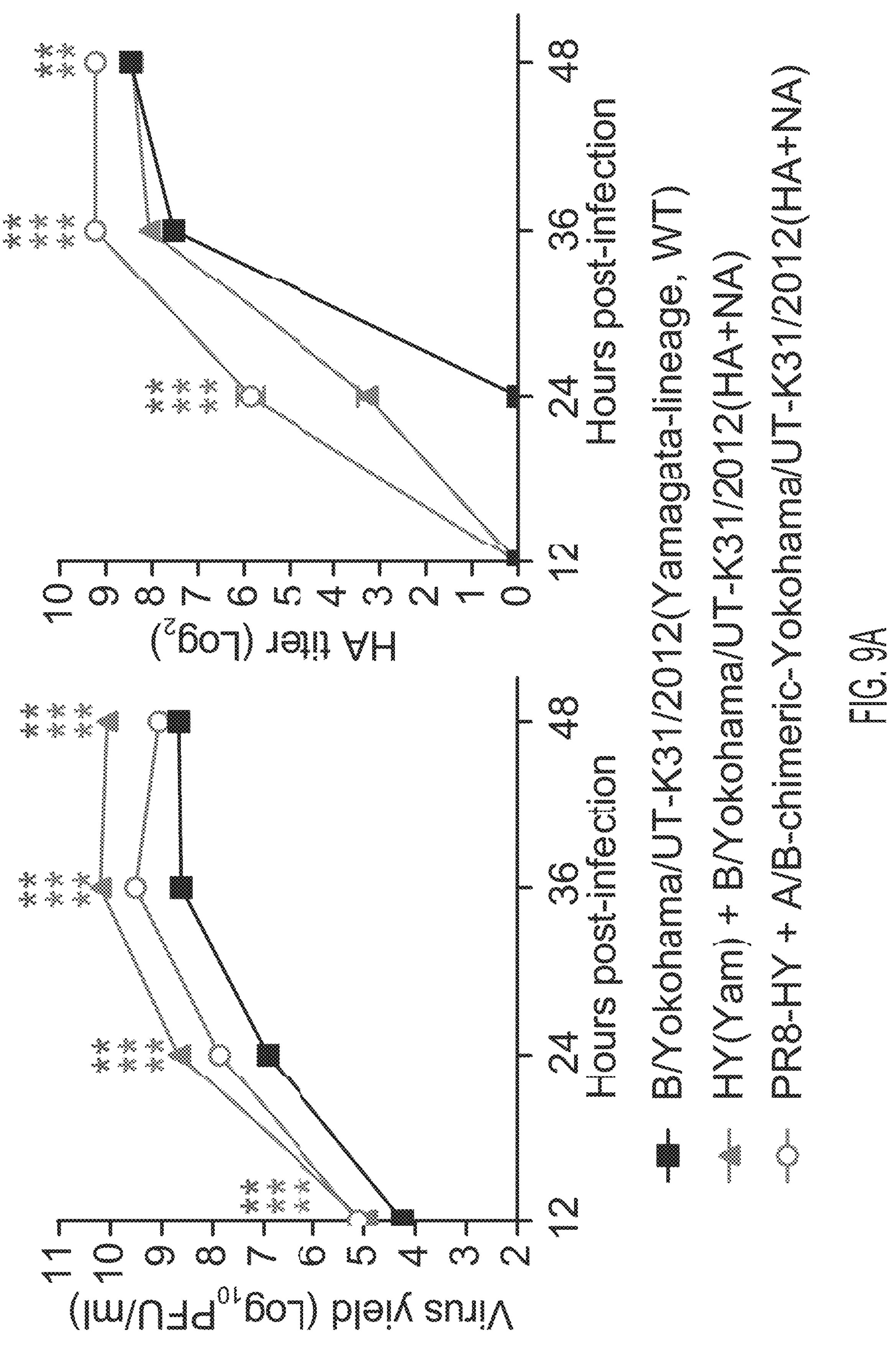
FIGS. 9A-F. Comparison of high-yield influenza A and B vaccine virus backbones. (A and B). The virus yield and hemagglutination titers of: (i) the indicated wild-type viruses; (ii) viruses possessing the indicated HA and NA vRNAs in combination with the internal genes of HY(Yam); and (iii) viruses possessing the indicated type A/B chimeric HA and NA vRNAs in combination with the internal genes of high-yield influenza A virus. (C and D), were compared. Similar experiments were carried out for viruses of the Victoria lineage. (E and F) Comparison of the indicated wild-type and hybrid viruses in embryonated chicken eggs. The values presented are the average of three independent experiments±SD. The statistical significance was determined by using the linear mixed model (A-D), or by two-way ANOVA, followed by Tukey's post hoc test (E and F) (*P<0.05; **P<0.01); P values are not shown if the titer of the high-yield vaccine candidate was lower than that of wild-type virus. Red and blue asterisks indicate the comparison of the respective virus with WT virus; beige asterisks indicate the comparison between the viruses depicted in red and blue.
Figure 9B:
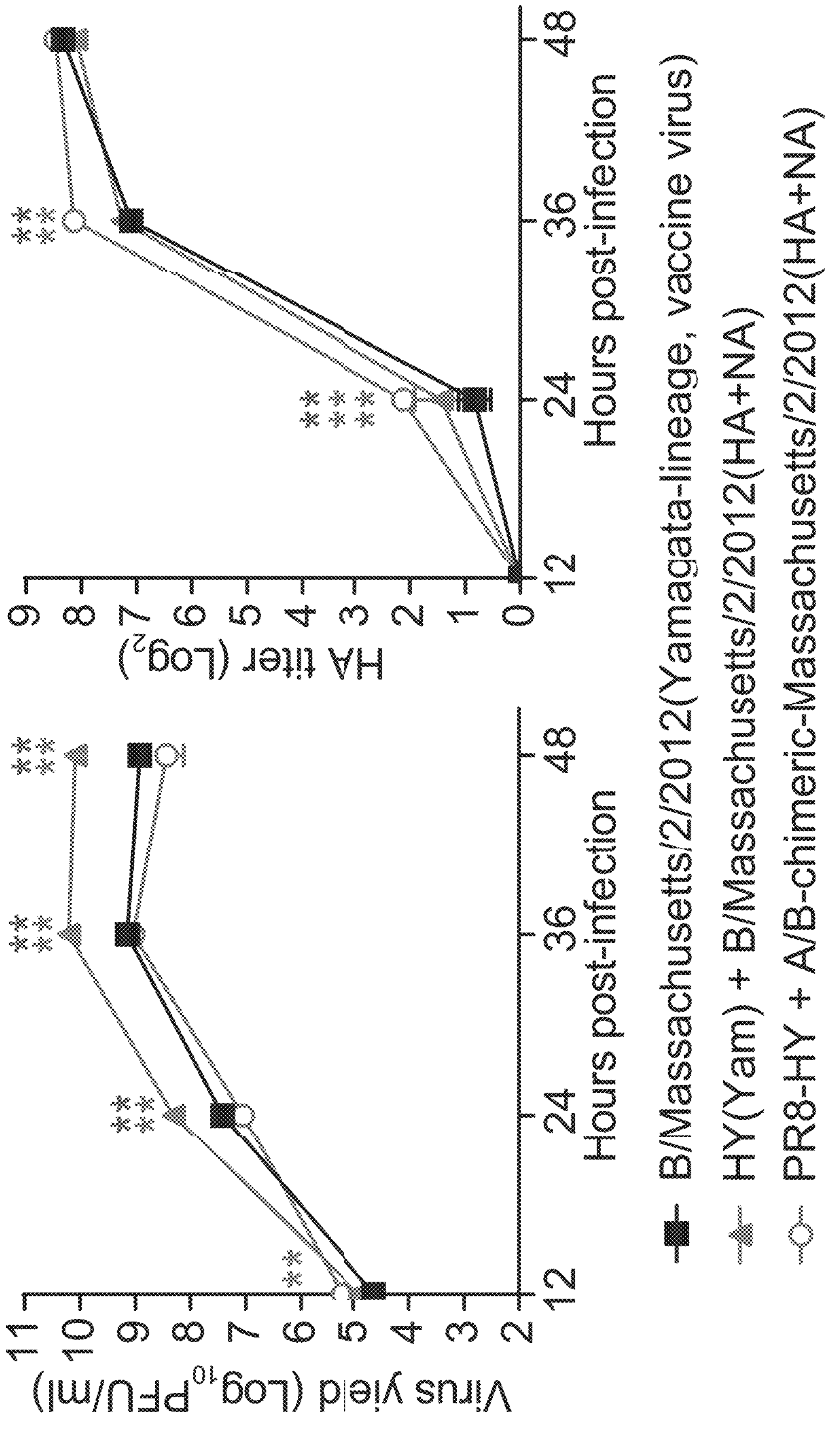
Figure 9C:
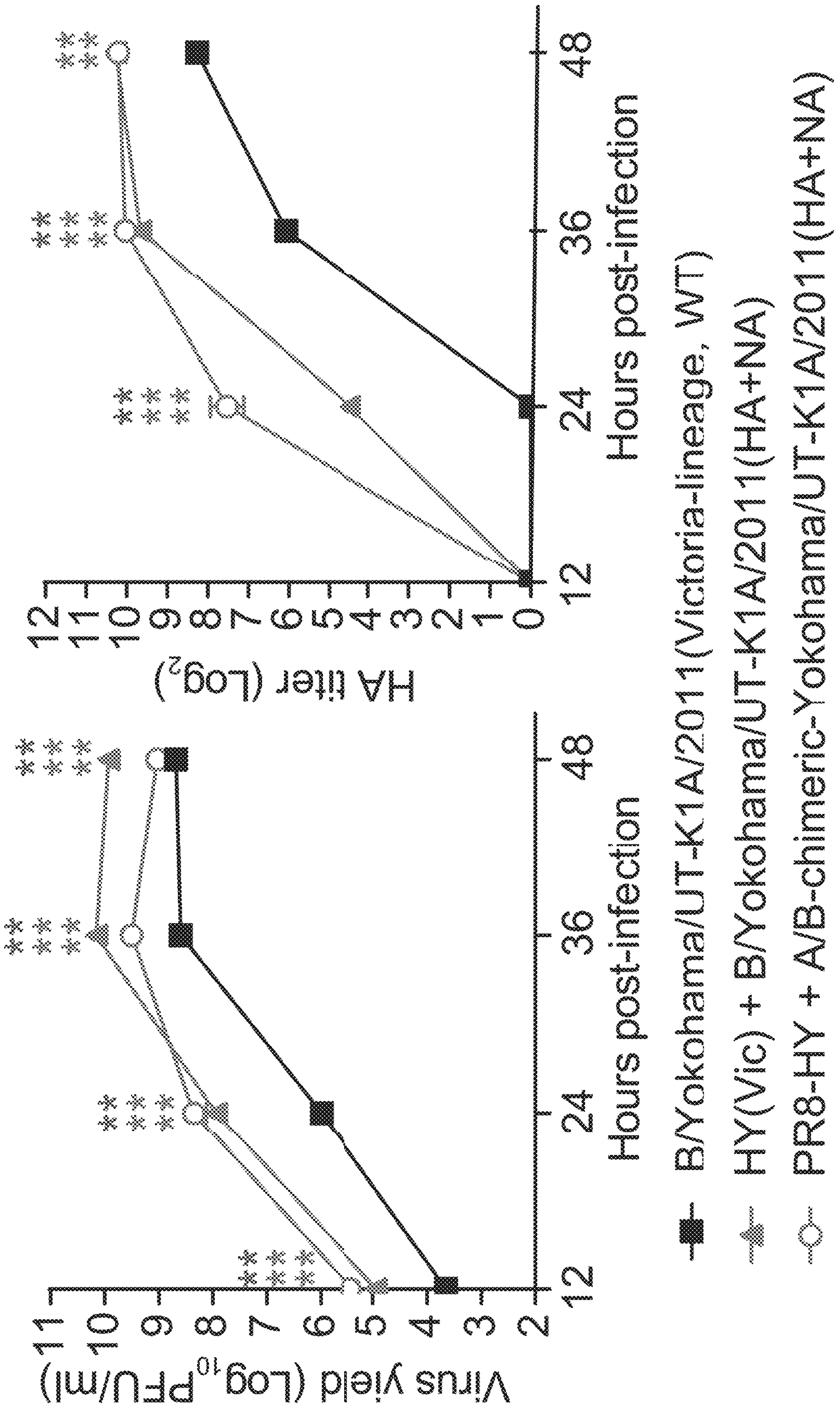
Figure 9D:
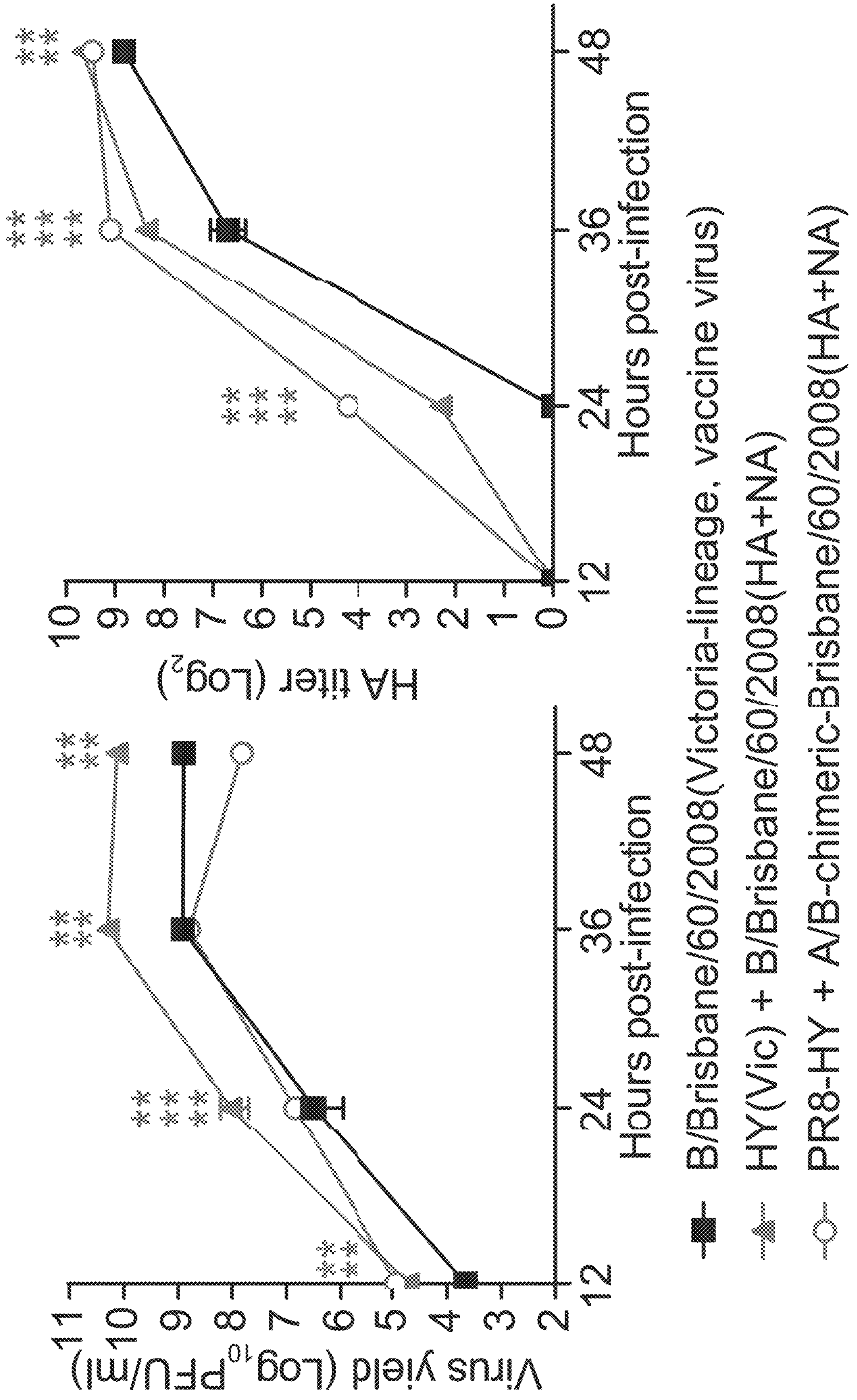
Figure 9E:
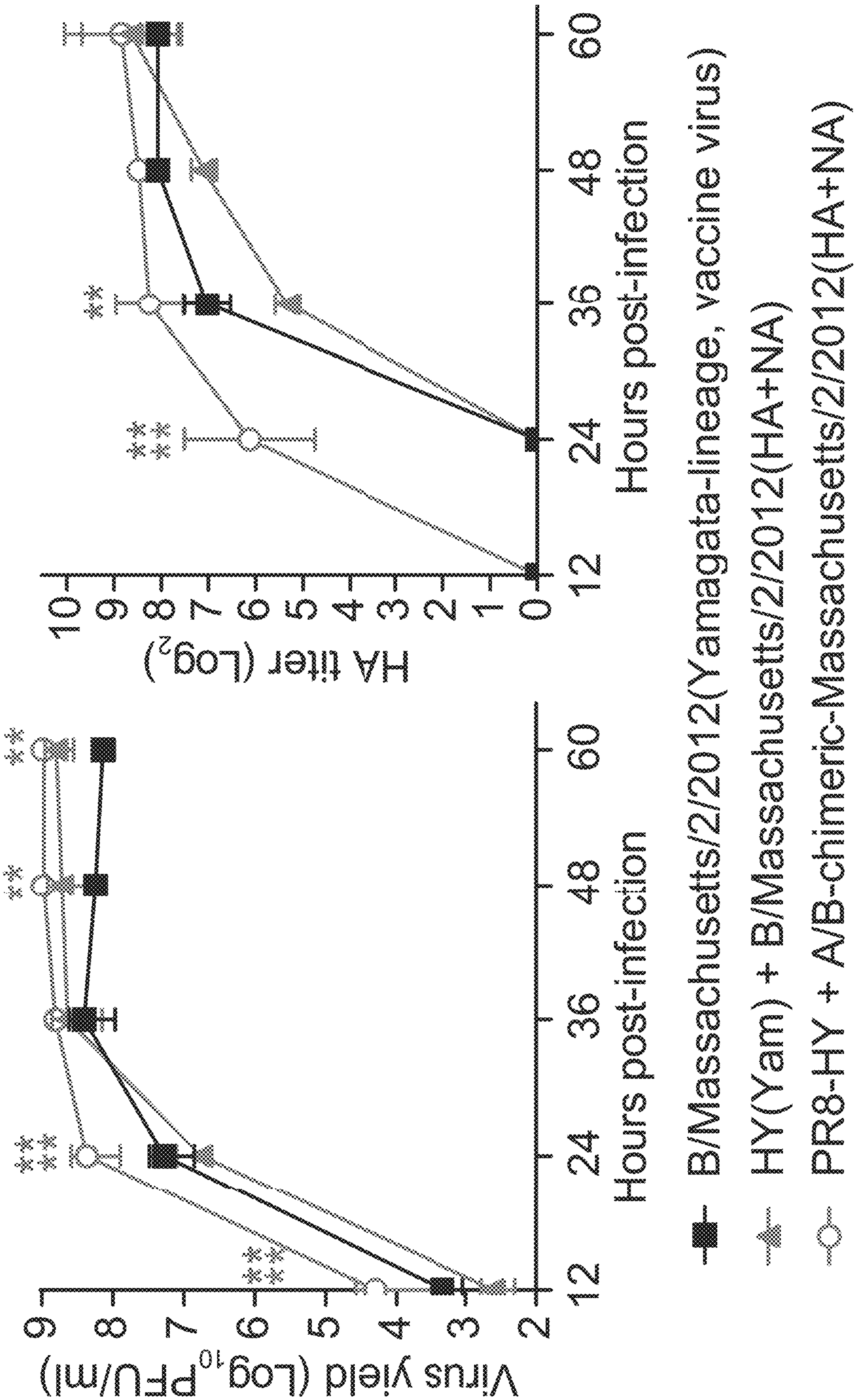
Figure 9F:
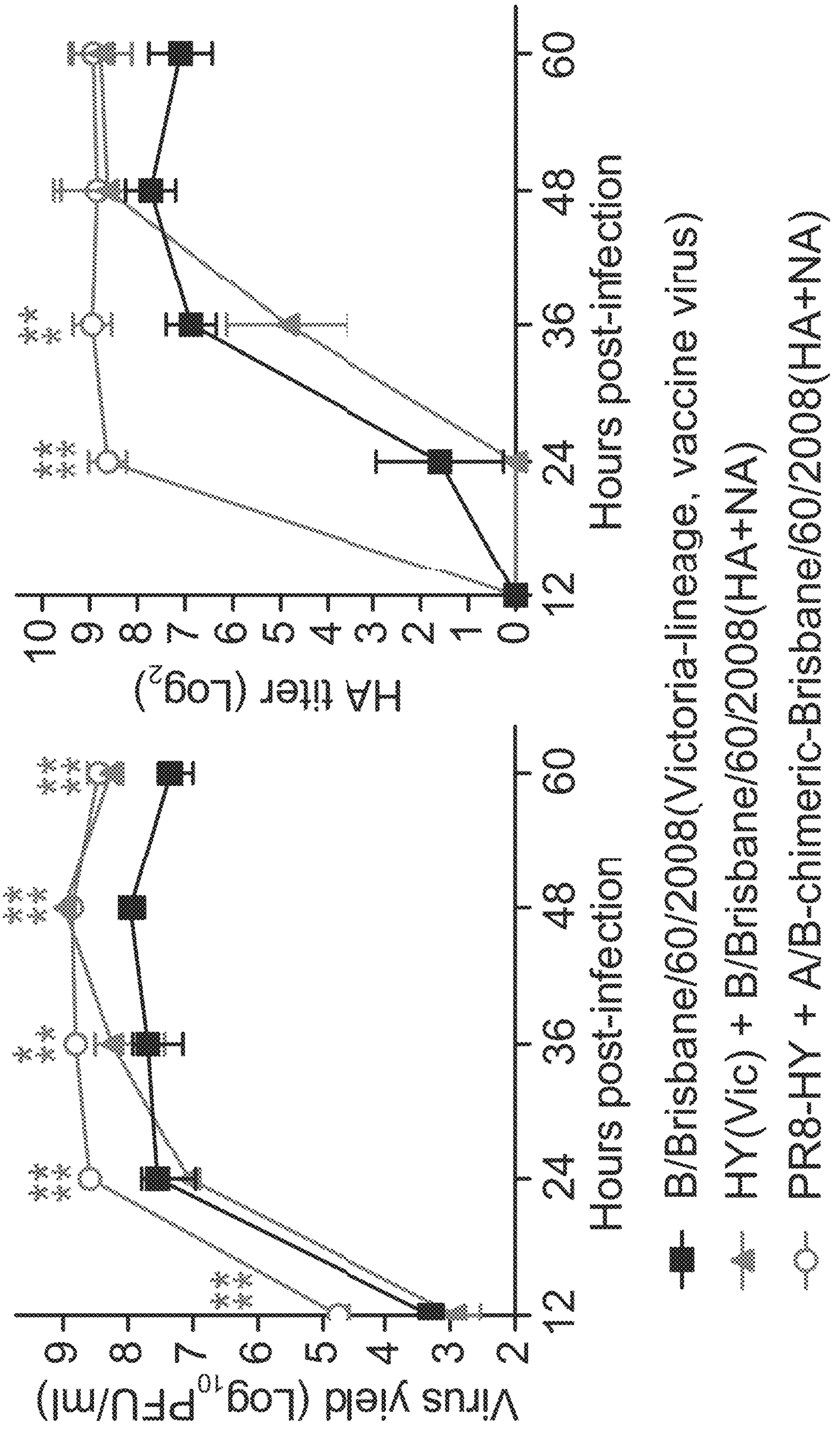

Comparison of Influenza A and B Virus Vaccine Backbones. Chimeric influenza A viruses possessing the HA and NA genes of an influenza B virus have been generated previously (Horimoto et al., 2004 and Flandorfer et al., 2003). The use of a universal backbone for both influenza A and B viruses would simplify the vaccine production process. Reassortants between influenza A and B viruses do not occur naturally, likely because of type-specific viral packaging signals located in the 5' and 3' terminal regions of influenza vRNA segments (Fujii et al., 2003; Baker et al., 2014). Therefore, vRNA segments were generated in which the ectodomains of the influenza A PR8 virus HA and NA proteins were replaced with influenza B virus counterparts (FIG. 5). Then the hemagglutination and viral titers of the following three viruses were compared: a wild-type Yamagata-lineage influenza B virus; HY(Yam) with the HA and NA genes of a Yamagata-lineage virus; and high-yield PR8 virus with type A/B chimeric HA and NA genes of a Yamagata-lineage virus (FIGS. 9A-B). Similar experiments were carried out for viruses of the Victoria-lineage (FIGS. 9C-D). At most time points tested, the high-yield influenza A or B vaccine virus backbones conferred significantly increased hemagglutination and viral titers compared with wild-type viruses. Comparison of the influenza A and B vaccine backbones revealed higher virus titers with the influenza B vaccine backbone but, interestingly, higher hemagglutination titers with the influenza A vaccine backbone. Moreover, for two influenza B viruses representing both lineages, the influenza A vaccine backbone was superior to the influenza B vaccine backbones with respect to hemagglutination and viral titers in embryonated chicken eggs (FIGS. 4E-F). Other influenza B viruses containing the HA and NA from B/Yokohama/UT-K1A/2011, B/Yokohama/P-2922/2005, B/Tokyo/UTE2/2008, or B/Tochigi/UT-T1/2014 did not grow well in embryonated chicken eggs regardless of the backbone (wild-type or high-yield), suggesting that the HA and NA genes of these human viruses may restrict efficient growth in embryonated chicken eggs.

Figure 10A:
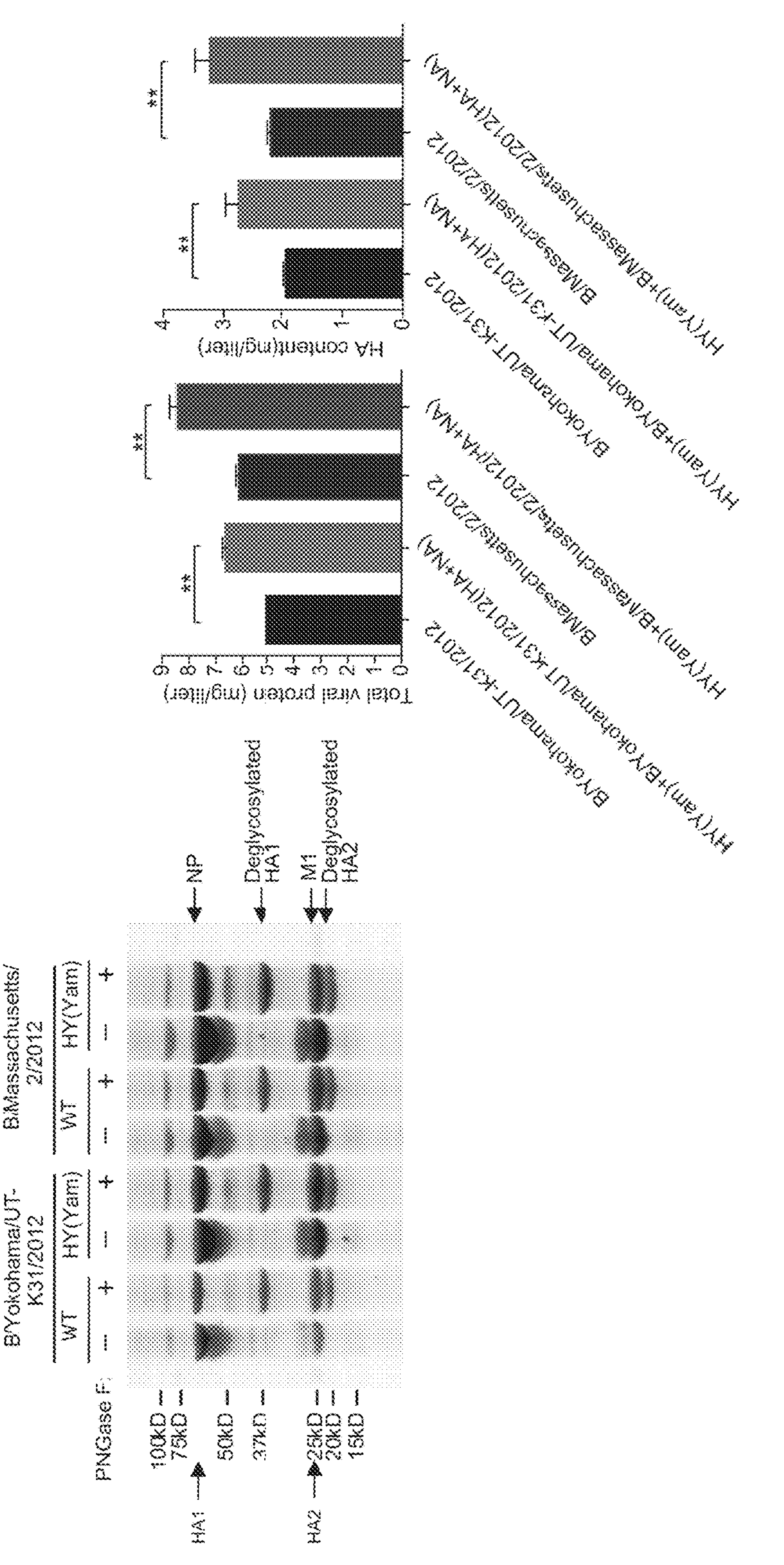
FIGS. 10A-B. Evaluation of the total viral protein yield and HA content of HY(Yam) and HY(Vic) viruses. A) Comparison of viruses possessing the HA and NA vRNAs of the indicated Yamagata-lineage viruses in combination with the internal vRNAs of the same natural wild-type virus (WT) or of HY(Yam). B) Comparison of viruses possessing the HA and NA vRNAs of the indicated Victoria-lineage viruses in combination with the internal vRNAs of the same wild-type virus (WT) or of HY(Vic). The total viral protein yield of MDCK cell-grown, sucrose gradient-purified virus samples is shown (Left and Center). PNGaseF treatment deglycosylates HA1 and HA2; this treatment was carried out because glycosylated HA2 migrates at a similar molecular weight as M1. The HA contents (Right) were calculated based on the total viral protein amounts and the relative amounts of HA. The values presented are the average of three independent experiments±SD. The statistical significance was assessed by using one-way ANOVA followed by Dunnett's test, comparing the total viral protein yield and HA content of wild-type viruses with that of recombinant high-yield vaccine viruses (*P<0.05; **P<0.01).
Figure 10B:
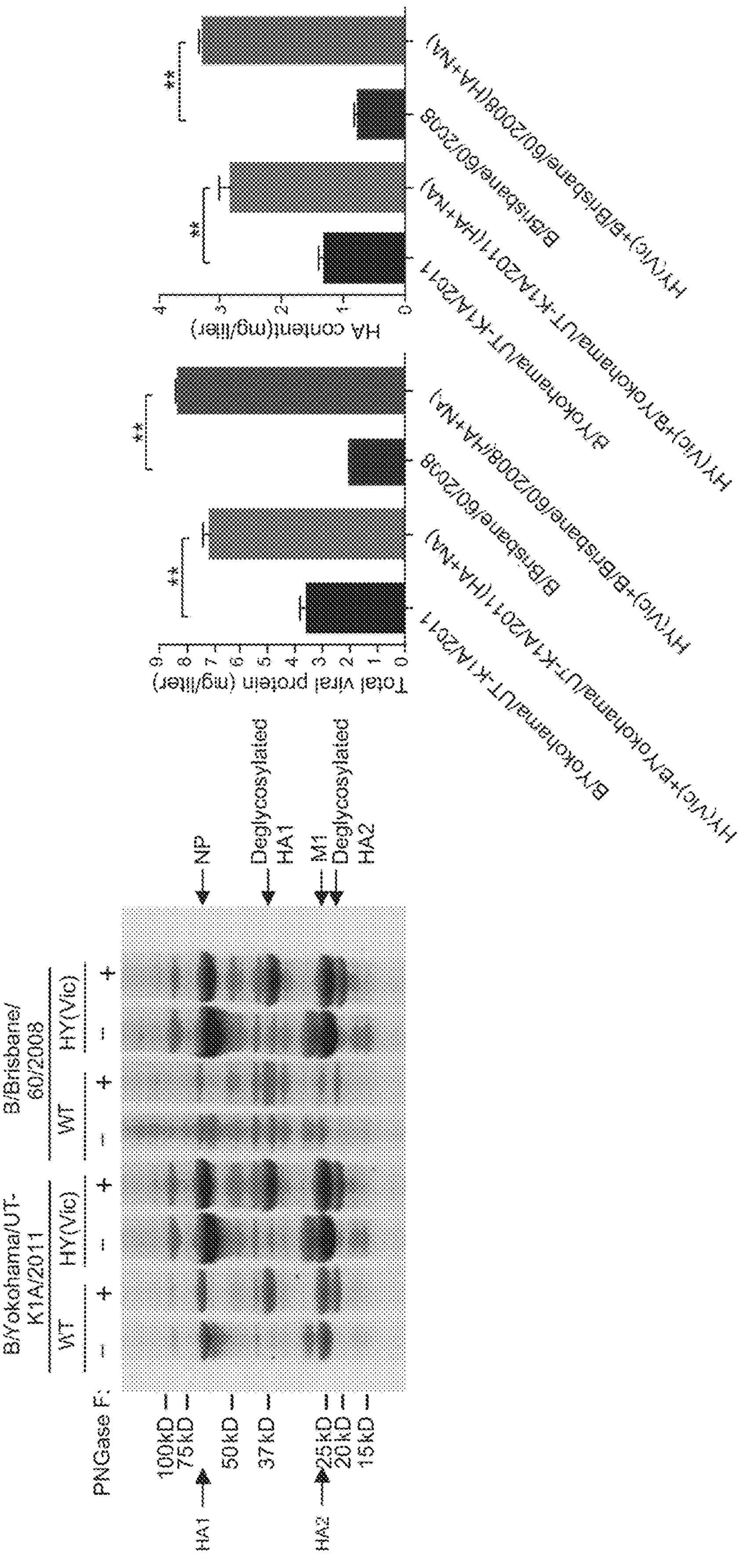

Evaluation of Total Viral Protein Field and HA Content. Most preparations of inactivated influenza vaccines contain 15 μg each of H1 HA, H3 HA, and type B HA proteins. For vaccine optimization, total viral protein yield and HA content are therefore important parameters, prompting us to compare the total viral protein yield and HA content of different HY(Yam) and HY(Vic) viruses with theft respective wild-type viruses in MDCK cells. Cell-culture supernatants were collected from infected cells, and viruses were concentrated and purified by use of sucrose gradient centrifugation. The total viral protein yield was then determined by using the Pierce BCA Protein Assay Kit (Thermo Scientific). In parallel, purified virus samples were treated with PNGase F, resulting in HA deglycosylation, which allows easier detection of HA2 (which in its glycosylated form is similar in size to M1). Samples were separated by using SDS/PAGE (FIGS. 10A-B) and the amounts of HA1, HA2, NP, and M1 were determined based on densitometric analysis. The HA content was calculated by dividing the HA amount (calculated by summing the amounts of HA1 and HA2) by the sum of the amounts of HA1, HA2, NP, and M1, and multiplying this value by the amount of total viral protein in the samples analyzed via gel electrophoresis (FIGS. 10A-B), For all viruses tested, total viral protein yield and HA content were significantly higher with the HY(Yam) and HY(Vic) vaccine backbones compared with the wild-type viruses from which the HA and NA vRNAs were derived.

Figure 11A:
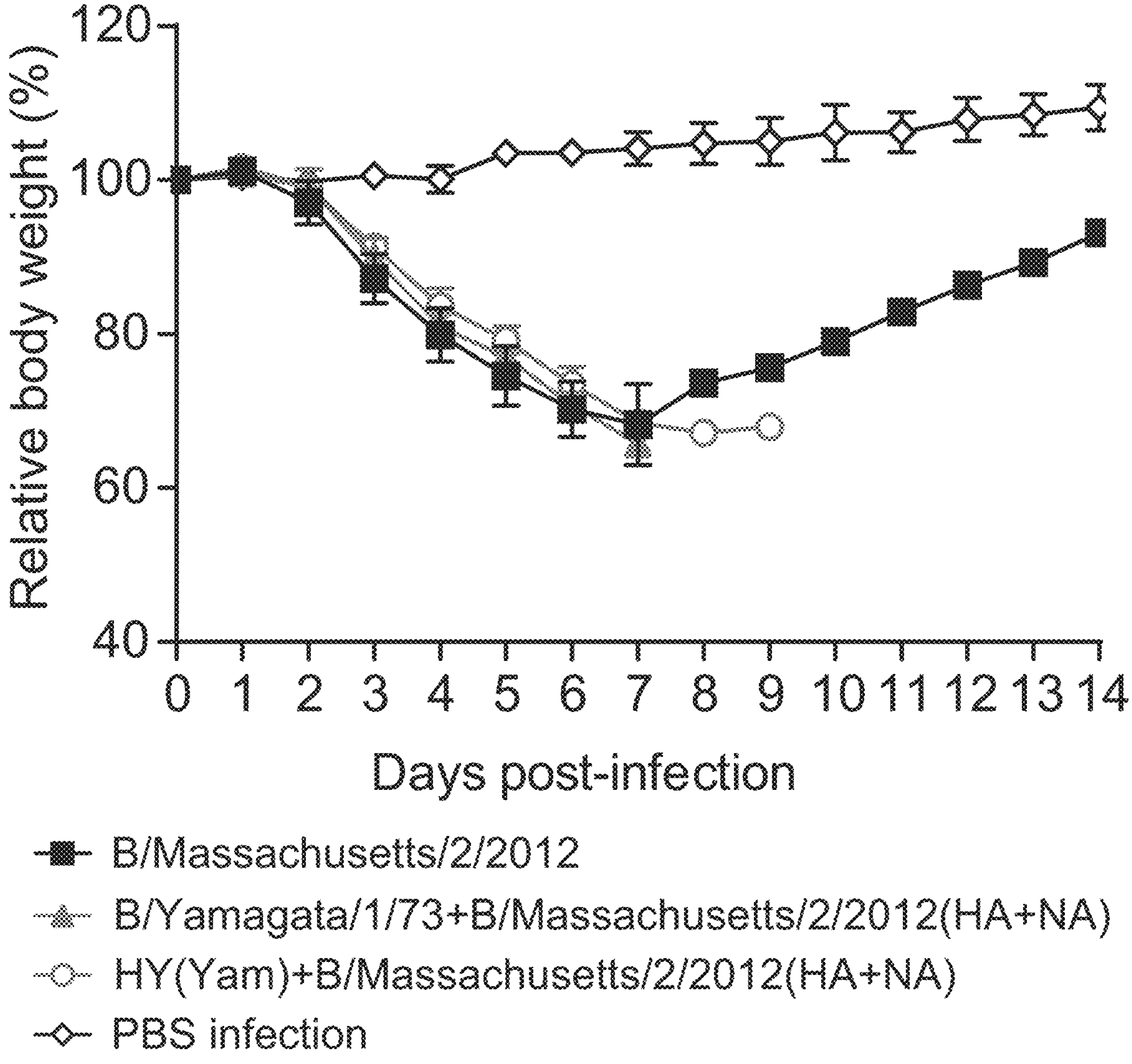
FIGS. 11A-F. Virulence of HY(Yam) and HY(Vic) viruses in mice. A-C) Comparison of a wild-type Yamagata-lineage virus (B/Massachusetts/2/2012), a virus possessing the B/Massachusetts/2/2012 HA and NA vRNAs in combination with the remaining vRNAs of B/Yamagata/1/73 (used for virus library generation), and a virus possessing the B/Massachusetts/2/2012 HA and NA vRNAs in combination with the remaining vRNAs of HY(Yam). D-F) Comparison of a wild-type Victoria-lineage virus (B/Brisbane/60/2008), a virus possessing the B/Brisbane/60/2008 HA and NA vRNAs in combination with the remaining vRNAs of B/Yamagata/1/73 (used for virus library generation), and a virus possessing the B/Brisbane/60/2008 HA and NA vRNAs in combination with the remaining vRNAs of HY(Vic). BALB/c mice (five per group) were inoculated intranasally with $10^6$ pfu of the indicated viruses and monitored daily for body weight changes (A and D) and survival (B and E). To assess virus replication in mice, $10^6$ pfu of the indicated viruses were used to infect 10 additional mice. On days 3 and 6 post-infection, five mice in each group were killed, and lung virus titers were determined by use of plaque assays in MDCK cells (C and F). Statistical significance was assessed by using one-way ANOVA followed by Dunnett's test (*P<0.05; **P<001).
Figure 11B:
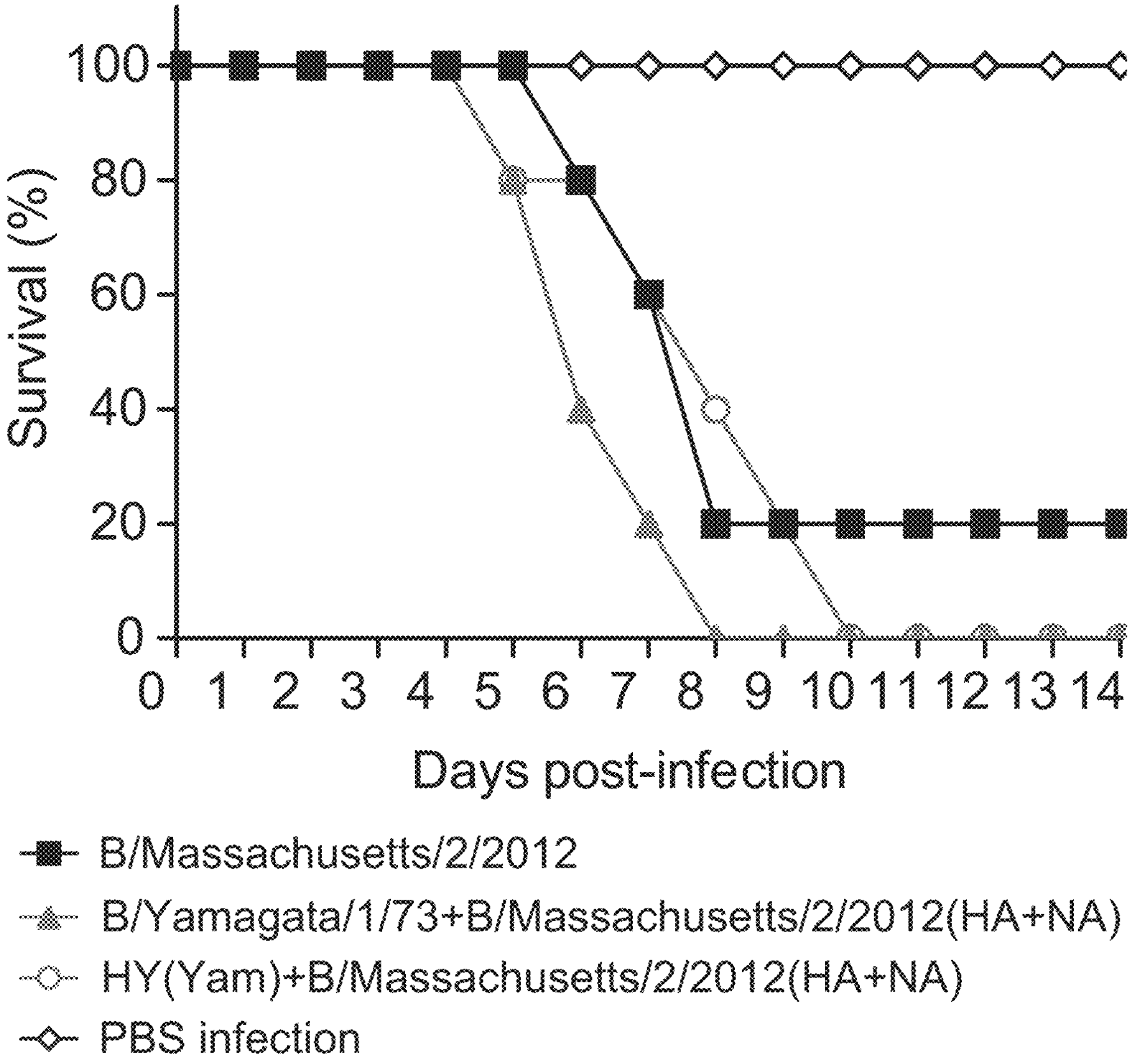
Figure 11C:
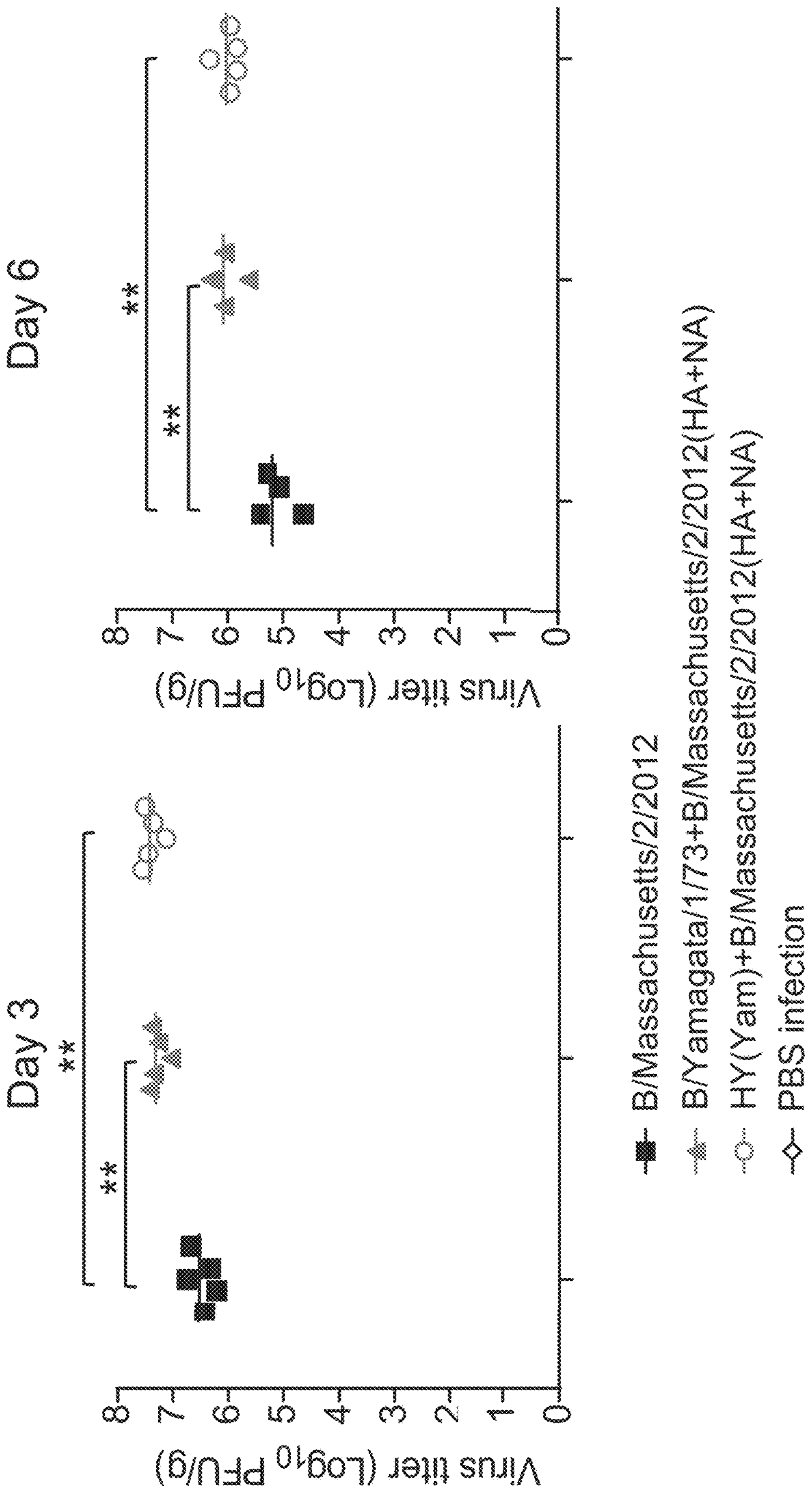
Figure 11D:
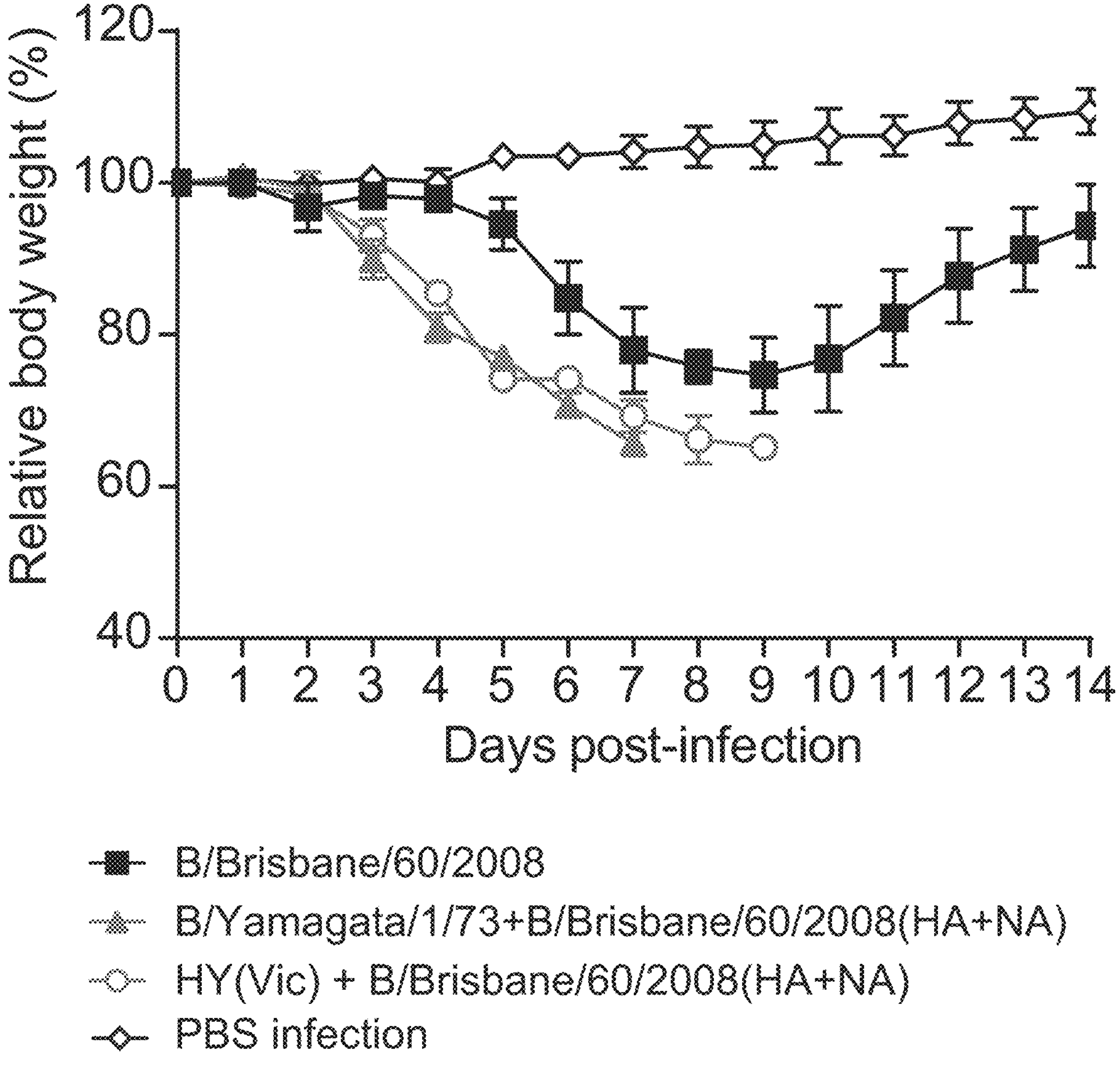
Figure 11E:
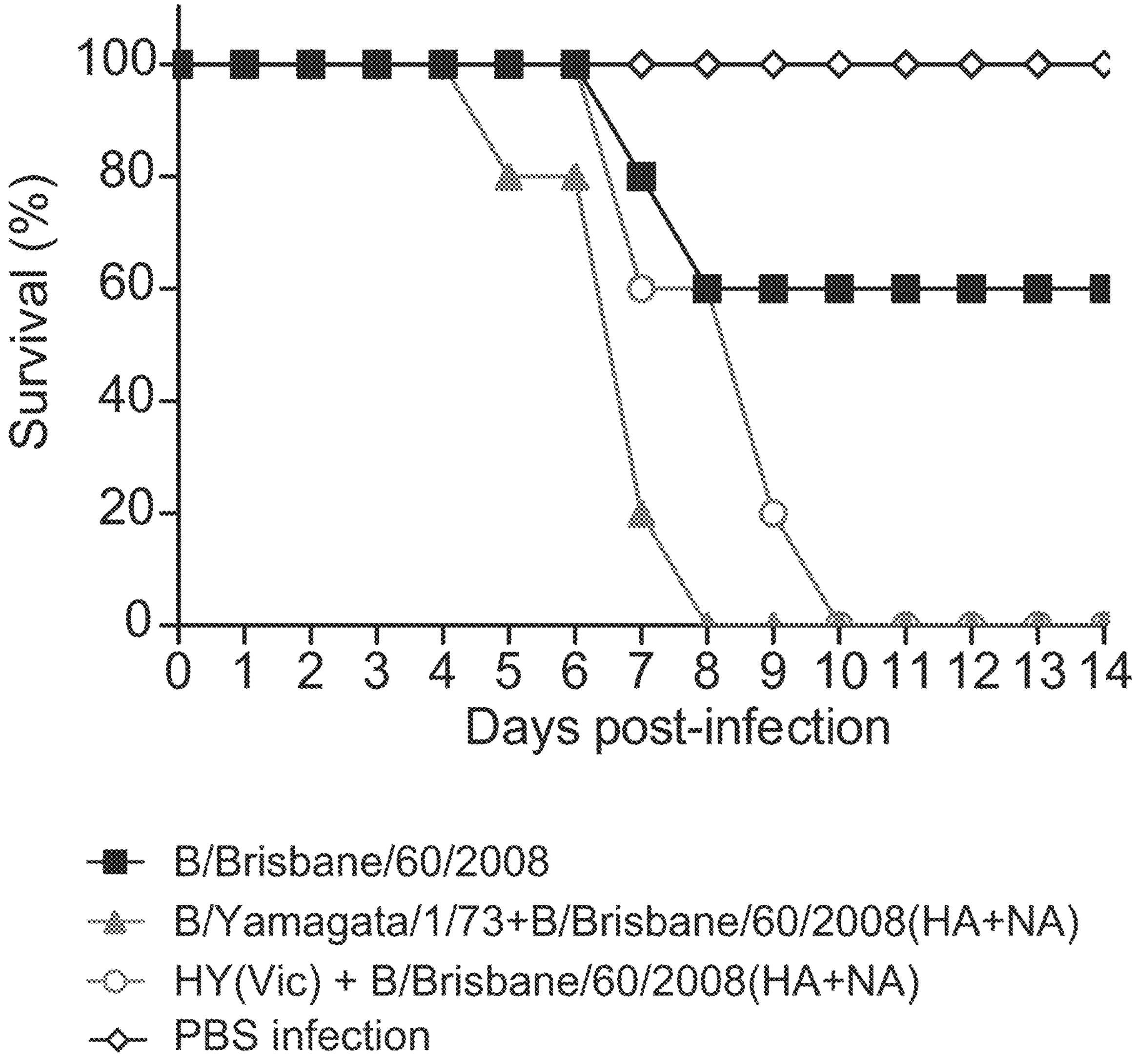
Figure 11F:
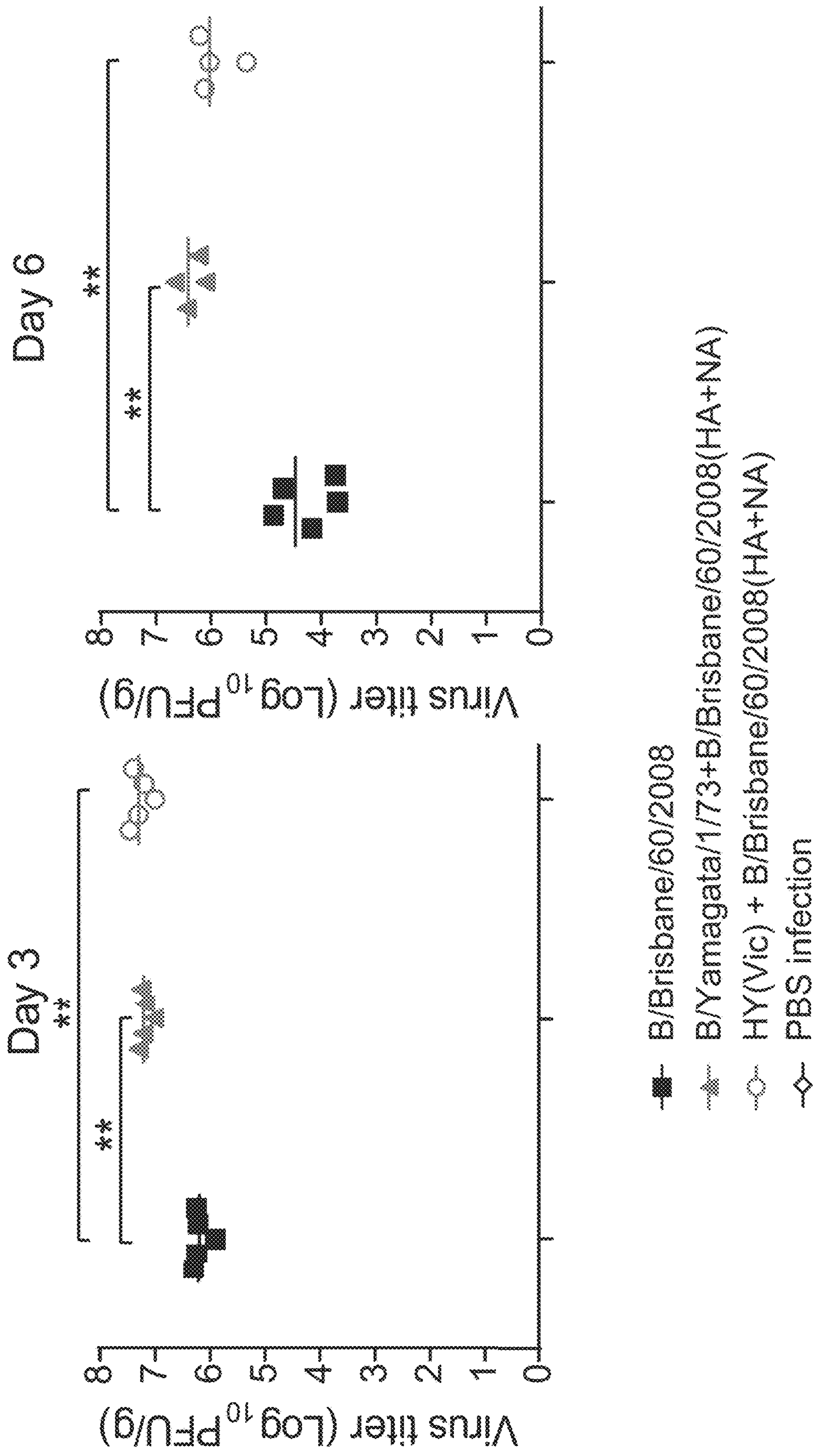

Virulence of PR8-HY-Based Vaccine Viruses in Mice. An experimental approach was designed to select mutants with increased replicative ability, which may also increase their virulence in mammals. To address this question, five mice per group were infected with $10^6$ pfu of a wild-type Yamagata-lineage virus, a virus possessing the HA and NA vRNAs of the Yamagata-lineage virus in combination with the remaining six genes of wild-type B/Yamagata/1/73 virus (which was used to generate the virus libraries), and a virus possessing the HA and NA vRNAs of the Yamagata-lineage virus in combination with the HY(Yam) vaccine virus backbone (FIGS. 11A-B). In parallel, groups of 10 mice were infected with $10^6$ pfu of the viruses described above, and five animals each were killed on days 3 and 6 post-infection to assess lung virus titers (FIG. 11C). Similarly, experiments were carried out with a Victoria-lineage viruses and the HY(Vic) vaccine backbone (FIGS. 11D-F). The wild-type B/Yamagata/1/73 virus backbone conferred higher pathogenicity than the B/Massachusetts/2/2012 and B/Brisbane/60/2008 backbones, respectively. However, the yield-enhancing mutations of HY(Yam) and HY(Vic) did not increase mouse virulence further; in fact, they had slightly attenuating effects compared with the B/Yamagata/1/73 backbone.

Genetic Stability of the HY(Yam) and HY(Vic) Vaccine Backbones. Vaccine viruses should be genetically stable so that their desired properties are maintained. To test the genetic stabilities of the high-yield candidates, 10 serial passages of a HY(Yam) virus were performed with the HA and NA vRNAs of B/Yokohama/UTK31/2012, and of a HY(Vic) virus with the HA and NA vRNAs of B/Yokohama/UT-K1A/2011 in MDCK cells. After each passage, the genomic sequences of the viruses were determined by Sanger sequencing. For the Yamagata-lineage virus, no mutations were detected. For the Victoria-lineage virus, mutations in the internal genes that define the high-yield properties of HY(Vic) were not detected. However, a mixed population encoding HA1-196T and -196I was detected after passage 5; after passage 10, only the HA1-196I mutant was detected.

Similarly, several wild-type and high-yield influenza B viruses of both lineages were passaged in embryonated chicken eggs (Table 7). After 5-10 consecutive passages, no egg-adapting mutations were detected in the internal genes. However, for viruses that possessed a glycosylation site at amino acids 194-196 of HA, mutations arose that resulted in the loss of that glycosylation site. This finding is consistent with the earlier finding of mutations at this glycosylation site in viruses of the Victoria-lineage (Table 2). Collectively, the data indicate that the yield-enhancing mutations in HY(Yam) and HY(Vic) were genetically stable for at least 5-10 consecutive passages in MDCK cells and embryonated chicken eggs.

Contribution of Individual vRNAs to High-Yield Properties of HY(Yam) and HY(Vic). The HY(Yam) and HY(Vic) vaccine backbones possess mutations in several vRNA. To better understand the contributions of these mutations to the HY(Yam) and HY(Vic) phenotypes, reverse genetics was used to generate viruses possessing individual mutant vRNA segments of HY(Yam) or HY(Vic): for example, viruses were generated in which the HA and NA vRNAs of a Yamagata-lineage virus were combined with the six remaining vRNAs of wild-type B/Yamagata/1/73 (used to generate virus libraries), of wild-type B/Yamagata/1/73 (also encoding the NP-P40S mutation found in HY(Yam)), or of HY(Yam) (FIG. 12). The resulting viruses were tested for their replicative abilities and hemagglutination titers in MDCK cells (FIG. 12). When tested individually, the NP-P40S, M1-R77K, and NS-a39g+NS1-K176Q mutations significantly increased the viral and hemagglutination titers of Yamagata-linage viruses at one or more time points compared with the reference virus. For Victoria-lineage viruses, each of the mutations tested had a statistically significant growth-enhancing effect at one or more time points. Most of the viruses possessing individual mutations found in HY(Yam) or HY(Vic) did not replicate as efficiently as the high-yield vaccine candidates, demonstrating that combinations of several mutations are important for the high-yield properties of HY(Yam) and HY(Vic).

Figure 12A:
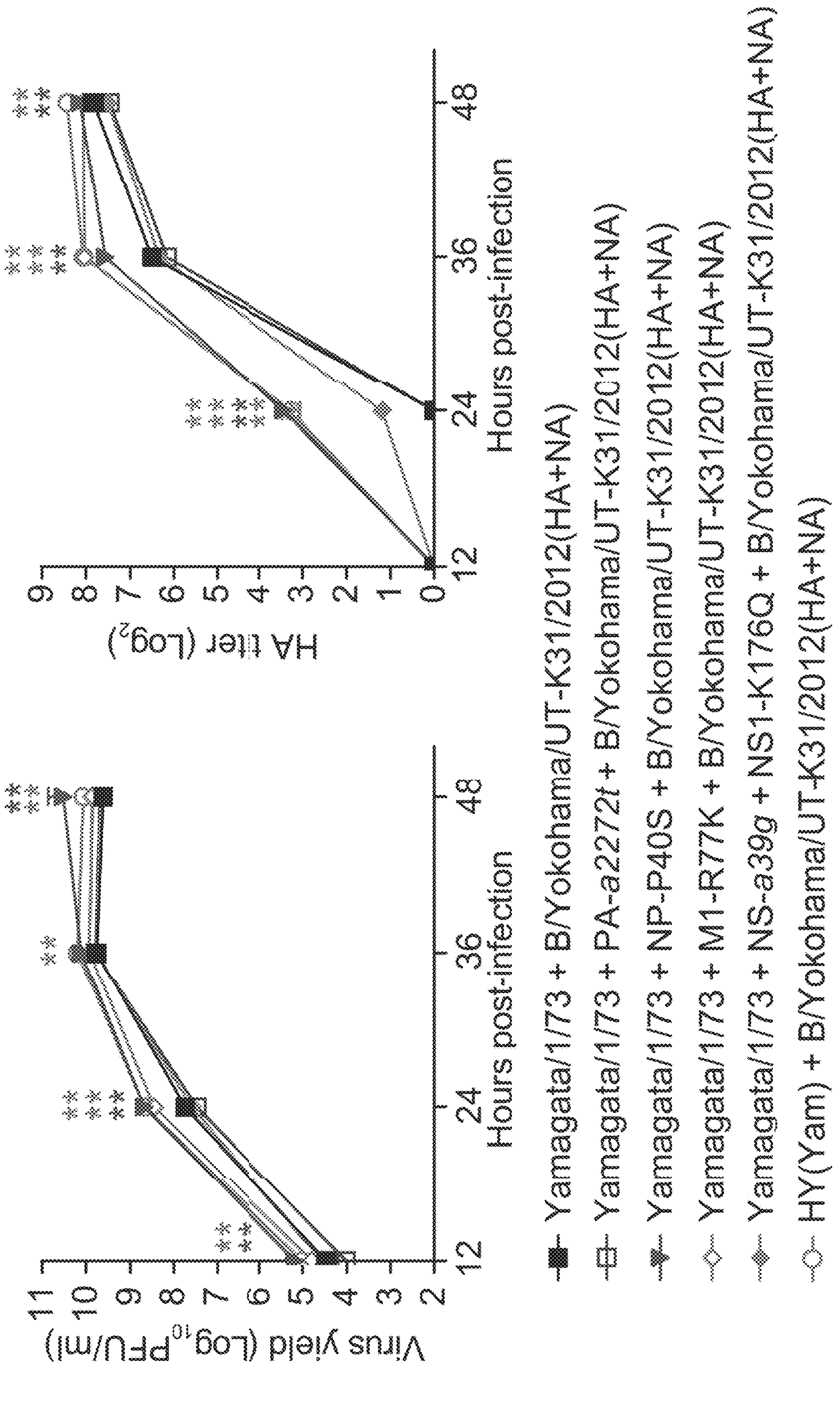
FIGS. 12A-B. Growth kinetics and hemagglutination titers of single reassortant viruses. A) Comparison of the parental virus used for Yamagata-lineage virus library generation (B/Yamagata/1/73 with the HA and NA vRNAs of B/Yokohama/UT-K31/2012) with viruses that also possess an individual vRNA of HY(Yam). B) Comparison of the parental virus used for Victoria-lineage virus library generation (i.e., B/Yamagata/1/73 with the HA and NA vRNAs of B/Yokohama/UT-K1A/2011) with viruses that also possess an individual vRNA of HY(Vic). Data were obtained from three independent experiments; shown are average titers±SD. The values presented are the average of three independent experiments±SD. Statistical significance was determined by using the linear mixed model (*P<0.05.
Figure 12B:
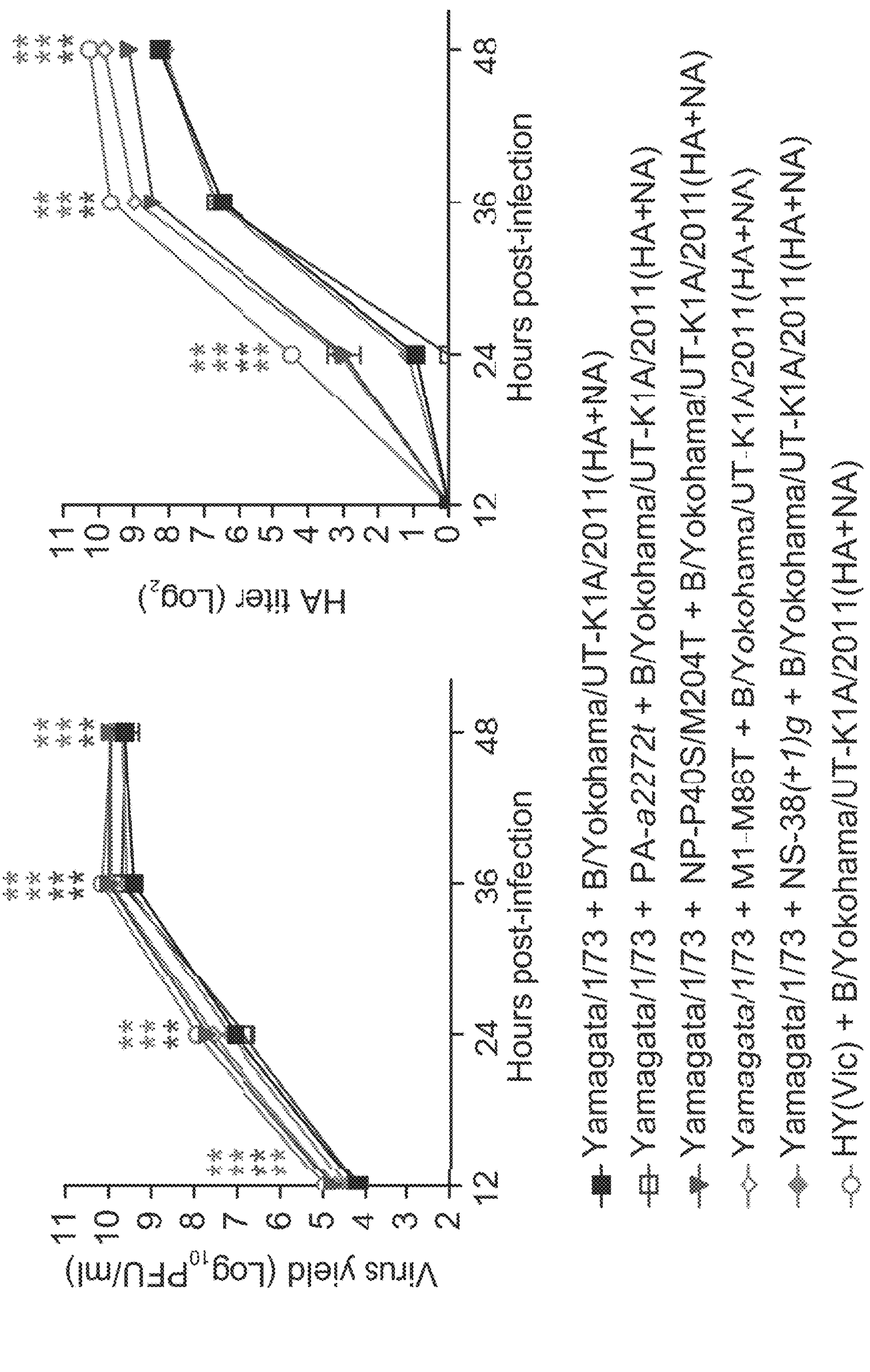
Figure 13A:
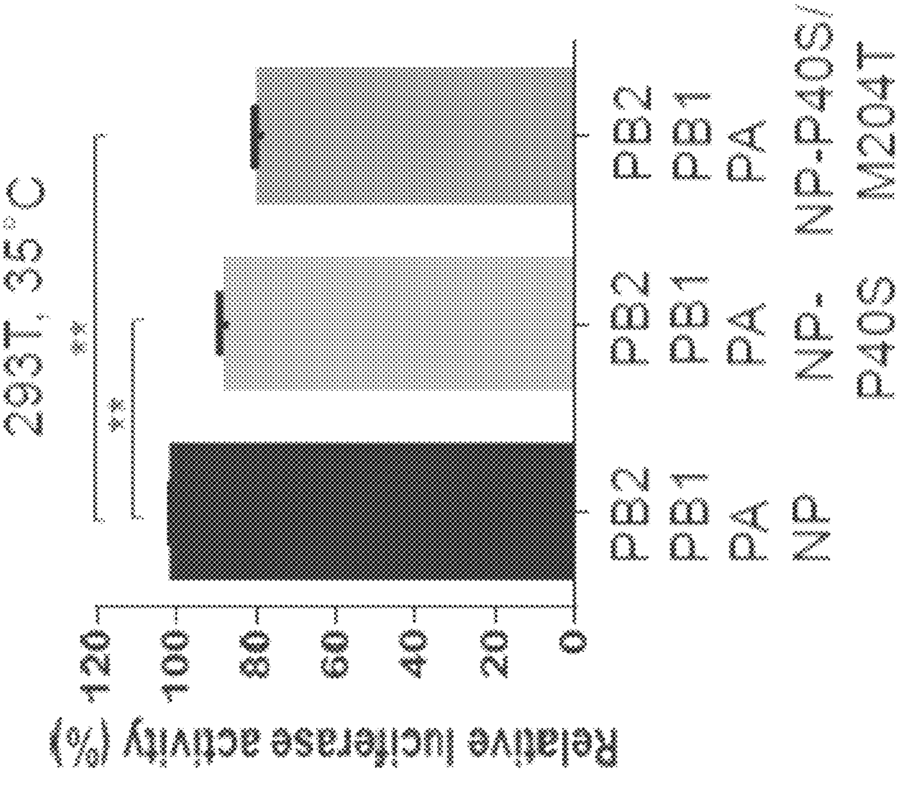
Figure 13B:
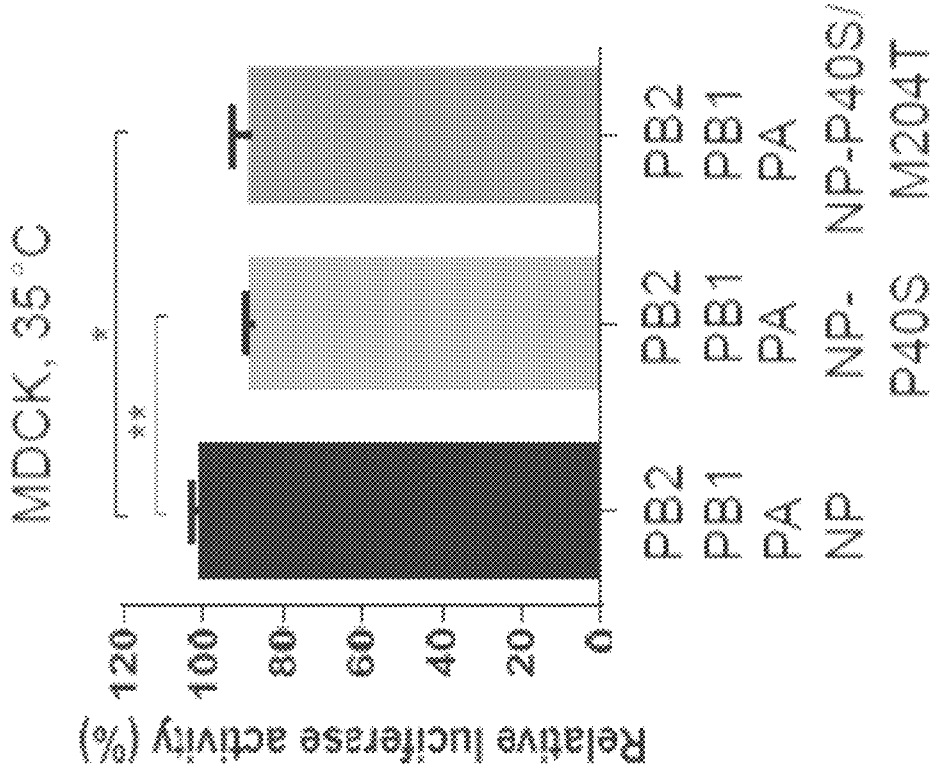
Figure 13D:
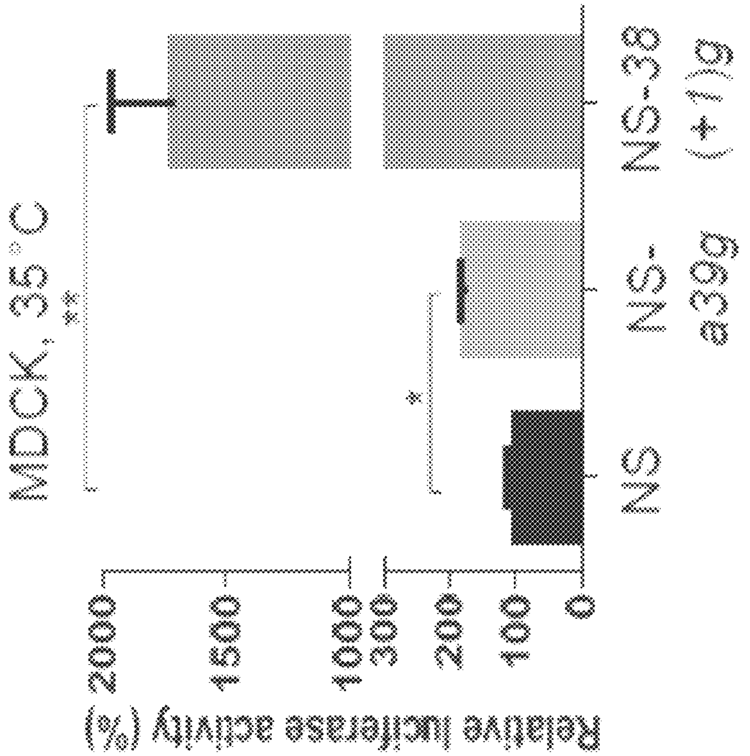
Figure 13C:
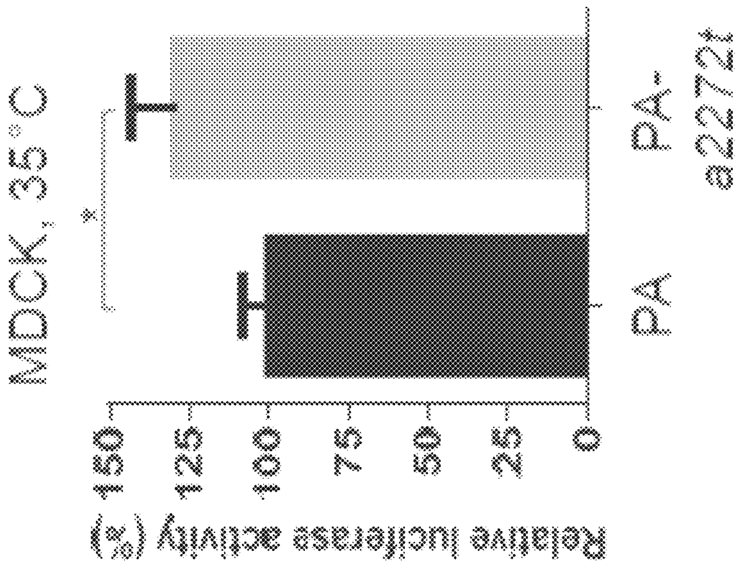

Effect of Individual Mutations in HY(Yam) and HY(Vic) on the Activity of the Viral Replication Complex. The NP-P40S mutation was selected individually and in combination with NP-M204T from the Yamagata- and Victoria-lineage libraries, respectively. Moreover, these mutations increased viral and hemagglutination titers when tested without the other growth-enhancing mutations (FIG. 12). To assess whether these mutations affect the activity of the viral replication complex, 293T and MDCK cells were transfected with plasmids expressing the three polymerase subunits of B/Yamagata/1/73 virus, wild-type or mutant B/Yamagata/1/73 NP, and an influenza B virus-like RNA expressing the luciferase reporter protein (the NP-M204T mutant was not tested separately because it was selected from the virus libraries only in combination with NP-P40S). Interestingly, the NP-P40S and -P40S/M204T mutations significantly reduced the replicative activity of the viral replication complex (FIG. 13A-B).

Figure 6A:
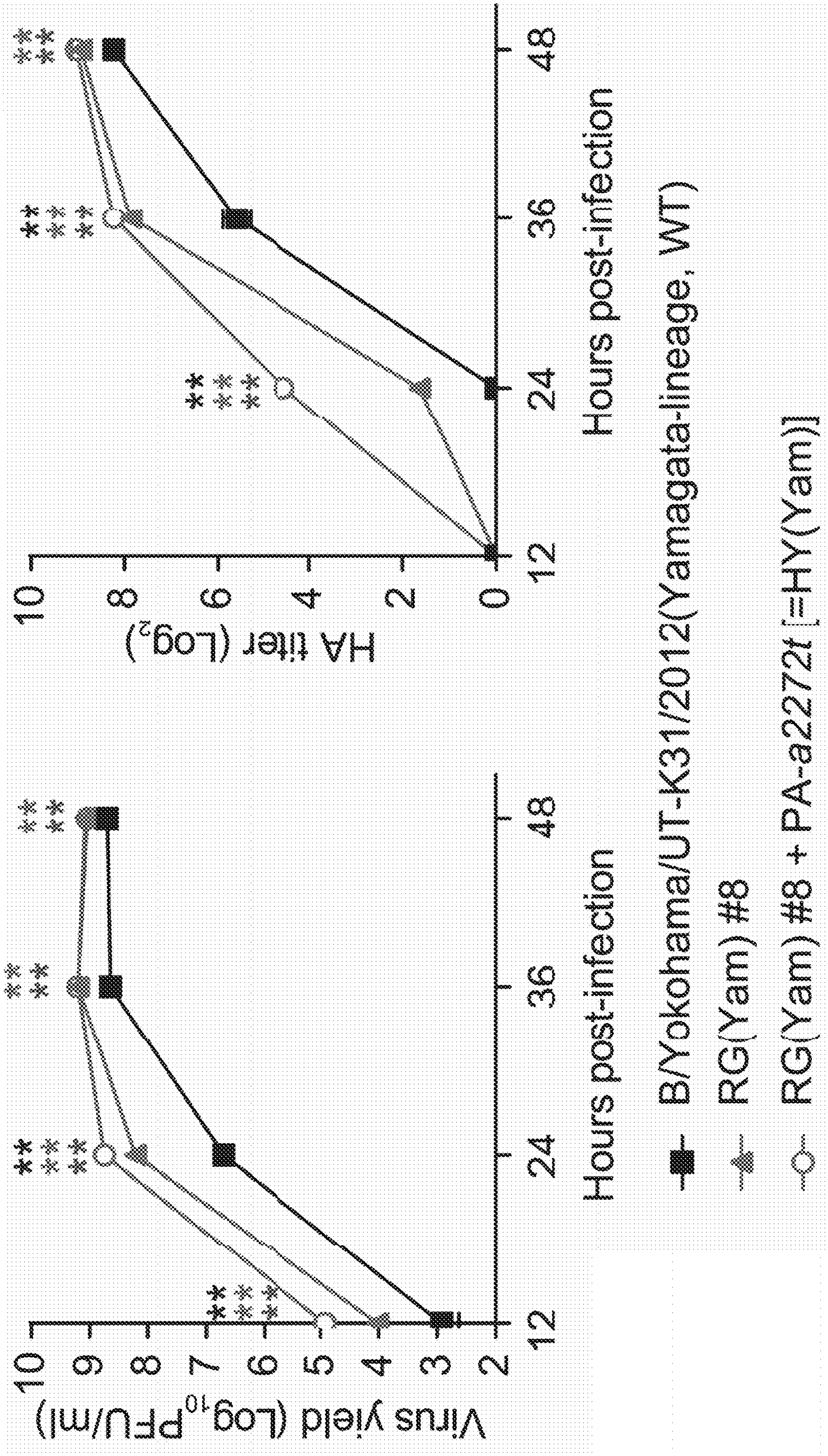
FIG. 6A-B. Growth kinetics and HA titers of high-yield Yamagata- and Victoria-lineage viruses. (A) The indicated Yamagata-lineage wild-type virus was compared with the Yamagata-lineage high-yield candidate RG(Yam) #8 (Table 3) and with RG(Yam) #8 possessing the PA-a2272t mutation; the latter virus was selected as lead candidate HY(Yam). (B) The indicated Victoria-lineage wild-type virus was compared with the Victoria-lineage high-yield candidate RG(Vic) #2 (Table 4) and with RG(Vic) #2 possessing the PA-a2272t mutation; the latter virus was selected as lead candidate HY(Vic). In both sets of experiments, MDCK cells were infected in triplicate with the indicated viruses at an MOI of 0.001 and incubated at 35° C. At the indicated time points, virus and hemagglutination titers were determined by performing plaque or hemagglutination assays, respectively. The values presented are the average of three independent experiments±SD. P values were calculated by using the linear mixed model (*P<0.05; **P<0.01). Red and blue asterisks indicate the comparison of the respective virus with WT virus; beige asterisks indicate the comparison between the viruses depicted in red and blue.
Figure 6B:
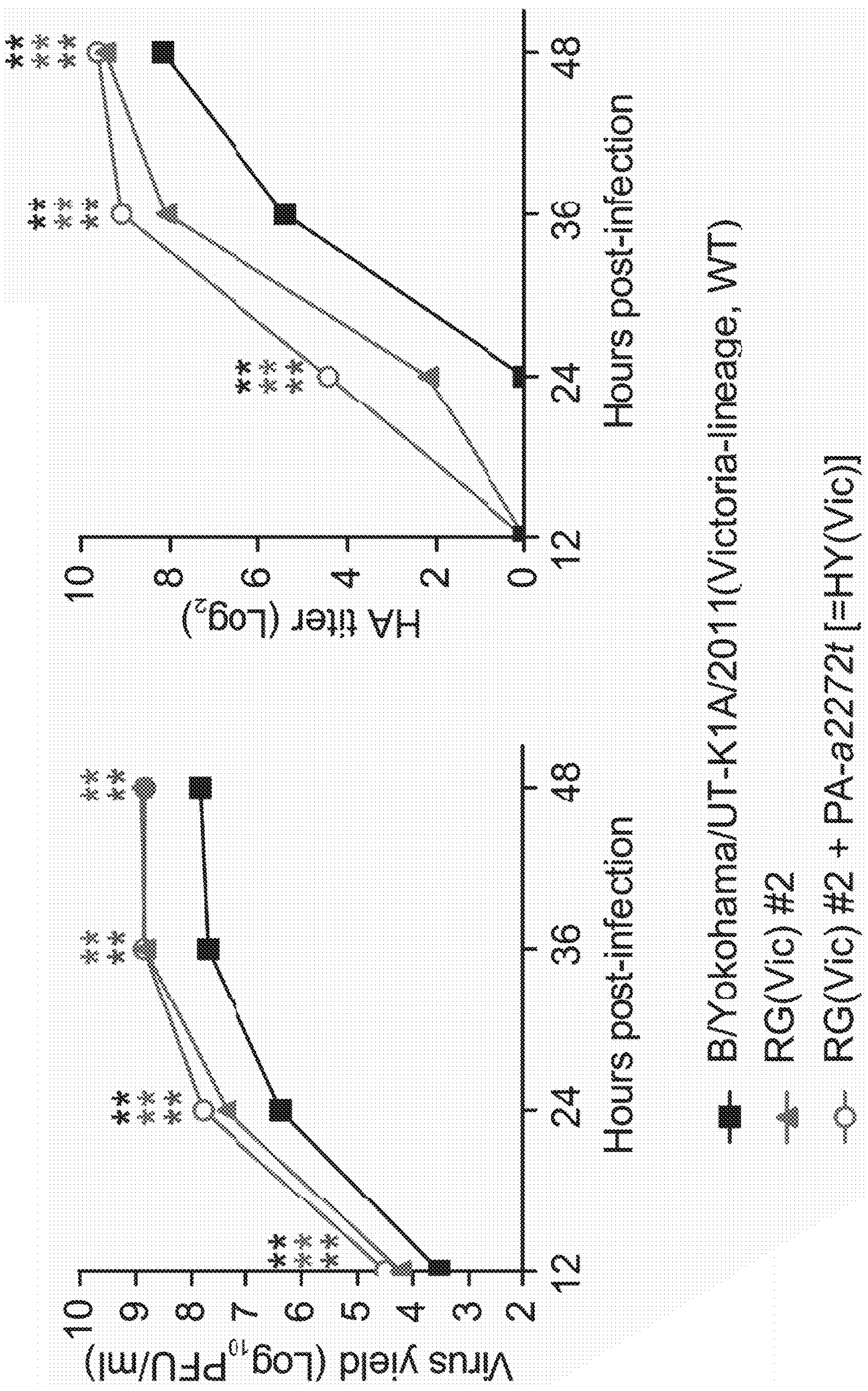
Figure 7A:
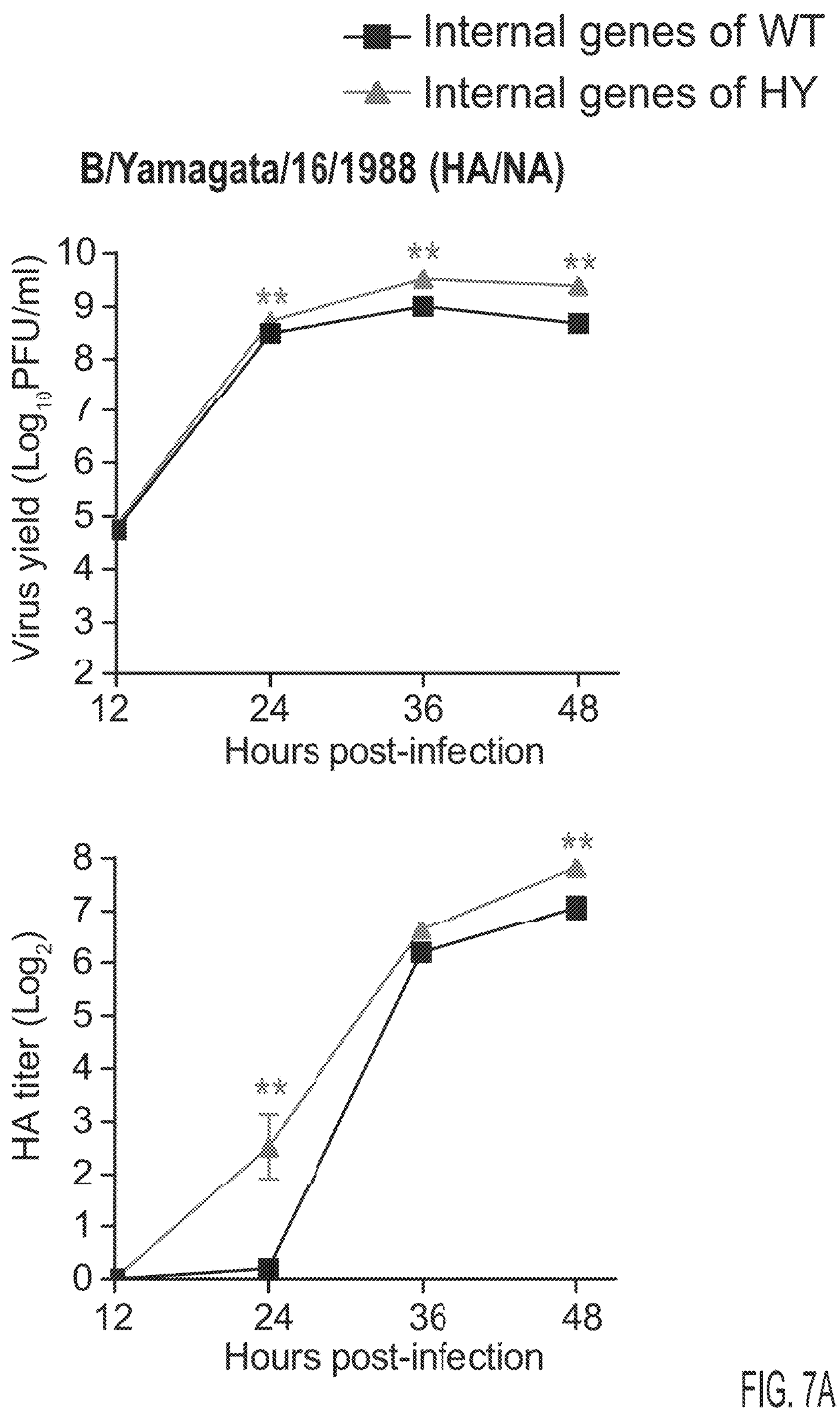
FIGS. 7A-F. Comparison of wild-type and high-yield viruses possessing different HA and NA vRNAs. Viruses possessing the HA and NA vRNAs of the indicated viruses in combination with the internal vRNA segments of the respective natural wild-type isolate (WT), or of HY(Yam) (A-C) or HY(Vic) (D-F) (the viruses indicated by the black graphs possess the eight wild-type vRNA segments of a human influenza B virus isolate). The values presented are the average of three independent experiments±SD. P values were calculated by using the linear mixed model described in the Methods section (*P<0.05; **p<0.01). Red asterisks indicate the comparison of the respective virus with WT virus.
Figure 7B:
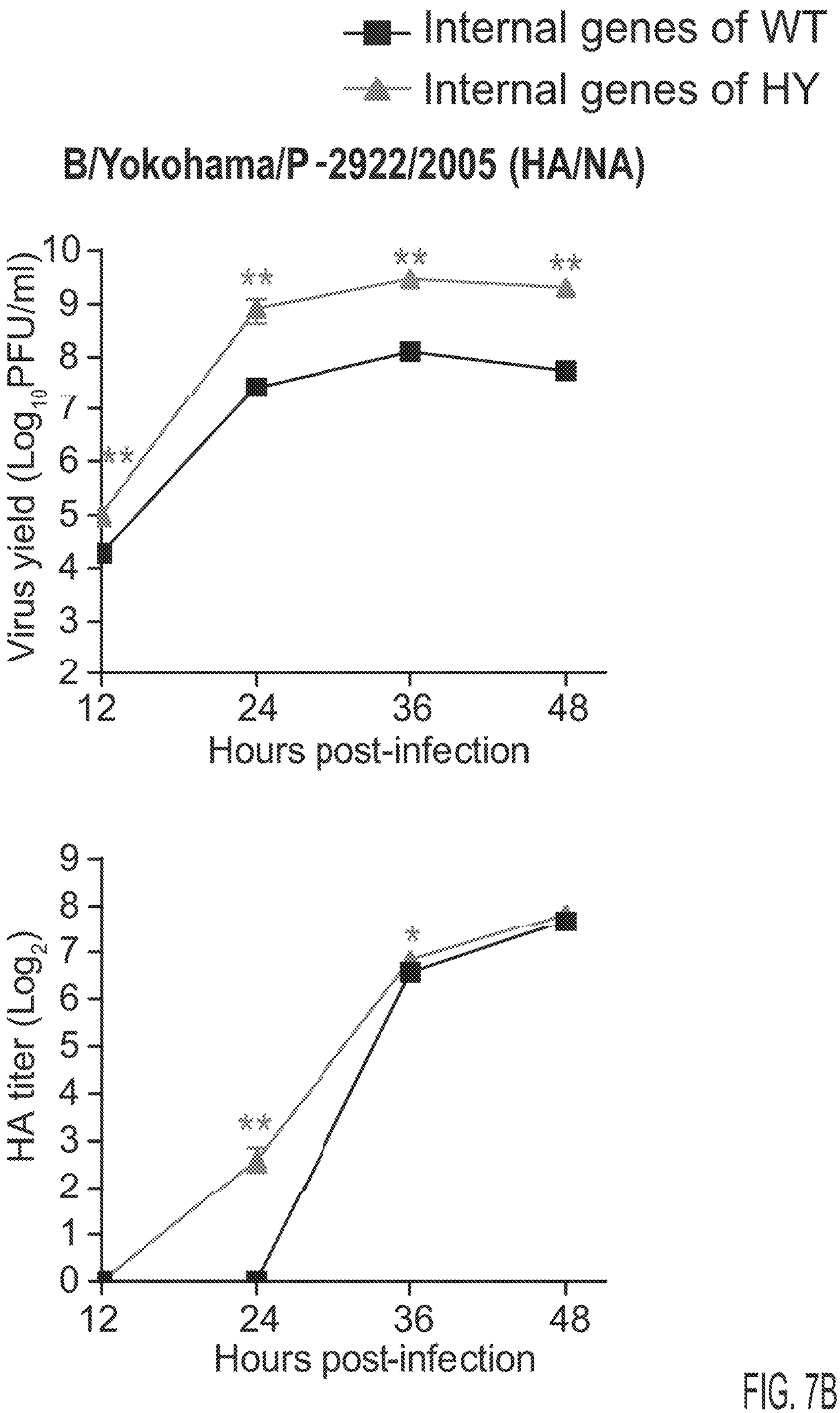
Figure 7C:
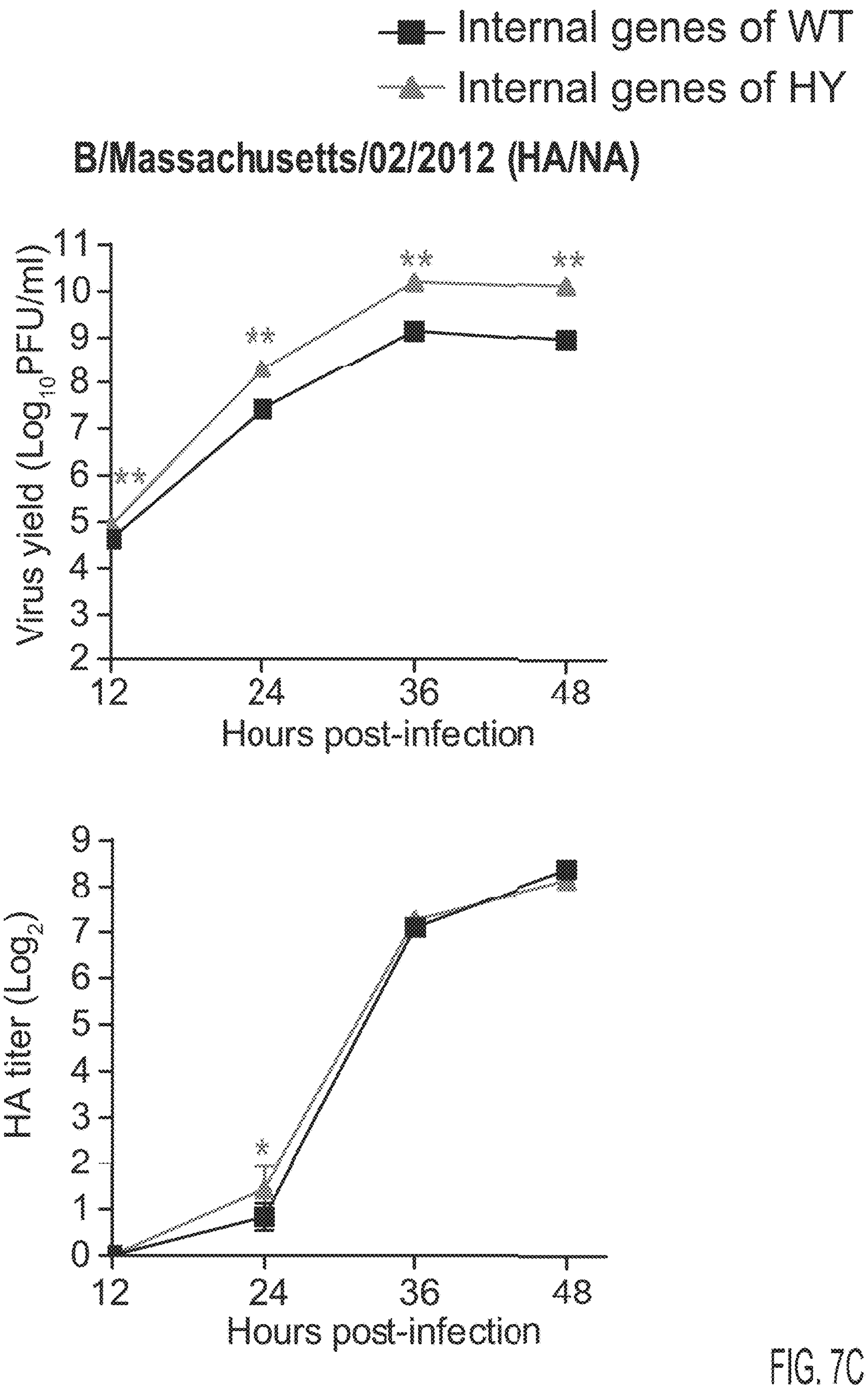
Figure 7D:
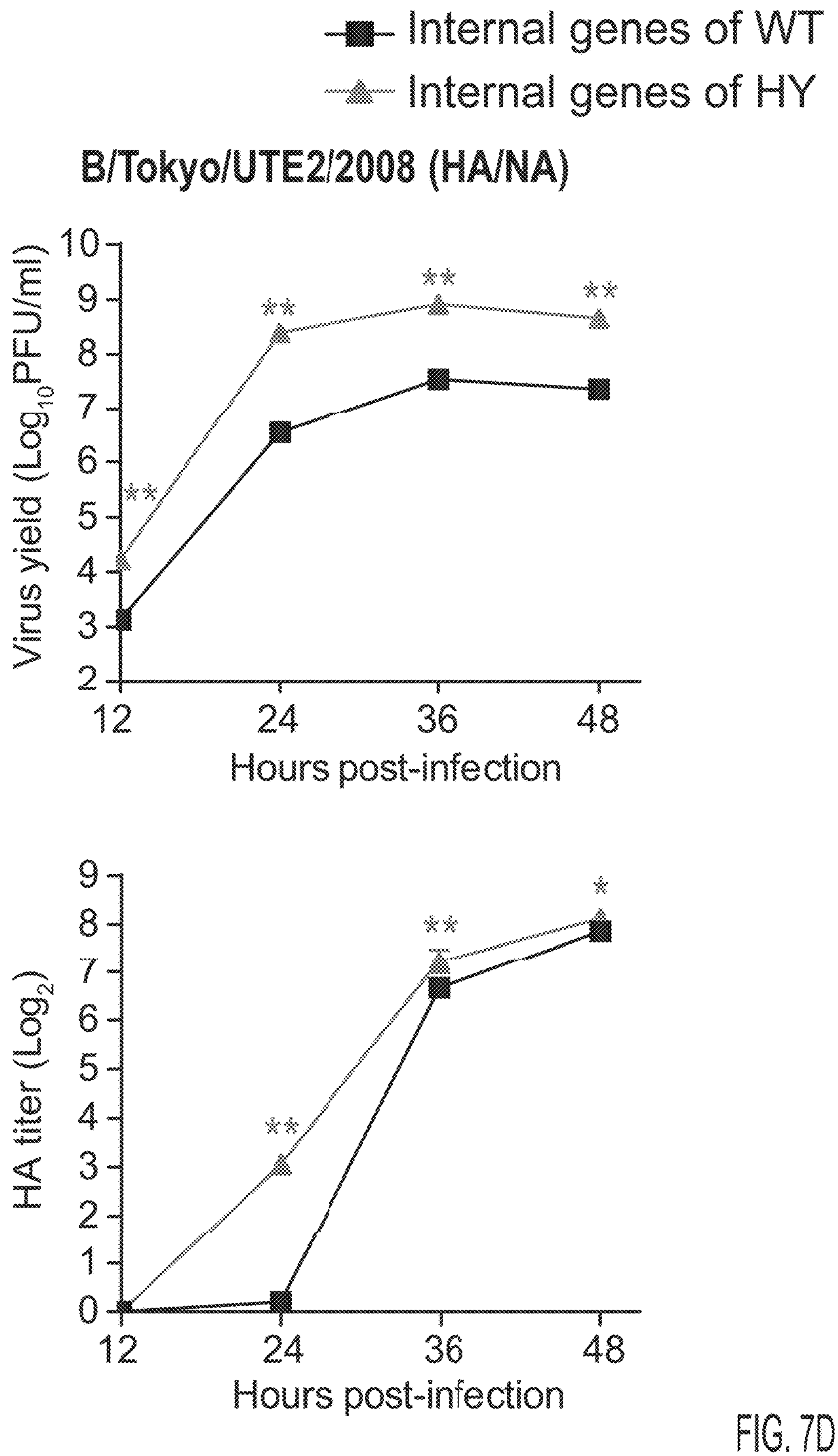
Figure 7E:
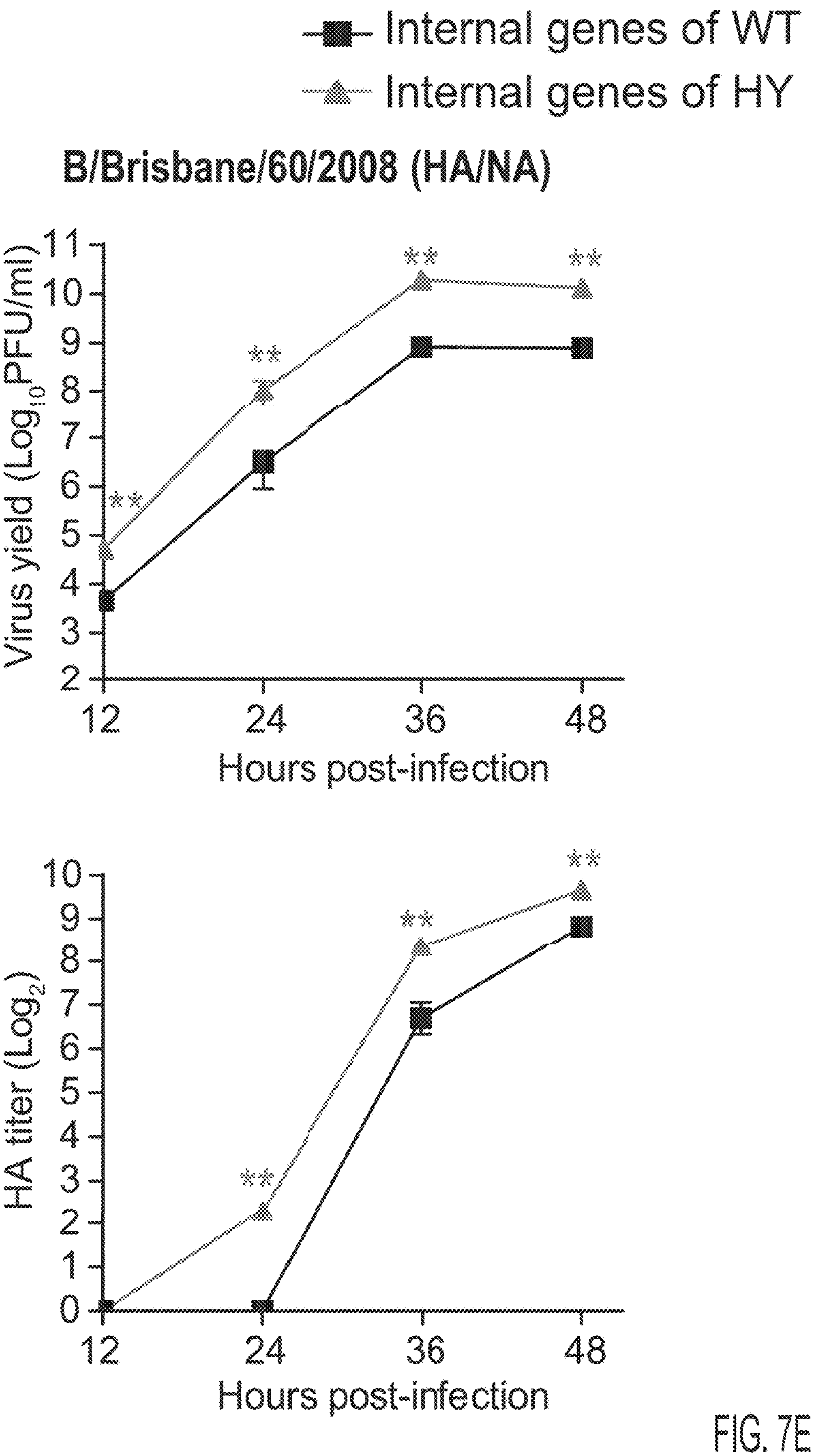
Figure 7F:
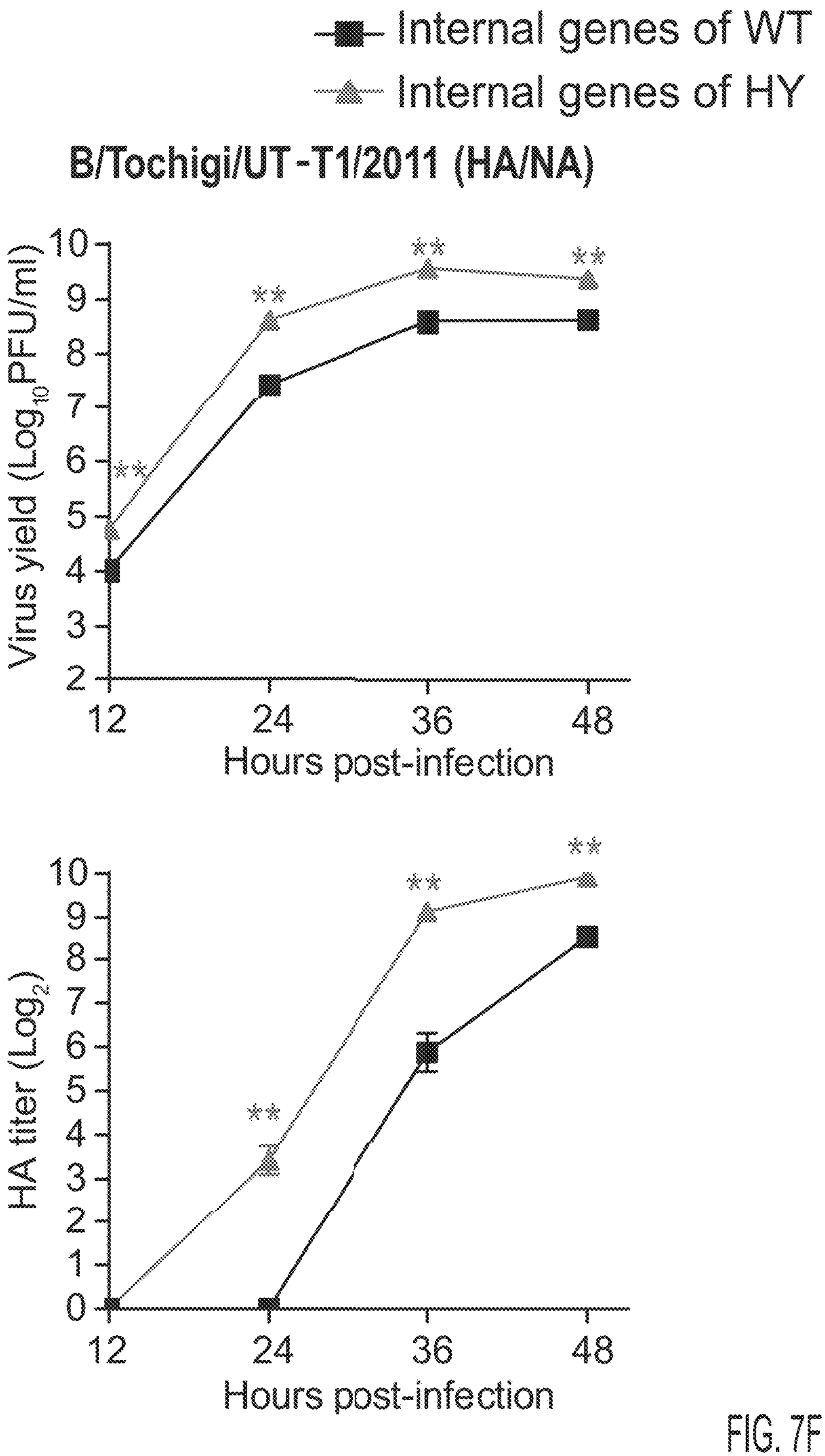
Figure 8A:
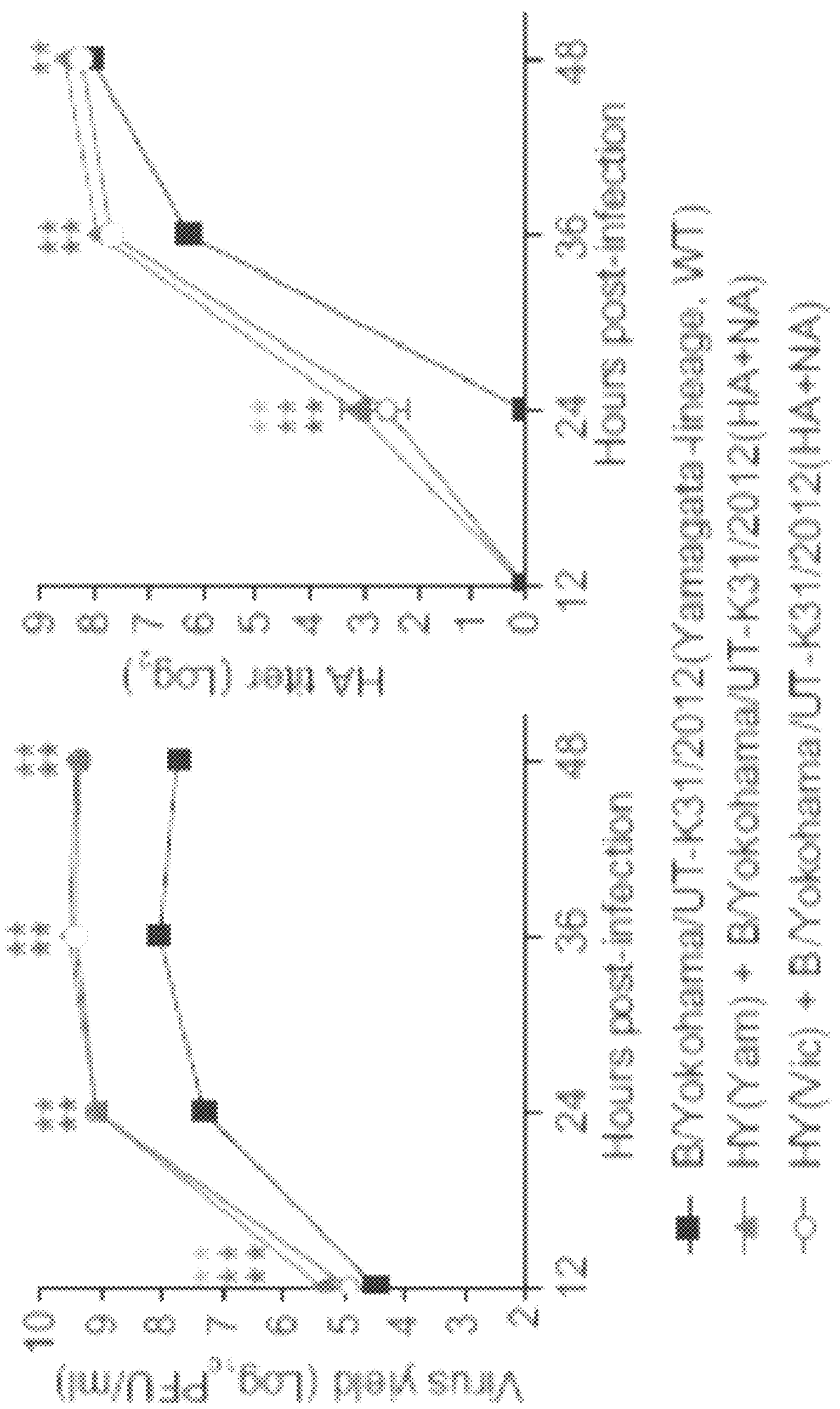
FIGS. 8A-D. Exchange of HY(Yam) and HY(Vic) backbones. (A and B) Comparison of the virus and hemagglutination titers of two wild-type Yamagata-lineage viruses with viruses possessing the same HA and NA vRNAs in combination with the internal genes of HY(Yam) or HY(Vic). (C and D) Comparison of the virus and hemagglutination titers of two wild-type Victoria-lineage viruses with viruses possessing the same HA and NA vRNAs in combination with the internal genes of HY(Yam) or HY(Vic). The values presented are the average of three independent experiments±SD. P values were calculated by using the linear mixed model (*P<0.05; **P<0.01). Red and blue asterisks indicate the comparison of the respective virus with WT virus; beige asterisks indicate the comparison between the viruses depicted in red and blue.
Figure 8B:
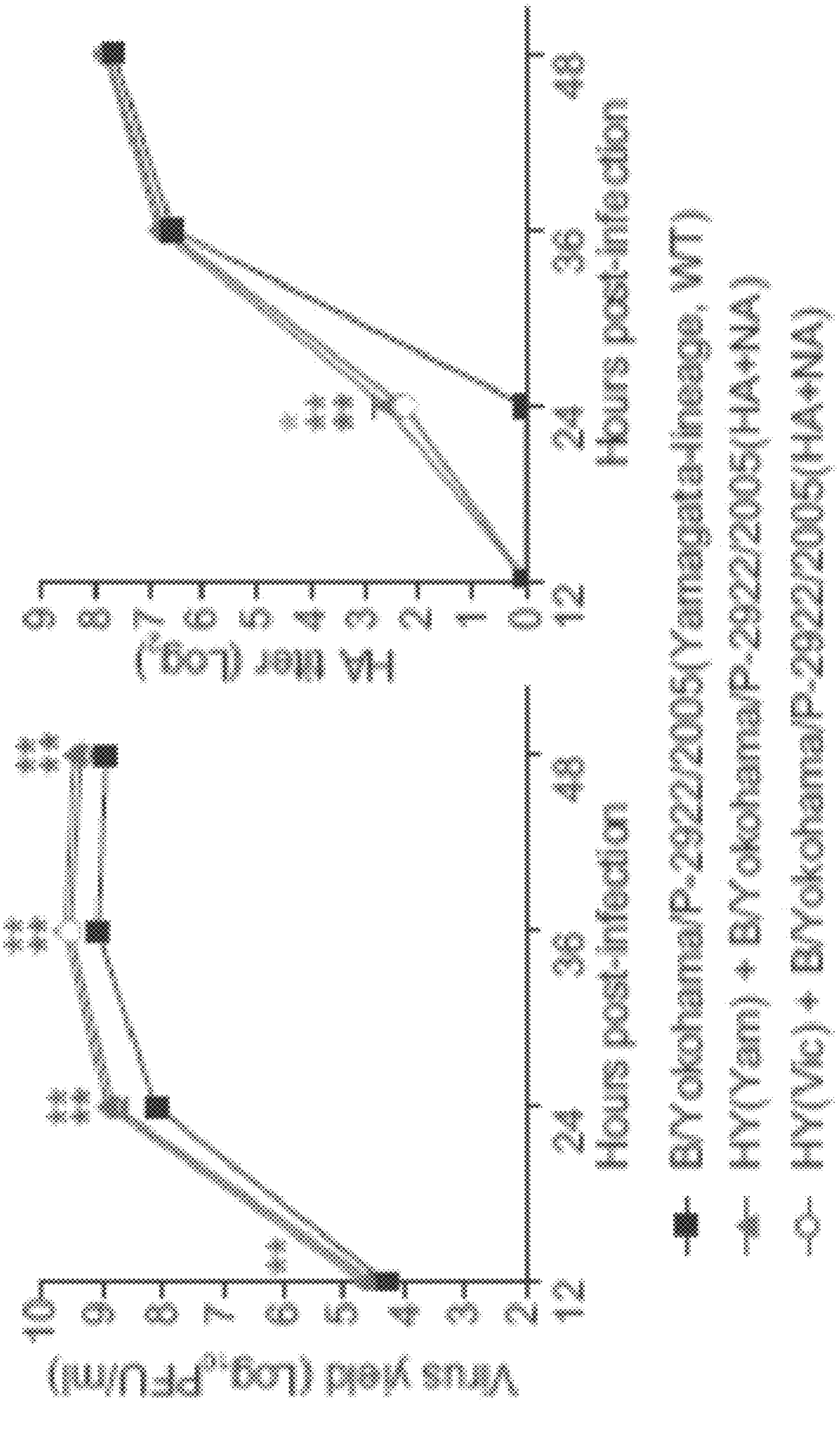
Figure 8C:
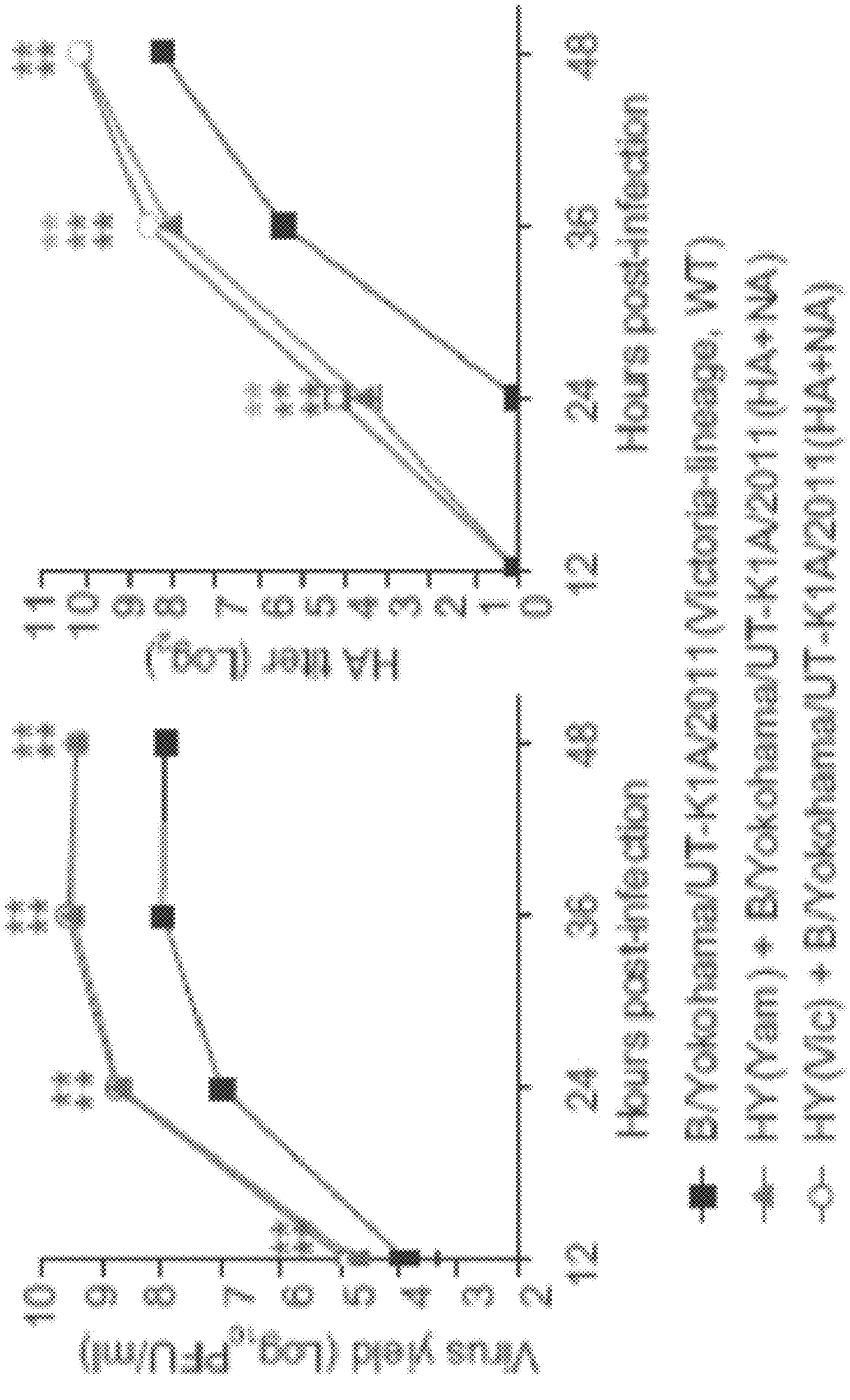
Figure 8D:
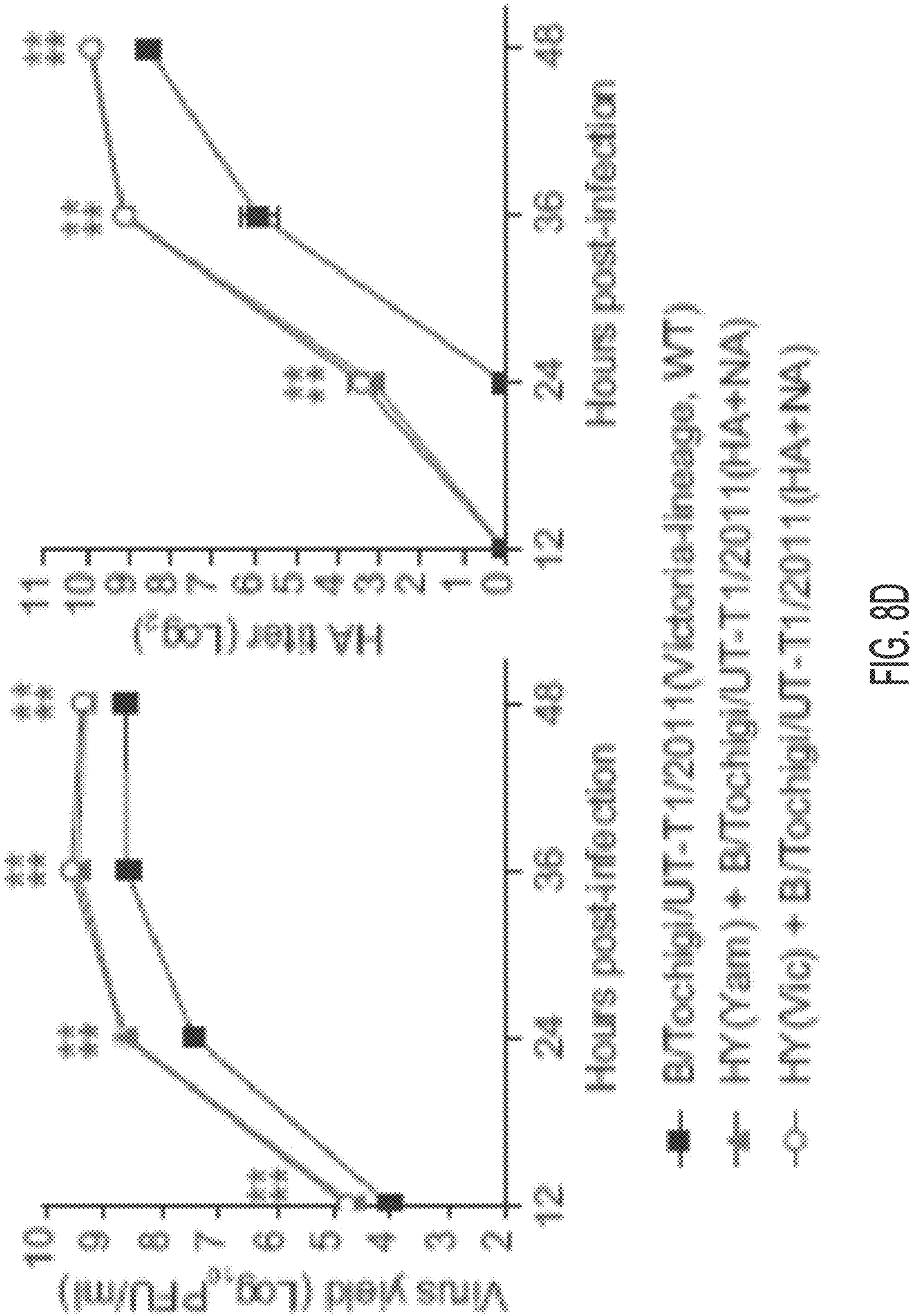

The PA-a2272t mutation emerged during passages of virus libraries in Vero cells (Tables 5 and 6) and significantly increased the viral and hemagglutination titers of a Victoria-lineage vaccine candidate (FIG. 6). This mutation was found to significantly increase the replication of a virus-like RNA in minireplicon assays (FIG. 105C). HY(Yam) and HY(Vic) possess NS-a39g and NS-38(+1)g mutations, respectively. These mutations were introduced into a virus-like RNA that expresses luciferase. Both mutations conferred significantly increased expression of the reporter protein from the virus-like RNA (FIG. 13D); this effect was substantially greater for the NS-38(+1)g mutation compared with the NS-a39g mutation.

Effect of Individual Mutations in HY(Yam) and HY(Vic) on the Composition of Virus-Like Particles. The M1-R77K and M1-M86T mutations in HY(Yam) and HY(Vic) affected viral and hemagglutination titers when tested individually (FIG. 12). M1 is the major structural component of virions and mutations in this protein could affect the composition of virions. 293T cells were transfected with plasmids for the expression of the B/Yamagata/1/73 HA, NA, NP, BM2, NS2, and wild-type or mutant M1 proteins; expression of this set of viral protein results in efficient virus-like particle (VLP) formation and release (Gomez-Puertas et al., 1999). Cell culture supernatant was collected and the VLP incorporation efficiency of viral proteins assessed (FIG. 14). Both mutations in M1 significantly increased the amount of viral HA, NP, and M1 proteins in the culture supernatant, which presumably resulted in the increased viral and hemagglutination titers conferred by the M1-R77K and -86T mutations.

Effect of a Mutation in the HY(Yam) NS1 Protein on IFN Antagonist Activity. The NS1 protein is the major influenza viral IFN antagonist (Yuan et al., 2001; Dauber et al., 2004). To assess the effect of the HY(Yam) NS1-K176Q mutation on NS1's ability to interfere with IFN-β synthesis, 293T cells were transfected with wild-type or mutant NS1 protein expression plasmids and with the reporter plasmid pGL-IFN-β, which encodes the firefly luciferase protein under the control of the IFN-β promoter (Bale et al., 2012). Cells were then infected with Sendai virus to stimulate IFN-β synthesis, resulting in increased reporter gene expression. Wild-type and mutant NS1 were comparable in their ability to down-regulate IFN-β synthesis (FIG. 12A). To determine the ability of wild-type and mutant NS1 to interfere with the expression of IFN-β-stimulated genes, 293T cells were transfected with wild-type or mutant NS1 protein expression plasmids and the reporter plasmid pISRE-Luc (Promega), which encodes the firefly luciferase protein under the control of an IFN-regulated promoter. Cells were stimulated with 24 hours later, incubated again for 24 hours, and then assayed for luciferase expression. The NS1-K176Q protein was slightly less efficient than wild-type NS1 in suppressing gene synthesis from an IFN-regulated promoter (FIG. 12B), suggesting that other mechanisms account for its growth-enhancing effect.

Discussion

To date, no systematic efforts have been carried out to develop a high-yield influenza B vaccine backbone. Vodeiko et al. (Vodeiko et al., 2003) compared two influenza B viruses that differed in their replicative ability in embryonated chicken eggs. Reassortment experiments revealed several vRNAs that contributed to the phenotypic differences (Vodeiko et al., 2003); however, the specific amino acids that determined the growth properties were not identified. Kim et al. (Kim et al., 2015) found that coldadaptation of influenza B viruses enhanced their growth properties. Several amino acid changes in HA, NA, and NP (not the mutations reported here) were responsible for the increased virus titers (Kim et al., 2015). Le et al. (2015) tested reassortants between B/Lee/40 and Yamagata- and Victoria-lineage influenza B viruses isolated in 2002-2007; all 14 high-yield candidates possessed the NP vRNA of B/Lee/40 virus, suggesting that this vRNA confers efficient replicative ability. Ping et al. (2015) published a more comprehensive strategy to develop high-yield influenza A vaccine backbones, which was applied here to influenza B viruses: from virus libraries possessing random mutations in the internal genes, candidates were selected that improved influenza B virus replication in MDCK and Vero cells. Combinations of mutations resulted in Yamagata- and Victoria-lineage vaccine candidates (encoding the NP-P40S, M1-R77K, NS1-K176Q, NS-a39g, and PA-a2272t mutations for the Yamagata-lineage vaccine and the NP-P40S/M204T, M1-M86T, NS-(38+1)g, and PA-a2272t mutations for the Victoria-lineage vaccine) with high yield in MDCK and Vero cells, and also in embryonated chicken eggs. Further studies in (semi)industrial settings would be necessary to determine whether lineage-specific vaccine backbones provide an advantage over a single backbone used for viruses of both lineages.

The total viral protein yield and HA content obtained from HY(Yam) and HY(Vic) were substantially higher than those from wild-type viruses (FIG. 10), High virus and HA yields are important for cost-effective vaccine production. More importantly, increases in vaccine virus yield may be imperative in years with high-vaccine demand and in years with shortened Virus yield vaccine production times. However, some of the observed differences in virus titers or HA yield were small (although statistically significant), and we currently do not know the extent by which HY(Yam) and HY(Vic) would increase vaccine virus yield in industrial vaccine production.

Evaluation of influenza B virus sequences revealed that the amino acid changes in HY(Yam) and HY(Vic) are rare among natural influenza B viruses (the NP-P40S, NF-M204T, and M1-M86T mutations have each been found in one isolate; the M1-R77K mutation has been reported in 14 isolates; and the NS1-K176Q mutation has not been detected). The 3D structure of an influenza B virus NP protein has been resolved (Ng et al., 2012), but position 40 (at which P-to-S mutations were selected from the Yamagata- and Victoria-lineage libraries) is part of the N-terminal 71 amino acids for which no structural data could be obtained, suggesting that this region is highly flexible. Sequence analysis of influenza B virus NP proteins revealed that the proline at position 40 is highly conserved: only 1 in 3,234 sequences does not encode NP-40P (the only exception, B/Tennessee/01/2015, encodes NP-40S, as found in this study). Interestingly, the NP P40S mutation reduced the activity of the viral replication complex in minireplicon assays, suggesting that the yield-enhancing effect of this mutation is mediated by functions other than replication and transcription. For example, this region in NP could interact with viral or cellular proteins during the export of viral ribonucleoprotein complexes from the nucleus to the cytoplasm, or during virion assembly.

Several mutations were also identified in the noncoding regions of vRNA segments that increased virus yield; some of these mutations conferred increased levels of replication and transcription, as measured in minireplicon assays. These mutations may, for example, increase the stability of the vRNA or affect its interaction with the viral polymerase complex. Further studies are needed to decipher the exact mechanistic functions of these mutations.

Collectively, influenza B vaccine virus backbones were developed that could increase the titers of seasonal influenza B vaccines in the propagation systems currently used for human influenza vaccine virus production.

TABLE 1

Amino acid changes of selected Yamagata lineage high yield clones.

| Yamagata lineage HY clones # | HA | NA | PB2 | PB1 | PA | NP | M1 | BM2 | NSI |
|---|---|---|---|---|---|---|---|---|---|
| #18, #19 | | | | | | | G34V, 197N | H58R, R80G | |
| #28 | K129E | | | | | | G34V, I97N | H58R, R80G | |
| #23 | N168D | | | | | | G34V, I97N | H58R, R80G | M117Y, S252T |
| #26 | | G434E | | | | | G34V, I97N | H58R, R80G | M117Y, S252T |
| #8 | | G434E | | | | | G34V, I97N | H58R, R80G | |
| #27 | | | | | | S57G | G34V, I97N | H58R, R80G | |
| #21 | | | | | | E52K | R77K | | |

TABLE 2

Amino acid changes of selected Victoria lineage high yield clones.

| Victoria lineage HY clones # | HA | NA | PB2 | PB1 | PA | NP | M1 | NS1 |
|---|---|---|---|---|---|---|---|---|
| #2 | T196P | | | | | P40S, M204T | M86T | |
| #4 | T196I | | | | | P40S, | M86T | |
| #27 | T196I | | | | | P40S | M86T | a39g, K176Q |
| #20 | T196A | | | | | P40S | D54G, M86T | Additional g insert after position 38* |
| #5 | T196P | | | | | P40S, P51Q | M86T | Additional g insert after position 38 |
| #25 | T34I, T196N | | | | | A28T, P40S, g1795a | M86T | Additional g insert after position 38 |

TABLE 2-continued

| Amino acid changes of selected Victoria lineage high yield clones. | | | | | | | | |
|---|---|---|---|---|---|---|---|---|
| Victoria lineage HY clones # | HA | NA | PB2 | PB1 | PA | NP | M1 | NS1 |
| #22 | T196P | N169T | | | | P40S, g1795a | M86T | Additional g insert after position 38 |
| #28 | | | | | | P40S, g1795a | M86T | Additional g insert after position 38 |

*Also referred to as 38(+1)g

Mutations in lowercase and italics in this and the following tables indicate nucleotide changes in the non-coding region

TABLE 3

| Amino acid changes of Yamagata lineage HY vaccine virus candidates generated by using reverse genetics. | | | | | | | | |
|---|---|---|---|---|---|---|---|---|
| Yamagata lineage canidates | HA &NA | PB2 | PB1 | PA | NP | M1 | BM2 | MS1 |
| RG(Yam)# 1 | B/Yokohama/UT-k31/2012 | | | | E52K | R77K | | |
| RG(Yam)# 2 | (Yamagata lineage) | | | | E52K | R77K | | M117Y, S252T |
| RG(Yam)# 3 | | | | | E52K | G34V, I97N | H58R, R82G | |
| RG(Yam)# 4 | | | | | S57G | R77K | | M117Y, S252T |
| RG(Yam)# 5 | | | | | P40S, g1795a | M86T | | Additional g insert after position 38 |
| RG(Yam)# 6 | | | | | P40S | D54G, M86T | | Additional g insert after position 38 |
| RG(Yam)# 7 | | | | | E52K | D54G, M86T | | M117Y, S252T |
| RG(Yam)# 8 | | | | | P40S | R77K | | a39g, K176Q |

TABLE 4

| Amino acid changes of Victoria lineage HY vaccine virus candidates generated by using reverse genetics. | | | | | | | | |
|---|---|---|---|---|---|---|---|---|
| Victoria lineage candidates | HA &NA | PB2 | PB1 | PA | NP | M1 | BM2 | NS1 |
| RG(Vic)#1 | B/Yokohama/UT-K1A/2011 | | | | P40S | D54G, M86T | | Addonal g insert after position 38 |
| RG(Vic)#2 | (Victoria lineage) | | | | P40S M204T | M86T | | Addonal g insert after position 38 |
| RG(Vic)#3 | | | | | P40S, g1795a | M86T | | Addonal g insert after position 38 |
| RG(Vic)#4 | | | | | P40S, P51Q | M86T | | Addonal g insert after position 38 |
| RG(Vic)#5 | | | | | P40S | M86T | | a39g, K176Q |
| RG(Vic)#6 | | | | | E52K | R77K | | |
| RG(Vic)#7 | | | | | E52K | D54G, M86T | | M117Y, S252T |
| RG(Vic)#8 | | | | | P40S | D54G, M86T | | Addonal ga insert after position 38 |

Virus libraries were passaged for a total of 12 times in MDCK cells, e.g., 2 passages after which the libraries may be mixed and then 10 more passages were carried out (FIG. 2). After passages in MDCK cells, plaque assays were performed and over 1,400 individual plaques were picked. High-yield candidates are shown in Tables 1-4.

Tables 5 and 6 show changes that resulted in enhanced growth in Vero cells using a similar protocol.

TABLE 5

Amino acid changes of Vero cell adapted HY Yamagata lineage viruses.

| Yamagata lineage clone | HA1 | HA2** | NA | PB2 | PBI | PA | NP | M1 | BM2 | NS1 |
|---|---|---|---|---|---|---|---|---|---|---|
| 1 | N194D | D112E | T436M | | | | | G34N, I97N | H58R | |
| 2 | T196P | D112E | E105K | N16S | | D494N | | G34N, I97N | H27R, H58R | |
| 3 | | D112E | T76M, P139S, D457N | N16S | | D494N | | G34N, I97N | H27R, H58R | |
| 4 | | D112E | R102K, T436M | | | a2272t | | G34N, I97N | H58R | |
| 5 | | D112E | T436M | | | a2272t | P343T | G34N, I97N | H58R | |
| 6 | | D112E | | | | g2213a, a2272t | P343T | G34N, I97N | G28R, H58R | |

**numbering begins at cleavage site

TABLE 6

Amino acid changes of Vero cell adapted HY Victoria lineage viruses.

| Victoria lineage clone | HA1 | HA2** | NA | PB2 | PB1 | PA | NP | M1 | BM2 | NS1 |
|---|---|---|---|---|---|---|---|---|---|---|
| 1 | T196A, | S56G, K61N | D457N | | | Y387H, V434A, T524A, a2272t | | | R80G | Y42N |
| 2 | T196A, | K39G, S56G | D457N | | | Y387H, V434A, a2272t | | | R80G | Y42N |
| 3 | T196A | S56G, K61N | D457N | | | Y387H, V434A, a2272t | | | R80G | Y42N |
| 4 | R98K, T196A | S56G | D457N | | | Y387H, V434A, a2272t | | | R80G | Y42N |
| 5 | T196A | K39G, S56G | D457N | | | Y387H, V434A, a2272t | | | R80G | Y42N |
| 6 | T196A | S56G | D457N | | | Y387H, V434A, a2272t | | | R80G | Y42N |

**numbering begins at cleavage site

TABLE 7

Amino acid changes detected after serial virus passages in embryonated chicken eggs

| Virus | Egg passage | Amino acid changes in HA |
|---|---|---|
| B/Massachusetts/2/2012 | P1 | None |
| | P2 | None |
| | P3 | None |
| | P4 | None |
| | P5 | None |
| | P6 | None |
| | P7 | None |
| | P8 | None |

TABLE 7-continued

Amino acid changes detected after serial virus passages in embryonated chicken eggs

| Virus | Egg passage | Amino acid changes in HA |
|---|---|---|
| | P9 | None |
| | P10 | None |
| HY(Yam) + B/Massachusetts/2/2012 (HA + NA) | P1 | None |
| | P2 | None |
| | P3 | None |
| | P4 | None |
| | P5 | None |
| | P6 | None |
| | P7 | None |

TABLE 7-continued

Amino acid changes detected after serial virus passages in embryonated chicken eggs

| Virus | Egg passage | Amino acid changes in HA |
|---|---|---|
| | P8 | None |
| | P9 | None |
| | P10 | None |
| B/Brisbane/60/2008 | P1 | None |
| | P2 | None |
| | P3 | None |
| | P4 | None |
| | P5 | None |
| | P6 | None |
| | P7 | None |
| | P8 | None |
| | P9 | None |
| | P10 | None |
| HY(Vic) + B/Brisbane/60/2008 (HA + NA) | P1 | None |
| | P2 | None |
| | P3 | None |
| | P4 | None |
| | P5 | None |
| | P6 | None |
| | P7 | None |
| | P8 | None |
| | P9 | None |
| | P10 | None |
| B/Yokohama/UT-K31/2012 | P1 | None |
| | P2 | N194K (loss of glycosylation site) |
| | P3 | N194K (loss of glycosylation site) |
| | P4 | N194K (loss of glycosylation site) |
| | P5 | N194K (loss of glycosylation site) |
| HY(Yam) + B/Yokohama/UT-K31/2012(HA + NA) | P1 | None |
| | P2 | N194N/S (N194S results in loss of glycosylation site) |
| | P3 | N194S (loss of glycosylation site) |
| | P4 | N194S (loss of glycosylation site) |
| | P5 | N194S (loss of glycosylation site) |
| B/Yokohama/UT-K1A/2011 | P1 | None |
| | P2 | T196I (loss of glycosylation site) |
| | P3 | T196I (loss of glycosylation site) |
| | P4 | T196I (loss of glycosylation site) |
| | P5 | T196I (loss of glycosylation site) |
| Hy(Vic) + B/Yokohama/UT-K1A/2011(HA + NA) | P1 | None |
| | P2 | T196T/I (T196I results in loss of glycosylation site) |
| | P3 | T196T/I (T196I results in loss of glycosylation site) |
| | P4 | T196I (loss of glycosylation site) |
| | P5 | T196I (loss of glycosylation site) |
| Hy(Vic) + B/Yokohama/UT-K1A/2011(HA + NA) (10 sequential passages in MDCK cells) | P1 | None (MDCK passages already resulted in loss of glycosylation site at positions 194-196) |
| | P2 | None (MDCK passages already resulted in loss of glycosylation site at positions 194-196) |
| | P3 | None (MDCK passages already resulted in loss of glycosylation site at positions 194-196) |
| | P4 | None (MDCK passages already resulted in loss of glycosylation site at positions 194-196) |
| | P5 | None (MDCK passages already resulted in loss of glycosylation site at positions 194-196) |
| B/Yokohama/P-2922/2005 | P1 | None |
| | P2 | N194D (loss of glycosylation site) |
| | P3 | N194D (loss of glycosylation site) |
| | P4 | N194D (loss of glycosylation site) |
| | P5 | N194D (loss of glycosylation site) |
| HY(Yam) + B/Yokohama/P-2922/2005 | P1 | None |
| | P2 | N194D (loss of glycosylation site) |
| | P3 | N194D (loss of glycosylation site) |
| | P4 | N194D (loss of glycosylation site) |
| | P5 | N194D (loss of glycosylation site) |
| B/Tokyo/UTE2/2008 | P1 | T196I (loss of glycosylation site) |
| | P2 | T196I (loss of glycosylation site) |
| | P3 | T196I (loss of glycosylation site) |
| | P4 | T196I (loss of glycosylation site) |
| | P5 | T196I (loss of glycosylation site) |
| HY(Vic) + B/Tokyo/UTE2/2008 (HA + NA) | P1 | None |
| | P2 | N194S (loss of glycosylation site) |
| | P3 | N194S (loss of glycosylation site) |
| | P4 | N194S (loss of glycosylation site) |
| | P5 | N194S (loss of glycosylation site) |

REFERENCES

Ambrose and Levin, *Hum. Vaccin. Immunother.,* 8:81 (2012).

*Avery's Drug Treatment: Principles and Practice of Clinical Pharmacology and Therapeutics,* 3rd edition, ADS Press, Ltd., Williams and Wilkins, Baltimore, MD (1987).

Aymard-Henry et al., *Virology: A Practical Approach*, Oxford IRL Press, Oxford, 119-150 (1985).

Bachmeyer, *Intervirology,* 5:260 (1975).

Baker et al., *J. Virol.,* 88:10778 (2014).

Bale et al., *PLoS Pathog.,* 8: e1002916 (2012).

Belshe et al., *Influenza Other Respi. Viruses.* 4:141 (2010).

Belshe, *Vaccine,* 28: D45 (2010).

Berkow et al., eds., *The Merck Manual,* 16th edition, Merck & Co., Rahway, NJ (1992).

Dauber et al., *J. Virol.,* 78:1865 (2004).

Flandorfer et al., *J. Virol.,* 77:9116 (2003).

Fujii et al., *Proc. Natl. Acad. Sci. U.S.A.,* 100:2002 (2003).

Glezen et al., *Am. J. Public Health,* 103: e43 (2013).

Gómez-Puertas et al., *J. Gen. Virol.,* 80:1635 (1999).

Hatta et al., *Science,* 293:1840 (2001).

Horimoto et al., *J. Virol.,* 68:3120 (1994).

Horimoto et al., *Microbes Infect.,* 6:579 (2004).

Horimoto et al., *Vaccine,* 24:3669 (2006).

Keitel et al., in Textbook of Influenza, eds. Nickolson, K. G., Webster, R. G., and Hay, A. (Blackwell, Oxford), pp. 373-390 (1998).

Kim et al., *Vaccine,* 33:5786 (2015).

Knipe et al., (Lippincott Williams & Wilkins, Philadelphia, PA), 6th Ed, vol 1, pp 1186-1243.

Laver & Webster, *Virology,* 69:511 (1976).

Le et al., *Vaccine,* 33:879 (2015).

Maassab, *J. Immunol.,* 102:728 (1969).

Neumann et al., *Adv. Virus Res.,* 53:265 (1999).

Neumann et al., *J. Gen. Virol.,* 83:2635 (2002).

Neumann et al., *J. Virol.,* 71:9690 (1997).

Neumann et al., *Proc. Natl. Acad. Sci. USA,* 96:9345 (1999).

Neumann et al., *Virology,* 287:243 (2001).

Ng, et al., *J. Virol.,* 86:6758 (2012).

Osol (ed.), *Remington's Pharmaceutical Sciences*, Mack Publishing Co., Easton, PA 1324-1341 (1980).

Ping et al., *Nat. Commun.,* 6:8148 (2015).
Ramanunninair, et al. *PLoS One,* 8: e65955 (2013).
Rota, et al., *Virology,* 175:59 (1990).
Sugawara et al., *Biologicals,* 30:303 (2002).
Tafalla et al., *Hum. Vaccin. Immunother.,* 12:993002 (2016).
van de Sandt et al., *Future Microbiol.,* 10:1447 (2015).
Vodeiko et al., *Vaccine,* 21:3867 (2003).
Webby & Webster et al., *Science,* 302:1519 (2003).
Wood & Robertson, *Nat. Rev. Microbiol.,* 2:842 (2004).
World Health Organization TSR No. 673 (1982).
World Health Organization. Confirmed human cases of avian influenza A (H5N1). http://www.who.int/csr/disease/avian_influenza/country/en/index.html
Wright et al., *Fields Virology*, eds (2013). Orthomyxoviruses.
Yuan and Krug, *EMBO. J.,* 20:362 (2001).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated recombinant influenza B virus having PA, PB1, PB2, NP, NS, and M viral segments, a heterologous or chimeric influenza virus NA viral segment, and a heterologous or chimeric HA viral segment, wherein the NP viral segment encodes a NP polypeptide having threonine at position 40, or a serine or threonine at position 40 and a threonine, valine, leucine, isoleucine or alanine at position 204, wherein the M viral segment encodes a M1 polypeptide with a lysine or histidine at position 77 or a M1 polypeptide with a threonine, glycine, valine, leucine, isoleucine or alanine at position 86, wherein the NS viral segment encodes a NS1 polypeptide with a glutamine or asparagine at position 176, and optionally the NS viral segment encodes a NS1 polypeptide having a residue other than Y at position 42, other than M at position 117, and/or other than S at position 252, and/or the NS viral segment has a nucleotide other than a at nucleotide position 39 or a nucleotide insertion after position 38, or any combination thereof; or optionally the M viral segment encodes a M1 polypeptide having a residue other than G at position 34, other than D at position 54, or other than I at position 97, or any combination thereof; or optionally the M viral segment encodes a BM2 polypeptide having a residue other than H at position 58, other than R at position 80, other than H at position 27, or other than G at position 26, or any combination thereof; or optionally the NP viral segment has a nucleotide other than g at nucleotide position 1795 or other than c at nucleotide position 500, or any combination thereof, or optionally the PA viral segment encodes a PA polypeptide having a residue other than Y at position 387, other than V at position 434, other than D at position 494, and/or other than T at position 524, and/or the PA viral segment has a nucleotide other than a at nucleotide 2272, other than a at position 1406, other than c at position 1445, or other than g at nucleotide 2213, or any combination thereof; or optionally the PB2 viral segment encodes a PB2 polypeptide having a residue other than N at position 16; or any combination thereof, wherein the position in the NP polypeptide is relative to a NP polypeptide encoded by SEQ ID NO: 4, wherein the position in the NS polypeptide is relative to a NS polypeptide encoded by SEQ ID NO: 6, wherein the position in the M1 polypeptide is relative to a M1 polypeptide encoded by SEQ ID NO: 5, wherein the position in the BM2 polypeptide is relative to a BM2 polypeptide encoded by SEQ ID NO: 5, wherein the position in the PA polypeptide is relative to a PA polypeptide encoded by SEQ ID NO: 3, or wherein the position in the PB2 polypeptide is relative to a BM2 polypeptide encoded by SEQ ID NO: 1.

2. The isolated virus of claim 1 wherein the NP polypeptide further has at least one of: T at position 28, Q at position 51, K at position 52, G at position 57, T at position 343, a at position 1795 or the NP viral segment hast at position 500.

3. The isolated virus of claim 1 wherein the M1 polypeptide has at least one of: V or N at position 34, G at position 54, K at position 77, T at position 86, or N at position 97.

4. The isolated virus of claim 1 wherein the BM2 polypeptide has at least one of: R at position 58, G at position 80, R at position 27 or R at position 26.

5. The isolated virus of claim 1 wherein the NS1 polypeptide has at least one of: N at position 42, Y at position 117, Q at position 176, T at position 252, or the NS segment has a nucleotide insertion of g after nucleotide position 38 or g at position 39.

6. The isolated virus of claim 1 wherein the PA viral segment has at least one of: H at position 387, A at position 434, N at position 494, A at position 524, g at position 1406, t at position 2272, t at position 1445, or any combination thereof.

7. The isolated virus of claim 1 wherein the NP polypeptide has T at position 40 and further comprises one or more of: the NP viral segment hast at nucleotide 500, the M1 polypeptide has K at position 77, the NS1 polypeptide has Q at position 176 and the NS viral segment has g at nucleotide 39, or the PA viral segment has g at nucleotide 1406, t at nucleotide 1445, and t at nucleotide 2272.

8. The isolated virus of claim 1 wherein the M1 polypeptide has T at position 86, the NS viral segment has an insertion of g after nucleotide 38, or the PA viral segment has g at nucleotide 1406, t at nucleotide 1445, or t at nucleotide 2272.

9. The isolated virus of claim 1 wherein the NA gene segment and the HA gene segment are from the same influenza virus isolate.

10. The isolated virus of claim 1 wherein the PA, PB1, PB2, NP, NS, and M viral segments comprise sequences encoding at least one of the following: a PB1 having the amino acid sequence encoded by SEQ ID NO: 2 or PB1 with at least 80% amino acid sequence identity to the PB1 encoded by SEQ ID NO: 2; a PB2 having the amino acid sequence encoded by SEQ ID NO: 3 or PB2 with at least 80% amino acid sequence identity to the PB2 encoded by SEQ ID NO: 3; a PA having the amino acid sequence encoded by SEQ ID NO: 1 or PA with at least 80% amino acid sequence identity to the PA encoded by SEQ ID NO: 1; a NP having the amino acid sequence encoded by SEQ ID NO: 4 or NP with at least 80% amino acid sequence identity to the NP encoded by SEQ ID NO: 4; a M having the amino acid sequence encoded by SEQ ID NO: 5 or M with at least 80% amino acid sequence identity to the M encoded by SEQ NO: 5; or a NS having the amino acid sequence encoded by SEQ ID NO: 6 or NS with at least 95% amino acid sequence identity to the NS encoded by SEQ ID NO: 6.

11. The isolated virus of claim 1 which has a heterologous HA gene segment or a heterologous NA gene segment.

12. The isolated virus of claim 1 wherein the M1 polypeptide has V at position 34, N at position 97, or T at position 86, or any combination thereof; or the BM2 polypeptide has R at position 58 and/or G at position 80; or the NP polypeptide bas S at position 40 or K at position 52.

13. A vaccine having the isolated recombinant virus of claim 1.

14. A method to prepare influenza virus, comprising: contacting a cell with:

a vector for vRNA or cRNA production comprising a promoter operably linked to an influenza virus PA DNA linked to a transcription termination sequence, a vector for vRNA or cRNA production comprising a promoter operably linked to an influenza virus PB1 DNA linked to a transcription termination sequence, a vector for vRNA or cRNA production comprising a promoter operably linked to an influenza virus PB2 DNA linked to a transcription termination sequence, a vector for vRNA or cRNA production comprising a promoter operably linked to an influenza virus HA DNA linked to a transcription termination sequence, a vector for vRNA or cRNA production comprising a promoter operably linked to an influenza virus NP DNA linked to a transcription termination sequence, a vector for vRNA or cRNA production comprising a promoter operably linked to an influenza virus NA DNA linked to a transcription termination sequence, a vector for vRNA or cRNA production comprising a promoter operably linked to an influenza virus M DNA linked to a transcription termination sequence, and a vector for vRNA or cRNA production comprising a promoter operably linked to an influenza virus NS DNA linked to a transcription termination sequence, wherein the PB1, PB2, PA, NP, NS, and M DNAs in the vectors for vRNA or CRNA production are from one or more influenza vaccine virus isolates, wherein the NA DNA in the vector for vRNA or cRNA production of NA has sequences for a heterologous or chimeric NA, and wherein the HA DNA in the vector for vRNA or cRNA production of HA has sequences for a heterologous or chimeric HA, wherein the NP viral segment encodes a NP polypeptide having threonine at position 40, or a serine or threonine at position 40 and a threonine, valine, leucine, isoleucine or alanine at position 204, wherein the M viral segment encodes a M1 polypeptide with a lysine or histidine at position 77 or a M1 polypeptide with a threonine, glycine, valine, leucine, isoleucine or alanine at position 86, wherein the NS viral segment encodes a NS1 polypeptide with a glutamine or asparagine at position 176, and optionally wherein the NS vRNA or cRNA encodes a NS1 polypeptide having a residue other than Y at position 42, other than M at position 117, and/or other than S at position 252, and/or a nucleotide other than an a at position 39 or a nucleotide insertion after position 38, or any combination thereof; or optionally the M vRNA or cRNA encodes a M1 polypeptide having a residue other than G at position 34, other than D at position 54, other than I at position 97, or any combination thereof; or optionally encoded by the M vRNA or cRNA encodes a BM2 polypeptide having a residue other than H at position 58, other than R at position 80, other than H at position 27, other than G at position 26, or any combination thereof; or optionally the NP vRNA or cRNA has a nucleotide other than g at position 1795 or other than c at position 500, or any combination thereof, or optionally the PA vRNA or cRNA encodes a PA polypeptide having a residue other than Y at position 387, other than V at position 434, other than D at position 494, and/or other than T at position 524, and/or the PA vRNA or cRNA has a nucleotide other than a at nucleotide 2272, other than a at position 1406, other than e at position 1445, and/or other than g at nucleotide 2213, or any combination thereof; or optionally the PB2 vRNA or cRNA encodes a PB2 polypeptide has a residue other than N at position 16, wherein the position in the NS polypeptide is relative to a NS polypeptide encoded by SEQ ID NO: 6, wherein the position in the M1 polypeptide is relative to a M1 polypeptide encoded by SEQ ID NO: 5, wherein the position in the BM2 polypeptide is relative to a BM2 polypeptide encoded by SEQ ID NO: 5, wherein the position in the PA polypeptide is relative to a PA polypeptide encoded by SEQ ID NO: 3, or wherein the position in the PB2 polypeptide is relative to a PB2 polypeptide encoded by SEQ NO: 1;

or any combination thereof, and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP; in an amount effective to yield infectious influenza virus.

15. The method of claim 14 wherein the cell is an avian cell or a mammalian cell.

16. The method of claim 15 wherein the cell is a Vero cell, a human cell or a MDCK cell.

17. The method of claim 14 wherein the NP polypeptide has T at position 40 and the NP vRNA hast at nucleotide 500, the M1 polypeptide has K at position 77, the NS1 polypeptide has Q at position 176 and the NS vRNA has g at nucleotide 39, or the PA vRNA has g at nucleotide 1406, t at nucleotide 1445, and t at nucleotide 2272.

18. The method of claim 14 wherein the NP vRNA has t at nucleotide 500, the M1 polypeptide has T at position 86, the NS vRNA has an insertion of g after nucleotide 38, or the PA vRNA has g at nucleotide 1406, t at nucleotide 1445, and t at nucleotide 2272.

19. The method of claim 14 further comprising isolating the infectious influenza virus.

* * * * *

SEQUENCE LISTING

```
<160> NUMBER OF SEQ ID NOS: 19

<210> SEQ ID NO 1
<211> LENGTH: 2396
<212> TYPE: DNA
<213> ORGANISM: Influenza B

<400> SEQUENCE: 1

agcagaagcg gagcgttttc aagatgacat tggctaaaat tgaattgtta aaacaactgt     60

taagggacaa cgaagccaaa acagtattga aacaaacaac ggtagaccaa tataacataa    120

taagaaaatt caatacatca agaattgaaa agaacccttc attaaggatg aagtgggcca    180

tgtgttctaa ttttcccttg gctctgacca agggtgatat ggcaaataga atccccttgg    240

aatacaaggg aatacaactt aaaacaaatg ctgaagacat aggaaccaaa ggccaaatgt    300

gctcaatagc agcagttacc tggtggaata catatggacc aataggagac actgaaggtt    360

tcgaaaaggt ctacgaaagc ttctttctca gaaagatgag acttgacaat gccacttggg    420

gccgaataac ttttggccca gttgaaagag taagaaaaag ggtactgcta aaccctctca    480

ccaaggaaat gcctccagat gaagcgagca atgtgataat ggaaatattg ttccctaagg    540

aagcaggaat accaagagaa tctacttgga tacataggga actgataaaa gaaaaaaagag    600

aaaaattgaa aggaacgatg ataactccca ttgtactggc atacatgctt gagagagaat    660

tggttgcccg aagaaggttc ctgccagtgg caggagcaac atcagctgag ttcatagaaa    720

tgctacactg cttacaaggt gaaaattgga gacaaatata tcacccagga gggaataaac    780

taactgaatc taggtctcaa tcaatgattg tagcttgtag aaaaataatc agaagatcaa    840

tagtcgcatc aaacccacta gagctagctg tagaaattgc aaacaagact gtgatagata    900

ctgaaccttt aaaatcatgt ctggcagcca tagacggagg tgatgtagcc tgtgacataa    960

tgagagctgc attaggacta aagatcagac aaagacaaag atttggacgg cttgaactaa   1020

agagaatatc aggaagagga ttcaaaaatg atgaagaaat attgatcggg aacggaacaa   1080

tacagaagat tggaatatgg gacggagaag aggagttcca tgtaagatgt ggtgaatgca   1140

ggggaatatt aaaaaagagc aaaatgagaa tggaaaaact actaataaat tcagccaaaa   1200

aggaggacat gaaagattta ataatcttgt gcatggtatt ttctcaagac actaggatgt   1260

tccaaggagt gagaggagaa ataaattttc ttaatcgagc aggccaactt ttatctccaa   1320

tgtaccaact ccaaagatat tttttgaata ggagcaacga tctttttgat caatgggggt   1380

atgaggaatc acccaaagca agtgaactac atgggataaa tgaattaatg aatgcatctg   1440

attatacgtt gaaaggggtt gtagtaacaa aaaatgtgat tgatgacttt agttctactg   1500

aaacagaaaa agtatctata acaaaaaatc ttagtttaat aaaaagaact ggggaagtca   1560
```

-continued

```
taatgggggc taatgacgta agtgaattag aatcacaagc tcagctaatg ataacatatg   1620

atacacctaa gatgtgggag atgggaacaa ccaaagaact ggtgcaaaac acctaccaat   1680

gggtgctaaa aaatttggta acactgaagg ctcagtttct tctaggaaaa gaagacatgt   1740

tccaatggga tgcatttgaa gcatttgaaa gcataatccc ccagaagatg gctggccagt   1800

acagtggatt tgcaagggca gtgctcaaac aaatgagaga ccaagaggtt atgaaaactg   1860

accagttcat aaagttgttg cctttctgtt tctcaccacc aaaattaagg agcaatgggg   1920

agccttatca attcttgagg cttatattga agggaggagg agaaaatttc atcgaagtaa   1980

ggaaagggtc ccctctattc tcctacaatc cacaaacaga agtcctaact atatgcggca   2040

gaatgatgtc attaaaaggg aaaattgaag atgaagaaag gaatagatca atggggaatg   2100

cagtattggc aggctttctc gttagtggca agtatgaccc agatcttgga gatttcaaaa   2160

ctattgaaga acttgaaaag ctaaaaccgg gggagaaagc aaacatctta ctttatcaag   2220

gaaagcccgt taaagtagtt aaaaggaaaa gatatagtgc tttatccaat gacatttcac   2280

aaggaattaa gagacaaaga atgacagttg agtccatggg gtgggccttg agctaatata   2340

aatttatcca ttaattcaat aaacacaatt gagtgaaaaa tgctcgtgtt tctact       2396
```

<210> SEQ ID NO 2
<211> LENGTH: 2369
<212> TYPE: DNA
<213> ORGANISM: Influenza B

<400> SEQUENCE: 2

```
agcagaagcg gagcctttaa gatgaatata aatccttatt ttctcttcat agatgtaccc     60

atacaggcag caatttcaac aacattccca tacaccggtg ttccccctta ttcccatgga    120

acgggaacag gctacacaat agacaccgtg atcagaacac atgagtactc aaacaaggga    180

aaacagtaca tttctgatgt tacaggatgt acaatggtag atccaacaaa tgggccatta    240

cccgaagaca atgagccgag tgcctatgca caattagatt gcgttctgga ggctttggat    300

agaatggatg aagaacatcc aggtctgttt caagcagcct cacagaatgc catggaggca    360

ctaatggtca caactgtaga caaattaacc caggggagac agacttttga ttggacagta    420

tgcagaaacc aacctgctgc aacggcactg aacacaacaa taacctcttt taggttgaat    480

gatttgaatg gagccgacaa gggtggatta gtacccttt gccaagatat cattgattca    540

ttggacagac ctgaaatgac tttcttctca gtaaagaata taaagaaaaa attgcctgct    600

aaaaacagaa agggtttcct cataaagaga ataccaatga aggtaaaaga cagaataacc    660

agagtggaat acatcaaaag agcattatca ttaaacacaa tgacaaaaga tgctgaaaga    720

ggcaaactaa aaagaagagc gattgccacc gctggaatac aaatcagagg gtttgtatta    780

gtagttgaaa acttggctaa aaatatctgt gaaaatctag aacaaagtgg tttgccagta    840

ggtggaaacg agaagaaggc caaactgtca aatgcagtgg ccaaaatgct cagtaactgc    900

ccaccaggag ggatcagcat gacagtaaca ggagacaata ccaaatggaa tgaatgctta    960

aatccaagaa tctttttggc tatgactgaa agaataacca gagacagccc aatttggttc   1020

cgggattttt gtagtatagc accggtcttg ttctccaata aaatagccag attgggaaaa   1080

gggtttatga taacaagcaa aacaaaaaga ctgaaggctc aaataccttg tcctgatctg   1140

tttagtatac cattagaaag atataatgaa gaaacaaggg caaaattgaa aaagctgaaa   1200

ccattcttca atgaagaagg aacggcatct ttgtcgcctg ggatgatgat gggaatgttt   1260

aatatgctat ctaccgtgtt gggagtagcc gcactaggta tcaaaaacat tggaaacaaa   1320
```

-continued

```
gaatacttat gggatggact gcaatcttct gatgattttg ctctgtttgt taatgcaaaa   1380
gatgaagaga catgtatgga aggaataaac gacttttacc gaacatgtaa actattggga   1440
ataaacatga gcaaaaagaa aagttactgt aatgaaactg gaatgtttga atttacaagc   1500
atgttctaca gagatggatt tgtatctaat tttgcaatgg aacttccttc atttggagtt   1560
gctggagtaa atgaatcagc agatatggca ataggaatga caataataaa gaacaatatg   1620
atcaacaatg ggatgggtcc agcaacagca caaacagcca tacaattatt catagctgat   1680
tatagataca cctacaaatg ccacagggga gattccaaag tggaaggaaa gagaatgaaa   1740
attataaagg agctatggga aaacactaaa ggaagagatg gtctgttagt agcagatggt   1800
gggcctaaca tttacaattt gagaaacttg catatcccag aaatagtatt aaagtacaac   1860
ctaatggacc ctgaatacaa agggcggtta cttcatcctc aaaatccctt tgtaggacat   1920
ttgtctattg agggcatcaa agaggcagat ataaccccag cacatggtcc agtaaagaaa   1980
atggactatg atgcggtgtc tggaactcat agttggagaa ccaaaaggaa cagatctata   2040
ctaaacactg atcagaggaa catgattctt gaggaacaat gctacgctaa gtgttgcaac   2100
ctttttgagg cctgttttaa cagtgcatca tacaggaaac cagtaggtca gcacagcatg   2160
cttgaggcta tggcccacag attaagaatg gatgcacgac tagattatga atcaggaaga   2220
atgtcaaagg atgattttga gaaagcaatg gctcaccttg gtgagattgg gtacatataa   2280
gcttcgaaga tgtctatggg gttattggtc atcattgaat acatgcggta cacaaatgat   2340
taaaatgaaa aaaggctcgt gtttctact                                    2369
```

<210> SEQ ID NO 3
<211> LENGTH: 2308
<212> TYPE: DNA
<213> ORGANISM: Influenza B

<400> SEQUENCE: 3

```
agcagaagcg gtgcgtttga tttgccataa tggatacttt tattacaaga aacttccaga     60
ctacaataat acaaaaggcc aaaaacacaa tggcagaatt tagtgaagat cctgaattac    120
aaccagcaat gctattcaac atctgcgtcc atctggaggt ctgctatgta ataagtgata    180
tgaattttct tgatgaagaa ggaaaagcat atacagcatt agaaggacaa ggaaaagaac    240
aaaacttgag accacaatat gaagtgattg agggaatgcc aagaaacata gcatggatgg    300
ttcaaagatc cttagcccaa gagcatggga tagagactcc aaggtatctg gctgatttgt    360
tcgattataa aactaagagg tttatagaag ttggaataac aaagggattg gctgatgatt    420
acttctggaa aaagaaagaa aagctgggga atagcatgga actgatgata ttcagctaca    480
atcaagacta ttcgttaagt aatgaatcct cattggatga ggaaggaaaa gggagagtgc    540
taagcagact cacagaactt caggctgagt taagtctgaa aaatctatgg caagttctca    600
taggagaaga agatattgaa aaaggaattg acttcaaact tggacaaaca atatctaaac    660
taagggatat atctgttcca gctggtttct ccaattttga aggaatgagg agctacatag    720
acaatataga tcctaaagga gcaatagaga gaaatctagc aaggatgtct ccccttagtat    780
cagttacacc taaaaagttg aaatgggagg acctaagacc aatagggcct cacatttaca    840
accatgagct accagaagtt ccatataatg cctttcttct aatgtctgat gaattggggc    900
tggctaatat gactgaaggg aagtccaaga aaccgaagac cttagccaaa gagtgcctag    960
aaaagtactc aacactacgg gatcaaactg acccaatatt aataatgaaa agcgaaaaag   1020
```

ctaatgaaca cttcctatgg aaactgtgga gggactgtgt aaatacaata agtaatgagg 1080
aaacaagtaa cgaattacag aaaaccaatt atgccaagtg ggccacagga gatggattaa 1140
catatcagaa aataatgaaa gaagtagcaa tagatgacga aacaatgtac caagaagagc 1200
ccaaaatacc taacaaatgt agagtggctg cttgggttca aacagagatg aatctattga 1260
gcactctgac aagtaaaagg gccctggatc tgccagaaat agggccagac gtagcacccg 1320
tggagcatgt agggagtgaa agaaggaaat actttgttaa tgaaatcaac tactgtaagg 1380
cctctaccgt tatgatgaag tatgtacttt ttcacacttc attattaaat gaaagcaatg 1440
ccagcatggg aaaatataaa gtaataccaa taaccaacag agtagtaaat gaaaagggag 1500
aaagttttga catgctttat ggtctagcgg ttaaagggca atctcatctg aggggagata 1560
ctgatgttgt aacagttgtg actttcgaat ttagtagtac agatcccaga gtggactcag 1620
gaaagtggcc aaaatatact gtatttagaa ttggctcctt atttgtgagt gggagggaaa 1680
aatctgtata cctatattgc cgagtgaatg gtacaaataa gatccaaatg aaatggggaa 1740
tggaagctag aagatgtctg cttcaatcaa tgcaacaaat ggaagcaatt gttgaacaag 1800
aatcatcgat acaaggatat gacatgacca aagcttgttt caagggagac agagtgaata 1860
gtccaaaaac tttcagtatt gggactcaag aaggaaaact agtgaaagga tcctttggga 1920
aagcactaag agtaatattc accaaatgtt tgatgcacta tgtatttgga aatgcccaat 1980
tggaggggtt tagtgccgaa tctaggagac ttctactgtt aattcaggca ttaaaagaca 2040
gaaagggccc ttgggtattc gacttagagg gaatgtattc tggaatagaa gaatgtatta 2100
gtaacaaccc ttgggtaata cagagtgcat actggtttaa tgaatggttg ggctttgaaa 2160
aagaggggag taaagtatta gaatcagtag atgaaataat ggatgaatga aagaagggca 2220
tagtgctcaa tttggtacta ttttgttcat tatgtatcta aacatccaat aaaaagaatt 2280
gagaattaaa aatgcacgtg tttctact 2308

<210> SEQ ID NO 4
<211> LENGTH: 1840
<212> TYPE: DNA
<213> ORGANISM: Influenza B

<400> SEQUENCE: 4
agcagaagca cagcattttc ttgtgaactt caagtaccaa caaaaaactg aaaatcaaaa 60
tgtccaacat ggacattgac ggcatcaaca ctggaataat tgacaaaaca ccagaagaaa 120
taacttccgg aaccagtggg gcaaccagac caatcatcag accagcaacc cttgccccac 180
caagcaacaa acgaaccaga aacccatccc cggaaagggc aaccacaagc agtgaagctg 240
atgtcggaag gaaaacccaa aagaaacaaa ctccgacaga gataaagaag agcgtctaca 300
atatggtagt gaaactgggt gaattctaca accagatgat ggtcaaagct ggactcaacg 360
atgacatgga gagaaaccta atccaaaatg cacatgctgt ggaaagaatt ctattggctg 420
ctactgatga caagaaaact gaattccaaa agaaaaagaa tgccagagac gtcaaagaag 480
ggaaagaaga aatagaccac aacaaaacag gaggcacctt ttacaagatg gtaagagatg 540
ataaaaccat ctacttcagc cctataagaa ttaccttttt aaaagaagag gtgaaaacaa 600
tgtacaaaac caccatgggg agtgacggtt tcagtggact aaatcacatc atgattgggc 660
attcacagat gaacgatgtc tgtttccaaa gatcaaaggc actaaaaaga gttggacttg 720
acccttcatt aatcagtact tttgcaggaa gcacactccc cagaagatca ggtacaactg 780
gtgttgcgac caaaggaggt ggaactttag tggcagaagc cattcgattt ataggaagag 840
caatggcaga cagagggcta ttgagagaca tcagagccaa gacggcctat gaaaagattc 900
ttctgaatct gaaaaacaag tgctctgcgc cccaacaaaa ggctctggtt gatcaagtga 960
tcggaagtag aaatccaggg attgcagaca tagaagatct caccctgctt gctcgaagta 1020
tggtcgttgt taggccctct gtagcaagca aagtggtgct tcccataagc atctatgcta 1080
aaatacctca actggggttc aacgttgaag aatactctat ggttgggtat gaagccatgg 1140
ctctttataa tatggcaaca cctgtttcca tattaagaat gggagacgat gcaaaagata 1200
aatcacaatt attcttcatg tcttgctttg gagctgccta tgaagaccta agagttctgt 1260
ctgcactaac aggcacggaa ttcaagccta ggtcagcatt aaagtgcaaa ggtttccacg 1320
ttccagcaaa ggagcaagtg gaaggaatgg gggcagctct gatgtccatc aagctccagt 1380
tttgggctcc aatgaccaga tctgggggga atgaagtagg tggagacgga gggtctggtc 1440
aaataagttg cagccccgtg tttgcagtag aaagacctat tgctctaagc aagcaagctg 1500
taagaagaat gctgtcaatg aatattgagg gacgtgatgc agatgtcaaa ggaaatctac 1560
tcaagatgat gaatgattca atggctaaga aaaccaatgg aaatgctttc attgggaaga 1620
aaatgttcca aatatcagac aaaaacaaaa ccaatcccgt tgagattcca attaagcaga 1680
ccatccccag tttcttcttt gggagggaca cagcagagga ttatgatgac ctcgattatt 1740
aaagcaacaa aatagacact atggctgtga ttgtttcagt acgtttggaa tgtgggtgtt 1800
tactcttatt gaaataaatg taaaaaatgc tgttgtttct 1840

<210> SEQ ID NO 5
<211> LENGTH: 1190
<212> TYPE: DNA
<213> ORGANISM: Influenza B

<400> SEQUENCE: 5
agcagaagca cgcactttct taaaatgtcg ctgtttggag acacaattgc ctacctgctt 60
tcactaacag aagatggaga aggcaaagca gaactagcgg aaaaattaca ctgttggttc 120
ggtgggaaag aattcgatct agactctgct ttggaatgga taaaaaacaa aagatgccta 180
actgatatac aaaaagcact aattggtgcc tctatctgct tttgaaacc caaagaccaa 240 gaaagaaaaa gaagattcat cacagagccc ctgtcaggaa tgggaacaac agcaacaaaa 300
aagaaaggcc tgattctagc tgaaagaaaa atgagaagat gtgtgagttt tcatgaggca 360
tttgaaatag cagaaggcca tgaaagctca gcactactat attgtctcat ggtcatgtac 420
ctgaaccctg gaaattattc aatgcaagta aaactaggaa cgctctgtgc tttatgcgag 480
aaacaagcat cacattcaca cagagctcat agcagagcag caagatcttc agtgcctgga 540
gtgaggcgag aaatgcaaat ggtttcagct atgaacacag caaaaacaat gaatggaatg 600
gggaagggag aagacgtcca aaaactggca gaagagctgc aaagcaacat tggagtattg 660
agatctctgg gggcaagtca aaagaatgga gaaggaattg caaaggatgt aatggaagtg 720
ctaaagcaga gctccatggg aaattcagct cttgtgaaga aatacctata atgctcgagc 780
catttcagat tctttcaatt tgctctttca ttttatcggc tctccatttc atgggctgga 840
caatagggca tttaaatcaa ataaaaagag gagtaaacct aaaaatacga ataagaaatc 900
caaataaaga gacaataaat agagaggtat caattttgag acacagttac caaaaagaaa 960
tccaagccaa agaaacaata aaggaagtac tctctgacaa catggagaga ttgagtgacc 1020
acatagtaat tgaggggctt tctgctgaag agataataaa aatgggtgaa acagttttgg 1080

-continued

```
aggtagaaga attgcattaa acccaatttt caccgtattt cttactatgc atttaagcaa   1140

attgtaatca atgtcagcaa ataaactgga aaaagtgcgt tgtttctact              1190


<210> SEQ ID NO 6
<211> LENGTH: 1098
<212> TYPE: DNA
<213> ORGANISM: Influenza B

<400> SEQUENCE: 6

agcagaagca gaggatttgt ttagtcactg gcaaacggaa aaaaatggcg gacaacatga     60

ccacaacaca aattgaggtg ggtccgggag caaccaatgc cactataaac tttgaagcag    120

gaattttgga gtgctatgaa aggctttcat ggcaaagagc ccttgactac cctggtcaag    180

accgcctaaa cagactaaag agaaaattag aatcaagaat aaagactcac aacaaaagtg    240

agcctgaaag taaaaggatg tctcttgaag agagaaaagc aattggggta aaaatgatga    300

aagtgctcct atttatgaac ccatctgctg gaattgaagg gtttgagcca tactgtatga    360

aaaattcctc caatagcaac tgcccaaact gcaattgggc cgattaccct ccaacatcag    420

gaaagtgcct tgatgacata gaagaagaac cggagaatgt tgatgaccca actgaaatag    480

tattaaggga catgaacaac aaagatgcaa ggcaaaagat aaaagaggaa gtaaacactc    540

agaaagaagg gaagttccgt ttgacaataa aaagggatat acgtaatgtg ttgtccttga    600

gagtgttggt aaacggaaca ttcctcaagc accctaatgg atacaagtcc ttatcaactc    660

tgcatagatt gaatgcatat gaccagagtg gaaggcttgt tgctaaactt gttgctactg    720

atgatcttac agtggaggat gaagaagatg gccatcggat cctcaactca ctcttcgagc    780

gttttaatga aggacattca aagccaattc gagcagctga aactgcggtg ggagtcttat    840

cccaatttgg tcaagagcac cgattatcac cagaggaggg agacaattag actggttacg    900

gaagaacttt atcttttaag taaaagaatt gatgataaca tattgttcca caaaacagta    960

atagctaaca gctccataat agctgacatg attgtatcat tatcattatt ggaaacattg   1020

tatgagatga aggatgtggt tgaagtgtac agcaggcagt gcttgtgaat ttaaaataaa   1080

aatcctcttg ttactact                                                 1098


<210> SEQ ID NO 7
<211> LENGTH: 583
<212> TYPE: PRT
<213> ORGANISM: Influenza B

<400> SEQUENCE: 7

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Met Gly Thr Ile Pro Ser Ala Lys Ala
                85                  90                  95

Ser Ile Leu His Glu Val Arg Pro Val Thr Ser Gly Cys Phe Pro Ile
            100                 105                 110
```

-continued

```
Met His Asp Arg Thr Lys Ile Arg Gln Leu Pro Asn Leu Leu Arg Gly
        115                 120                 125

Tyr Glu Asn Ile Arg Leu Ser Thr His Asn Val Ile Asn Ala Glu Arg
    130                 135                 140

Ala Pro Gly Gly Pro Tyr Arg Leu Gly Thr Ser Gly Ser Cys Pro Asn
145                 150                 155                 160

Val Thr Ser Arg Asn Gly Phe Phe Ala Thr Met Ala Trp Ala Val Pro
                165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
        195                 200                 205

Asp Asp Lys Thr Gln Met Lys Asn Leu Tyr Gly Asp Ser Asn Pro Gln
    210                 215                 220

Lys Phe Thr Ser Ser Ala Asn Gly Val Thr Thr His Tyr Val Ser Gln
225                 230                 235                 240

Ile Gly Asp Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525
```

```
Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580


<210> SEQ ID NO 8
<211> LENGTH: 466
<212> TYPE: PRT
<213> ORGANISM: Influenza B

<400> SEQUENCE: 8

Met Leu Pro Ser Thr Ile Gln Thr Leu Thr Leu Phe Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Ile Leu Leu Lys Phe Ser Pro Thr Glu Ile Thr Ala Pro
        35                  40                  45

Lys Val Pro Leu Asp Cys Ala Asn Ala Ser Asn Val Gln Ala Val Asn
    50                  55                  60

Arg Ser Ala Thr Lys Gly Met Thr Leu Leu Leu Ser Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Thr Arg Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Ile Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Lys Cys Arg Phe Leu Lys Ile
                245                 250                 255

Arg Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300
```

-continued

Leu Asn Val Glu Thr Asp Thr Ala Glu Ile Arg Leu Met Cys Thr Glu
305 310 315 320

Thr Tyr Leu Asp Thr Pro Arg Pro Asp Asp Gly Ser Ile Thr Gly Pro
325 330 335

Cys Glu Ser Asn Gly Asp Lys Gly Arg Gly Gly Ile Lys Gly Gly Phe
340 345 350

Val His Gln Arg Met Ala Ser Lys Ile Gly Arg Trp Tyr Ser Arg Thr
355 360 365

Met Ser Lys Thr Glu Arg Met Gly Met Glu Leu Tyr Val Lys Tyr Asp
370 375 380

Gly Asp Pro Trp Thr Asp Ser Asp Ala Leu Ala Pro Ser Gly Val Met
385 390 395 400

Val Ser Met Lys Glu Pro Gly Trp Tyr Ser Phe Gly Phe Glu Ile Lys
405 410 415

Asp Lys Lys Cys Asp Val Pro Cys Ile Gly Ile Glu Met Val His Asp
420 425 430

Gly Gly Lys Lys Thr Trp His Ser Ala Ala Thr Ala Ile Tyr Cys Leu
435 440 445

Met Gly Ser Gly Gln Leu Leu Trp Asp Thr Val Thr Gly Val Asp Met
450 455 460

Ala Leu
465

<210> SEQ ID NO 9
<211> LENGTH: 1843
<212> TYPE: DNA
<213> ORGANISM: Influenza B

<400> SEQUENCE: 9
tttctaatat ccacaaaatg aaggcaataa ttgtactact catggtagta acatccaacg 60
cagatcgaat ctgcactggg ataacatctt caaactcacc tcatgtggtc aaaacagcta 120
ctcaagggga agttaatgtg actggtgtga taccactgac aacaacacca acaaaatctc 180
attttgcaaa tctcaaagga acaaagacca gagggaaact atgcccaaac tgtctcaact 240
gcacagatct ggatgtggcc ttgggcagac caatgtgtat ggggaccata ccttcggcaa 300
aagcttcaat actccacgaa gtcagacctg ttacatccgg gtgctttcct ataatgcacg 360
acagaacaaa aatcagacag ctacccaatc ttctcagagg atatgaaaat atcagattat 420
caacccataa cgttatcaac gcagaaaggg caccaggagg accctacaga cttggaacct 480
caggatcttg ccctaacgtt accagtagaa acggattctt cgcaacaatg gcttgggctg 540
tcccaaggga caacaaaaca gcaacgaatc cactaacagt agaagtacca tacatttgca 600
caaaaggaga agaccaaatt actgtttggg ggttccattc tgatgacaaa acccaaatga 660
aaaacctcta tggagactca aatcctcaaa agttcacctc atctgccaat ggagtaacca 720
cacattatgt ttctcagatt ggtgacttcc caaatcaaac agaagacgga gggctaccac 780
aaagcggcag aattgttgtt gattacatgg tgcaaaaacc tgggaaaaca ggaacaattg 840
tctatcaaag aggtgttttg ttgcctcaaa aggtgtggtg cgcaagtggc aggagcaagg 900
taataaaagg gtccttgcct ttaattggtg aagcagattg ccttcacgaa aaatacggtg 960
gattaaacaa aagcaagcct tactacacag gagaacatgc aaaagccata ggaaattgcc 1020
caatatgggt gaaaacacct ttgaagcttg ccaatggaac caaatataga cctcctgcaa 1080
aactattaaa ggaaaggggt ttcttcggag ctattgctgg tttcttagag ggaggatggg 1140

```
aaggaatgat tgcaggttgg cacggataca catctcatgg agcacatgga gtggcagtgg   1200
cagcagacct taagagcacg caagaagcca taaacaagat aacaaaaaat ctcaattctt   1260
tgagtgagct agaagtaaag aatcttcaaa gactaagtgg tgccatggat gaactccaca   1320
acgaaatact cgagctggat gagaaagtgg atgatctcag agctgacaca ataagctcgc   1380
aaatagagct tgcagtcttg ctttccaacg aaggaataat aaacagtgaa gatgagcatc   1440
tattggcact tgagagaaaa ctaaagaaaa tgctgggtcc ctctgctgta gacataggga   1500
atggatgctt cgaaaccaaa cacaagtgca accagacctg cttagacagg atagctgctg   1560
gcacctttaa tgcaggagaa ttttctcttc ccacttttga ttcactgaat attactgctg   1620
catctttaaa tgatgatgga ttggataatc atactatact gctctactac tcaactgctg   1680
cttctagttt ggccgtaaca ttgatgatag ctatttttat tgtttatatg gtctccagag   1740
acaatgtttc ttgctccatc tgtctataag gaaaattaag ccctgtattt tcctttattg   1800
tagtgcttgt ttgcttgtta ccattacaaa gaaacgttat tga                     1843
```

<210> SEQ ID NO 10
<211> LENGTH: 1504
<212> TYPE: DNA
<213> ORGANISM: Influenza B

<400> SEQUENCE: 10

```
aaactgaggc aaataggcca aaaatgaaca atgctacctt caactataca aacgttaacc     60
ctatttctca catcaggggg agtgttatta tcactatatg tgtcagcttc actgtcatac    120
ttactgtatt cggatatatt gctaaaattt tcaccaacag aaataactgc accaaaagtg    180
ccattggatt gtgcaaacgc atcaaatgtt caggctgtga accgttctgc aacaaaaggg    240
atgacacttc ttctctcaga accggagtgg acataccctc gtttatcttg ccagggctca    300
acctttcaga aagcactcct aattagccct catagattcg gagaaaccag aggaaactca    360
gctcccttga taataaggga accttttatt gcttgtggac caaaggaatg caaacacttt    420
gctctaaccc attatgcagc tcaaccaggg ggatactaca atggaacaag agaggacaga    480
aacaagctga ggcatctgat ttcagtcaaa ttgggcaaaa tcccaacagt agaaaactcc    540
attttccaca tggcagcttg gagcgggtcc gcatgccatg atggtagaga atggacatat    600
atcggagttg atggccctga cagtaatgca ttgatcaaaa taaaatatgg agaagcatat    660
actgacacat accattccta tgcaaacaac atcctaagaa cacaagaaag tgcctgcaat    720
tgcatcgggg gagattgtta tcttatgata actgatggct cagcttcagg aattagtaaa    780
tgcagatttc ttaagattcg agagggtcga ataataaaag aaatatttcc aacaggaaga    840
gtagaacata ctgaagaatg cacatgcgga tttgccagca ataaaaccat agaatgtgcc    900
tgtagagata acagttacac agcaaaaaga ccctttgtca aattaaatgt ggagactgat    960
acagctgaaa taagattgat gtgcacagag acttatttgg acacccccag accagatgat   1020
ggaagcataa cagggccttg cgaatctaat ggggacaaag ggcgtggagg catcaaggga   1080
ggatttgttc atcaaagaat ggcatccaag attggaagat ggtactctcg aacgatgtct   1140
aaaactgaaa gaatggggat ggaactgtat gtcaagtatg atggagaccc atggactgac   1200
agtgacgccc ttgctcctag tggagtaatg gtttcaatga aagaacctgg ttggtattcc   1260
tttggcttcg aaataaaaga taagaaatgt gatgtcccct gtattgggat agagatggta   1320
catgatggtg gaaaaaagac ttggcactca gcagcaacag ccatttactg tttaatgggc   1380
```

-continued tcaggacaat tgctatggga cactgtcaca ggtgttgata tggctctgta atggaggaat 1440
ggttgagtct gttctaaacc ctttgttcct attttgtttg aacaattgtc cttactgaac 1500
ttaa 1504

<210> SEQ ID NO 11
<211> LENGTH: 2396
<212> TYPE: DNA
<213> ORGANISM: Influenza B

<400> SEQUENCE: 11
agcagaagcg gagcgttttc aagatgacat tggctaaaat tgaattgtta aaacaactgt 60
taagggacaa cgaagccaaa acagtattga aacaaacaac ggtagaccaa tataacataa 120
taagaaaatt caatacatca agaattgaaa agaacccttc attaaggatg aagtgggcca 180
tgtgttctaa ttttcccttg gctctgacca agggtgatat ggcaaataga atccccttgg 240
aatacaaggg aatacaactt aaaacaaatg ctgaagacat aggaaccaaa ggccaaatgt 300
gctcaatagc agcagttacc tggtggaata catatggacc aataggagac actgaaggtt 360
tcgaaaaggt ctacgaaagc ttctttctca gaaagatgag acttgacaat gccacttggg 420
gccgaataac ttttggccca gttgaaagag taagaaaaag ggtactgcta aaccctctca 480
ccaaggaaat gcctccagat gaagcgagca atgtgataat ggaaatattg ttccctaagg 540
aagcaggaat accaagagaa tctacttgga tacataggga actgataaaa gaaaaaagag 600
aaaaattgaa aggaacgatg ataactccca ttgtactggc atacatgctt gagagagaat 660
tggttgcccg aagaaggttc ctgccagtgg caggagcaac atcagctgag ttcatagaaa 720
tgctacactg cttacaaggt gaaaattgga gacaaatata tcacccagga gggaataaac 780
taactgaatc taggtctcaa tcaatgattg tagcttgtag aaaaataatc agaagatcaa 840
tagtcgcatc aaacccacta gagctagctg tagaaattgc aaacaagact gtgatagata 900
ctgaaccttt aaaatcatgt ctggcagcca tagacggagg tgatgtagcc tgtgacataa 960
tgagagctgc attaggacta aagatcagac aaagacaaag atttggacgg cttgaactaa 1020
agagaatatc aggaagagga ttcaaaaatg atgaagaaat attgatcggg aacggaacaa 1080
tacagaagat tggaatatgg gacggagaag aggagttcca tgtaagatgt ggtgaatgca 1140
ggggaatatt aaaaaagagc aaaatgagaa tggaaaaact actaataaat tcagccaaaa 1200
aggaggacat gaaagattta ataatcttgt gcatggtatt ttctcaagac actaggatgt 1260
tccaaggagt gagaggagaa ataaattttc ttaatcgagc aggccaactt ttatctccaa 1320
tgtaccaact ccaaagatat tttttgaata ggagcaacga tctttttgat caatgggggt 1380
atgaggaatc acccaaagca agtgaactac atgggataaa tgaattaatg aatgcatctg 1440
attatacgtt gaaaggggtt gtagtaacaa aaaatgtgat tgatgacttt agttctactg 1500
aaacagaaaa agtatctata acaaaaaatc ttagtttaat aaaaagaact ggggaagtca 1560
taatgggggc taatgacgta agtgaattag aatcacaagc tcagctaatg ataacatatg 1620
atacacctaa gatgtgggag atgggaacaa ccaaagaact ggtgcaaaac acctaccaat 1680
gggtgctaaa aaatttggta acactgaagg ctcagtttct tctaggaaaa gaagacatgt 1740
tccaatggga tgcatttgaa gcatttgaaa gcataatccc ccagaagatg gctggccagt 1800
acagtggatt tgcaagggca gtgctcaaac aaatgagaga ccaagaggtt atgaaaactg 1860
accagttcat aaagttgttg cctttctgtt tctcaccacc aaaattaagg agcaatgggg 1920
agccttatca attcttgagg cttatattga agggaggagg agaaaatttc atcgaagtaa 1980

-continued ggaaagggtc ccctctattc tcctacaatc cacaaacaga agtcctaact atatgcggca 2040
gaatgatgtc attaaaaggg aaaattgaag atgaagaaag gaatagatca atggggaatg 2100
cagtattggc aggctttctc gttagtggca agtatgaccc agatcttgga gatttcaaaa 2160
ctattgaaga acttgaaaag ctaaaaccgg gggagaaagc aaacatctta ctttatcaag 2220
gaaagcccgt taaagtagtt aaaaggaaaa gatatagtgc tttatccaat gacatttcac 2280
aaggaattaa gagacaaaga atgacagttg agtccatggg gtgggccttg agctaatata 2340
aatttatcca ttaattcaat aaacacaatt gagtgaaaaa tgctcgtgtt tctact 2396

<210> SEQ ID NO 12
<211> LENGTH: 2369
<212> TYPE: DNA
<213> ORGANISM: Influenza B

<400> SEQUENCE: 12
agcagaagcg gagcctttaa gatgaatata aatccttatt ttctcttcat agatgtaccc 60
atacaggcag caatttcaac aacattccca tacaccggtg ttccccctta ttcccatgga 120
acgggaacag gctacacaat agacaccgtg atcagaacac atgagtactc aaacaaggga 180
aaacagtaca tttctgatgt tacaggatgt acaatggtag atccaacaaa tgggccatta 240
cccgaagaca atgagccgag tgcctatgca caattagatt gcgttctgga ggctttggat 300
agaatggatg aagaacatcc aggtctgttt caagcagcct cacagaatgc catggaggca 360
ctaatggtca caactgtaga caaattaacc caggggagac agacttttga ttggacagta 420
tgcagaaacc aacctgctgc aacggcactg aacacaacaa taacctcttt taggttgaat 480
gatttgaatg gagccgacaa gggtggatta gtaccctttt gccaagatat cattgattca 540
ttggacagac ctgaaatgac tttcttctca gtaaagaata taaagaaaaa attgcctgct 600
aaaaacagaa agggtttcct cataaagaga ataccaatga aggtaaaaga cagaataacc 660
agagtggaat acatcaaaag agcattatca ttaaacacaa tgacaaaaga tgctgaaaga 720
ggcaaactaa aaagaagagc gattgccacc gctggaatac aaatcagagg gtttgtatta 780
gtagttgaaa acttggctaa aaatatctgt gaaaatctag aacaaagtgg tttgccagta 840
ggtggaaacg agaagaaggc caaactgtca aatgcagtgg ccaaaatgct cagtaactgc 900
ccaccaggag ggatcagcat gacagtaaca ggagacaata ccaaatggaa tgaatgctta 960
aatccaagaa tctttttggc tatgactgaa agaataacca gagacagccc aatttggttc 1020
cgggattttt gtagtatagc accggtcttg ttctccaata aaatagccag attgggaaaa 1080
gggtttatga taacaagcaa aacaaaaaga ctgaaggctc aaataccttg tcctgatctg 1140
tttagtatac cattagaaag atataatgaa gaaacaaggg caaaattgaa aaagctgaaa 1200
ccattcttca atgaagaagg aacggcatct ttgtcgcctg ggatgatgat gggaatgttt 1260
aatatgctat ctaccgtgtt gggagtagcc gcactaggta tcaaaaacat tggaaacaaa 1320
gaatacttat gggatggact gcaatcttct gatgattttg ctctgtttgt taatgcaaaa 1380
gatgaagaga catgtatgga aggaataaac gacttttacc gaacatgtaa actattggga 1440
ataaacatga gcaaaaagaa aagttactgt aatgaaactg gaatgtttga atttacaagc 1500
atgttctaca gagatggatt tgtatctaat tttgcaatgg aacttccttc atttggagtt 1560
gctggagtaa atgaatcagc agatatggca ataggaatga caataataaa gaacaatatg 1620
atcaacaatg ggatgggtcc agcaacagca caaacagcca tacaattatt catagctgat 1680
tatagataca cctacaaatg ccacagggga gattccaaag tggaaggaaa gagaatgaaa 1740
attataaagg agctatggga aaacactaaa ggaagagatg gtctgttagt agcagatggt 1800
gggcctaaca tttacaattt gagaaacttg catatcccag aaatagtatt aaagtacaac 1860
ctaatggacc ctgaatacaa agggcggtta cttcatcctc aaaatccctt tgtaggacat 1920
ttgtctattg agggcatcaa agaggcagat ataaccccag cacatggtcc agtaaagaaa 1980
atggactatg atgcggtgtc tggaactcat agttggagaa ccaaaaggaa cagatctata 2040
ctaaacactg atcagaggaa catgattctt gaggaacaat gctacgctaa gtgttgcaac 2100
ctttttgagg cctgttttaa cagtgcatca tacaggaaac cagtaggtca gcacagcatg 2160
cttgaggcta tggcccacag attaagaatg gatgcacgac tagattatga atcaggaaga 2220
atgtcaaagg atgattttga gaaagcaatg gctcaccttg gtgagattgg gtacatataa 2280
gcttcgaaga tgtctatggg gttattggtc atcattgaat acatgcggta cacaaatgat 2340
taaaatgaaa aaaggctcgt gtttctact 2369

<210> SEQ ID NO 13
<211> LENGTH: 2308
<212> TYPE: DNA
<213> ORGANISM: Influenza B

<400> SEQUENCE: 13
agcagaagcg gtgcgtttga tttgccataa tggatacttt tattacaaga aacttccaga 60
ctacaataat acaaaaggcc aaaaacacaa tggcagaatt tagtgaagat cctgaattac 120
aaccagcaat gctattcaac atctgcgtcc atctggaggt ctgctatgta ataagtgata 180
tgaattttct tgatgaagaa ggaaaagcat atacagcatt agaaggacaa ggaaaagaac 240
aaaacttgag accacaatat gaagtgattg agggaatgcc aagaaacata gcatggatgg 300
ttcaaagatc cttagcccaa gagcatggga tagagactcc aaggtatctg gctgatttgt 360
tcgattataa aactaagagg tttatagaag ttggaataac aaagggattg gctgatgatt 420
acttctggaa aaagaaagaa aagctgggga atagcatgga actgatgata ttcagctaca 480
atcaagacta ttcgttaagt aatgaatcct cattggatga ggaaggaaaa gggagagtgc 540
taagcagact cacagaactt caggctgagt taagtctgaa aaatctatgg caagttctca 600
taggagaaga agatattgaa aaaggaattg acttcaaact tggacaaaca atatctaaac 660
taagggatat atctgttcca gctggtttct ccaattttga aggaatgagg agctacatag 720
acaatataga tcctaaagga gcaatagaga gaaatctagc aaggatgtct cccttagtat 780
cagttacacc taaaaagttg aaatgggagg acctaagacc aatagggcct cacatttaca 840
accatgagct accagaagtt ccatataatg cctttcttct aatgtctgat gaattggggc 900
tggctaatat gactgaaggg aagtccaaga aaccgaagac cttagccaaa gagtgcctag 960
aaaagtactc aacactacgg gatcaaactg acccaatatt aataatgaaa agcgaaaaag 1020
ctaatgaaca cttcctatgg aaactgtgga gggactgtgt aaatacaata agtaatgagg 1080
aaacaagtaa cgaattacag aaaaccaatt atgccaagtg ggccacagga gatggattaa 1140
catatcagaa aataatgaaa gaagtagcaa tagatgacga aacaatgtac caagaagagc 1200
ccaaaatacc taacaaatgt agagtggctg cttgggttca aacagagatg aatctattga 1260
gcactctgac aagtaaaagg gccctggatc tgccagaaat agggccagac gtagcacccg 1320
tggagcatgt agggagtgaa agaaggaaat actttgttaa tgaaatcaac tactgtaagg 1380
cctctaccgt tatgatgaag tatgtgcttt ttcacacttc attattaaat gaaagcaatg 1440

```
ccagtatggg aaaatataaa gtaataccaa taaccaacag agtagtaaat gaaaagggag   1500

aaagttttga catgctttat ggtctagcgg ttaaagggca atctcatctg aggggagata   1560

ctgatgttgt aacagttgtg actttcgaat ttagtagtac agatcccaga gtggactcag   1620

gaaagtggcc aaaatatact gtatttagaa ttggctcctt atttgtgagt gggagggaaa   1680

aatctgtata cctatattgc cgagtgaatg gtacaaataa gatccaaatg aaatggggaa   1740

tggaagctag aagatgtctg cttcaatcaa tgcaacaaat ggaagcaatt gttgaacaag   1800

aatcatcgat acaaggatat gacatgacca aagcttgttt caagggagac agagtgaata   1860

gtccaaaaac tttcagtatt gggactcaag aaggaaaact agtgaaagga tcctttggga   1920

aagcactaag agtaatattc accaaatgtt tgatgcacta tgtatttgga aatgcccaat   1980

tggaggggtt tagtgccgaa tctaggagac ttctactgtt aattcaggca ttaaaagaca   2040

gaaagggccc ttgggtattc gacttagagg gaatgtattc tggaatagaa gaatgtatta   2100

gtaacaaccc ttgggtaata cagagtgcat actggtttaa tgaatggttg ggctttgaaa   2160

aagaggggag taaagtatta gaatcagtag atgaaataat ggatgaatga aagaagggca   2220

tagtgctcaa tttggtacta ttttgttcat tatgtatcta aacatccaat ataaagaatt   2280

gagaattaaa aatgcacgtg tttctact                                      2308


<210> SEQ ID NO 14
<211> LENGTH: 1843
<212> TYPE: DNA
<213> ORGANISM: Influenza B

<400> SEQUENCE: 14

agcagaagca cagcattttc ttgtgaactt caagtaccaa caaaaaactg aaaatcaaaa     60

tgtccaacat ggacattgac ggcatcaaca ctggaataat tgacaaaaca ccagaagaaa    120

taacttccgg aaccagtggg gcaaccagac caatcatcag accagcaacc cttgcctcac    180

caagcaacaa acgaaccaga aacccatccc cggaaagggc aaccacaagc agtgaagctg    240

atgtcggaag gaaaacccaa aagaaacaaa ctccgacaga gataaagaag agcgtctaca    300

atatggtagt gaaactgggt gaattctaca accagatgat ggtcaaagct ggactcaacg    360

atgacatgga gagaaaccta atccaaaatg cacatgctgt ggaaagaatt ctattggctg    420

ctactgatga caagaaaact gaattccaaa agaaaaagaa tgccagagac gtcaaagaag    480

ggaaagaaga aatagaccat aacaaaacag gaggcacctt ttacaagatg gtaagagatg    540

ataaaaccat ctacttcagc cctataagaa ttaccttttt aaaagaagag gtgaaaacaa    600

tgtacaaaac caccatgggg agtgacggtt tcagtggact aaatcacatc atgattgggc    660

attcacagat gaacgatgtc tgtttccaaa gatcaaaggc actaaaaaga gttggacttg    720

acccttcatt aatcagtact tttgcaggaa gcacactccc cagaagatca ggtacaactg    780

gtgttgcgac caaaggaggt ggaactttag tggcagaagc cattcgattt ataggaagag    840

caatggcaga cagagggcta ttgagagaca tcagagccaa gacggcctat gaaaagattc    900

ttctgaatct gaaaaacaag tgctctgcgc cccaacaaaa ggctctggtt gatcaagtga    960

tcggaagtag aaatccaggg attgcagaca tagaagatct caccctgctt gctcgaagta   1020

tggtcgttgt taggccctct gtagcaagca aagtggtgct tcccataagc atctatgcta   1080

aaatacctca actggggttc aacgttgaag aatactctat ggttgggtat gaagccatgg   1140

ctctttataa tatggcaaca cctgtttcca tattaagaat gggagacgat gcaaaagata   1200
```

-continued

```
aatcacaatt attcttcatg tcttgctttg gagctgccta tgaagaccta agagttctgt   1260

ctgcactaac aggcacggaa ttcaagccta ggtcagcatt aaagtgcaaa ggtttccacg   1320

ttccagcaaa ggagcaagtg gaaggaatgg gggcagctct gatgtccatc aagctccagt   1380

tttgggctcc aatgaccaga tctgggggga atgaagtagg tggagacgga gggtctggtc   1440

aaataagttg cagccccgtg tttgcagtag aaagacctat tgctctaagc aagcaagctg   1500

taagaagaat gctgtcaatg aatattgagg gacgtgatgc agatgtcaaa ggaaatctac   1560

tcaagatgat gaatgattca atggctaaga aaaccaatgg aaatgctttc attgggaaga   1620

aaatgttcca aatatcagac aaaaacaaaa ccaatcccgt tgagattcca attaagcaga   1680

ccatccccag tttcttcttt gggagggaca cagcagagga ttatgatgac ctcgattatt   1740

aaagcaacaa aatagacact atggctgtga ttgtttcagt acgtttggaa tgtgggtgtt   1800

tactcttatt gaaataaatg taaaaaatgc tgttgtttct act                    1843


<210> SEQ ID NO 15
<211> LENGTH: 1843
<212> TYPE: DNA
<213> ORGANISM: Influenza B

<400> SEQUENCE: 15

agcagaagca cagcattttc ttgtgaactt caagtaccaa caaaaaactg aaaatcaaaa     60

tgtccaacat ggacattgac ggcatcaaca ctggaataat tgacaaaaca ccagaagaaa    120

taacttccgg aaccagtggg gcaaccagac caatcatcag accagcaacc cttgcctcac    180

caagcaacaa acgaaccaga aacccatccc cggaaagggc aaccacaagc agtgaagctg    240

atgtcggaag gaaaacccaa aagaaacaaa ctccgacaga gataaagaag agcgtctaca    300

atatggtagt gaaactgggt gaattctaca accagatgat ggtcaaagct ggactcaacg    360

atgacatgga gagaaaccta atccaaaatg cacatgctgt ggaaagaatt ctattggctg    420

ctactgatga caagaaaact gaattccaaa agaaaaagaa tgccagagac gtcaaagaag    480

ggaaagaaga aatagaccat aacaaaacag gaggcacctt ttacaagatg gtaagagatg    540

ataaaaccat ctacttcagc cctataagaa ttaccttttt aaaagaagag gtgaaaacaa    600

tgtacaaaac caccatgggg agtgacggtt tcagtggact aaatcacatc atgattgggc    660

attcacagac gaacgatgtc tgtttccaaa gatcaaaggc actaaaaaga gttggacttg    720

acccttcatt aatcagtact tttgcaggaa gcacactccc cagaagatca ggtacaactg    780

gtgttgcgac caaaggaggt ggaactttag tggcagaagc cattcgattt ataggaagag    840

caatggcaga cagagggcta ttgagagaca tcagagccaa gacggcctat gaaaagattc    900

ttctgaatct gaaaaacaag tgctctgcgc cccaacaaaa ggctctggtt gatcaagtga    960

tcggaagtag aaatccaggg attgcagaca tagaagatct caccctgctt gctcgaagta   1020

tggtcgttgt taggccctct gtagcaagca aagtggtgct tcccataagc atctatgcta   1080

aaatacctca actggggttc aacgttgaag aatactctat ggttgggtat gaagccatgg   1140

ctctttataa tatggcaaca cctgtttcca tattaagaat gggagacgat gcaaaagata   1200

aatcacaatt attcttcatg tcttgctttg gagctgccta tgaagaccta agagttctgt   1260

ctgcactaac aggcacggaa ttcaagccta ggtcagcatt aaagtgcaaa ggtttccacg   1320

ttccagcaaa ggagcaagtg gaaggaatgg gggcagctct gatgtccatc aagctccagt   1380

tttgggctcc aatgaccaga tctgggggga atgaagtagg tggagacgga gggtctggtc   1440

aaataagttg cagccccgtg tttgcagtag aaagacctat tgctctaagc aagcaagctg   1500
```

taagaagaat gctgtcaatg aatattgagg gacgtgatgc agatgtcaaa ggaaatctac 1560
tcaagatgat gaatgattca atggctaaga aaaccaatgg aaatgctttc attgggaaga 1620
aaatgttcca aatatcagac aaaaacaaaa ccaatcccgt tgagattcca attaagcaga 1680
ccatccccag tttcttcttt gggagggaca cagcagagga ttatgatgac ctcgattatt 1740
aaagcaacaa aatagacact atggctgtga ttgtttcagt acgtttggaa tgtgggtgtt 1800
tactcttatt gaaataaatg taaaaaatgc tgttgtttct act 1843

<210> SEQ ID NO 16
<211> LENGTH: 1190
<212> TYPE: DNA
<213> ORGANISM: Influenza B

<400> SEQUENCE: 16
agcagaagca cgcactttct taaaatgtcg ctgtttggag acacaattgc ctacctgctt 60
tcactaacag aagatggaga aggcaaagca gaactagcgg aaaaattaca ctgttggttc 120
ggtgggaaag aattcgatct agactctgct ttggaatgga taaaaaacaa aagatgccta 180
actgatatac aaaaagcact aattggtgcc tctatctgct tttgaaacc caaagaccaa 240 gaaagaaaaa gaaaattcat cacagagccc ctgtcaggaa tgggaacaac agcaacaaaa 300
aagaaaggcc tgattctagc tgaaagaaaa atgagaagat gtgtgagttt tcatgaggca 360
tttgaaatag cagaaggcca tgaaagctca gcactactat attgtctcat ggtcatgtac 420
ctgaaccctg gaaattattc aatgcaagta aaactaggaa cgctctgtgc tttatgcgag 480
aaacaagcat cacattcaca cagagctcat agcagagcag caagatcttc agtgcctgga 540
gtgaggcgag aaatgcaaat ggtttcagct atgaacacag caaaaacaat gaatggaatg 600
gggaagggag aagacgtcca aaaactggca gaagagctgc aaagcaacat tggagtattg 660
agatctctgg gggcaagtca aaagaatgga gaaggaattg caaaggatgt aatggaagtg 720
ctaaagcaga gctccatggg aaattcagct cttgtgaaga aatacctata atgctcgagc 780
catttcagat tctttcaatt tgctctttca ttttatcggc tctccatttc atgggctgga 840
caatagggca tttaaatcaa ataaaaagag gagtaaacct aaaaatacga ataagaaatc 900
caaataaaga gacaataaat agagaggtat caattttgag acacagttac caaaaagaaa 960
tccaagccaa agaaacaata aaggaagtac tctctgacaa catggagaga ttgagtgacc 1020
acatagtaat tgaggggctt tctgctgaag agataataaa aatgggtgaa acagttttgg 1080
aggtagaaga attgcattaa acccaatttt caccgtattt cttactatgc atttaagcaa 1140
attgtaatca atgtcagcaa ataaactgga aaaagtgcgt tgtttctact 1190

<210> SEQ ID NO 17
<211> LENGTH: 1190
<212> TYPE: DNA
<213> ORGANISM: Influenza B

<400> SEQUENCE: 17
agcagaagca cgcactttct taaaatgtcg ctgtttggag acacaattgc ctacctgctt 60
tcactaacag aagatggaga aggcaaagca gaactagcgg aaaaattaca ctgttggttc 120
ggtgggaaag aattcgatct agactctgct ttggaatgga taaaaaacaa aagatgccta 180
actgatatac aaaaagcact aattggtgcc tctatctgct tttgaaacc caaagaccaa 240 gaaagaaaaa gaagattcat cacagagccc ctgtcaggaa cgggaacaac agcaacaaaa 300

-continued

```
aagaaaggcc tgattctagc tgaaagaaaa atgagaagat gtgtgagttt tcatgaggca    360
tttgaaatag cagaaggcca tgaaagctca gcactactat attgtctcat ggtcatgtac    420
ctgaaccctg gaaattattc aatgcaagta aaactaggaa cgctctgtgc tttatgcgag    480
aaacaagcat cacattcaca cagagctcat agcagagcag caagatcttc agtgcctgga    540
gtgaggcgag aaatgcaaat ggtttcagct atgaacacag caaaaacaat gaatggaatg    600
gggaagggag aagacgtcca aaaactggca gaagagctgc aaagcaacat tggagtattg    660
agatctctgg gggcaagtca aaagaatgga gaaggaattg caaaggatgt aatggaagtg    720
ctaaagcaga gctccatggg aaattcagct cttgtgaaga aatacctata atgctcgagc    780
catttcagat tctttcaatt tgctctttca ttttatcggc tctccatttc atgggctgga    840
caatagggca tttaaatcaa ataaaaaagag gagtaaacct aaaaatacga ataagaaatc    900
caaataaaga gacaataaat agagaggtat caattttgag acacagttac caaaaagaaa    960
tccaagccaa agaaacaata aaggaagtac tctctgacaa catggagaga ttgagtgacc   1020
acatagtaat tgaggggctt tctgctgaag agataataaa aatgggtgaa acagttttgg   1080
aggtagaaga attgcattaa acccaatttt caccgtattt cttactatgc atttaagcaa   1140
attgtaatca atgtcagcaa ataaactgga aaaagtgcgt tgtttctact              1190
```

<210> SEQ ID NO 18
<211> LENGTH: 1098
<212> TYPE: DNA
<213> ORGANISM: Influenza B

<400> SEQUENCE: 18

```
agcagaagca gaggatttgt ttagtcactg gcaaacggga aaaaatggcg gacaacatga     60
ccacaacaca aattgaggtg ggtccgggag caaccaatgc cactataaac tttgaagcag    120
gaattttgga gtgctatgaa aggctttcat ggcaaagagc ccttgactac cctggtcaag    180
accgcctaaa cagactaaag agaaaattag aatcaagaat aaagactcac aacaaaagtg    240
agcctgaaag taaaaggatg tctcttgaag agagaaaagc aattggggta aaaatgatga    300
aagtgctcct atttatgaac ccatctgctg gaattgaagg gtttgagcca tactgtatga    360
aaaattcctc caatagcaac tgcccaaact gcaattgggc cgattaccct ccaacatcag    420
gaaagtgcct tgatgacata gaagaagaac cggagaatgt tgatgaccca actgaaatag    480
tattaaggga catgaacaac aaagatgcaa ggcaaaagat aaaagaggaa gtaaacactc    540
agaaagaagg gaagttccgt ttgacaatac aaagggatat acgtaatgtg ttgtccttga    600
gagtgttggt aaacggaaca ttcctcaagc accctaatgg atacaagtcc ttatcaactc    660
tgcatagatt gaatgcatat gaccagagtg gaaggcttgt tgctaaactt gttgctactg    720
atgatcttac agtggaggat gaagaagatg gccatcggat cctcaactca ctcttcgagc    780
gttttaatga aggacattca aagccaattc gagcagctga aactgcggtg ggagtcttat    840
cccaatttgg tcaagagcac cgattatcac cagaggaggg agacaattag actggttacg    900
gaagaacttt atcttttaag taaaagaatt gatgataaca tattgttcca caaaacagta    960
atagctaaca gctccataat agctgacatg attgtatcat tatcattatt ggaaacattg   1020
tatgagatga aggatgtggt tgaagtgtac agcaggcagt gcttgtgaat ttaaaataaa   1080
aatcctcttg ttactact                                                 1098
```

<210> SEQ ID NO 19
<211> LENGTH: 1099

-continued

```
<212> TYPE: DNA
<213> ORGANISM: Influenza B

<400> SEQUENCE: 19

agcagaagca gaggatttgt ttagtcactg gcaaacggga aaaaaatggc ggacaacatg      60

accacaacac aaattgaggt gggtccggga gcaaccaatg ccactataaa ctttgaagca     120

ggaattttgg agtgctatga aaggctttca tggcaaagag cccttgacta ccctggtcaa     180

gaccgcctaa acagactaaa gagaaaatta gaatcaagaa taaagactca caacaaaagt     240

gagcctgaaa gtaaaaggat gtctcttgaa gagagaaaag caattggggt aaaaatgatg     300

aaagtgctcc tatttatgaa cccatctgct ggaattgaag ggtttgagcc atactgtatg     360

aaaaattcct ccaatagcaa ctgcccaaac tgcaattggg ccgattaccc tccaacatca     420

ggaaagtgcc ttgatgacat agaagaagaa ccggagaatg ttgatgaccc aactgaaata     480

gtattaaggg acatgaacaa caaagatgca aggcaaaaga taaaagagga agtaaacact     540

cagaaagaag ggaagttccg tttgacaata aaaagggata tacgtaatgt gttgtccttg     600

agagtgttgg taaacggaac attcctcaag caccctaatg gatacaagtc cttatcaact     660

ctgcatagat tgaatgcata tgaccagagt ggaaggcttg ttgctaaact tgttgctact     720

gatgatctta cagtggagga tgaagaagat ggccatcgga tcctcaactc actcttcgag     780

cgttttaatg aaggacattc aaagccaatt cgagcagctg aaactgcggt gggagtctta     840

tcccaatttg gtcaagagca ccgattatca ccagaggagg gagacaatta gactggttac     900

ggaagaactt tatcttttaa gtaaaagaat tgatgataac atattgttcc acaaaacagt     960

aatagctaac agctccataa tagctgacat gattgtatca ttatcattat tggaaacatt    1020

gtatgagatg aaggatgtgg ttgaagtgta cagcaggcag tgcttgtgaa tttaaaataa    1080

aaatcctctt gttactact                                                 1099
```